(12) United States Patent
Jiang et al.

(10) Patent No.: US 9,533,006 B2
(45) Date of Patent: Jan. 3, 2017

(54) MARINE COATINGS

(71) Applicant: University of Washington, Seattle, WA (US)

(72) Inventors: Shaoyi Jiang, Redmond, WA (US); Xuewei Xu, Seattle, WA (US); Yuting Li, Seattle, WA (US); Andrew Keefe, Seattle, WA (US); Hong Xue, Pleasanton, CA (US); Shengfu Chen, Hangzhou (CN)

(73) Assignee: University of Washington, Seattle, WA (US)

( * ) Notice: Subject to any disclaimer, the term of this patent is extended or adjusted under 35 U.S.C. 154(b) by 71 days.

(21) Appl. No.: 13/692,958

(22) Filed: Dec. 3, 2012

(65) Prior Publication Data

US 2013/0178125 A1  Jul. 11, 2013

Related U.S. Application Data

(63) Continuation-in-part of application No. 12/780,251, filed on May 14, 2010, now Pat. No. 8,349,966, which is a continuation of application No. PCT/US2008/084098, filed on Nov. 19, 2008.

(60) Provisional application No. 60/989,073, filed on Nov. 19, 2007, provisional application No. 61/074,913, filed on Jun. 23, 2008, provisional application No. 61/566,476, filed on Dec. 2, 2011, provisional application No. 61/566,549, filed on Dec. 2, 2011.

(51) Int. Cl.
- *C08F 20/56* (2006.01)
- *A61K 31/785* (2006.01)
- *C09D 5/16* (2006.01)

(52) U.S. Cl.
CPC ............ *A61K 31/785* (2013.01); *C09D 5/165* (2013.01); *C09D 5/1668* (2013.01); *C09D 5/16* (2013.01); *C09D 5/1606* (2013.01); *C09D 5/1637* (2013.01); *C09D 5/1656* (2013.01); *C09D 5/1662* (2013.01); *C09D 5/1675* (2013.01); *Y10T 428/3154* (2015.04); *Y10T 428/31511* (2015.04); *Y10T 428/31551* (2015.04); *Y10T 428/31663* (2015.04); *Y10T 428/31725* (2015.04); *Y10T 428/31786* (2015.04); *Y10T 428/31844* (2015.04); *Y10T 428/31938* (2015.04); *Y10T 428/31942* (2015.04); *Y10T 442/10* (2015.04)

(58) Field of Classification Search
None
See application file for complete search history.

(56) References Cited

U.S. PATENT DOCUMENTS

| | | | |
|---|---|---|---|
| 2,777,872 A | 1/1957 | Shacklett | |
| 3,671,502 A | 6/1972 | Samour | |
| 4,075,183 A | 2/1978 | Kawakami | |
| 4,138,446 A | 2/1979 | Kawakami | |
| 4,415,388 A | 11/1983 | Korpman | |
| 4,493,926 A | 1/1985 | Williams, Jr. | |
| 4,569,798 A | 2/1986 | Nieh | |
| 4,985,023 A | 1/1991 | Blank | |
| 5,204,060 A | 4/1993 | Allenmark | |
| 5,695,552 A * | 12/1997 | Taylor | 106/15.05 |
| 5,714,360 A | 2/1998 | Swan | |
| 5,919,523 A | 7/1999 | Sundberg | |
| 5,986,042 A | 11/1999 | Irizato | |
| 6,361,768 B1 | 3/2002 | Galleguillos | |
| 6,486,333 B1 | 11/2002 | Murayama | |
| 6,864,314 B1 * | 3/2005 | Yeung et al. | 525/91 |
| 6,897,263 B2 | 5/2005 | Hell | |
| 6,924,338 B1 * | 8/2005 | Davies | A61L 27/34 525/203 |
| 7,056,532 B1 | 6/2006 | Kabanov | |
| 7,291,427 B2 | 11/2007 | Kawamura | |
| 7,306,625 B1 | 12/2007 | Stratford | |
| 7,335,248 B2 | 2/2008 | Abou-Nemeh | |
| 7,737,224 B2 | 6/2010 | Willis | |
| 2003/0195133 A1* | 10/2003 | Shefer et al. | 510/444 |
| 2004/0063587 A1 | 4/2004 | Horton | |
| 2004/0063881 A1 | 4/2004 | Lewis | |
| 2004/0067503 A1 | 4/2004 | Tan | |
| 2005/0004661 A1* | 1/2005 | Lewis et al. | 623/1.42 |
| 2005/0058689 A1 | 3/2005 | McDaniel | |
| 2006/0183863 A1 | 8/2006 | Huang | |
| 2006/0217285 A1* | 9/2006 | Destarac | 510/475 |
| 2006/0240072 A1 | 10/2006 | Chudzik | |
| 2007/0021569 A1 | 1/2007 | Willis | |
| 2007/0042198 A1 | 2/2007 | Schonemyr | |
| 2007/0104654 A1 | 5/2007 | Hsieh | |
| 2008/0131393 A1 | 6/2008 | Yeung | |
| 2008/0181861 A1 | 7/2008 | Jiang | |

(Continued)

FOREIGN PATENT DOCUMENTS

| | | |
|---|---|---|
| DE | 10 2006 004 111 A1 | 8/2007 |
| EP | 0 354 984 A2 | 2/1990 |

(Continued)

OTHER PUBLICATIONS

Zhang "Superlow Fouling Sulfobetaine and Carboxybetaine Polymers on Glass Slides", 2006, Langmuir, 22, pp. 10072-10077.*

Patent Examination Report No. 1 mailed May 28, 2013, issued in corresponding Australian Application No. 2008326438, filed Nov. 19, 2008, 3 pages.

International Search Report and Written Opinion mailed Jul. 7, 2009, issued in corresponding International Application No. PCT/US2008/084098, filed Nov. 19, 2008, 10 pages.

(Continued)

*Primary Examiner* — James Rogers
(74) *Attorney, Agent, or Firm* — Christensen O'Connor Johnson Kindness PLLC

(57) ABSTRACT

Marine coatings including cationic polymers hydrolyzable to nonfouling zwitterionic polymers, coated marine surfaces, and methods for making and using the marine coatings.

14 Claims, 83 Drawing Sheets

(56) References Cited

U.S. PATENT DOCUMENTS

| | | | |
|---|---|---|---|
| 2008/0299177 | A1 | 12/2008 | Hardy |
| 2009/0197791 | A1* | 8/2009 | Balastre et al. ............. 510/407 |

FOREIGN PATENT DOCUMENTS

| | | | |
|---|---|---|---|
| EP | 0 419 654 A1 | 4/1991 | |
| EP | 0 479 245 A2 | 4/1992 | |
| FR | 2894585 A1 | 6/2007 | |
| FR | 2898067 A1 | 9/2007 | |
| JP | 51-147581 A | 12/1976 | |
| JP | 53-124538 | 10/1978 | |
| JP | 59-199696 A | 11/1984 | |
| JP | 63-234007 A | 9/1988 | |
| JP | 03-166272 A | 7/1991 | |
| JP | 06-118399 A | 4/1994 | |
| JP | 10-330687 A | 12/1998 | |
| JP | 2000-0265110 A | 9/2000 | |
| JP | 2001-294810 A | 10/2001 | |
| JP | 2003-504476 A | 6/2002 | |
| JP | 2007130194 A | 5/2007 | |
| JP | 2009-528440 A | 9/2007 | |
| JP | 2009-102314 A | 5/2009 | |
| SU | 1780673 A1 | 12/1992 | |
| WO | 00/39176 A1 | 7/2000 | |
| WO | 2004/058837 A2 | 7/2004 | |
| WO | 2004/100666 A1 | 11/2004 | |
| WO | 2007/068744 A1 | 6/2007 | |
| WO | WO 2007068744 A1 * | 6/2007 | |
| WO | 2007/084452 A2 | 7/2007 | |
| WO | 2007/099239 A2 | 9/2007 | |
| WO | 2008/083390 A2 | 7/2008 | |

OTHER PUBLICATIONS

International Preliminary Report on Patentability mailed Jun. 3, 2010, issued in corresponding International Application No. PCT/US2008/084098, filed Nov. 19, 2008, 8 pages.
"Betaine," Wikipedia, The Free Encyclopedia, <http://en.wikipedia.org/wiki/Betaine> [retrieved Jul. 31, 2011], 1 page.
"Bromide," Wikipedia, The Free Encyclopedia, <http://en.wikipedia.org/wiki/Bromide> [retrieved Jul. 27, 2011], 3 pages.
Chang, Y., et al., "Highly Protein-Resistant Coatings From Well-Defined Diblock Copolymers Containing Sulfobetaines," Langmuir 22(5):2222-2226, Feb. 2006.
Chen, S., et al., "Controlling Antibody Orientation on Charged Self-Assembled Monolayers," Langmuir 19(7):2859-2864, Apr. 2003.
Chen, S., et al., "Strong Resistance of Oligo(phosphorylcholine) Self-Assembled Monolayers to Protein Adsorption," Langmuir 22(6):2418-2421, Mar. 2006.
Chen, S., et al., "Strong Resistance of Phosphorylcholine Self-Assembled Monolayers to Protein Adsorption: Insights Into Nonfouling Properties of Zwitterionic Materials," Journal of the American Chemical Society 127(41):14473-14478, Oct. 2005.
Feng, W., et al., "Adsorption of Fibrinogen and Lysozyme on Silicon Grafted With Poly(2-methacryloyloxyethyl phosphorylcholine) Via Surface-Initiated Atom Transfer Radical Polymerization," Langmuir 21(13):5980-5987, Jun. 2005.
Feng., W., et al., "Atom-Transfer Radical Grafting Polymerization of 2-Methacryloyloxyethyl Phosphorylcholine From Silicon Wafer Surfaces," Journal of Polymer Science: Part A: Polymer Chemistry 42(12):2931-2942, Jun. 2004.
Jiang, Y., et al., "Blood Compatibility of Polyurethane Surface Grafted Copolymerization With Sulfobetaine Monomer," Colloids and Surfaces B: Biointertaces 36(1):27-33, Jul. 2004.
Jun, Z., et al., "Surface Modification of Segmented Poly(ether urethane) by Grafting Sulfo Ammonium Zwitterionic Monomer to Improve Hemocompatibilities," Colloids and Surfaces B: Biointerfaces 28(1):1-9, Apr. 2003.
Li, L., et al., "Protein Adsorption on Alkanethiolate Self-Assembled Monolayers: Nanoscale Surface Structural and Chemical Effects," Langmuir 19(7):2974-2982, Apr. 2003.
Li, L., et al., "Protein Adsorption on Oligo(ethylene glycol)-Terminated Alkanethiolate Self-Assembled Monolayers: The Molecular Basis for Nonfouling Behavior," Journal of Physical Chemistry B 109(7):2934-2941, Feb. 2005.
Lowe, A.B., et al., "Well-Defined Sulfobetaine-Based Statistical Copolymers as Potential Antibioadherent Coatings," Journal of Biomedical Materials Research 52(1):88-94, Jul. 2000.
"Nail Infections," Health911, <http://www.health911.com/nail-infections> [retrieved Aug. 29,2011], 3 pages.
Yuan, J., et al., "Chemical Graft Polymerization of Sulfobetaine Monomer on Polyurethane Surface for Reduction in Platelet Adhesion," Colloids and Surfaces B: Biointerfaces 39(1-2):87-94, Nov. 2004.
Yuan, J., et al., "Improvement of Blood Compatibility on Cellulose Membrane Surface by Grafting Betaines," Colloids and Surfaces B: Biointerfaces 30(1-2):147-155, Jul. 2003.
Yuan, J., "Platelet Adhesion Onto Segmented Polyurethane Surfaces Modified by Carboxybetaine," Journal of Biomatenal Science, Polymer Edition 14(12):1339-1349, Dec. 2003.
Yuan, Y., et al., "Grafting Sulfobetaine Monomer Onto Silicone Surface to Improve Haemocompatability," Polymer International 53 (1):121-126, Jan. 2004.
Yuan, Y., et al. "Grafting Sulfobetaine Monomer Onto the Segmented Poly(ether-urethane) Surface to Improve Hemocompatability," Journal of Biomaterials Science, Polymer Edition 13(10):1081-1092, Oct. 2002.
Yuan, Y., et al., "Polyurethane Vascular Catheter Surface Grafted With Zwitterionic Sulfobetaine Monomer Activated by Ozone," Colloids and Surfaces B: Biointerfaces 35(1):1-5, May 2004.
Yuan, Y., et al., "Surface Modification of SPEU Films by Ozone Induced Graft Copolymerization to Improve Hemocompatibility," Colloids and Surfaces B: Biointerfaces 29(4):247-256, Jun. 2003.
Zhang, J., et al., "Chemical Modification of Cellulose Membranes With Sulfo Ammonium Zwitterionic Vinyl Monomer to Improve Hemocompatibility," Colloids and Surfaces B: Biointerfaces 30(3):249-257, Jul. 2003.
Zhang, Z., et al., "Superflow Fouling Sulfobetaine and Carboxybetaine Polymers on Glass Slides," Langmuir 22(24):10072-10077, Nov. 2006.
Zhang, Z., "Surface Grafted Sulfobetaine Polymers Via Atom Transfer Radical Polymerization as Superlow Fouling Coatings," Journal of Physical Chemistry B 110(22)10799-10804, Jun. 2006.
Zheng, J., "Molecular Simulation Study of Water Interactions With Oligo (Ethylene Glycol)-Terminated Alkanethiol Self-Assembled Monolayers," Langmuir 20(20):8931-8938, Sep. 2004.
Zheng, J., "Strong Repulsive Forces Between Protein and Oligo (Ethylene Glycol) Self-Assembled Monolayers: A Molecular Simulation Study," Biophysical Journal 89(1):158-166, Jul. 2005.
Zhou, J., et al., "Platelet Adhesion and Protein Adsorption on Silicone Rubber Surface by Ozone-Induced Grafted Polymerization With Carboxybetaine Monomer," Colloids and Surfaces B: Biointerfaces 41(1):55-62, Mar. 2005.
Communication from Mexican Associate dated Jan. 17, 2014, that a second Office Action was issued by the Mexican Institute of Industrial Property in related Mexican Application No. MX/a/2010/005295, filed Nov. 19, 2008, 5 pages.
Notice of Reasons for Rejection dated Jul. 25, 2013, issued in corresponding Japanese Application No. 2010-534290, filed Nov. 19, 2008, 7 pages.
Zauner, W., et al., "Polylysine-Based Transfection Systems Utilizing Receptor-Mediated Delivery," Advanced Drug Delivery Reviews 30(1-3):97-113, Mar. 1998.
Zhang, L., et al., "Imaging and Cell Targeting Characteristics of Magnetic Nanoparticles Modified by a Functionalizable Zwitterionic Polymer With Adhesive 3,4-Dihydroxyphenyl-L-alanine Linkages," Biomaterials 31(25):6582-6588, Sep. 2010.
Zhang, L.M., et al., "New Water-Soluble Ampholytic Polysaccharides for Oilfield Drilling Treatment: A Preliminary Study," Carbohydrate Polymers 44(3):255-260, Mar. 2001.
Zhang, Z., et al., "Biocompatible, Functionalizable, and Nonfouling Surfaces and Materials for Biomedical and Engineering Applications," doctoral dissertation, University of Washington, Seattle, Wash., 2008, 214 pages.

(56) References Cited

OTHER PUBLICATIONS

Zhang, Z., et al., "Dual-Functional Biomimetic Materials: Nonfouling Poly(carboxybetaine) With Active Functional Groups for Protein Immobilization," Biomacromolecules 7(12):3311-3315, Dec. 2006.

Zhang, Z., et al., "Nonfouling Behavior of Polycarboxybetaine-Grafted Surfaces: Structural and Environmental Effects," Biomacromolecules 9(10):2686-2692, Sep. 2008.

Zhang, Z., et al., "Polysulfobetaine-Grafted Surfaces as Environmentally Benign Ultralow Fouling Marine Coatings," Langmuir 25(23):13516-13521, Aug. 2009.

Zhang, Z., et al., "The Hydrolysis of Cationic Polycarboxybetaine Esters to Zwitterionic Polycarboxybetaines With Controlled Properties," Biomaterials 29(36):4719-4725, Dec. 2008.

Zuidam, N.J., et al., "Effects of Physicochemical Characteristics of Poly(2-(dimethylamino)ethyl methacrylate)-Based Polyplexes on Cellular Association and Internalization," Journal of Drug Targeting 8(1):51-66, Jan. 2000.

Abel, T., et al., "Preparation and Investigation of Antibacterial Carbohydrate-Based Surfaces," Carbohydrate Research 337(24):2495-2499, Nov. 2002.

Ahlström, B., and L. Edebo, "Hydrolysis of the Soft Amphiphilic Antimicrobial Agent Tetradecyl Betainate is Retarded After Binding to and Killing Salmonella typhimurium," Microbiology 144(9):2497-2504, Sep. 1998.

Ahlström, B., et al., "The Effect of Hydrocarbon Chain Length, Ph, and Temperature on the Binding and Bactericidal Effect of Amphiphilic Betaine Esters on Salmonella typhimurium," Acta Pathologica Microbiologica et Immunologica Scandinavica 107(3):318-324, Mar. 1999.

Akesso, L., et al., "Deposition Parameters to Improve the Fouling-Release Properties of Thin Siloxane Coatings Prepared by PACVD," Applied Surface Science 255(13-14):6508-6514, Apr. 2009.

Al-Lohedan, H.A., "Reactions of Betaine Esters With Hydroxide Ion in Surfactant With Reactive and Unreactive Counterions," Tetrahedron 43(2):345-350, 1987.

Berge, S.M., et al., "Pharmaceutical Salts," Journal of Pharmaceutical Sciences 66(1):1-19, Jan. 1977.

Brault, N.D., et al., "Ultra-Low Fouling and Functionalizable Zwitterionic Coatings Grafted Onto $SiO_2$ via a Biomimetic Adhesive Group for Sensing and Detection in Complex Media," Biosensors & Bioelectronics 25(10):2276-2282, Jun. 2010.

Breiting, V., et al., "A Study on Patients Treated With Polyacrylamide Hydrogel Injection for Facial Corrections," Aesthetic Plastic Surgery 28(1):45-53, Jan. 2004.

Bronich, T.K., et al., "Recognition of DNA Topology in Reactions Between Plasmid DNA and Cationic Copolymers," Journal of the American Chemical Society 122(35):8339-8343, Sep. 2000.

Cao, L., et al., "Glow Discharge Plasma Treatment of Polyethylene Tubing With Tetraglyme Results in Ultralow Fibrinogen Adsorption and Greatly Reduced Platelet Adhesion," Journal of Biomedical Materials Research Part A 79A(4):788-803, Dec. 2006.

Chang, Y., et al., "Development of Biocompatible Interpenetrating Polymer Networks Containing a Sulfobetaine-Based Polymer and a Segmented Polyurethane for Protein Resistance," Biomacromolecules 8(1):122-127, 2007.

Chang, Y., et al., "A Systematic SPR Study of Human Plasma Protein Adsorption Behavior on the Controlled Surface Packing of Self-Assembled Poly(ethylene oxide) Triblock Copolymer Surfaces," Journal of Biomedical Materials Research Part A 93A(1):400-408, Apr. 2010.

Chen, G.H., and A.S. Hoffman, "Graft-Copolymers That Exhibit Temperature-Induced Phase-Transitions Over a Wide-Range of pH," Nature 373(6509):49-52, Jan. 1995.

Cheng, G., et al., "Inhibition of Bacterial Adhesion and Biofilm Formation on Zwitterionic Surfaces," Biomaterials 28(29):4192-4199, Oct. 2007.

Cheng, G., et al., "A Switchable Biocompatible Polymer Surface With Self-Sterilizing and Non-Fouling Capabilities," Angewandte Chemie International Edition 47(46):8831-8834, 2008.

Cheng, G., et al., "Zwitterionic Carboxybetaine Polymer Surfaces and Their Resistance to Long-Term Biofilm Formation," Biomaterials 30(28):5234-5240, Oct. 2009.

Cheng, J., et al., "Formulation of Functionalized PLGA-PEG Nanoparticles for In Vivo Targeted Drug Delivery," Biomaterials 28(5):869-876, Feb. 2007.

Chung, K.K. et al., "Impact of Engineered Surface Microtopography on Biofilm Formation of Staphylococcus aureus," Biointerphases 2(2):89-94, Jun. 2007.

Cogan, N.G., "Two-Fluid Model of Biofilm Disinfection," Bulletin of Mathematical Biology 70(3):800-819, Apr. 2008.

Communication Pursuant to Article 94(3) EPC, mailed Oct. 19, 2010, issued in corresponding European Application No. 08851463.3, filed Nov. 19, 2008, 4 pages.

Eberl, H.J., and R. Sudarsan, "Exposure of Biofilms to Slow Flow Fields: The Convective Contribution to Growth and Disinfection," Journal of Theoretical Biology 253(4):788-807, Aug. 2008.

Edebo, L., et al., "Betaine Esters: Quaternary Ammonium Compounds With Time-Limited Activity," Proceedings of the Industrial Applications of Surfactants III, Royal Society of Chemistry, University of Salford, U.K., Sep. 16-18, 1991, Special Publication No. 107, 1992, pp. 184-207.

Extended European Search Report dated Nov. 2, 2010, issued in European Application No. EP 08851866.7, filed Nov. 19, 2008, 4 pages.

Gaberc-Porekar, V., et al., "Obstacles and Pitfalls in the PEGylation of Therapeutic Proteins," Current Opinion in Drug Discovery & Development 11(2):242-250, Mar. 2008.

Gao, C.L., et al., "Functionalizable and Ultra-Low Fouling Zwitterionic Surfaces via Adhesive Mussel Mimetic Linkages," Biomaterials 31(7):1486-1492, Mar. 2010.

Gottenbos, B., et al., "In Vitro and In Vivo Antimicrobial Activity of Covalently Coupled Quaternary Ammonium Silane Coatings on Silicone Rubber," Biomaterials 23(6):1417-1423, Mar. 2002.

Gray, T. et al., "Molecular Mobility and Transitions in Complex Organic Systems Studied by Shear Force Microscopy," Nanotechnology 18(4):044009, Jan. 2007,9 pages.

Green, R.J., et al., "Adsorption of PEO-PPO-PEO Triblock Copolymers at the Solid/Liquid Interface: A Surface Plasmon Resonance Study," Langmuir 13(24):6510-6515, Nov. 1997.

Haldar, J., et al., "Polymeric Coatings That Inactivate Both Influenza Virus and Pathogenic Bacteria," Proceedings of the National Academy of Sciences USA (PNAS) 103(47):17667-17671, Nov. 2006.

Harder, P., et al., "Molecular Conformation in Oligo(ethylene glycol)-Terminated Self-Assembled Monolayers on Gold and Silver Surfaces Determines Their Ability to Resist Protein Adsorption," Journal of Physical Chemistry B 102(2):426-436, Jan. 1998.

He, M., et al., "Effect of Interfacial Liquid Structuring on the Coherence Length in Nanolubrication," Physical Review Letters 88(15):154302, Apr. 2002, 4 pages.

He, Y., et al., "Molecular Simulation Studies of Protein Interactions With Zwitterionic Phosphorylcholine Self-Assembled Monolayers in the Presence of Water," Langmuir 24(18):10358-10364, Aug. 2008.

He, Y., et al., "Origin of Repulsive Force and Structure/Dynamics of Interfacial Water in OEG-Protein Interactions: A Molecular Simulation Study," Physical Chemistry Chemical Physics 10(36):5539-5544, Aug. 2008.

Herold, D.A., et al., "Oxidation of Polyethylene Glycols by Alcohol Dehydrogenase," Biochemical Pharmacology 38(1):73-76, Jan. 1989.

Hirota, K., et al., "Coating of a Surface With 2-Methacryloyloxyethyl Phosphorylcholine (MPC) Co-Polymer Significantly Reduces Retention of Human Pathogenic Microorganisms," FEMS Microbiology Letters 248(1):37-45, Jul. 2005.

Holmberg, K., et al., "Effects on Protein Adsorption, Bacterial Adhesion and Contact Angle of Grafting PEG Chains to Polystyrene," Journal of Adhesion Science and Technology 7(6):503-517, Jun. 1993.

(56) References Cited

OTHER PUBLICATIONS

Holmlin, R.E., et al., "Zwitterionic SAMs That Resist Nonspecific Adsorption of Protein From Aqueous Buffer," Langmuir 17(9):2841-2850, Apr. 2001.
Horbett, T.A., "Principles Underlying the Role of Adsorbed Plasma Proteins in Blood Interactions With Foreign Materials," Cardiovascular Pathology 2(Suppl. 3):137S-148S, Jul.-Sep. 1993.
Horbett, T.A., et al., "The Role of Adsorbed Proteins in Animal Cell Adhesion," Colloids and Surfaces B: Biointerfaces 2(1-3):225-240, Mar. 1994.
Huang, S., and M.G. Hadfield, "Composition and Density of Bacterial Biofilms Determine Larval Settlement of the Polychaete Hydroides elegans," Marine Ecology Progress Series 260:161-172, Sep. 2003.
Hutter, J.L., and J. Bechhoefer, et al., "Measurement and Manipulation of van der Walls Forces in Atomic-Force Microscopy," Journal of Vacuum Science & Technology B 12(3):2251-2253, May-Jun. 1994.
Huxtable, R.J., "Physiological Actions of Taurine," Physiological Reviews 72(1):101-163, Jan. 1992.
Ilker, M.F., et al., "Tuning the Hemolytic and Antibacterial Activities of Amphiphilic Polynorbornene Derivatives," Journal of the American Chemical Society 126(48):15870-15875, Dec. 2004.
International Preliminary Report on Patentability mailed May 8, 2012, issued in related International Application No. PCT/US2010/055887, filed Nov. 8, 2010, 8 pages.
International Search Report and Written Opinion dated Jan. 29, 2009, issued in PCT/US2008/084095, filed Nov. 19, 2008, 12 pages.
International Search Report and Written Opinion mailed Jul. 28, 2011, issued in related International Application No. PCT/US2010/055887, filed Nov. 8, 2010, 12 pages.
Ishihara, K., et al., "Inhibition of Fibroblast Cell Adhesion on Substrate by Coating With 2-Methacryloyloxyethyl Phosphorylcholine Polymers," Journal of Biomaterials Science, Polymer Edition 10(10):1047-1061, 1999.
Japanese Office Action mailed Apr. 24, 2013, issued in Japanese Application No. 2010-534289, filed Nov. 19, 2008, 12 pages.
Jiang, S., and Z. Cao, "Ultralow-Fouling, Functionalizable, and Hydrolyzable Zwitterionic Materials and Their Derivatives for Biological Applications," Advanced Materials 22(9):920-932, Mar. 2010.
Johnston, E.E., et al., "Interactions Between Pseudomonas aeruginosa and Plasma-Deposited PEO-Like Thin Films During Initial Attachment and Growth," American Chemical Society Polymer Preprints, 38(1):1016-1017, Apr. 1997.
Database WPI, Week 199351 Thomson Scientific, London, AN 1993-412215 and SU 1780673 A1 (Centr Asia Sericulture Res Inst), Dec. 15, 1992.
First Examination Report mailed Sep. 22, 2015, issued in corresponding Indian Application No. 2206/KOLNP/2010, filed Jun. 17, 2010, 2 pages.
Juo, P.-S., "Concise Dictionary of Biomedicine and Molecular Biology," 2nd ed., CRC Press LLC, Boca Raton, Fla., p. 173, 2002.
Kawabata, N., et al., "Removal of Micro-Organisms by Filtration Through Unwoven Cloth Coated With a Pyridinium-Type Polymer," Epidemiology and Infection 108(1):123-134, Feb. 1992.
Kenawy, E.-R., et al., "The Chemistry and Applications of Antimicrobial Polymers: A State-of-the-Art Review," Biomacromolecules 8(5):1359-1384, May 2007.
Kingshott, P., et al., "Covalent Attachment of Poly(ethylene glycol) to Surfaces, Critical for Reducing Bacterial Adhesion," Langmuir 19(17):6912-6921, Jul. 2003.
Klibanov, A.M., "Permanently Microbicidal Materials Coatings," Journal of Materials Chemistry 17(24):2479-2482, May 2007.
Kuroda, K., and W.F. DeGrado, "Amphiphilic Polymethacrylate Derivatives as Antimicrobial Agents," Journal of the American Chemical Society 127(12):4128-4129, Mar. 2005.
Ladd, J., et al., "Zwitterionic Polymers Exhibiting High Resistance to Nonspecific Protein Adsorption From Human Serum and Plasma," Biomacromolecules 9(5):1357-1361, May 2008.

Ledley, F.D., "Nonviral Gene Therapy: The Promise of Genes as Pharmaceutical Products," Human Gene Therapy 6(9):1129-1144, Sep. 1995.
Lee, J.H., et al., "Polyplexes Assembled With Internally Quaternized PAMAM-OH Dendrimer and Plasmid DNA Have a Neutral Surface and Gene Delivery Potency," Bioconjugate Chemistry 14(6):1214-1221, Nov.-Dec. 2003.
Lee, S.B., et al., "Permanent, Nonleaching Antibacterial Surfaces. 1. Synthesis by Atom Transfer Radical Polymerization," Biomacromolecules 5(3):877-882, Feb. 2004.
Lewis, A.L., "Phosphorylcholine-Based Polymers and Their Use in the Prevention of Biofouling," Colloids and Surfaces B: Biointerfaces 18(3-4):261-275, Oct. 2000.
Li, G., et al., "Ultralow Fouling Zwitterionic Polymers Grafted From Surfaces Covered With an Initiator via an Adhesive Mussel Mimetic Linkage," Journal of Physical Chemistry B 112(48):15269-15274, Nov. 2008.
Li, G., et al., "Ultra Low Fouling Zwitterionic Polymers With a Biomimetic Adhesive Group," Biomaterials 29(35):4592-4597, Dec. 2008.
Li, L., et al., "Protein Interactions With Oligo(ethylene glycol) (OEG) Self-Assembled Monolayers: OEG Stability, Surface Packing Density and Protein Adsorption," Journal of Biomaterials Science, Polymer Edition 18(11):1415-1427, 2007.
Lindstedt, M., et al., "Antimicrobial Activity of Betaine Esters, Quaternary Ammonium Amphiphiles Which Spontaneously Hydrolyze Into Nontoxic Components," Antimicrobial Agents and Chemotherapy 34(10):1949-1954, Oct. 1990.
Loose, C., et al., "A Linguistic Model for the Rational Design of Antimicrobial Peptides," Nature 443(7113):867-869, Oct. 2006.
Lowe, A.B., and C.L. McCormick, "Synthesis and Solution Properties of Zwitterionic Polymers," Chemical Reviews 102(11):4177-4189, Nov. 2002.
Luo, D., and W.M. Saltzman, "Synthetic DNA Delivery Systems," Nature Biotechnology 18(1):33-37, Jan. 2000.
Lynn, D.M., and R. Langer, "Degradable Poly(β-amino esters): Synthesis, Characterization, and Self-Assembly With Plasmid DNA," Journal of the American Chemical Society 122(44):10761-10768, Oct. 2000.
Ma, H., et al., "'Non-Fouling' Oligo(ethylene glycol)-Functionalized Polymer Brushes Synthesized by Surface-Initiated Atom Transfer Radical Polymerization," Advanced Materials 16(4):338-341, Feb. 2004.
Notification of the First Office Action, dated Aug. 21,2013, issued in corresponding Chinese Application No. 201080055964.6, filed Nov. 8, 2010,8 pages.
Nyyssölä, A., "Pathways of Glycine Betaine Synthesis in Two Extremely Halophilic Bacteria, Actinopolyspora halophila and Ectothiorhodospira halochloris," doctoral dissertation, Department of Chemical Technology, Helsinki University of Technology, Espoo, Finland, Oct. 2001, 68 pages.
Ostuni, E., et al., "A Survey of Structure-Property Relationships of Surfaces That Resist the Adsorption of Protein," Langmuir 17(18):5605-5620, Jul. 2001.
Ostuni, E., et al., "Self-Assembled Monolayers That Resist the Adsorption of Proteins and the Adhesion of Bacterial and Mammalian Cells," Langmuir 17(20):6336-6343, Aug. 2001.
Overney, R.M., et al., "Compliance Measurements of Confined Polystyrene Solutions by Atomic Force Microscopy," Physical Review Letters 76(8):1272-1275, Feb. 1996.
Pasquier, N., et al., "From Multifunctionalized Poly(ethylene imine)s Toward Antimicrobial Coatings," Biomacromolecules 8(9):2874-2882, Sep. 2007.
Patel, J.D., et al., "Phospholipid Polymer Surfaces Reduce Bacteria and Leukocyte Adhesion Under Dynamic Flow Conditions," Journal of Biomedical Materials Research, Part A 73A(3):359-366, Jun. 2005.
Prata, C.A.H., et al., "Charge-Reversal Amphiphiles for Gene Delivery," Journal of the American Chemical Society 126(39):12196-12197, Oct. 2004.
Roland, C.M., and R. Casalini, "Temperature Dependence of Local Segmental Motion in Polystyrene and Its Variation With Molecular Weight," Journal of Chemical Physics 119(3):1838-1842, Jul. 2003.

(56) References Cited

OTHER PUBLICATIONS

Roosjen, A., et al., "Microbial Adhesion to Poly(ethylene oxide) Brushes: Influence of Polymer Chain Length and Temperature," Langmuir 20(25):10949-10955, Nov. 2004.

Russell, T.P., "Surface-Responsive Materials," Science 297(5583):964-967, Aug. 2002.

Schumacher, J.F., et al., "Engineered Antifouling Microtopographies—Effect of Feature Size, Geometry, and Roughness on Settlement of Zoospores of the Green Alga Ulva," Biofouling 23(1):55-62, 2007.

Shen, M., et al., "PEO-Like Plasma Polymerized Tetraglyme Surface Interactions With Leukocytes and Proteins: In Vitro and In Vivo Studies," Journal of Biomaterials Science, Polymer Edition 13(4):367-390, 2002.

Shikuma, N.J., and M.G. Hadfield, "Temporal Variation of an Initial Marine Biofilm Community and Its Effects on Larval Settlement and Metamorphosis of the Tubeworm Hydroides elegans," Biofilms 2(4):231-238, Oct. 2005 (8 pages).

Sills, S., et al., "Molecular Dissipation Phenomena of Nanoscopic Friction in the Heterogeneous Relaxation Regime of a Glass Former," Journal of Chemical Physics 123:134902, Oct. 2005, 7 pages.

Tegoulia, V.A., and S.L. Cooper, "*Staphylococcus aureus* Adhesion to Self-Assembled Monolayers: Effect of Surface Chemistry and Fibrinogen Presence," Colloids and Surfaces B: Biointerfaces 24(3-4):217-228, Apr. 2002.

Tiller, J.C., et al., "Designing Surfaces That Kill Bacteria on Contact," Proceedings of the National Academy of Sciences USA (PNAS) 98(11):5981-5985, May 2001.

Tsai, W.-B., et al., "Human Plasma Fibrinogen Adsorption and Platelet Adhesion to Polystyrene," Journal of Biomedical Materials Research 44(2):130-139, Feb. 1999.

Ueda, T., et al., "Preparation of 2-Methacryloyloxyethyl Phosphorylcholine Copolymers With Alkyl Methacrylates and Their Blood Compatibility," Polymer Journal 24(11):1259-1269, Nov. 1992.

Ueland, P.M., et al., "Betaine: A Key Modulator of One-Carbon Metabolism and Homocysteine Status," Clinical Chemistry and Laboratory Medicine 43(10):1069-1075, Oct. 2005.

Vaisocherová, H., et al., "Ultralow Fouling and Functionalizable Surface Chemistry Based on a Zwitterionic Polymer Enabling Sensitive and Specific Protein Detection in Undiluted Blood Plasma," Analytical Chemistry 80(20):7894-7901, Oct. 2008.

Vallee-Rehel, K., et al., "A New Approach in the Development and Testing of Antifouling Paints Without Organotin Derivatives," Journal of Coatings Technology 70(880):55-63, May 1998.

Wei, J.H., et al., "Direct Measurement of Nanofluxes and Structural Relaxations of Perfluorinated Ionomer Membranes by Scanning Probe Microscopy," Journal of Membrane Science 279(1-2):608-614, Aug. 2006.

West, S.L., et al., "The Biocompatibility of Crosslinkable Copolymer Coatings Containing Sulfobetaines and Phosphobetaines," Biomaterials 25(7-8):1195-1204, Mar.-Apr. 2004.

Wolfert, M.A., et al., "Polyelectrolyte Vectors for Gene Delivery: Influence of Cationic Polymer on Biophysical Properties of Complexes Formed With DNA," Bioconjugate Chemistry 10(6):993-1004, Nov.-Dec. 1999.

Wright, M.R., "Arrhenius Parameters for the Alkaline Hydrolysis of Esters in Aqueous Solution. Part III. Methyl Betaine Methyl Ester," Journal of the Chemical Society B: Physical Organic, 1968, pp. 548-550.

Yang, W., et al., "Film Thickness Dependence of Protein Adsorption From Blood Serum and Plasma Onto Poly (sulfobetaine)-Grafted Surfaces," Langmuir 24(17):9211-9214, Aug. 2008.

Yang, W., et al., "Functionalizable and Ultra Stable Nanoparticles Coated With Zwitterionic Poly(carboxybetaine) in Undiluted Blood Serum," Biomaterials 30(29):5617-5621, Oct. 2009.

Yang, W., et al., "Pursuing 'Zero' Protein Adsorption of Poly(carboxybetaine) from Undiluted Blood Serum and Plasma," Langmuir 25(19):11911-11916, Jul. 2009.

Yebra, D.M., et al., "Antifouling Technology—Past, Present and Future Steps Towards Efficient and Environmentally Friendly Antifouling Coatings," Progress in Organic Coatings 50(2):75-104, Jul. 2004.

\* cited by examiner

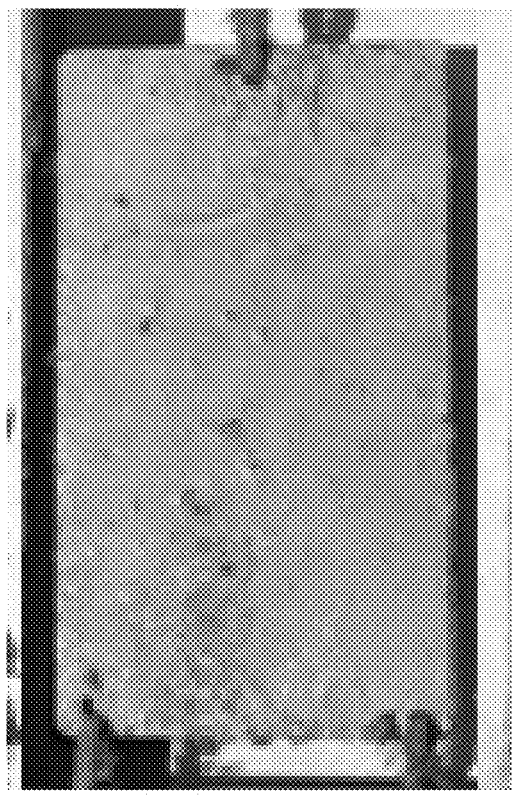
*Fig. 20C.*
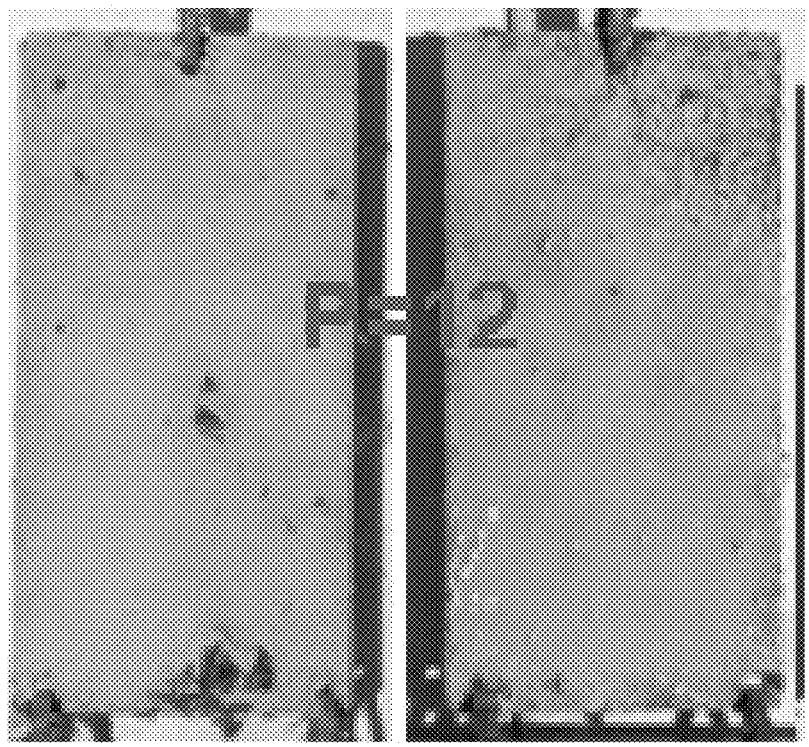
*Figs. 20D-E*

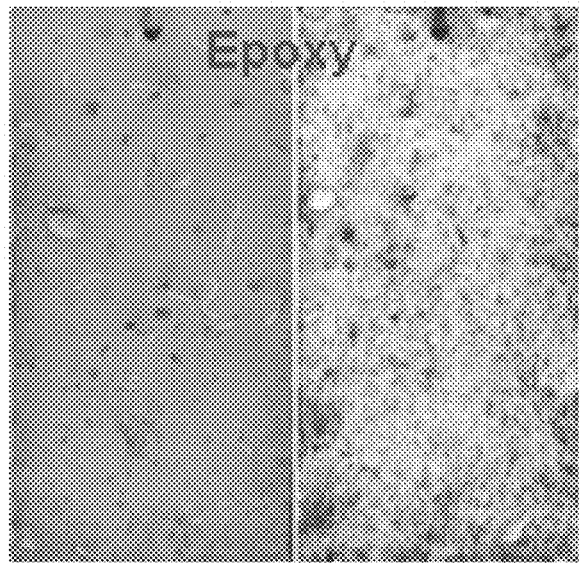
*Figs. 22A-B.*
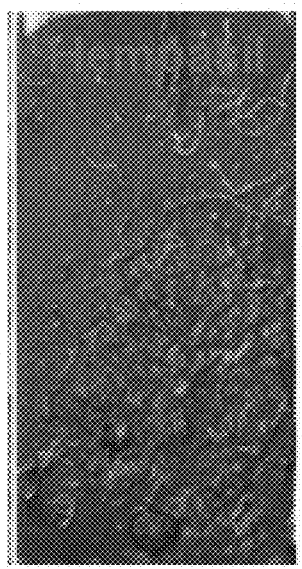
*Fig. 22C.*
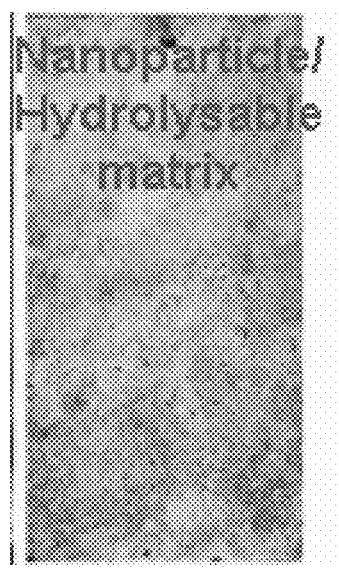
*Fig. 22D.*

| | Measured structure | Nanoparticles stability | | |
|---|---|---|---|---|
| | | 1% | 2% | 5% |
| YTL006 | SBMA$_{42}$-LMA$_{83}$ | ok | ok | ok |
| YTL007 | SBMA$_{49}$-LMA$_{63}$ | ok | ok | ok |
| YTL012 | SBMA$_{43}$-LMA$_{73}$ | ok | ok | ■ |
| YTL003 | SBMA$_{49}$-LMA$_{30}$ | ■ | ■ | ■ |
| YTL004 | SBMA$_{47}$-LMA$_{37}$ | ■ | ■ | ■ |
| YTL005 | SBMA$_{47}$-LMA$_{22}$ | ■ | ■ | ■ |
| YTL013 | SBMA$_{42}$-HMA$_{58}$ | ok | ok | ■ |

*Fig.32.*

| Name | Structure |
|---|---|
| YTL012 | PLMA41-PSBMA63 |
| YTL051 | PHMA70-PSBMA40 |
| YTL054 | PHMA41-PSBMA52 |
| YTL064 | PHMA41-PSBMA150 |
| YTL065 | PHMA41-PSBMA70 |

*Fig.34.*

|        | MMA  | TBSMA |
|--------|------|-------|
| YTL020 | 0.90 | 0.10  |
| YTL029 | 0.85 | 0.15  |
| YTL022 | 0.80 | 0.20  |
| YTL030 | 0.75 | 0.25  |

*Fig.36.*

| Name | Structure |
|---|---|
| YTL033 | $MMA_{0.8}/TBSMA_{0.2}$ |
| XUE327 | $PCB\ ester_{0.2}/MMA_{0.8}$ |
| YTL059 | $PCB\ ester_{0.5}/MMA_{0.3}/HMA_{0.2}$ |
| YTL058 | $PCB\ ester_{0.3}/MMA_{0.5}/HMA_{0.2}$ |
| YTL063 | $PCB\ ester_{0.25}/MMA_{0.5}/HMA_{0.25}$ |

*Fig.42.*

| Sample No. | Base coating composition | Nanoparticle composition | Nanoparticle amount | Protein adsorption |
|---|---|---|---|---|
| Control | | | | 1 |
| YTL054-7 | PCB ester50/MMA30/HMA20 | HMA41-SBMA52 | 10 | 0.6571 |
| YTL054-8 | PCB ester25/MMA50/HMA25 | HMA41-SBMA52 | 10 | 0.545 |
| YTL054-9 | PCB ester50/MMA30/HMA20 | HMA41-SBMA52 | 20 | 0.547 |
| YTL054-10 | PCB ester25/MMA50/HMA25 | HMA41-SBMA52 | 20 | 0.2468 |
| YTL064-1 | PCB ester50/MMA30/HMA20 | PHMA41-SBMA150 | 10 | 0.4869 |
| YTL064-2 | PCB ester25/MMA50/HMA25 | PHMA41-SBMA150 | 10 | 0.3064 |
| YTL064-3 | PCB ester50/MMA30/HMA20 | PHMA41-SBMA150 | 20 | 0.4488 |
| YTL064-4 | PCB ester25/MMA50/HMA25 | PHMA41-SBMA150 | 20 | 0.2355 |
| YTL065-1 | PCB ester50/MMA30/HMA20 | PHMA41-SBMA70 | 10 | 0.6221 |
| YTL065-2 | PCB ester25/MMA50/HMA25 | PHMA41-SBMA70 | 10 | 0.5692 |
| YTL065-3 | PCB ester50/MMA30/HMA20 | PHMA41-SBMA70 | 20 | 0.5851 |
| YTL065-4 | PCB ester25/MMA50/HMA25 | PHMA41-SBMA70 | 20 | 0.328 |

*Fig. 45.*

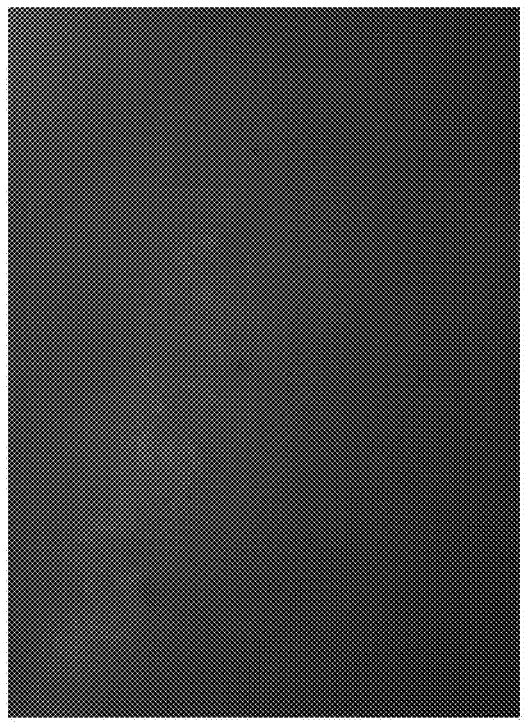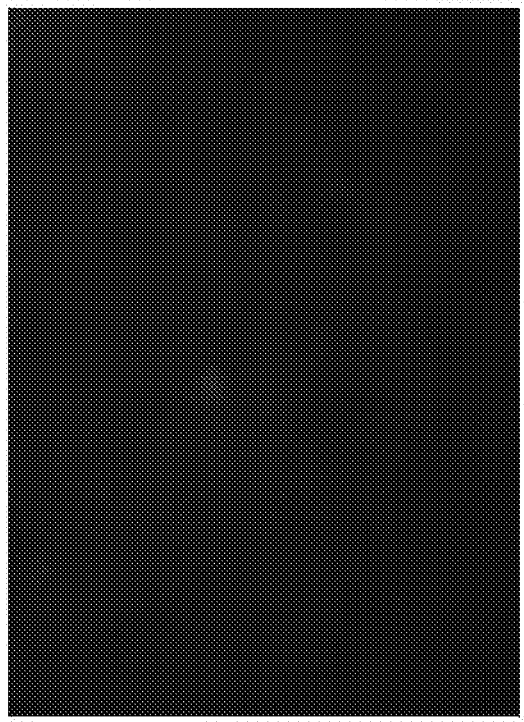
Fig. 46.

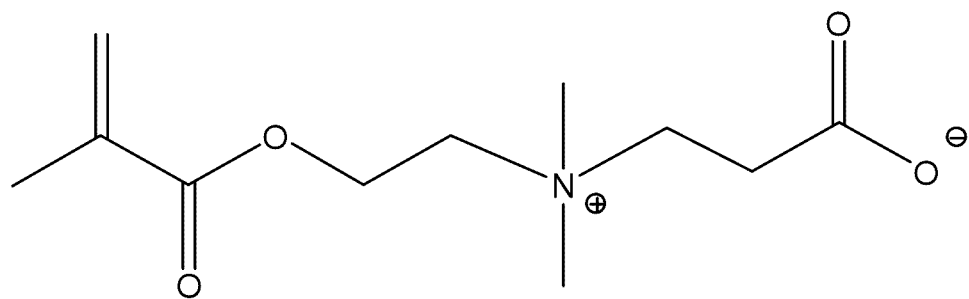
CBMA
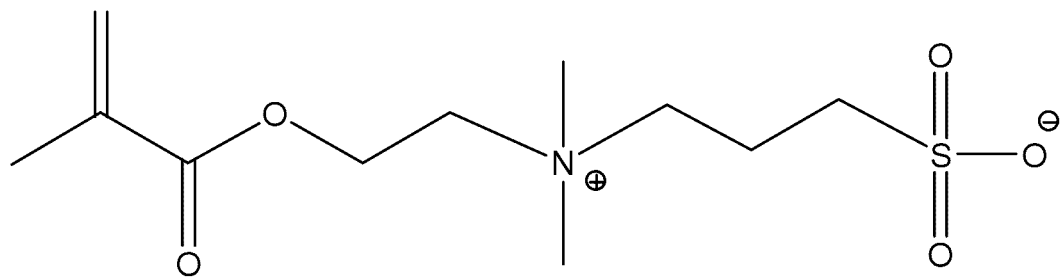
SBMA
*Fig.54.*

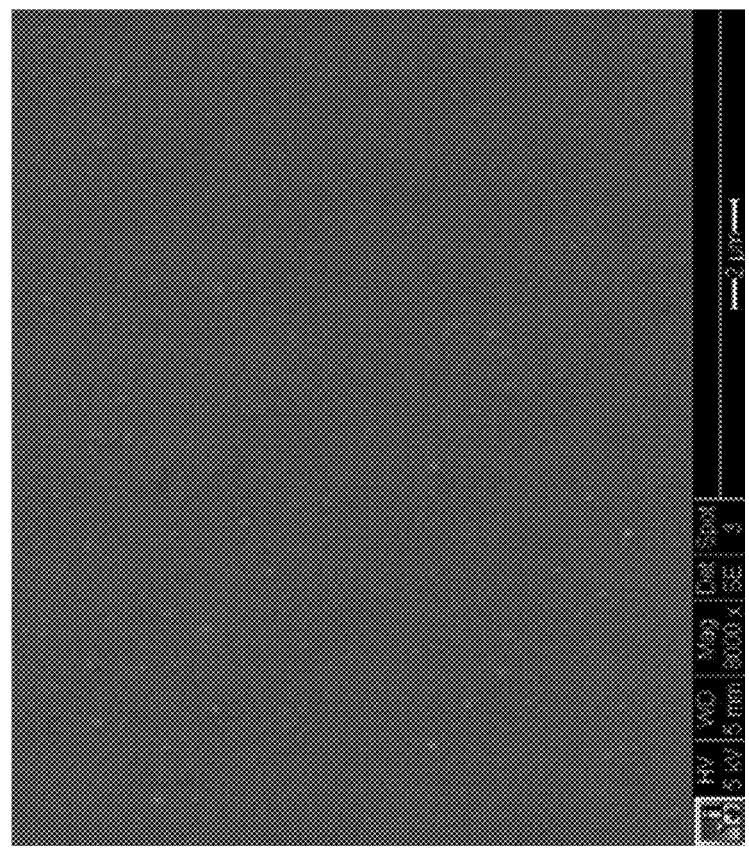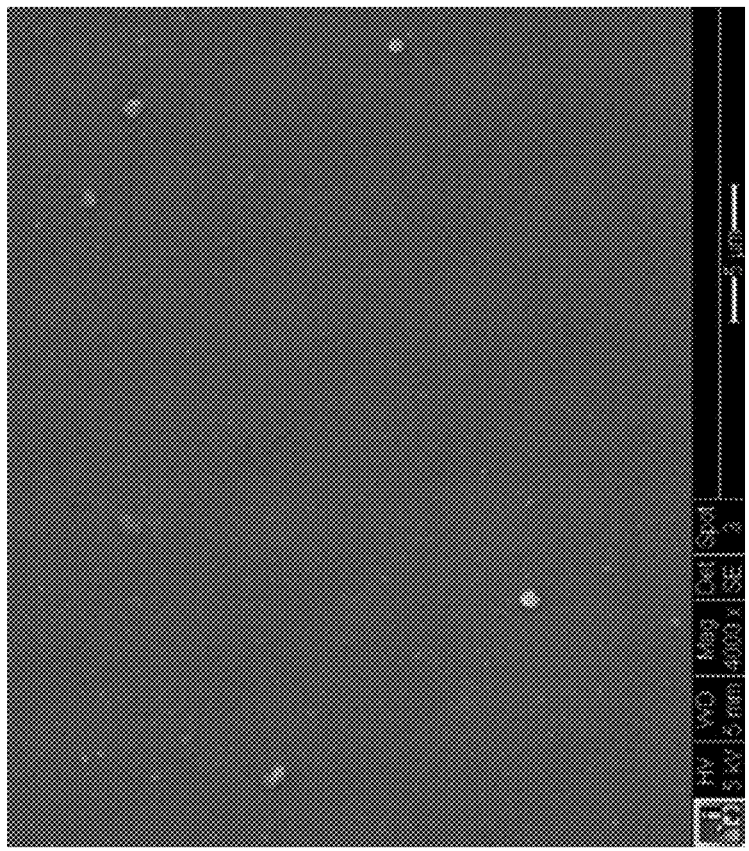
Fig. 60.

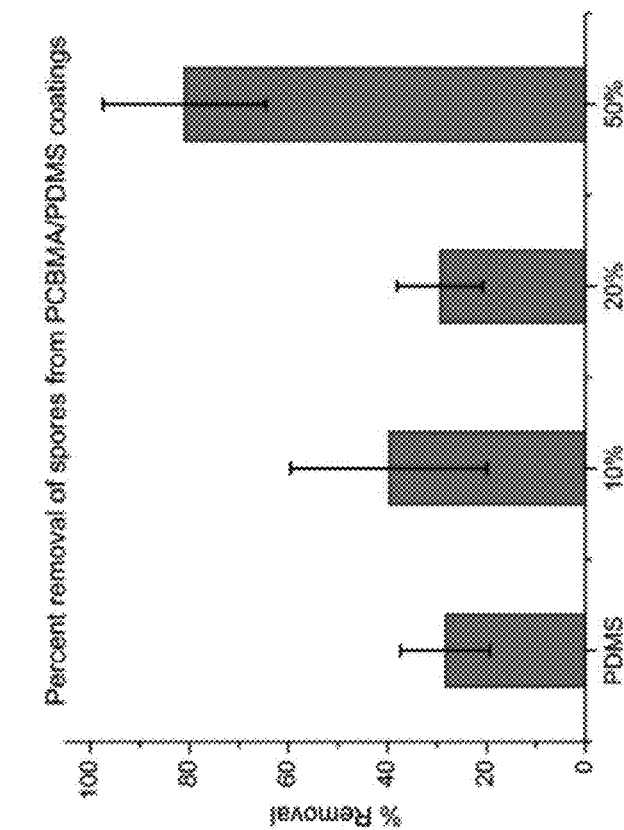
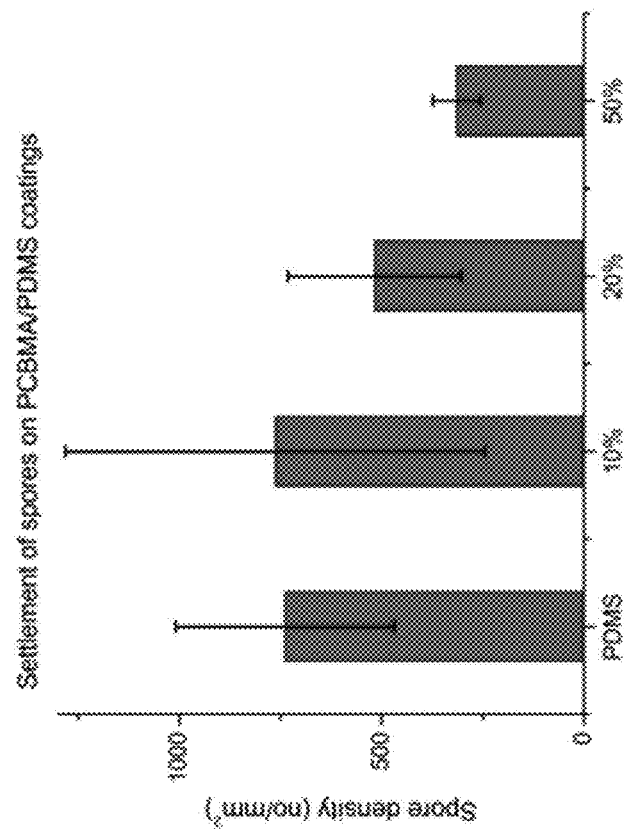
*Fig. 65B.*
*Fig. 65A.*

MARINE COATINGS

CROSS-REFERENCE TO RELATED APPLICATIONS

This application is a continuation-in-part of U.S. patent application Ser. No. 12/780,251, filed May 14, 2010, which is a continuation of International Application No. PCT/US2008/084098, filed Nov. 19, 2008, which claims the benefit of U.S. Provisional Application No. 60/989,073, filed Nov. 19, 2007, and U.S. Provisional Application No. 61/074,913, filed Jun. 23, 2008; and this application also claims the benefit of U.S. Provisional Application No. 61/566,476, filed Dec. 2, 2011, and U.S. Provisional Application No. 61/566,549, filed Dec. 2, 2011. Each application is incorporated herein by reference in its entirety.

STATEMENT OF GOVERNMENT LICENSE RIGHTS

This invention was made with Government support under Grant Numbers N00014-04-1-0409, N00014-07-1036, N000141010631, and N000141210441 awarded by Office of Naval Research and Grant Number HDTRA1-10-1-0074 awarded by the Defense Threat Reduction Agency. The Government has certain rights in the invention.

BACKGROUND OF THE INVENTION

Biofouling on ship hulls and other marine surfaces has become a global environmental and economic issue. Currently, the majority of marine coating products are based on antifouling coatings (i.e., release of biocides to kill marine microorganisms). As biocides are harmful to the marine environment, their application is highly limited. Nontoxic fouling-release coatings based on silicone compounds have been marketed, but have not gained popularity yet. These coatings are only effective on vessels moving at high speeds (greater than 14 knots). Furthermore, these coatings are expensive in terms of material, application, and maintenance.

Superlow fouling zwitterionic materials and coatings enables the development of nonfouling marine coatings. Poly(ethylene glycol) (PEG) derivatives or zwitterionic polymers have been extensively used as nonfouling materials to reduce bacterial attachment and biofilm formation. However, the susceptibility of PEG to oxidation damage has limited its long-term application in complex media. Zwitterionic materials such as poly(sulfobetaine methacrylate) (pSBMA) are able to dramatically reduce bacterial attachment and biofilm formation and are highly resistant to nonspecific protein adsorption.

Despite the advances made in marine coatings, there exists a need for new marine coatings that offer advantageous properties of self-polishing/non-fouling and superhydrophobic/nonfouling. The present invention seeks to fulfill this need and provides further related advantages.

SUMMARY OF THE INVENTION

The invention provides marine coatings that include copolymers, methods for making the coatings, marine surface coated with the coatings, and methods for applying the coatings to marine vessels.

In one aspect, the invention provides a marine coating composition. In one embodiment, the composition comprises (a) a copolymer, comprising a zwitterionic component and a hydrophobic component, wherein the zwitterionic component comprises repeating units derived from zwitterionic monomers, and wherein the hydrophobic component comprises repeating units derived from hydrophobic monomers; and (b) a polymeric matrix.

In certain embodiments, the copolymer forms a nanostructure (e.g., a nanoparticle, a micelle, or a vesicle).

In one embodiment, the copolymer is a block copolymer and the zwitterionic component is a zwitterionic block and the hydrophobic component is a hydrophobic block. Representative zwitterionic monomers include polymerizable carboxybetaines, polymerizable sulfobetaines, and polymerizable phosphobetaines. In certain embodiments, the block polymer has the formula:

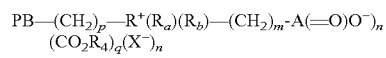

Wherein R, $R_2$, and $R_3$ taken together form a cationic center selected from imidazolium, triazaolium, pyridinium, morpholinium, oxazolidinium, pyrazinium, pyridazinium, pyrimidinium, piperazinium, and pyrrolidinium; or when R is N, $R_2$ and $R_3$ are independently selected from the group consisting of hydrogen, C1-C20 alkyl and fluoroalkyl, and C6-C12 aryl; A is C or SO; $R_4$ is selected from the group consisting of C1-C20 alkyl, C6-C12 aryl, and tri(C1-C8 alkyl)silyl; m is an integer from 1 to 20; n is an integer from 5 to about 100,000; p is an integer from 1 to 20; and q is an integer from 5 to about 100,000.

The polymeric matrix can either be a self-polishing matrix or fouling release matrix to provide self-polishing and fouling release coatings, respectively.

In one embodiment, the polymeric matrix comprises a polymer selected from the group consisting of rosins, acrylic polymers, polyesters, amino resins, polyurethanes, polyamides, polyimides, epoxy and phenolic resins, alkyd resins, polyphosphazenes, polysiloxanes, fluorinated polymers, and mixtures thereof.

In another embodiment, the polymeric matrix comprises a polymer comprising:
(a) a polymeric backbone;
(b) a plurality of cationic centers, each cationic center covalently coupled to the polymer backbone by a first linker;
(c) a counter ion associated with each cationic center; and
(d) a hydrolyzable group covalently coupled to each cationic center through a second linker, wherein the hydrolyzable group is hydrolyzable to an anionic center to provide a zwitterionic polymer having the anionic center covalently coupled to the cationic center through the second linker. In certain embodiments, the polymer of the matrix has the formula:

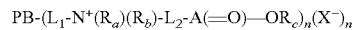

wherein PB is the polymer backbone having n pendant groups $L_1$-$N^+$($R_a$)($R_b$)-$L_2$-A(=O)—$OR_c$); $N^+$($R_a$)($R_b$) is the cationic center; A(=O)—$OR_c$ is the hydrolyzable group, wherein A is selected from the group consisting of C, S, SO, P, or PO, and $R_c$ is an alkyl, aryl, acyl, or silyl group that may be further substituted with one or more substituents; $L_1$ is a linker that covalently couples the cationic center to the polymer backbone; $L_2$ is a linker that covalently couples the cationic center to the hydrolyzable group; $X^-$ is the counter ion associated with the cationic center; and n is an integer from about 10 to about 10,000. Representative counterions include C1-C20 carboxylates and C1-C20 alkylsulfonates; antimicrobial, antibacterial, and antifungal agents; as well as counterions such as halide, carboxylate, alkylsulfonate, sulfate, nitrate, perchlorate, tetrafluoroborate, hexafluorophosphate, trifluoromethylsulfonate, bis(trifluoromethylsulfonyl)amide, lactate, and salicylate. In certain embodiments, the hydrolyzable group releases a C1-C20 carboxylate on hydrolysis. In other embodiments, the hydrolyzable group releases an antimicrobial, an antibacterial, or an antifungal agent on hydrolysis. Representative cationic centers can be is selected from ammonium, imidazolium, triazaolium, pyridinium, morpholinium, oxazolidinium, pyrazinium, pyridazinium, pyrimidinium, piperazinium, and pyrrolidinium. In certain embodiments, $R_a$ and $R_b$ are independently selected from the group consisting of hydrogen, C1-C10 straight chain and branched alkyl groups, and C6-C12 aryl groups. In certain embodiments, $L_1$ is selected from the group consisting of —C(=O)O—$(CH_2)_n$— and —C(=O)NH—$(CH_2)_n$—, wherein n is an integer from 1 to 20, and $L_2$ is —$(CH_2)_n$—, where n is an integer from 1 to 20.

In certain embodiments, the copolymer is an amphiphilic copolymer. Suitable amphiphilic copolymers include copolymers having hydrophobic repeating units and hydrophilic repeating units selected from anionic repeating units, cationic repeating units, and zwitterionic repeating units. Suitable copolymers include block copolymers, random copolymers, and graft copolymers. Representative hydrophilic repeating units comprise repeating units having carboxyl groups, sulfonate groups, phosphate groups, and amine groups. Representative hydrophobic repeating units are derived from acrylic acids and esters, alkyl acrylic acids and esters, acrylamides, alkyl acrylamides, polysiloxane repeating units, polyester repeating units, polyurethane repeating units, polystyrene repeating units, and fluorinated derivatives thereof. In certain embodiments, the copolymer further comprises neutral hydrophilic repeating units (e.g., alkylene oxide repeating units). In one embodiment, the copolymer is a block copolymer having a hydrophilic block comprising zwitterionic or mixed charge repeating units and a hydrophobic block comprising siloxane repeating units. Representative copolymers include PDMS-b-PCBMA and PDMS-b-PSBMA diblock copolymers. In certain embodiments, the copolymer is a triblock copolymer having a first hydrophilic block comprising zwitterionic or mixed charge repeating units, a hydrophobic block comprising siloxane repeating units, and a second hydrophilic block comprising neutral hydrophilic repeating units. Representative copolymers include PDMS-PEGMA-PCBMA and PDMS-PEGMA-PSBMA triblock copolymers. In other embodiments, the copolymer is a triblock copolymer, comprising a first hydrophilic block having repeating units comprising anionic, cationic, or zwitterionic repeating units; a second block having neutral repeating units; and a third hydrophilic block having repeating units comprising anionic, cationic, or zwitterionic repeating units. In one embodiment, the first hydrophilic block comprises zwitterionic repeating units, the second hydrophilic block comprises alkylene oxide repeating units, and the third hydrophilic block comprises zwitterionic repeating units. Representative copolymers include PCBMA-PPO-PCBMA, PCBMA-PEO-PCBMA, PSBMA-PPO-PSBMA, PSBMA-PEO-PSBMA, PCBMA-PPO-PSBMA, and PCBMA-PEO-PSBMA triblock copolymers.

The marine coating compositions of the invention may further include a biocide or antifouling agent such as those known in conventional marine coatings.

In another aspect, the invention provides a surface of a marine substrate treated with a marine coating of the invention. Representative substrates include marine vessel hulls and marine structures such as propellers, periscopes, and sensors. Other marine structures that can be advantageously coated with a marine coating of the invention include bridges and fish nets. In certain embodiments, the marine substrates are coated with a composition of the invention in which the copolymer is dispersed within the polymer matrix. In other embodiments, the marine substrate is first treated the polymer matrix and then treated with the copolymer (e.g., the copolymer is applied to the polymeric matrix on the marine substrate).

In a further aspect of the invention, a method for treating a surface of a marine substrate is provided. In the method, a marine coating of the invention is applied to a surface of a marine substrate. In one embodiment, applying the coating includes spraying the coating. In another embodiment, applying the coating comprises painting the coating.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 20A-20F are photographs comparing Florida field test panels: FIG. 20A is an epoxy panel; FIG. 20B is a PVC panel; and FIGS. 20C-20F are panels treated with a representative cationic polymer of the invention illustrated in FIG. 23 (m=11).

FIGS. 22A-22D are photographs comparing Hawaii field test panels: FIGS. 22A and 22B are epoxy panels; FIG. 22C is a Hempasil panel; and FIG. 22D is a panel treated with the representative block copolymer of the invention illustrated in FIG. 28 (p=11) (block copolymer nanoparticles mixed with hydrolyzable silyl ester binder polymers).

FIG. 32 tabulates representative nanoparticles synthesized via the group transfer polymerization and their stability in THF solution.

FIG. 34 tabulates representative diblock copolymer synthesized via RAFT polymerization.

FIG. 36 tabulates representative base coating structures synthesized via the radical polymerization of MMA and TBSMA.

FIG. 42 tabulates representative hydrolyzable base coatings synthesized via the copolymerization of MMA, HMA and a hydrolysable zwitterionic monomer precursor.

FIG. 45 tabulates representative self-polishing marine coating formulations and their nonfouling properties.

FIG. 46 compares the self-polishing marine coating's low fouling properties before (0 days) and after (14 days) hydrolysis under artificial seawater conditions.

FIG. 54 illustrates the structures of two representative zwitterionic monomers for making zwitterionic polymers: CBMA and SBMA.

FIG. 60 compares SEM images of a representative diblock copolymer, PDMA-b-PCBMA, incorporated in a PDMS matrix.

FIGS. 65A and 65B illustrates settlement densities of spores of Ulva on PCBMA/PDMS composites (PDMS, commercial SYLGARD 184 PDMS control; 10%-50%, weight percentage of PDMS-PCBMA in PDMS matrix) (65A) and percentage removal of sporelings of Ulva from the PCBMA/PDMS composites following exposure to a wall shear stress of 8 Pa (65B).

FIG. 72A: PDMS surfaces coated with different CBMA-PPO-CBMA triblock copolymers. FIG. 72B: PDMS surface coated with $CBMA_{40}$-$PPO_{48}$-$CBMA_{40}$ compared to unmodified PDMS. Once the surface is activated by EDC/NHS chemistry, the surface is able to be functionalized with fibrinogen by covalent immobilization, by treating a surface with pH 10 buffer, an activated surface is able to regenerate its nonfouling properties.

DETAILED DESCRIPTION OF THE INVENTION

Figure 1:
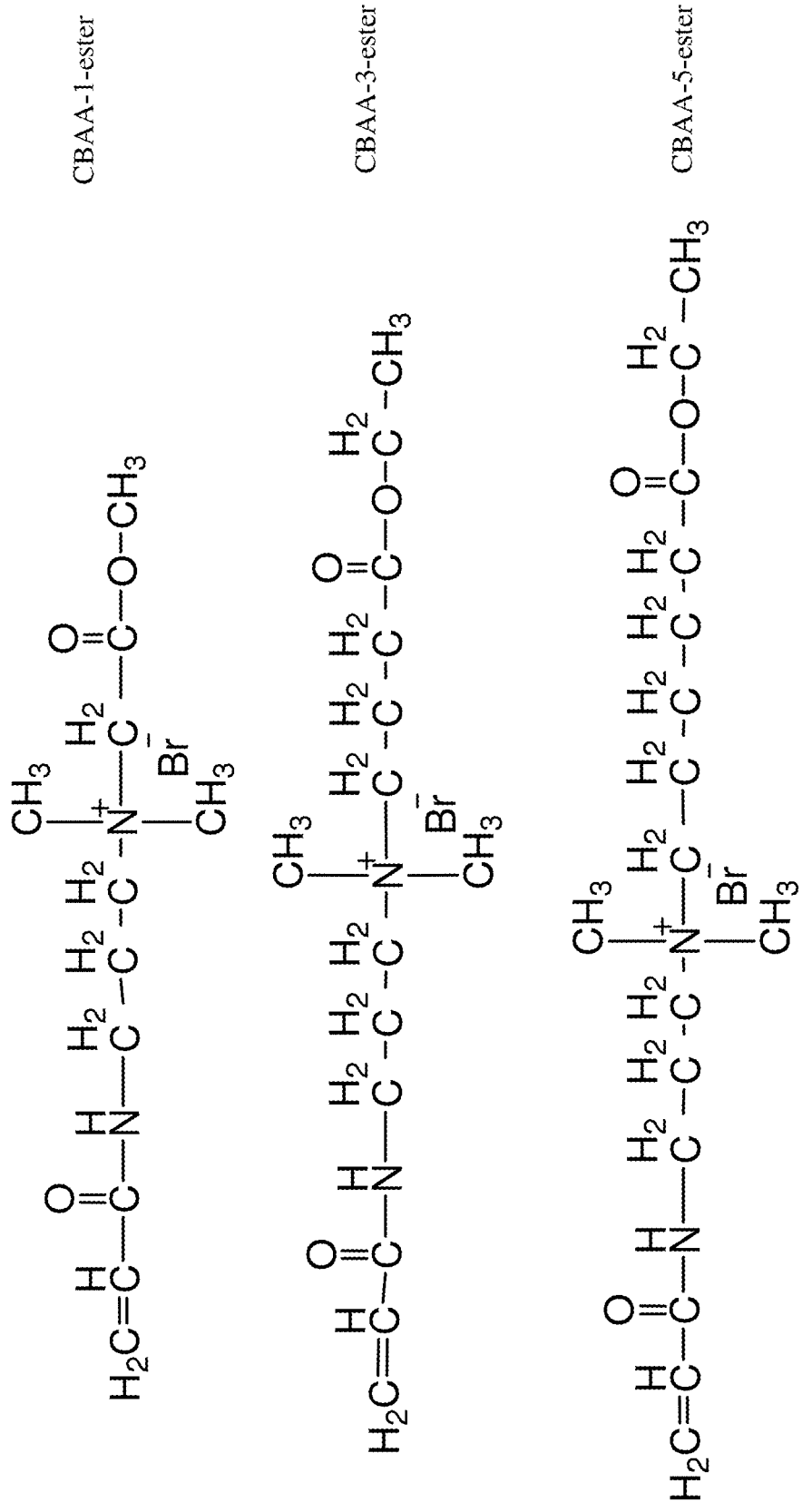
FIG. 1 illustrates the structures of three representative cationic monomers useful for making cationic polymers useful in the invention: three acrylamide monomers with different carboxybetaine ester groups; CBAA-1-ester, CBAA-3-ester, and CBAA-5-ester.

The invention provides marine coatings that include cationic polymers having hydrolyzable groups, methods for making the coatings, and methods for applying the coatings to marine vessels.

In one aspect of the invention, marine coatings that include cationic polymers are provided. The cationic polymers useful in the invention include hydrolyzable groups that can be hydrolyzed to provide zwitterionic polymers. Zwitterionic polymers are polymers having a balance of positive and negative charge. Zwitterionic polymers can be highly resistant to protein adsorption and bacterial adhesion. Due to their biomimetic nature, zwitterionic polymers, such as phosphobetaine, sulfobetaine, and carboxybetaine polymers, exhibit high biocompatibility and are environmentally benign.

Controlled Hydrolysis.

The variation of the structural features of the cationic polymers allows for their controlled hydrolysis and the control of the biological, chemical, and mechanical properties. The rate of hydrolysis can be significantly affected and controlled by the selection of the nature of the hydrolyzable group (e.g., for esters, —OR).

As described below, in certain embodiments, the cationic polymers useful in the invention advantageously release functional groups on hydrolysis. For example, for cationic esters useful in the invention, hydrolysis ester releases an —OR group. In these embodiments, the released group can be a therapeutic agent (e.g., an antimicrobial, antibacterial, an antifungal agent). Similarly, in certain embodiments, the cationic polymers can release their counter ions ($X^-$), which can also be biologically active (e.g., antimicrobial and antibacterial agents).

It will be appreciated that the hydrolyzable group can be cleaved not only by hydrolysis, but also by cleavage (e.g., degradation or erosion) that occurs by other means. The cationic polymers can be converted to their corresponding zwitterionic polymers by environmental changes due to enzymatic catalysis, redox, heat, light, ionic strength, pH, and hydrolysis, among others.

Representative cationic polymers useful in the invention and their corresponding zwitterionic polymer counterparts are described below.

Cationic Polymers

The cationic polymers useful in the invention include hydrolyzable groups that, when hydrolyzed, provide anionic groups that render the polymer zwitterionic. In each polymer, the number of hydrolyzable groups is substantially equal to the number of cationic groups such that, when the hydrolyzable groups are hydrolyzed, in the resulting polymer is zwitterionic. As used herein, the term "zwitterionic polymer" refers to a polymer having substantially equal numbers of cationic groups and anionic groups.

Representative cationic polymers useful in the invention have formula (I):

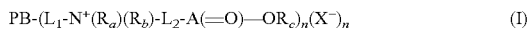

$$\text{PB-}(L_1\text{-}N^+(R_a)(R_b)\text{-}L_2\text{-}A(=O)\text{—}OR_c)_n(X^-)_n \qquad (I)$$

wherein PB is the polymer backbone having n pendant groups (i.e., $L_1\text{-}N^+(R_a)(R_b)\text{-}L_2\text{-}A(=O)\text{—}OR_c$); $N^+$ is the cationic center; $R_a$ and $R_b$ are independently selected from hydrogen, alkyl, and aryl groups; $A(=O)\text{—}OR_c$ is the hydrolyzable group, wherein A is C, S, SO, P, or PO, and $R_c$ is an alkyl, aryl, acyl, or silyl group that may be further substituted with one or more substituents; $L_1$ is a linker that covalently couples the cationic center to the polymer backbone; $L_2$ is a linker that covalently couples the cationic center to the hydrolyzable group; $X^-$ is the counter ion associated with the cationic center; and n is from about 10 to about 10,000. The average molecular weight of the polymers of formula (I) is from about 1 kDa to about 1,000 kDa.

Hydrolysis of the cationic polymer of formula (I) provides zwitterionic polymer having formula (II):

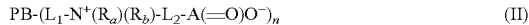

wherein PB, $L_1$, $N^+$, $R_a$, $R_b$, $L_2$, A, and n are as described above, and $A(=O)O^-$ is the anionic group.

In this embodiment, the polymer of formula (I) includes n pendant groups and can be prepared by polymerization of monomers having formula (III):

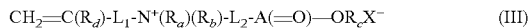

wherein $L_1$, $N^+$, $R_a$, $R_b$, $A(=O)OR_c$, and $L_2$, and $X^-$ are as described above, $R_d$ is selected from hydrogen, fluorine, trifluoromethyl, C1-C6 alkyl, and C6-C12 aryl groups.

The following is a description of the polymers and monomers of formulas (I)-(III) described above.

In formulas (I) and (II), PB is the polymer backbone. Representative polymer backbones include vinyl backbones (i.e., —C(R')(R'')—C(R''')(R'''')—, where R', R'', R''', and R'''' are independently selected from hydrogen, alkyl, and aryl) derived from vinyl monomers (e.g., acrylate, methacrylate, acrylamide, methacrylamide, styrene). Other suitable backbones include polymer backbones that provide for pendant cationic groups that include hydrolyzable groups that can be converted to zwitterionic groups, and backbones that include cationic groups and that provide for pendant hydrolyzable groups that can be converted to zwitterionic groups. Other representative polymer backbones include peptide (polypeptide), urethane (polyurethane), and epoxy backbones.

Similarly, in formula (III), $CH_2=C(R_d)$— is the polymerizable group. It will be appreciated that other polymerizable groups, including those noted above, can be used to provide the monomers and polymers of the invention.

In formulas (I)-(III), $N^+$ is the cationic center. In certain embodiments, the cationic center is a quaternary ammonium (N bonded to $L_1$; $R_a$, $R_b$, and $L_2$). In addition to ammonium, other useful cationic centers include imidazolium, triazaolium, pyridinium, morpholinium, oxazolidinium, pyrazinium, pyridazinium, pyrimidinium, piperazinium, and pyrrolidinium.

$R_a$ and $R_b$ are independently selected from hydrogen, alkyl, and aryl groups. Representative alkyl groups include C1-C10 straight chain and branched alkyl groups. In certain embodiments, the alkyl group is further substituted with one of more substituents including, for example, an aryl group (e.g., —$CH_2C_6H_5$, benzyl). In one embodiment, $R_a$ and $R_b$ are methyl. Representative aryl groups include C6-C12 aryl groups including, for example, phenyl. For certain embodiments of formulas (I)-(III), $R_2$ or $R_3$ is absent.

$L_1$ is a linker that covalently couples the cationic center to the polymer backbone. In certain embodiments, $L_1$ includes a functional group (e.g., ester or amide) that couples the remainder of $L_1$ to the polymer backbone (or polymerizable moiety for the monomer of formula (III)). In addition to the functional group, $L_1$ can include an C1-C20 alkylene chain. Representative $L_1$ groups include —C(=O)O—$(CH_2)_n$— and —C(=O)NH—$(CH_2)_n$—, where n is 1-20 (e.g., 3).

$L_2$ is a linker that covalently couples the cationic center to the hydrolyzable group (or anionic group for the zwitterionic polymer of formula (II)). $L_2$ can be a C1-C20 alkylene chain. Representative $L_2$ groups include —$(CH_2)_n$—, where n is 1-20 (e.g., 1, 3, or 5).

The hydrophobicity and the rate of hydrolysis of the cationic polymers of formula (I) can be controlled by $L_1$ and/or $L_2$. The greater the hydrophobicity of $L_1$ or $L_2$, the slower the hydrolysis of the hydrolyzable group and the conversion of the cationic polymer to the zwitterionic polymer.

$A(=O)$—$OR_c$ is the hydrolyzable group. The hydrolyzable group can be an ester, such as a carboxylic acid ester (A is C), a sulfinic acid ester (A is S), a sulfonic acid ester (A is SO), a phosphinic acid ester (A is P), or a phosphonic acid ester (A is PO). The hydrolyzable group can also be an anhydride. $R_1$ is an alkyl, aryl, acyl, or silyl group that may be further substituted with one or more substituents.

Representative alkyl groups include C1-C30 straight chain and branched alkyl groups. In certain embodiments, the alkyl group is further substituted with one of more substituents including, for example, an aryl group (e.g., —$CH_2C_6H_5$, benzyl). In certain embodiments, $R_c$ is a C1-C20 straight chain alkyl group. In one embodiment, $R_c$ is methyl. In another embodiment, $R_c$ is ethyl. In one embodiment, $R_c$ is a C3-C20 alkyl. In one embodiment, $R_c$ is a C4-C20 alkyl. In one embodiment, $R_c$ is a C5-C20 alkyl. In one embodiment, $R_c$ is a C6-C20 alkyl. In one embodiment, $R_c$ is a C8-C20 alkyl. In one embodiment, $R_c$ is a C10-C20 alkyl. For applications where relatively slow hydrolysis is desired, $R_c$ is a C4-C20 n-alkyl group or a C4-C30 n-alkyl group.

Representative aryl groups include C6-C12 aryl groups including, for example, phenyl including substituted phenyl groups (e.g., benzoic acid).

Representative acyl groups (—C(=O)$R_c$) include acyl groups where $R_c$ is C1-C20 alkyl or C6-C12 aryl.

Representative silyl groups (—$SiR_3$) include silyl groups where R is C1-C20 alkyl or C6-C12 aryl).

In certain embodiments of the invention, the hydrolysis product $R_cO^-$ (or $R_cOH$) is biologically active (e.g., an antimicrobial agent, such as salicylic acid (2-hydroxybenzoic acid), benzoate, lactate, and the anion form of an antibiotic or antifungal drug).

In certain other embodiments, the hydrolysis product $R_cO^-$ (or $R_cOH$) is a lactate, glycolate, or an amino acid.

The rate of hydrolysis of the cationic polymers of formula (I) can also be controlled by $R_c$. The slower the hydrolysis of the hydrolyzable group due to, for example, steric and/or kinetic effects due to $R_c$, the slower the conversion of the cationic polymer to the zwitterionic polymer.

$X^-$ is the counter ion associated with the cationic center. The counter ion can be the counter ion that results from the synthesis of the cationic polymer of formula (I) or the monomers of formula (III) (e.g., $Cl^-$, $Br^-$, $I^-$). The counter ion that is initially produced from the synthesis of the cationic center can also be exchanged with other suitable counter ions to provide polymers having controllable hydrolysis properties and other biological properties.

The rate of hydrolysis of the cationic polymers of formula (I) can be controlled by the counter ion. The more hydrophobic the counter ion, the slower the hydrolysis of the hydrolyzable group and the slower the conversion of the cationic polymer to the zwitterionic polymer. Representative hydrophobic counter ions include carboxylates, such as benzoic acid and fatty acid anions (e.g., $CH_3(CH_2)_nCO_2^-$ where n=1-19); alkyl sulfonates (e.g., $CH_3(CH_2)_nSO_3^-$ where n=1-19); salicylate; lactate; bis(trifluoromethylsulfonyl)amide anion ($N^-(SO_2CF_3)_2$); and derivatives thereof. Other counter ions also can be chosen from chloride, bromide, iodide, sulfate; nitrate; perchlorate ($ClO_4$); tetrafluoroborate ($BF_4$); hexafluorophosphate ($PF_6$); trifluoromethylsulfonate ($SO_3CF_3$); and derivatives thereof.

Other suitable counter ions include hydrophobic counter ions and counter ions having biological activity (e.g., an antimicrobial agent, such as salicylic acid (2-hydroxybenzoic acid), benzoate, lactate, and the anion form of an antibiotic or and antifungal drug).

For the monomer of formula (III), $R_d$ is selected from hydrogen, fluoride, trifluoromethyl, and C1-C6 alkyl (e.g., methyl, ethyl, propyl, butyl). In one embodiment, $R_d$ is hydrogen. In one embodiment, $R_d$ is methyl. In another embodiment, $R_d$ is ethyl.

The variation of the structural features of the cationic polymers allows for their controlled hydrolysis and the control of the biological, chemical, and mechanical properties. The structural features of the cationic polymers noted above that can be varied to achieve the desired controlled hydrolysis of the polymer include $L_1$, $L_2$, $R_a$, $R_b$, A, $R_c$, and $X^-$. In general, the more hydrophobic the polymer or the noted structural feature, the slower the hydrolysis of the cationic polymer to the zwitterionic polymer.

Homopolymers, Random Copolymers, Block Copolymers.

The cationic polymers useful in the invention include homopolymers, random copolymers, and block copolymers.

In one embodiment, the invention provides cationic homopolymers, such as defined by formula (I), prepared by polymerizing a cationic monomer, such as defined by formula (III). It will be appreciated that the advantageous properties associated with cationic polymers useful in the invention including those polymers defined by formula (I) can be imparted to other polymeric materials.

In one embodiment, the invention provides random copolymers prepared by copolymerizing two different cationic monomers of formula (III).

In another embodiment, the invention provides random copolymers that include cationic repeating units prepared by copolymerizing one or more cationic monomers of the invention defined by formula (III) with one or more other monomers (e.g., hydrophobic monomers, anionic monomers, or zwitterionic monomers, such as phosphorylbetaine, sulfobetaine, or carboxybetaine monomers).

In one embodiment, the invention provides block copolymers having one or more blocks comprising cationic repeating units and one or more other blocks. In this embodiment, the one or more blocks that include cationic repeating units include only cationic repeating units (e.g., homo- or copolymer prepared from cationic monomers of formula (III)). Alternatively, the one or more blocks that include cationic repeating units include cationic repeating units and other repeating units (e.g., hydrophobic, anionic, zwitterionic repeating units).

Other Suitable Polymers

The invention also provides the following polymers.

In one embodiment, the cationic polymer has the following structure:

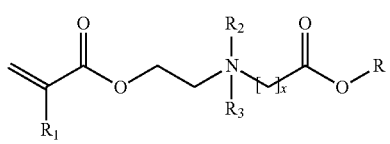

$R_1$=—H, —CH$_3$, —C$_2$H$_5$
$R_2$=no atom, —H, —CH$_3$, —C$_2$H$_5$
$R_3$=—H, —CH$_3$, —C$_2$H$_5$
x=1-8.

R=any alkyl chain, aromatic or lactate or glycolate

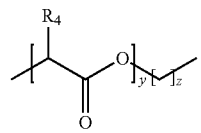

$R_4$=—H, —CH$_3$, —C$_2$H$_5$
Y=1-10
Z=0-22
or C(=O)R'
R'=any alkyl chain or aromatic group.

In another embodiment, the cationic polymer has the following structure:

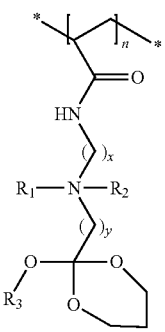

n>5
x=1-5
y=1-5
$R_1$=H, or alkyl chain
$R_2$=no atom, H, or alkyl chain
$R_3$=alkyl chain.

In another embodiment, the invention provides a polymer having the following structure:

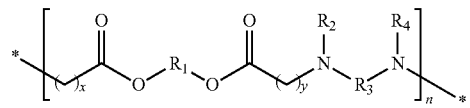

$R_1$ is any alkyl chain
$R_3$ is any alkyl chain
$R_2$, $R_4$ is any alkyl chain
x=1-18
y=1-18
n>3.

In another embodiment, the invention provides a polymer having the following structure:

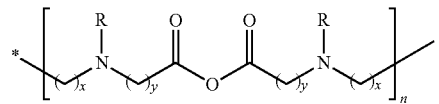

R is alkyl chain
x=1-18
y=1-18
n>3.

In another embodiment, the invention provides a polymer having the following structure:

[chemical structure]

R=any alkyl chain
x=0-11
n>3.

In another embodiment, the invention provides a polymer having the following structure:

[chemical structure]

n>3
x=1-10
R=any alkyl chain, aromatic or lactate or glycolate.

[chemical structure]

$R_4$=—H, —$CH_3$, —$C_2H_5$
y=1-10
z=0-22
or C(=O)R'
R'=any alkyl chain, aromatic group.

In another embodiment, the invention provides polymers having the following structure:

[chemical structures]

n>3
x=1-6
y=0-6
R=any alkyl chain, aromatic or lactate or glycolate)

[chemical structure]

$R_4$=—H, —$CH_3$, —$C_2H_5$
y=1-10
z=0-22
or C(=O)R'
R'=any alkyl chain, aromatic group.

In another embodiment, the invention provides a polymer having the following structure:

[chemical structure]

n>5
x=0-5.

In another embodiment, the invention provides a polymer having the following structure:

[chemical structure]

x=0-17
n>5
R=H or alkyl chain.

In another embodiment, the invention provides a polymer having the following structure:

[chemical structure]

n>5
$R_2$=H or any alkyl chain, e.g., methyl
x, y=1-6
$R_1$=any alkyl chain,

[chemical structure]

$R_4$=—H, —$CH_3$, —$C_2H_5$
y=1-10
z=0-22

In another embodiment, the invention provides a polymer having the following structure:

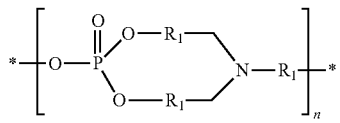

n>3

$R_1$=any alkyl chain.

Three representative cationic monomers of formula (III) useful for making cationic polymers of formula (I), and ultimately the zwitterionic polymers of formula (II) are illustrated in FIG. 1. Referring to FIG. 1, three positively charged polyacrylamides having pendant groups that bear cationic carboxybetaine ester groups are illustrated. The three monomers have different spacer groups ($L_2$: —$CH_2$)$_n$—) between the quaternary ammonium groups (cationic center) and the ester (hydrolyzable) groups: CBAA-1-ester (n=1); CBAA-3-ester (n=3); and CBAA-5-ester (n=5). Polymerization of the monomers provides the corresponding cationic polymers. The three monomers were polymerized using free radical polymerization to form linear polymers, or using surface-initiated ATRP to prepare polymer brushes on SPR sensors. The polymers with different spacer groups ($L_2$) and ester groups were expected to have different chemical, physical and biological properties. The synthesis of the three monomers and their polymerizations are described in Example 1.

Figure 2:
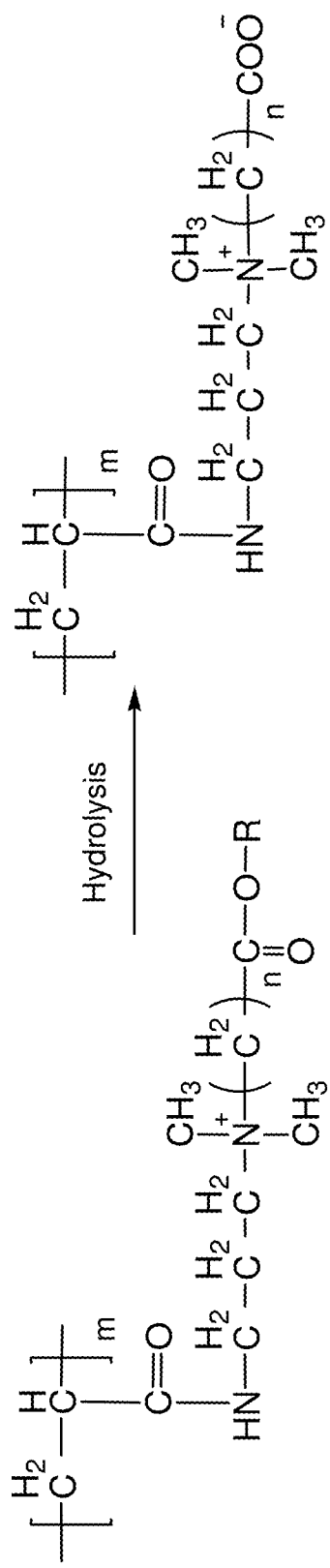
FIG. 2 illustrates the hydrolysis of a representative cationic polymer of the invention: hydrolysis of a cationic polycarboxybetaine ester to zwitterionic polycarboxybetaine.
Figure 3:
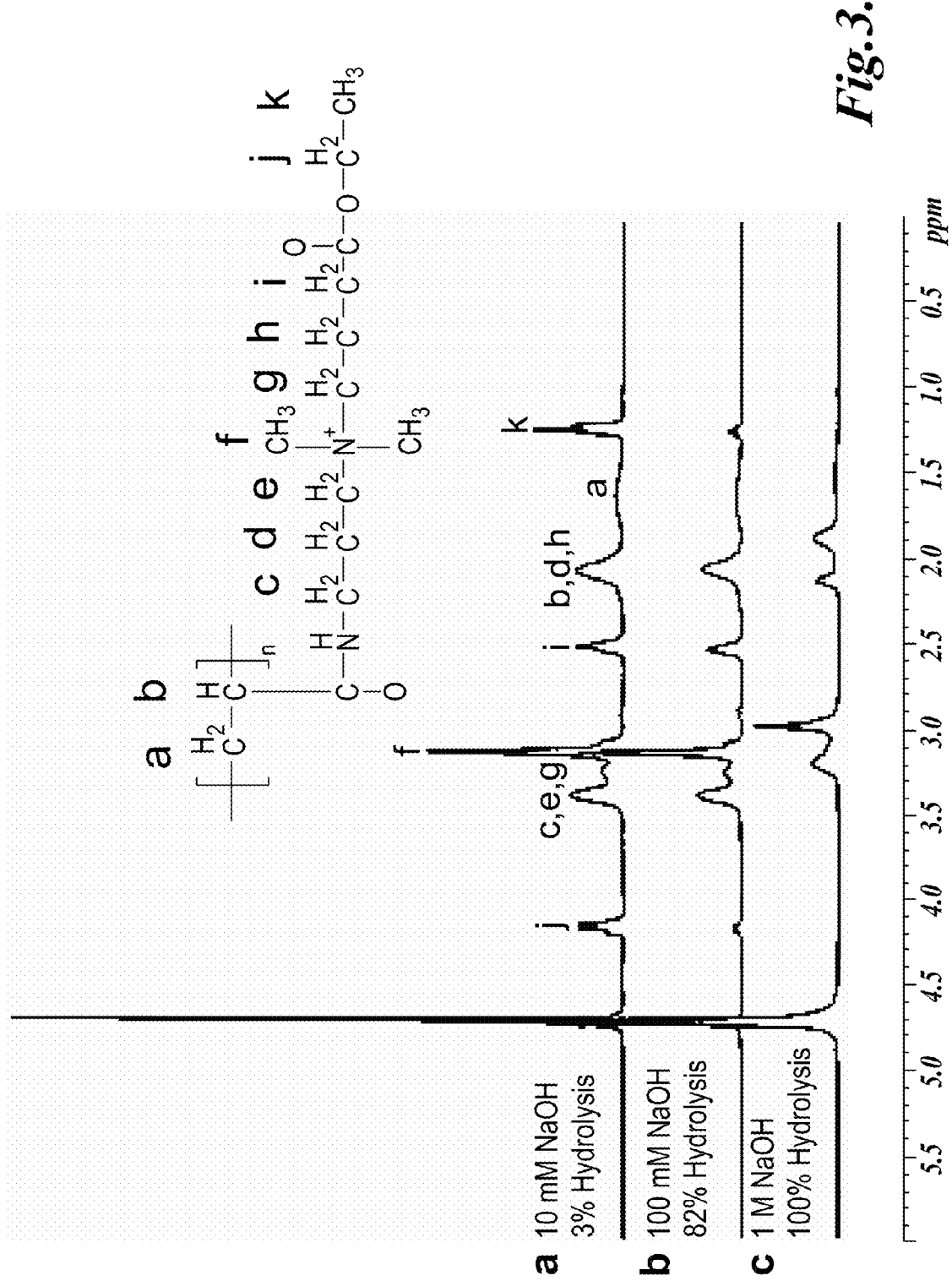
FIG. 3 compares the 'H NMR spectra of the hydrolysis of a representative cationic polymer of the invention, poly-CBAA-3-ester, after one-hour treatment in a solution with the sodium hydroxide concentration of (a) 10 mM (3% hydrolysis), (b) 100 mM (82% hydrolysis), and (c) 1 M (100% hydrolysis).
Figure 4:
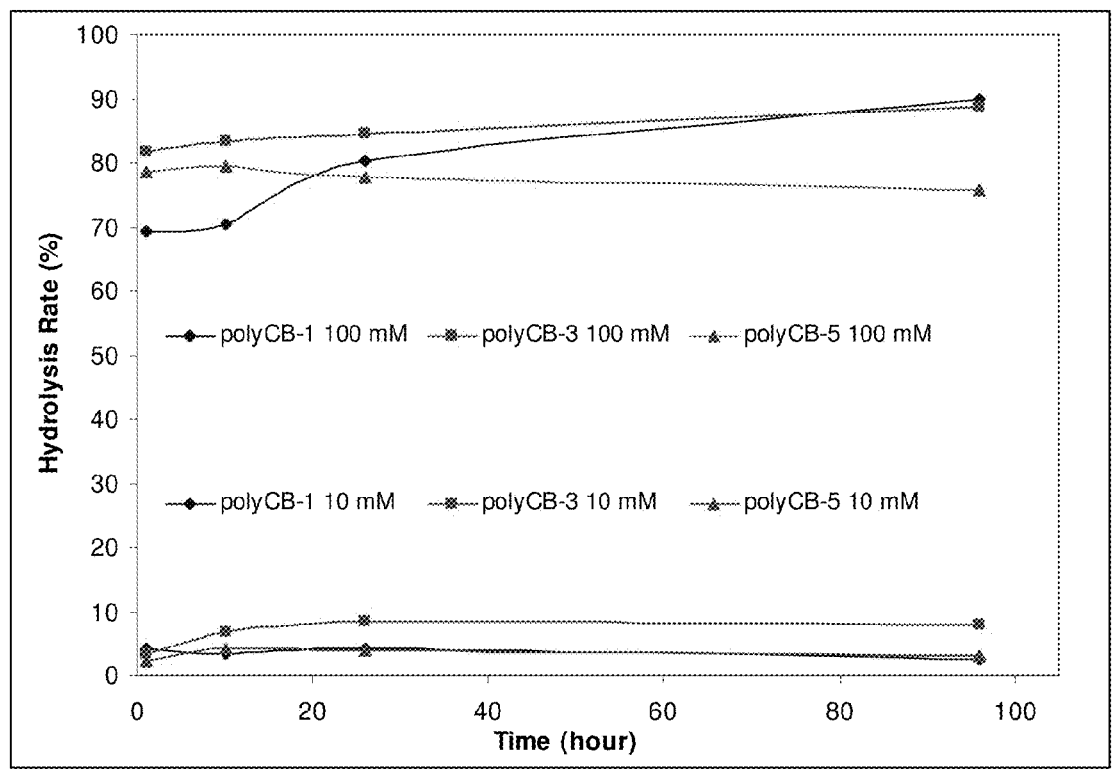
FIG. 4 compares the hydrolysis rates of representative cationic polymers useful in the invention at 10 mM and 100 mM aqueous sodium hydroxide.

For the linear polymers polymerized via free radical polymerization, their molecular weights were measured using gel permeation chromatography (GPC) in aqueous solutions. PolyCBAA-1-ester, polyCBAA-3-ester, and polyCBAA-5-ester had average molecular weights of 14 kDa, 13 kDa, and 9.6 kDa, respectively Hydrolysis of the cationic polymers provides the zwitterionic polymers (i.e., zwitterionic polycarboxybetaines). The hydrolysis of representative cationic polymer of the invention is described in Example 2 and illustrated schematically in FIG. 2. In FIG. 2, n is 1, 3, or 5 (corresponding to polyCBAA-1-ester, polyCBAA-3-ester, and polyCBAA-5-ester, respectively). The three carboxybetaine ester polymers were dissolved under different sodium hydroxide concentrations and their hydrolysis behavior was studied. After a period of time, the hydrolysis rate of the polymers was analyzed by measuring the retaining ester groups on the polymer using $^1$H NMR. All the three polymers are stable in water and no evident hydrolysis was detected after four days. The concentration of NaOH is crucial for the hydrolysis of the carboxybetaine ester polymers. FIG. 3 illustrates the NMR spectra of polyCBAA-3-ester after a one-hour treatment with three different concentrations of NaOH. For NaOH solution with a concentration of 10 mM, only slightly hydrolysis was detected (ca. 3%). For 100 mM NaOH solution, about 82% polymer was hydrolyzed. For the NaOH concentration of 1 M, the polymer was totally hydrolyzed in one hour. FIG. 4 graphs the hydrolysis rate under 100 mM or 10 mM NaOH as a function of time. Referring to FIG. 4, under these two NaOH concentrations, most hydrolysis happens in the first hour. After that, the hydrolysis rate changes only slightly with the time.

As noted above, the hydrolysis rate of the cationic polymers useful in the invention can be controlled by modifying their structures. To obtain the different hydrolysis behavior, cationic polymers having varying structure parameters such as ester groups (hydrolyzable groups), spacer groups ($L_1$ and $L_2$), and counter ions ($X^-$). Hydrolysis behavior can also be controlled by varying polymer molecular weight or copolymerizing with other monomers. Hydrolyzable ester groups (such as t-butyl and alkyl substituted silyl) or anhydride groups can be easily hydrolyzed under acidic or basic condition. Changing spacer groups ($L_2$: —$CH_2$)$_n$—) between the quaternary ammonium groups (cationic center) and the ester (hydrolyzable) groups also can tune the hydrolysis rate. Short spacers can increase the hydrolysis rate. In addition, counter ions, such as hydrophilic anions (e.g., $Cl^-$, $Br^-$, $I^-$, $SO_4^-$) also increase the hydrolysis rate, and low polymer molecular weight and copolymerization with other hydrophilic monomers also help to increase the hydrolysis rate.

Protein Adsorption

The hydrolyzable cationic polymers useful in the invention can advantageously be used as materials effective in reducing protein adsorption to surfaces treated with the polymers. The cationic polymers can be used to prepare low-fouling surfaces. These surfaces can be advantageously employed for devices in environments where the protein adsorption to device surfaces are detrimental.

To demonstrate the utility of representative cationic polymers useful in the invention in providing surfaces having low protein adsorption, polymer brushes were prepared from representative cationic polymers as described in Example 3 and their protein adsorption measured.

The three monomers (CBAA-1-ester, CBAA-3-ester, and CBAA-5-ester) were grafted on the surfaces of a SPR sensor using surface-initiated ATRP. The polymer brushes had a thickness of 5-20 nm estimated from XPS analysis. Protein adsorption from a 1 mg/mL fibrinogen solution on the three polymer brushes was measured using SPR. Fibrinogen is a sticky protein and plays an important role in platelet aggregation and blood clotting on biomaterials. Fibrinogen adsorption was 195 ng/cm$^2$, 255 ng/cm$^2$, and 600 ng/cm$^2$ for polyCBAA-1-ester, polyCBAA-3-ester, and polyCBAA-5-ester, respectively (see FIGS. 5A-5C). All three polymers have evident protein adsorption due to their positive charges. PolyCBAA-1-ester had relatively lower fibrinogen adsorption due to its higher hydrophilicity compared to the other two esters having more hydrophobic $L_2$ (i.e., C3 and C5, respectively). With the increase in $L_2$ from methylene to propylene to pentylene, the hydrophobicity of the polymer increases, leading to higher fibrinogen adsorption.

Figure 5A:
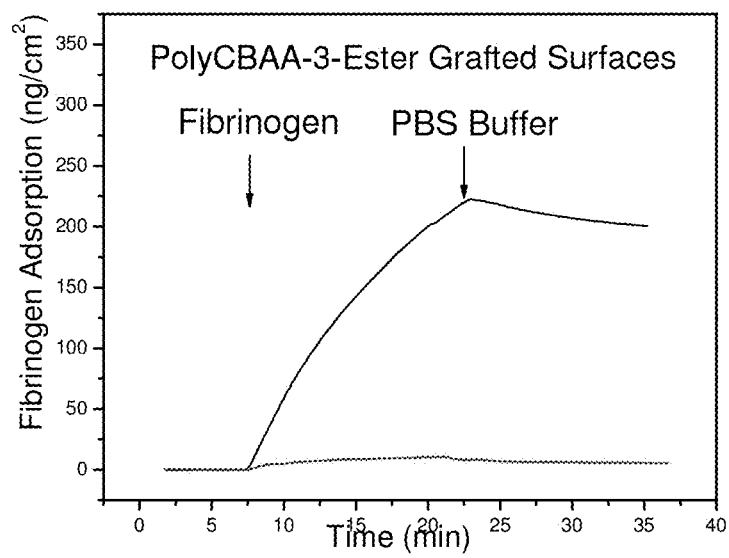
FIGS. 5A-5C are SPR sensorgrams for fibrinogen adsorption on the surfaces grafted with representative polymers useful in the invention: polycarboxybetaine esters before and after hydrolysis; (a) polyCBAA-1-ester, (b) polyCBAA-3-ester, and (c) polyCBAA-5-ester. The surfaces with polymer brushes were hydrolyzed with a 100 mm NaOH solution for 1-2 h.
Figure 5B:
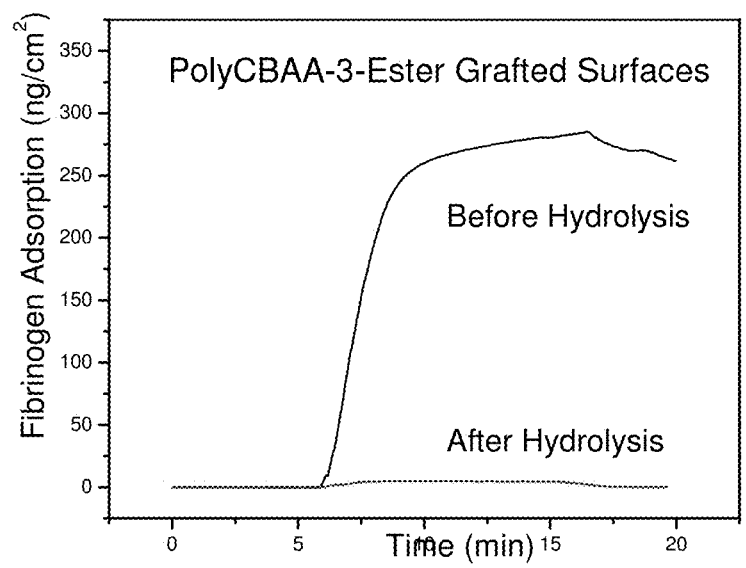
Figure 5C:
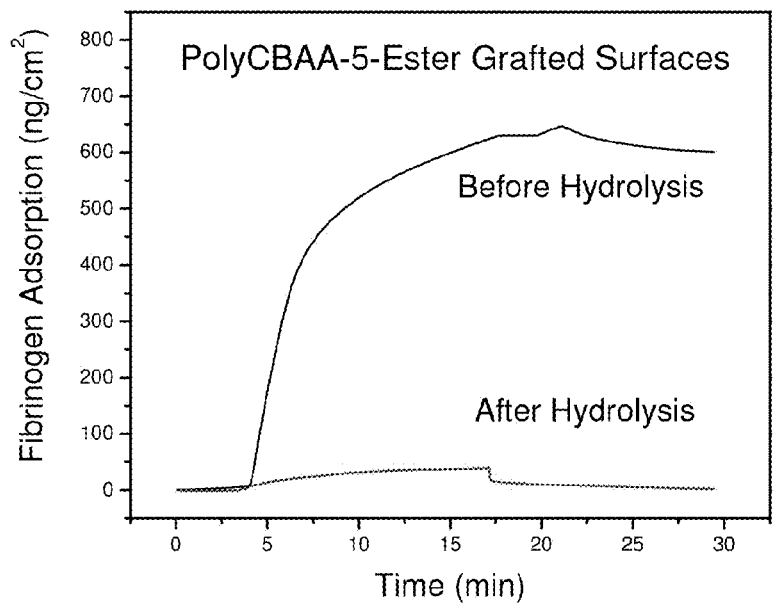

After hydrolysis at 100 mM for 1-2 hours, surface properties were dramatically changed. FIGS. 5A-5C illustrate that the surfaces grafted with each of the three polymers were converted to surfaces that were highly resistant to fibrinogen adsorption. On the surfaces with hydrolyzed polyCBAA-1-ester and hydrolyzed polyCBAA-3-ester, fibrinogen adsorption is less than 0.3 ng/cm$^2$, which is the detection limit of the SPR. Fibrinogen adsorption on hydrolyzed polyCBAA-5-ester was about 1.5 ng/cm$^2$. By controlling hydrolysis, the polymer-grafted surfaces can change their properties from high protein adsorption to strongly resistant to protein adsorption. Moreover, resulting surfaces with zwitterionic polymers after hydrolysis are biocompatible and highly resistant to nonspecific protein adsorption from blood plasma/serum and bacterial adhesion/biofilm formation.

Antimicrobial Properties

The hydrolyzable cationic polymers useful in the invention exhibit antimicrobial properties. The evaluation of antimicrobial properties of representative cationic polymers useful in the invention is described in Example 4.

To evaluate the antimicrobial properties of the cationic polycarboxybetaine esters, polymer solutions of poly-CBAA-1-ester, polyCBAA-3-ester, and polyCBAA-5-ester were incubated with *E. coli*. It was found that at a concentration of 2 mM (repeat unit molar concentration), poly-CBAA-1-ester, polyCBAA-3-ester, and polyCBAA-5-ester present a live cell percentage of 95%, 87.3%, and 46.2%, respectively (see FIG. 6). Antimicrobial activities appears to increase with the increase in the length of $L_2$. After hydrolysis, the zwitterionic polymers, polyCBAA-1, polyCBAA-3, and polyCBAA-5, exhibit a live cell percentage of 93.7%, 96.3% and 95.3%, respectively, indicating that the antimicrobial activity decreases with the hydrolysis of the cationic polymers (i.e., polycarboxybetaine esters) to the zwitterionic polymers (i.e., polycarboxybetaines).

Several amphiphilic polycations have been investigated for their antibacterial activities. The alkyl pendent chain length of the polycations was studied to compare the bactericidal efficiency of different polycations. It is found that the polymers with quaternary amine groups and longer hydrophobic pendant chains have better antimicrobial activities due to higher hydrophobicity. Small molecular quaternary ammonium compounds (QMCs) with carboxybetaine esters were found to have rapid bactericidal action when they have longer hydrocarbon groups. These QMCs could bind to the outer membrane and cytoplasmic membrane of enterobacteria and permeate into the bacterial membranes. The antimicrobial effect is increased with increasing the spacer length ($L_2$) of the cationic polymers (e.g., polycarboxybetaine esters) of the invention.

The antimicrobial efficacy of the polyCBAA-5-ester is comparable to that of other quaternized polymers with similar alkyl chain length. Higher antimicrobial efficacy can be achieved with longer alkyl chain lengths (e.g., C1-C20).

For conventional antimicrobial coatings, the killed microbes and adsorbed proteins usually accumulate on the surfaces and dramatically decrease their antimicrobial activities. In contrast, antimicrobial coatings made from the cationic polymers useful in the invention are hydrolyzed to zwitterionic polymers to provide surfaces that are highly resistant to the adsorption of various biomolecules. These zwitterionic polymers are nontoxic, biocompatible, and nonfouling, both as bulk materials and surface coatings.

Representative crosslinked zwitterionic polymers useful in the invention, polycarboxybetaines hydrogels, were non-cytotoxic and contain less than 0.06 units (EU)/mL of endotoxin using a *Limulus Amebocyte* Lysate (LAL) endotoxin assay kit (Cambrex Bioscience. Walkerville, Md.). The polycarboxybetaine hydrogels were implanted subcutaneously within mice for up to four weeks. The results showed that the polycarboxybetaines have in vivo biocompatibility comparable to that of poly(2-hydroxyethyl methacrylate (polyHEMA) hydrogels, a well-accepted model biomaterial for implantation. The nontoxic properties of the zwitterionic polymers convert the toxicity of their cationic polymer precursors and further provide nonfouling properties that can prevent dead microbes and adsorbed proteins from accumulating on the surface.

Switchable Polymer Coatings and their Use in Marine Coatings

The cationic polymers useful in the invention, hydrolyzable to zwitterionic polymers, can be advantageously used as coatings for the surfaces of a variety of devices including, for example, marine coatings. In this embodiment, the cationic polymers useful in the invention provide switchable biocompatible polymer surfaces having self-polishing and nonfouling capabilities.

Figure 7:
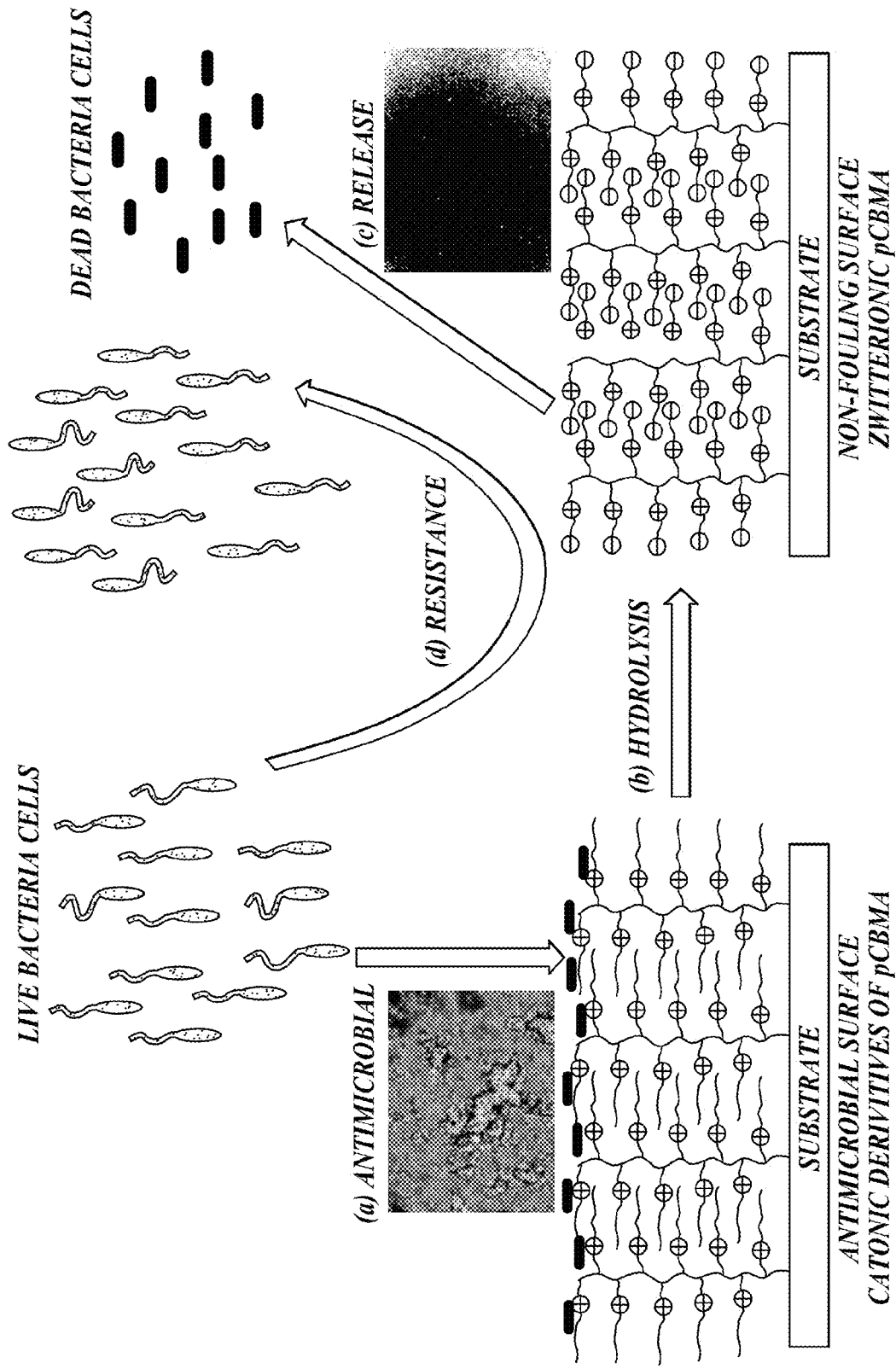
FIG. 7 is a schematic illustration of a representative surface of the invention coated with a cationic polymer. The surface switches from an antibacterial surface to a non-fouling surface upon hydrolysis: (a) antimicrobial cationic pCBMA-1 C2 effectively kills bacteria, (b) pCBMA-1 C2 is converted to non-fouling zwitterionic pCBMA-1 upon hydrolysis, (c) killed bacteria remaining on the surface is released from non-fouling zwitterionic pCBMA-1 demonstrating that (d) zwitterionic pCBMA-1 itself is highly resistant to bacterial adhesion.
Figure 8:
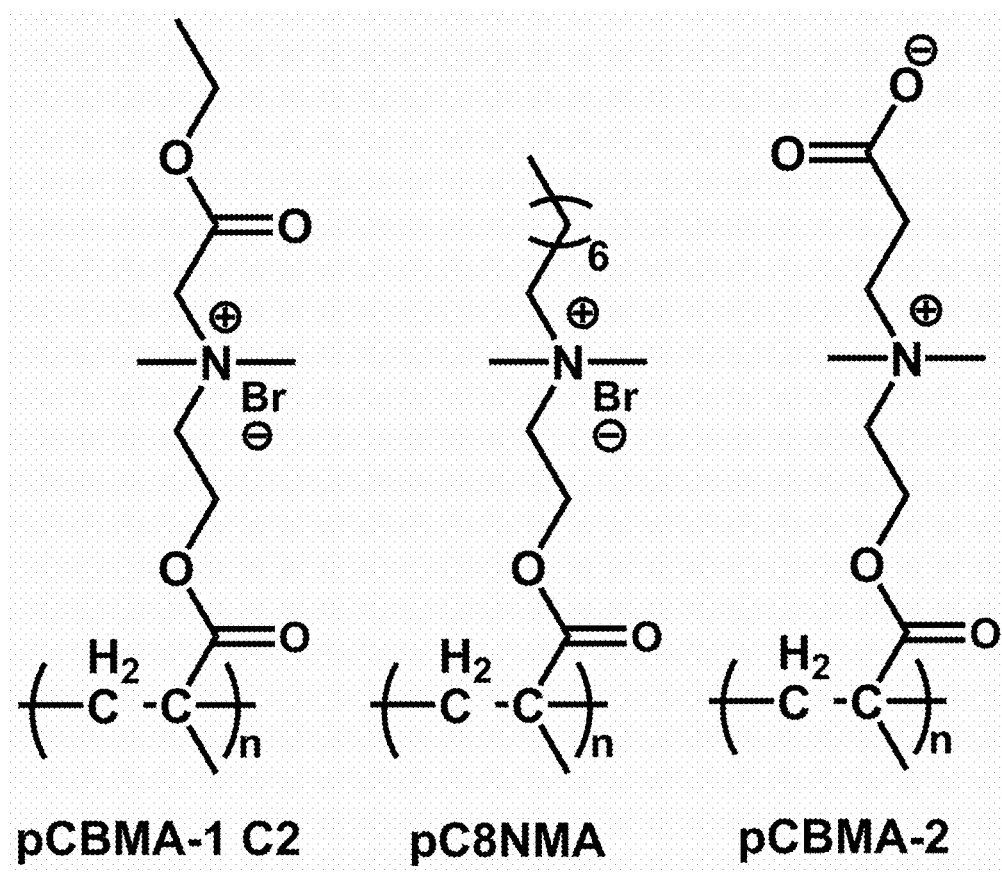
FIG. 8 illustrates the chemical structures of a representative cationic polymer of the invention, switchable pCBMA-1 C2; antimicrobial cationic pC8NMA; and non-fouling zwitterionic pCBMA-2.

FIG. 7 is a schematic illustration of a switchable biocompatible polymer surfaces having self-polishing and nonfouling capabilities. Referring to FIG. 7, antimicrobial surface (a) is a surface coated with a representative cationic polymer of the invention (i.e., pCBMA-1 C2, see FIG. 8) that effectively kills bacteria. On hydrolysis (b) the representative cationic polymer is converted to a nonfouling zwitterionic polymer (i.e., pCBMA-1, the carboxylate corresponding to pCBMA-1 C2 ester) and dead bacteria remaining on the surface are released (c) from the nonfouling zwitterionic polymer (i.e., pCBMA-1) to provide a surface coated with the zwitterionic polymer, which is highly resistant to bacterial adhesion (d).

The materials noted above are advantageously used to coat marine surfaces to provide biocompatible, antimicrobial, and nonfouling surfaces. Accordingly, in another aspect, the invention provides marine devices and materials having a surface (i.e., one or more surfaces) to which have been applied (e.g., coated, covalently coupled, ionically associated, hydrophobically associated) one or more materials noted above. Representative marine devices that may be advantageously treated with the material, modified to include the material, or that incorporates the material include marine vessels (e.g., boat or ship hulls).

As noted above, in one embodiment, the present invention provides a switchable polymer surface coating that combines the advantages of both nonfouling surface and that can kill greater than 99.9% of *Escherichia coli* K12 in one hour, with 98% of the dead bacterial cells released when the cationic derivatives are hydrolyzed to nonfouling zwitterionic polymers. pCBMA-1-C2 (cationic polymer of formula (I) where $L_1$ is —C(=O)OCH$_2$CH$_2$—, $L_2$ is —CH$_2$—, $R_c$ is CH$_2$CH$_3$, and X$^-$ is Br$^-$) control coatings were grafted by surface-initiated atom transfer radical polymerization (ATRP) onto a gold surface covered with initiators. The thicknesses of the obtained polymer coatings, as measured by atomic force microscopy (AFM), were 26-32 nm (Table 1).

TABLE 1

Film thicknesses (av ± std dev.) of pCBMA-1 C2, pC8NMA, and pCBMA-2 grafted onto gold-coated glass slides by ATRP and fibrinogen adsorption on these surfaces measured by SPR before and after hydrolysis under different conditions.

|  | pCBMA-1 Cl | pC8NMA | pCBMA-2 |
|---|---|---|---|
| polymer brush thickness (nm) | (31.2 ± 2.4) | (27.8 ± 2.8) | (26.1 ± 2.5) |
| protein adsorption (ng cm$^{-2}$) | | | |
| 0 h | 229.2 | 243.4 | 1.5 |
| 24 h H$_2$O | 189.9 | — | — |
| 24 h CHES (pH 9.0) | 114.9 | — | — |
| 24 h CAPS (pH 10.0) | 0 | 285.1 | 0.7 |

Figure 9:
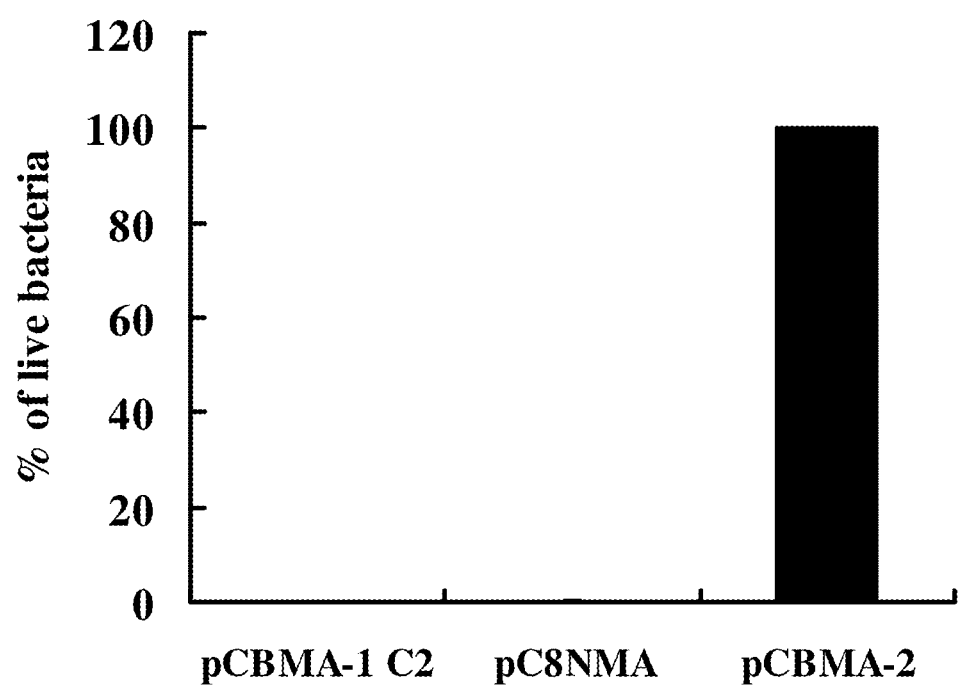
FIG. 9 is a graph comparing bactericidal activity of pCBMA-1 C2 and pC8NMA against *E. coli* K12. The percentage of live *E. coli* K12 colonies that grew on the surfaces coated with antimicrobial polymers is relative to the number of colonies that grew on the pCBMA-2 control (n=3).
Figures 10A, 10B, 10C, 10D, 10E, 10F:
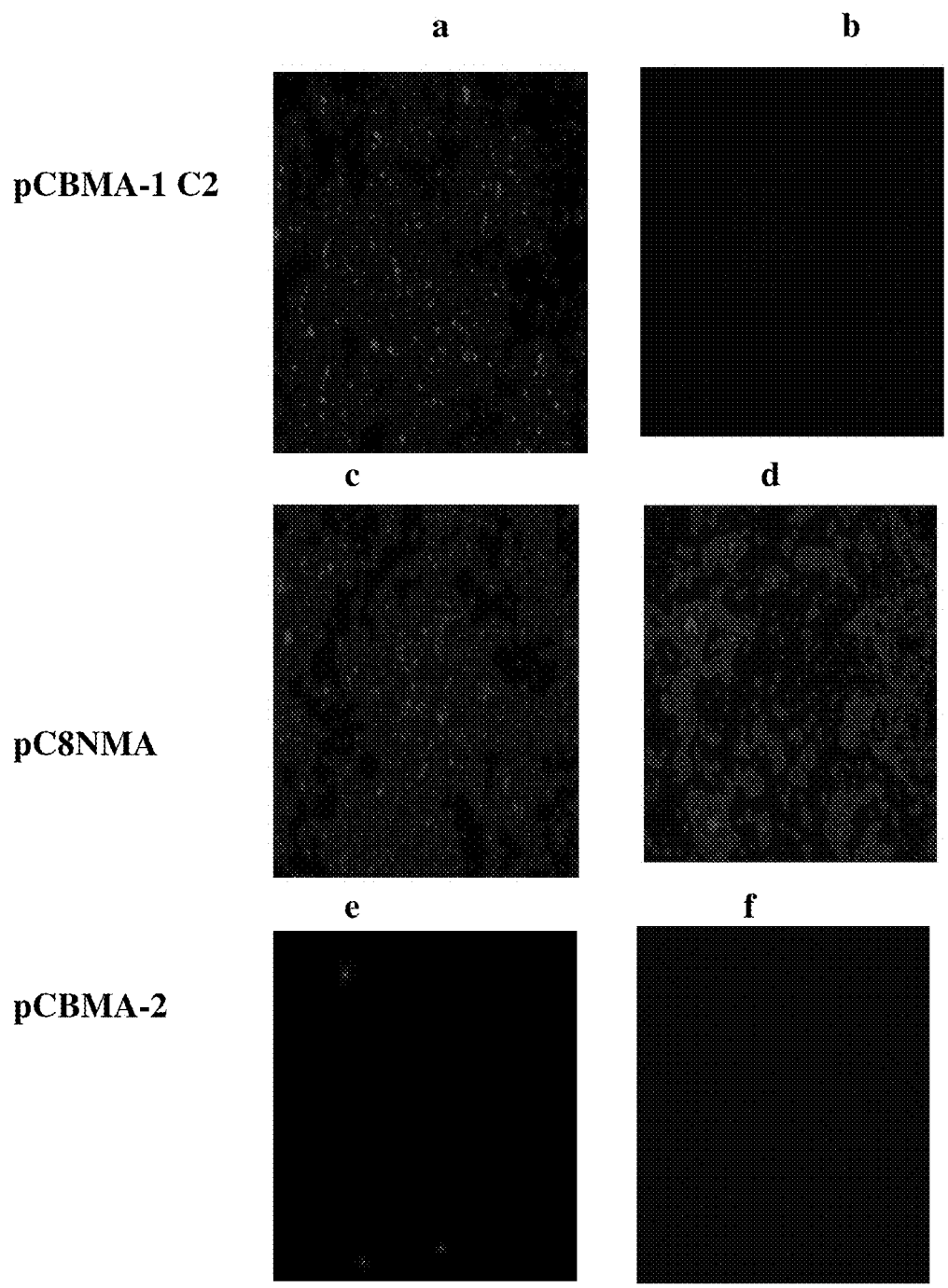
FIGS. 10A-10F are fluorescence microscopy images of attached *E. coli* K12 cells (red color) from a suspension with $10^{10}$ cellsmL$^{-1}$ for one-hour exposure to the surfaces covered with various polymers: (a), (c), and (e) are for pCBMA-1 C2, pC8NMA and pCBMA-2, respectively, before hydrolysis and (b), (d), and (f) are for the same polymers, respectively, after hydrolysis. Hydrolysis was for 8 days with 10 mM CAPS (pH 10.0).

The bactericidal activity of pCBMA-1 C2 surfaces was determined using *E. coli* K12, according to a modified literature procedure (Tiller et al., *Proc. Natl. Acad. Sci. USA* 98:5981, 2001). The permanently cationic poly(methacryloyloxyethyl-dimethyloctylammonium bromide) (pC8NMA, cationic control, (see FIG. 8) and the zwitterionic poly(2-carboxy-N,N-dimethyl-N-[2'-(methacryloyloxy)ethyl]ethanaminium) (pCBMA-2, zwitterionic control, see FIG. 8) were used as the positive and the negative control surfaces, respectively. The antimicrobial efficiency was defined as the amount of live cells on the tested surfaces relative to those on the pCBMA-2 surface. FIG. 9 shows that pCBMA-1 C2 and pC8NMA surfaces kill greater than 99.9% and 99.6%, respectively, of the *E. coli* in one hour relative to pCBMA-2 surfaces. The total number of live bacterial cells on the gold surface, which was also used as a negative-control surface, is similar to that on the pCBMA-2 surface.

Figure 11:
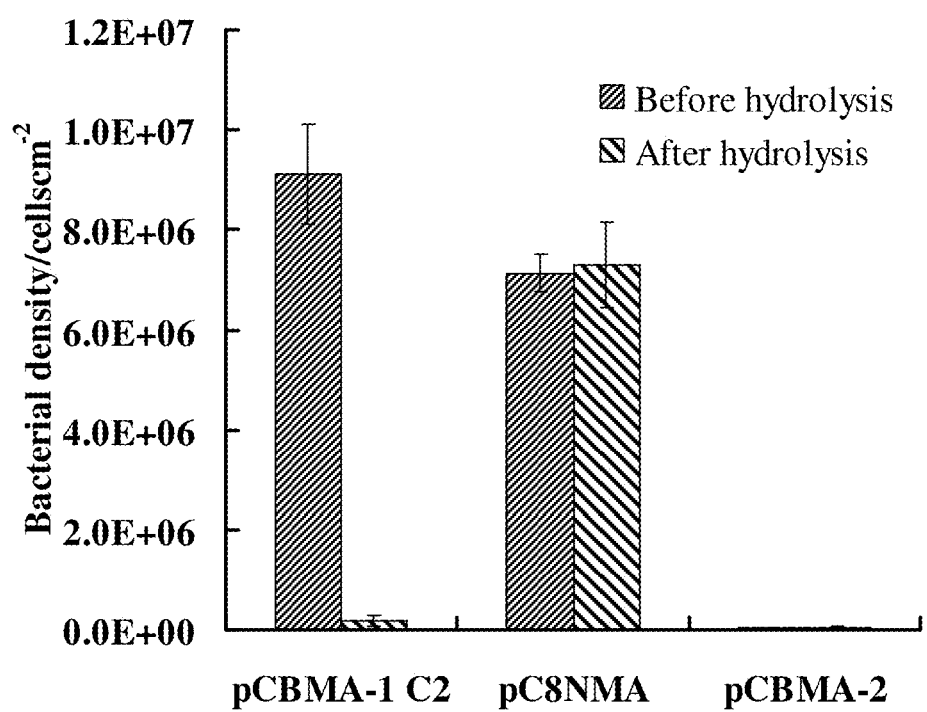
FIG. 11 is a graph comparing the attachment of *E. coli* K12 from a suspension with $10^{10}$ cells mL$^{-1}$ for one-hour exposure to pCBMA-1 C2, pC8NMA, and pCBMA-2 before and after hydrolysis (n=3).

The attachment and release of *E. coli* K12 were tested on the pCBMA-1 C2 surfaces before and after hydrolysis. Cationic pC8NMA and zwitterionic pCBMA-2 were used as the negative and the positive nonfouling control surfaces, respectively, and as the positive and the negative antimicrobial control surfaces, respectively. FIGS. 10A-10F show that large amounts of bacteria were attached to the cationic pCBMA-1 C2 and pC8NMA surfaces before hydrolysis, whereas very few bacterial cells were attached to the zwitterionic pCBMA-2 surface. In contrast to pC8NMA, pCBMA-1 C2 released the majority of cells after hydrolysis while pCBMA-2 remained nonfouling. FIG. 11 shows quantitative data for the amount of bacterial cells remaining on all three polymer surfaces before and after hydrolysis. There were similar amounts of bacterial residues on both cationic pCBMA-1 C2 and pC8NMA surfaces before hydrolysis, while the amount of attached cells on the pCBMA-2 surface is less than 0.3% of that on both cationic pCBMA-1 C2 and pC8NMA surfaces. To test the release of bacterial residues, the three surfaces were incubated in N-cyclohexyl-3-aminopropanesulfonic acid (CAPS) buffer (10 mM, pH 10.0) at 37° C. for 8 days. The pCBMA-1 C2 surfaces were hydrolyzed to poly(N-(carboxymethyl)-N,N-dimethyl-2-[(2-methyl-1-oxo-2-propen-1-yl)-oxy]ethanaminium) (pCBMA-1) and 98% of the dead bacterial cells were released. In contrast, no release of the dead cells was observed on pC8NMA surfaces (p>0.1) while pCBMA-2 surfaces retained very low bacterial adhesion.

The release of the attached bacterial cells is dependent on the conversion of cationic pCBMA-1 C2 into zwitterionic pCBMA-1. Hydrolysis rate of betaine esters is influenced by several factors, such as the length of the spacer ($L_2$) between the quaternary amine and the carboxyl groups, the nature of the hydrolyzable group, temperature,[1] and pH value. The majority of polymer chains of the ester group used were hydrolyzed. The hydrolysis rate of the betaine esters is also slower after bacterial cells and proteins are attached to the surface. pCBMA-1 C2, which has one methylene spacer ($L_2$), was chosen and the experimental temperature was set at 37° C. to achieve a fast hydrolysis rate and to provide a physiologically relevant temperature. The protein adsorption results (see Table 2) showed that the clean, cationic pCBMA-1 C2 surface was hydrolyzed into a nonfouling zwitterionic surface after only 24 h at 37° C. and pH 10.0, while it took 48 h to form a nonfouling surface and release bacterial residues after the attachment of bacteria from an *E. coli* K12 suspension of $10^7$ cells mL$^{-1}$. When bacterial cells were attached to the pCBMA-1 C2 surface from a suspension of $10^{10}$ cells mL$^{-1}$, the release of attached bacteria took eight days under the same hydrolysis conditions.

Figure 12A:
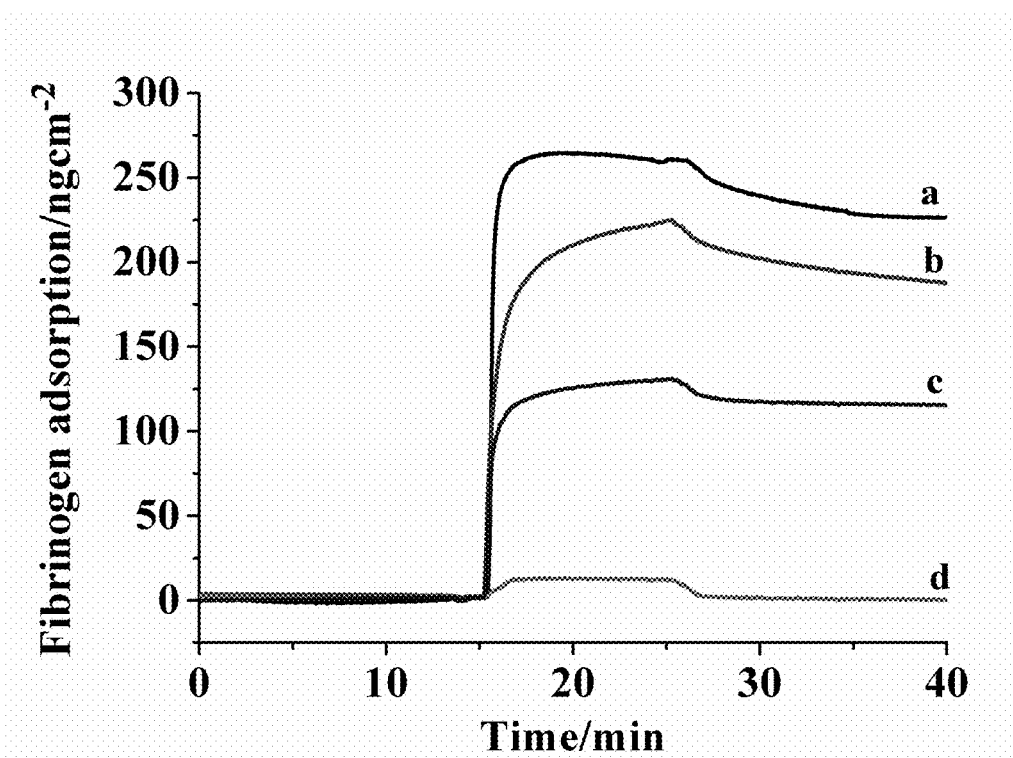
FIG. 12A compares SPR sensorgrams showing the adsorption of 1 mg mL$^{-1}$ fibrinogen in PBS buffer on the surfaces grafted with pCBMA-1 C2 via ATRP (a) before hydrolysis, and (b), (c) and (d) after 24 hr hydrolysis with water, 10 mM CEHS at pH 9.0, and 10 mM CAPS at pH 10.0, respectively.
Figure 12B:
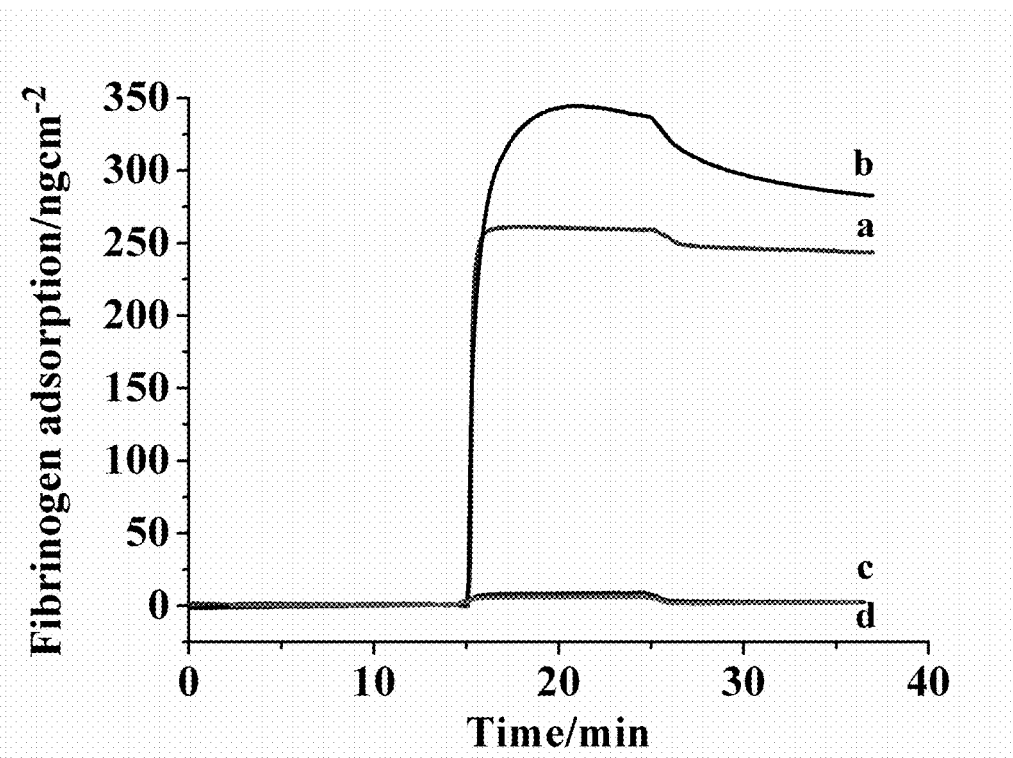
FIG. 12B compares SPR sensorgrams showing the adsorption of 1 mgmL$^{-1}$ fibrinogen in PBS buffer on the surfaces grafted with pC8NMA (a) before and (b) after 24 hr incubation with 10 mM CAPS at pH 10.0, and on the surfaces grafted with pCBMA-2 (c) before hydrolysis and (d) after 24 h of hydrolysis with 10 mM CAPS at pH 10.0.

Nonspecific protein adsorption on various surfaces was measured by a surface plasmon resonance (SPR) sensor to determine the nonfouling characteristics of the surfaces (see Table 2). Hydrolysis conditions for pCBMA-1 C2 and control surfaces were investigated in situ in the SPR sensor. FIGS. 12A and 12B show representative SPR sensorgrams for fibrinogen adsorption on pCBMA-1 C2 and control surfaces over time. The fibrinogen adsorption on pCBMA-1 C2 before hydrolysis was 229.2 ng cm$^{-2}$. After 24 h of incubation with CAPS buffer (pH 10.0), there was no measurable protein adsorption on the pCBMA-1 C2 surface, which indicated that pCBMA-1 C2 was completely hydrolyzed to nonfouling zwitterionic pCBMA-1. In contrast, hydrolysis of pCBMA-1 C2 was not complete after 24 h incubation in either water or N-cyclohexyl-2-aminoethanesulfonic acid (CEHS) buffer (pH 9.0). As shown in FIG. 12B, high fibrinogen adsorption was observed on the pC8NMA surface before and after the surface was incubated with CAPS buffer (pH 10.0) for 24 h at 37° C. However, under identical conditions, the pCBMA-2 surface still exhibited excellent nonfouling properties, with less than 2 ng cm$^{-2}$ fibrinogen absorption. This result indicates that the obtained zwitterionic surfaces are highly resistant to protein adsorption and are qualified as ultralow fouling surfaces.

In this embodiment, the invention provides a switchable polymer surface that integrates antimicrobial and nonfouling properties and is biocompatible. The representative cationic polymer (i.e., precursor of pCBMA) is able to kill bacterial cells effectively and switches to a zwitterionic nonfouling surface and releases dead bacterial cells upon hydrolysis. Moreover, the resulting nonfouling zwitterionic surface can further prevent the attachment of proteins and microorganisms and reduce the formation of a biofilm on the surface. The switchable process from antimicrobial to nonfouling surfaces can be tuned through adjusting the hydrolysis rate of these polymers for specific requirements of applications.

Figure 13:
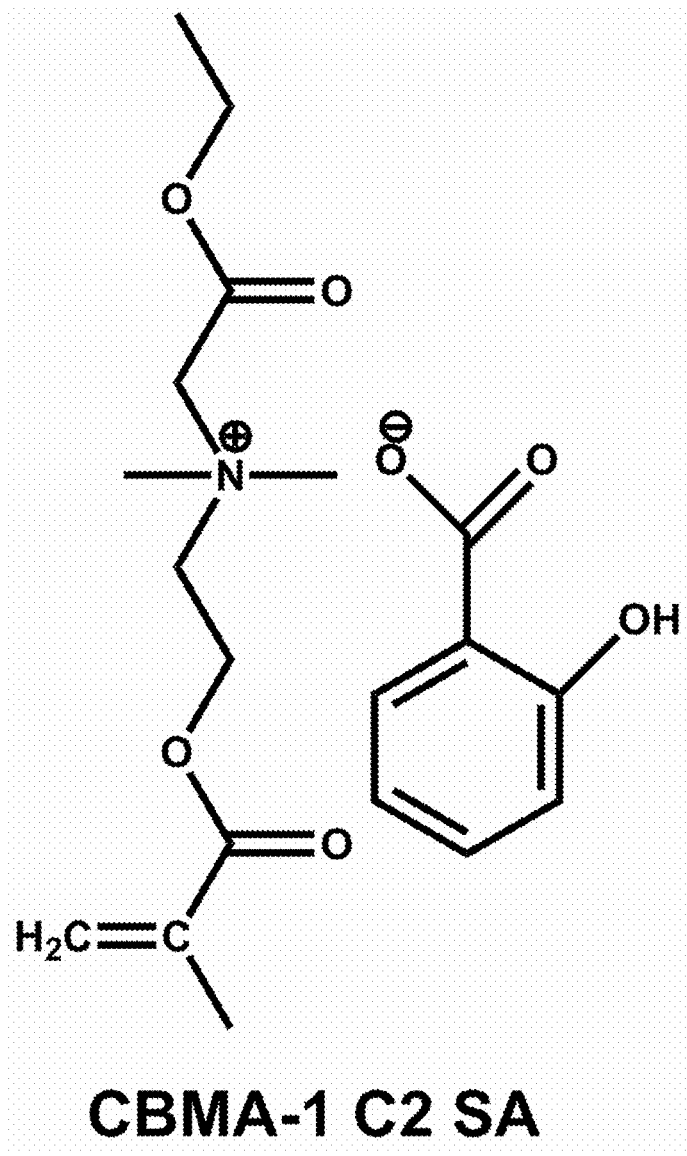
FIG. 13 illustrates the structure of a representative cationic monomers useful for making cationic polymers useful in the invention: CBMA-1 C2 SA, the ethyl ester of CBMA-1 having a salicylate counter ion.
Figure 14:
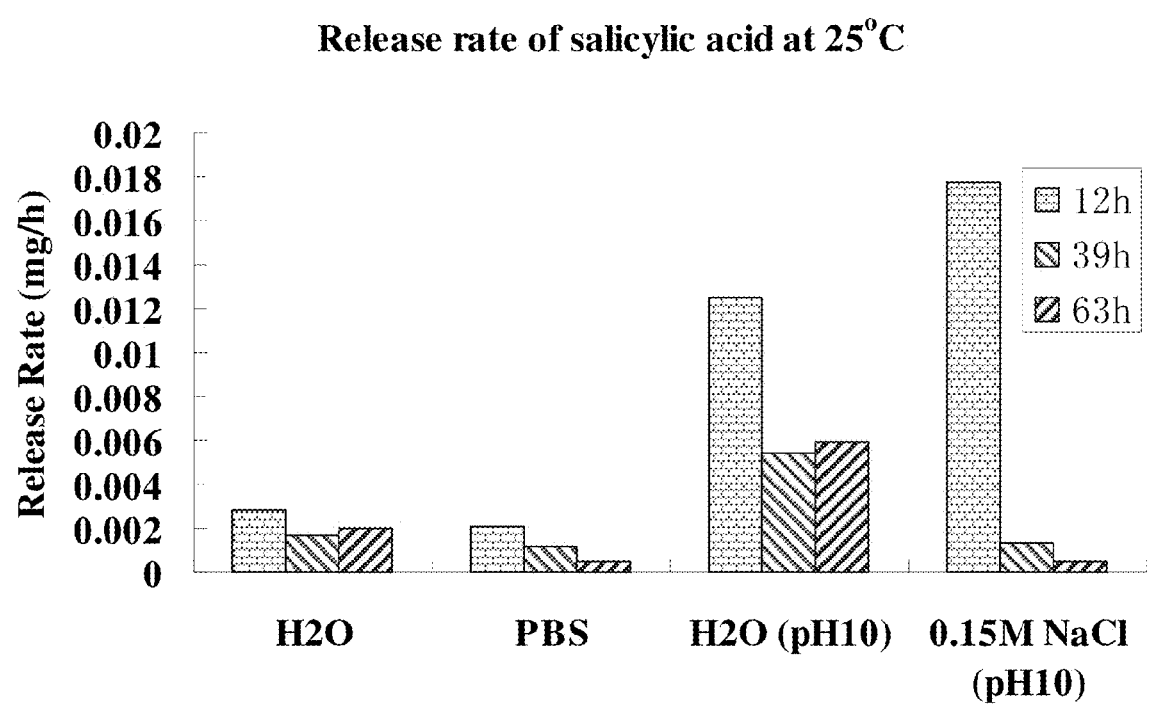
FIG. 14 compares the release rate (mg/h) of salicylic acid over time (12 h, 39 h, and 63 h) at 25° C. under four conditions from hydrogels prepared by polymerizing CBMA-1 C2 SA: (a) water, neutral pH; (b) phosphate buffered saline (PBS); (c) water, pH 10; and (d) 0.15 M aqueous sodium chloride, pH 10.
Figure 15:
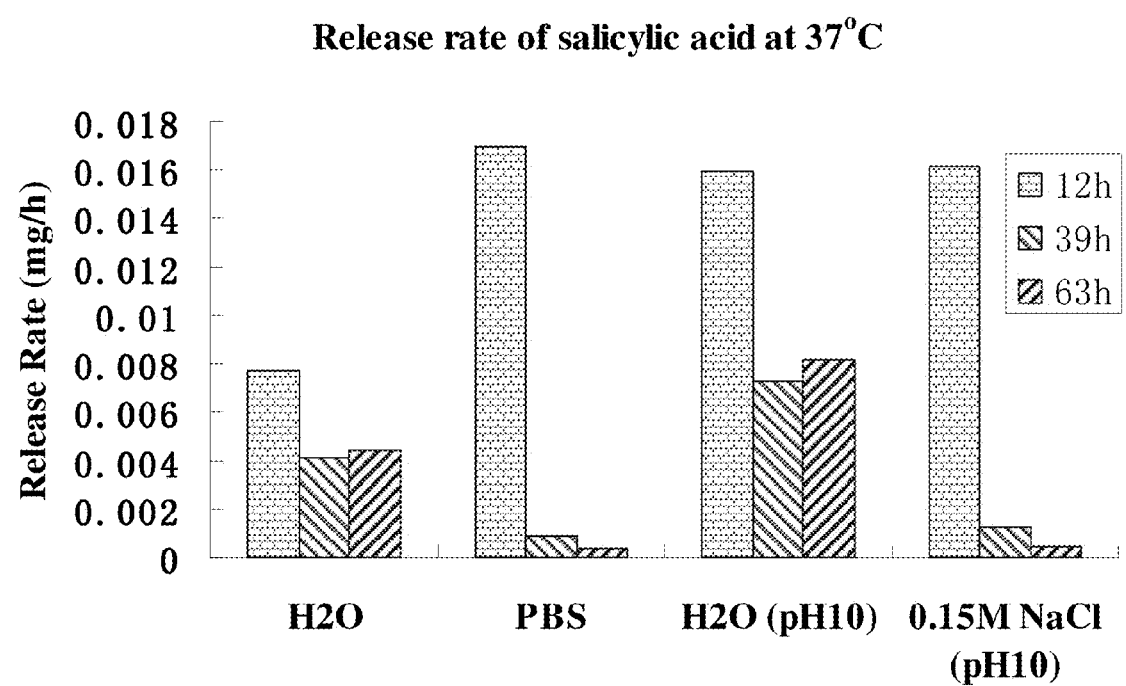
FIG. 15 compares the release rate (mg/h) of salicylic acid over time (12 h, 39 h, and 63 h) at 37° C. under four conditions from hydrogels prepared by polymerizing CBMA-1 C2 SA: (a) water, neutral pH; (b) phosphate buffered saline (PBS); (c) water, pH 10; and (d) 0.15 M aqueous sodium chloride, pH 10.

As noted above, the cationic polymers useful in the invention can include a hydrophobic counter ion or a counter ion having therapeutic activity (e.g., antimicrobial or antibacterial activity. A representative polymer having a salicylate counter ion (polyCBMA-1 C2) can be prepared from the monomer illustrated in FIG. 13: CBMA-1 C2 ("1" indicates one carbon between two charged groups and "C2" indicates C2 ester). PolyCBMA-1 C2 hydrogel loaded with salicylic acid (SA) as its counter ion was prepared by copolymerizing 1 mM CBMA-1 C2 SA monomer (FIG. 13) with 0.05 mM tetraethylenglycoldimethacrylate in 1 ml of solvent (ethylene glycol:water:ethanol=1:2:1) at 65° C. for 2 hours. The resulting hydrogel was soaked in DI water for 12 hours. The hydrogel was cut into round disks with 1 cm diameter. The hydrogel disks were then transferred into solutions with different pH and ionic strength and incubated at 25° C. or 37° C. At different time points the aqueous phase was completely removed and new solutions were added. The release of SA into the aqueous phase was measured by high performance liquid chromatography (HPLC). The release rate of SA is defined as the amount of released SA divided by time (mg/h). The release rate of SA from pCBMA-1 C2 SA hydrogel depends on temperature, ionic strength, and pH. FIG. 14 and FIG. 15 indicated that higher pH promotes the release of SA and that increased ionic strength can slightly increase the release rate of SA. By comparing FIG. 14 and FIG. 15, it can be observed that the elevated temperature results in a faster release of SA in water and phosphate buffered saline (PBS). The release rate of SA decreases as a function of time for all the conditions.

The cationic polymers useful in the invention, hydrolyzable to zwitterionic polymers, can be advantageously used as coatings or components of coatings for the surfaces of a variety of marine devices including, for example, boat and ship hulls. In this embodiment, the cationic polymers useful in the invention provide switchable biocompatible polymer surfaces having self-sterilizing and nonfouling capabilities. The cationic polymers applied as marine coatings convert to hydrophilic nonfouling coatings (zwitterionic coatings) on contact with seawater.

FIG. 7 is a schematic illustration of a switchable biocompatible polymer surfaces having self-sterilizing and nonfouling capabilities. Referring to FIG. 7, antimicrobial surface (a) is a surface coated with a representative cationic polymer of the invention (i.e., pCBMA-1 C2, see FIG. 8). On hydrolysis (b) the representative cationic polymer is converted to a nonfouling zwitterionic polymer (i.e., pCBMA-1, the carboxylate corresponding to pCBMA-1 C2 ester) to provide a surface coated with the zwitterionic polymer, which is highly resistant to bacterial adhesion (d).

In marine coating applications, the functional leaving/hydrolysable groups or functional counter ions are particularly useful. In these embodiment, the leaving/hydrolysable groups and/or counter ions are advantageously antimicrobial or biocide agents. The marine coating compositions of the invention are effective to store and release biocides.

The present invention provides nonfouling marine coatings for long-term applications. These durable, nonfouling marine coatings are self-polished at the outermost layer upon contact with seawater. The coating can be combined with fouling-release or anti-fouling technologies.

In one embodiment, the marine coating includes cationic polymers useful in the invention having a hydrophobic ion for counter ion X⁻. In this embodiment, the nonfouling marine coatings include one or more of the following polymers: (1) cationic homopolymers (i.e., polymers prepared by polymerization of hydrolysable precursors of zwitterionic monomers); (2) copolymers prepared by copolymerization of the cationic monomers of the invention (i.e., hydrolysable precursors of zwitterionic monomers) and zwitterionic or hydrophobic monomers; and (3) copolymers prepared by polymerization of hydrolysable precursors of mixed charged monomers.

Representative cationic homopolymers include the cationic polymers useful in the invention described above as well as the cationic homopolymers of formulas (IV) and (V) below.

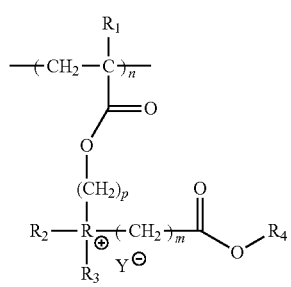

(IV)

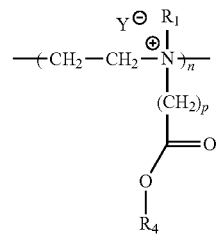

(V)

The cationic polymers of formula (IV) have the cationic center in the pendant group attached to the polymer backbone. The cationic polymers of formula (V) have the cationic center in the polymer backbone.

For the polymers of formulas (V) and (VI), $R_1$ is selected from hydrogen, methyl, and ethyl; $R_2$ and $R_3$ are independently selected from $C_1$-$C_{20}$ alkyl and fluoroalkyl; $R_4$ is selected from $C_1$-$C_{20}$ alkyl, $C_6$-$C_{12}$ aryl, tri($C_1$-$C_8$ alkyl) silyl, alkyl copper, and alkyl zinc; m is an integer from 1 to 10; p is an integer from 1 to 10; R is a cationic center selected from ammonium, imidazolium, triazaolium, pyridinium, morpholinium, oxazolidinium, pyrazinium, pyridazinium, pyrimidinium, piperazinium, and pyrrolidinium, and other nitrogen bases; Y is chloride, bromide, iodide, sulfate, nitrate, perchlorate ($ClO_4$), tetrafluoroborate ($BF_4$), hexafluorophosphate ($PF_6$), bis(trifluoromethylsulfonyl)amide ($N[SO_2CF_3]_2$), trifluoromethylsulfonate ($SO_3CF_3$), C1-C20 carboxylate (R—C(=O)O⁻), C1-C20 sulfonate (R—$SO_3^-$), lactate, salicylate, and derivatives thereof; and n is 5 to about 100,000.

The preparation of representative cationic homopolymers useful in the invention having formula (IV) having a hydrophobic counter ion and their self-polishing and nonfouling properties are described in Example 5. The water solubilities of representative cationic polymers useful in the invention having formula (IV) is summarized in Table 2.

TABLE 2

Water Solubility of Representative Cationic Polymers.

| Y | p | | | | | |
|---|---|---|---|---|---|---|
| | 2 | 4 | 6 | 8 | 12 | 18 |
| Cl or Br | s | s | ps | ps | ps | ns |
| Salicylate | s | ns | ns | ns | ns | ns | s = soluble,
ns = not soluble,
ps = partially soluble.

Representative copolymers prepared by copolymerization of the cationic monomers of the invention (i.e., hydrolysable precursors of zwitterionic monomers) and zwitterionic monomers include the copolymers of formula (VI) below.

(VI)

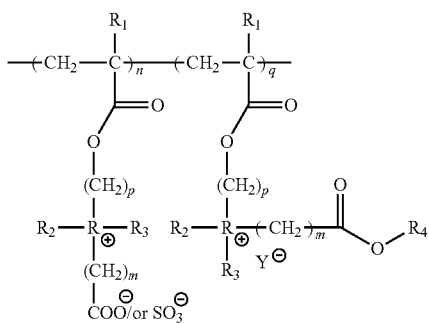

Representative copolymers prepared by polymerization of hydrolysable precursors of mixed charged monomers include the copolymers of formula (VII) below.

(VII)

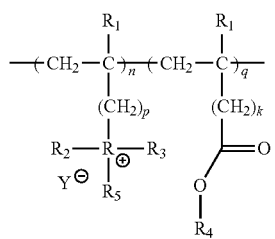

For the polymers of formulas (VI) and (VII), $R_1$ is selected from hydrogen, methyl, and ethyl; $R_2$ and $R_3$ are independently selected from C1-C20 alkyl and fluoroalkyl; $R_4$ is selected from C1-C20 alkyl, C6-C12 aryl, tri(C1-C8 alkyl)silyl, alkyl copper, and alkyl zinc; m is an integer from 1 to 10; p is an integer from 1 to 10; k is an integer from 1 to 10; R is a cationic center selected from ammonium, imidazolium, triazaolium, pyridinium, morpholinium, oxazolidinium, pyrazinium, pyridazinium, pyrimidinium, piperazinium, and pyrrolidinium, and other nitrogen bases; Y is chloride, bromide, iodide, sulfate, nitrate, perchlorate ($ClO_4$), tetrafluoroborate ($BF_4$), hexafluorophosphate ($PF_6$), bis(trifluoromethylsulfonyl)amide ($N[SO_2CF_3]_2$), trifluoromethylsulfonate ($SO_3CF_3$), C1-C20 carboxylate (R—C(=O)O$^-$), C1-C20 sulfonate (R—$SO_3^-$), lactate, salicylate, and derivatives thereof; n is 5 to about 100,000 and q is 5 to about 100,000.

In a further embodiment, the marine coating includes amphiphilic polymers containing zwitterionic and fluorine-containing and/or silicone polymers. Amphiphilic polymers include fluorine-containing or/and silicone polymers combining zwitterionic monomer units or groups.

Representative amphiphilic polymers with grafted zwitterionic side chains containing perfluoroalkyl groups pendant to silicone main chains include the copolymers of formulas (IX) and (X) below.

(IX)

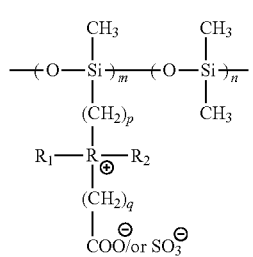

(X)

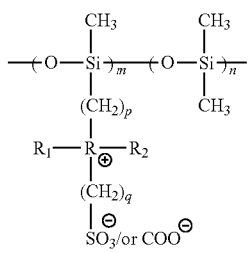

For polymers of formulas (IX) and (X), $R_1$ and $R_2$ are independently selected from C1-C20 alkyl and fluoroalkyl; p is an integer from 1 to 20; q is an integer from 1 to 20; and R is a cationic center selected from ammonium, imidazolium, triazaolium, pyridinium, morpholinium, oxazolidinium, pyrazinium, pyridazinium, pyrimidinium, piperazinium, and pyrrolidinium, and other nitrogen bases; m is 5 to about 100,000 and n is 2 to about 100,000. In one embodiment, p is an integer from 1 to 10. In one embodiment, q is an integer from 1 to 10.

The preparation of a representative polymer of the invention having a fluorinated zwitterionic pendant group grafted to a siloxane backbone is described in Example 7.

Representative amphiphilic polymers with grafted zwitterionic side chains containing perfluoroalkyl groups pendant to the polymer backbone include the copolymers of formulas (XI) and (XII) below.

(XI)

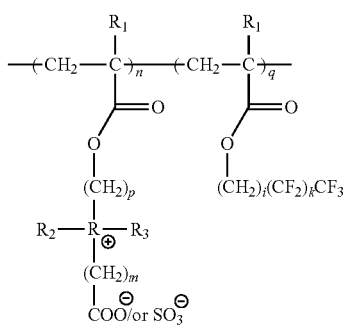

(XII)

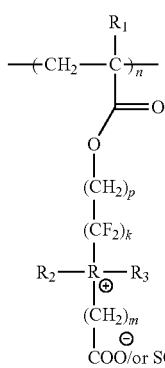

For the polymers of formulas (XI) and (XII), $R_1$ is selected from hydrogen, methyl, and ethyl; $R_2$ and $R_3$ are independently selected from C1-C20 alkyl and fluoroalkyl; m is an integer from 1 to 10; p is an integer from 1 to 10; k is an integer from 1 to 20; i is an integer from 1 to 20; and R is a cationic center selected from ammonium, imidazolium, triazaolium, pyridinium, morpholinium, oxazolidinium, pyrazinium, pyridazinium, pyrimidinium, piperazinium, and pyrrolidinium, and other nitrogen bases; n is 5 to about 100,000 and q is 5 to about 100,000.

As noted above, the nonfouling marine coatings include one or more of the following polymers: (1) cationic homopolymers (i.e., polymers prepared by polymerization of hydrolysable precursors of zwitterionic monomers); and (2) copolymers prepared by copolymerization of the cationic monomers of the invention (i.e., hydrolysable precursors of zwitterionic monomers) and zwitterionic or hydrophobic monomers. For these embodiments, the zwitterionic monomers are independently selected from polymerizable carboxybetaines, polymerizable sulfobetaines, polymerizable phosphobetaines, and other polymerizable zwitterionic compounds. The hydrolyzable precursors of zwitterionic monomers are selected from polymerizable cationic monomers containing hydrolyzable functional groups that on hydrolysis provide zwitterionic groups. The counterions of polymerizable cationic monomers noted above are selected from hydrophilic and/or hydrophobic anions, their mixtures, or modified hydrophilic and/or hydrophobic anions thereof. The mixed charged monomers are selected from polymerizable monomers having positively-charged cationic moieties and negatively-charged anionic moieties. The mixed charged monomers are selected from hydrolysable precursors of mixed charged monomer units, which can be hydrolyzed to mixed charged polymers. The backbones of the polymers noted above can be selected from acrylic polymers, acrylamide polymers, polyesters, amino resins, polyurethanes, polyamides, polyimides, epoxy and phenolic resins, alkyd resins, polyphosphazenes, polysiloxanes, and their mixtures or their modified polymers thereof.

The marine compositions of the invention can further include other fouling release materials (e.g., silicone and/or fluorine-containing coating materials) and/or antifouling materials (e.g., metallic compounds or biocides).

In one aspect, the present invention provides a marine coating comprising a copolymer and a base polymer (i.e., polymer matrix). The copolymer comprises at least one hydrophobic component and one hydrophilic component (e.g., PCB-PMMA, which is advantageously used in self-polishing coatings, or PCB-PDMS, which is advantageously used in fouling release coatings). The base polymer can include any one of a variety of polymers or copolymers described herein (e.g., polymers and copolymers containing esters that are used in self-polishing coatings; or PDMS, which is useful in fouling release coatings.

As used herein, the term "self-polishing coating" refers to coatings that include a copolymer of the invention (e.g., a copolymer of the invention organized into a nanostructure) in a self-polishing polymer base (e.g., polymers and copolymers containing hydrolyzable groups, such as esters, that upon use are hydrolyzable to produce zwitterionic or mixed charge polymers and copolymers that are hydrophilic and non-fouling and are thus regenerative or self-polishing). The term "fouling release coating" refers to coatings that include a copolymer of the invention (e.g., a copolymer of the invention organized into a nanostructure) in a stable-polymer base (e.g., PDMS).

Self-polishing polymer coatings embedded with a copolymer (e.g., self-organized nanostructure, such as a nanoparticle) are provided. As noted above, in one embodiment, the marine coating includes nanostructures (e.g., nanoparticles) formed from zwitterionic (hydrophilic) and hydrophobic copolymers contained in a matrix containing binder polymers. The nanostructures are formed from polymers or copolymers having zwitterionic and hydrophobic components (e.g., block copolymers having zwitterionic and hydrophobic blocks, or random copolymerization of zwitterionic monomers with hydrophobic monomers). The zwitterionic component or block comprises repeating units derived from zwitterionic monomers and the hydrophobic component or block comprises repeating units derived from hydrophobic monomers.

The nanostructures can be mixed with binder polymers, including hydrolyzable polymers, as nonfouling marine coating compositions. The binder polymers are selected from rosins, acrylic polymers, polyesters, amino resins, polyurethanes, polyamides, polyimides, epoxy and phenolic resins, alkyd resins, polyphosphazenes, polysiloxanes, and their mixtures or their modified polymers thereof.

Representative copolymers prepared by having zwitterionic and hydrophobic blocks or a random copolymer prepared by copolymerization of zwitterionic and hydrophobic monomers include the copolymers of formula (VIII) below.

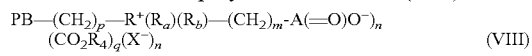

(VIII)

wherein

R, $R_2$, and $R_3$ taken together form a cationic center selected from imidazolium, triazaolium, pyridinium, morpholinium, oxazolidinium, pyrazinium, pyridazinium, pyrimidinium, piperazinium, and pyrrolidinium; or when R is N, $R_2$ and $R_3$ may be independently selected from the group consisting of hydrogen, C1-C20 alkyl and fluoroalkyl, and C6-C12 aryl;

A is C or SO;

$R_4$ is selected from the group consisting of C1-C20 alkyl, C6-C12 aryl, and tri(C1-C8 alkyl)silyl;

m is an integer from 1 to 20;

n is an integer from 5 to about 100,000;

p is an integer from 1 to 20; and q is an integer from 5 to about 100,000.

The preparation of representative cationic copolymers useful in the invention having formula (VII) and their nonfouling properties are described in Example 6.

In one embodiment, the invention provides a marine coating, comprising copolymers (e.g., nanoparticles) dispersed in a polymeric matrix. The nanoparticle comprise a plurality of block copolymers, wherein the block polymer comprises a zwitterionic block and a hydrophobic block, wherein the zwitterionic block comprises repeating units derived from zwitterionic monomers, and wherein the hydrophobic block comprises repeating units derived from hydrophobic monomers.

Suitable zwitterionic monomers useful for making the block copolymers include polymerizable carboxybetaines, polymerizable sulfobetaines, polymerizable phosphobetaines. Mixtures of monomers can also be used.

In certain embodiments, the block polymer has the formula:

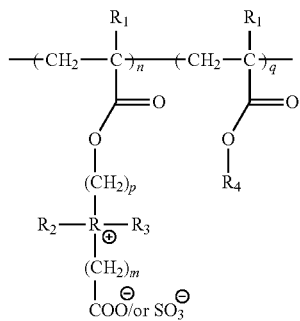

wherein R, $R_2$, and $R_3$ taken together form a cationic center selected from imidazolium, triazaolium, pyridinium, morpholinium, oxazolidinium, pyrazinium, pyridazinium, pyrimidinium, piperazinium, and pyrrolidinium; or when R is N, $R_2$ and $R_3$ are independently selected from the group consisting of hydrogen and C1-C20 alkyl and fluoroalkyl, and C6-C12 aryl; $R_1$ is independently at each occurrence selected from the group consisting of hydrogen, methyl, and ethyl; $R_4$ is selected from the group consisting of C1-C20 alkyl, C6-C12 aryl, and tri(C1-C8 alkyl)silyl; m is an integer from 1 to 20; n is an integer from 5 to about 100,000; p is an integer from 1 to 20; and q is an integer from 5 to about 100,000. In one embodiment, $R_4$ is C4-C12 alkyl.

Suitable polymeric matrices include polymers such as rosins, acrylic polymers, polyesters, amino resins, polyurethanes, polyamides, polyimides, epoxy and phenolic resins, alkyd resins, polyphosphazenes, polysiloxanes. Mixtures of polymers are also useful. In certain embodiments, the polymeric matrix is a hydrolysable, self-polishing polymer. In one embodiment, the polymeric matrix includes a cationic polymer having:

(a) a polymeric backbone;
(b) a plurality of cationic centers, each cationic center covalently coupled to the polymer backbone by a first linker;
(c) a counter ion associated with each cationic center; and
(d) a hydrolyzable group covalently coupled to each cationic center through a second linker, wherein the hydrolyzable group is hydrolyzable to an anionic center to provide a zwitterionic polymer having the anionic center covalently coupled to the cationic center through the second linker.

In certain of these embodiments, the polymeric matrix has the formula:

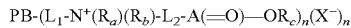

wherein

PB is the polymer backbone having n pendant groups $L_1$-$N^+$($R_a$)($R_b$)-$L_2$-A(=O)—$OR_c$);

$N^+$($R_a$)($R_b$) is the cationic center;

A(=O)—$OR_c$ is the hydrolyzable group, wherein A is selected from the group consisting of C, S, SO, P, or PO, and $R_c$ is an alkyl, aryl, acyl, or silyl group that may be further substituted with one or more substituents;

$L_1$ is a linker that covalently couples the cationic center to the polymer backbone;

$L_2$ is a linker that covalently couples the cationic center to the hydrolyzable group;

$X^-$ is the counter ion associated with the cationic center; and n is an integer from about 10 to about 10,000.

In certain embodiments, the counter ion is a hydrophobic organic counter ion. Suitable the hydrophobic counter ions include C1-C20 carboxylates and C1-C20 alkylsulfonates. In other embodiments, the counter ion is biologically active. Suitable biologically active counter ions include antimicrobial, antibacterial, and antifungal agents. In one embodiment, the counter ion is salicylate.

In certain embodiments, the hydrolyzable group releases a hydrophobic organic group on hydrolysis. In one embodiment, the hydrolyzable group releases a C1-C20 carboxylate on hydrolysis. In another embodiment, the hydrolyzable group releases a biological active on hydrolysis.

$N^+$($R_a$)($R_b$) taken together provide the cationic center. Representative cationic centers include ammonium, imidazolium, triazaolium, pyridinium, morpholinium, oxazolidinium, pyrazinium, pyridazinium, pyrimidinium, piperazinium, and pyrrolidinium centers. Alternatively, in certain embodiments, $R_a$ and $R_b$ are independently selected from the group consisting of hydrogen and C1-C10 straight chain and branched alkyl groups, and C6-C12 aryl groups.

In certain embodiments, $L_1$ is —C(=O)O—$(CH_2)_n$— or —C(=O)NH—$(CH_2)_n$—, wherein n is an integer from 1 to 20.

In certain embodiments, $L_2$ is —$(CH_2)_n$—, where n is an integer from 1 to 20.

In certain embodiments, A is C, SO, and PO. In certain embodiments, $R_c$ is C1-C20 alkyl.

In certain embodiments, $X^-$ is a halide, a carboxylate, an alkylsulfonate, a sulfate; a nitrate, a perchlorate, a tetrafluoroborate, a hexafluorophosphate, a trifluoromethylsulfonate, a bis(trifluoromethylsulfonyl)amide, a lactate, and a salicylate.

In another aspect, the invention provides a surface of a marine substrate treated with a marine coating of the invention comprising nanoparticles dispersed in a polymeric matrix as described above. Representative substrates include marine structures such as a vessel hull, a propeller, periscope, sensor, fish net, or bridge.

In a further aspect of the invention, a method for treating a surface of a marine substrate is provided. In one embodiment, the method includes applying a marine coating of the invention comprising copolymers dispersed in a polymeric matrix as described above to a surface of a marine substrate. In certain embodiments, applying the composition comprises spraying or painting.

The invention provides a stable coating that can be self-polished in seawater layer-by-layer (i.e., surface erosion) without sacrificing its mechanical properties at controllable hydrolysis rates.

Thus, in one embodiment, the invention provides self-polishing zwitterionic precursor-based polymer coatings. Such embodiments may further comprise homopolymers from various monomers with different hydrolysable groups, spacers between two charged groups and hydrophobic ions and copolymers with another hydrophobic monomer.

In a further embodiment, self-polishing nanoparticle-embedded polymer coatings are provided. Such embodiments may further comprise a self-polishing zwitterionic precursor-based polymer coatings embedded with zwitterionic nanoparticles. These coatings are capable of lasting three years or longer under static conditions.

PolySB and polyCB have been grafted onto surfaces via ATRP. While these are excellent model systems useful to study their interactions with marine microorganisms, these hydrophilic materials have no mechanical properties. Zwitterionic-based paints (non-hydrolysable) containing both hydrophilic zwitterionic for nonfouling and hydrophobic compounds for mechanical properties have been developed. While these panels have shown their effectiveness to defer biofouling in 1-3 months and further improvements may extend their life span a few more months, it is unrealistic to expect these (non-hydrolysable) coated panels to meet the requirements of 3 or 12 year life cycle needed by U.S. Navy.

Self-polishing zwitterionic coatings with an aim for long-term application provide an effective alternative. The key is to adjust its hydrolysis rate so that the coating peels layer-by-layer (i.e., surface erosion from its outer-most layers) at the appropriate time (just before severe biofouling occurs on the coating surface) while maintaining its mechanical properties.

Approaches to Realize Self-Polishing Zwitterionic Coatings.

As important as the discovery of ultra low fouling zwitterionic materials, hydrophobic hydrolysable zwitterionic precursors were developed by replacing carboxyl groups by hydrophobic hydrolysable esters. These hydrophobic hydrolysable zwitterionic precursors can be applied onto a ship surface at any film thickness (e.g., 150 μm) with strong mechanical properties using a sprayer. When they are in contact with seawater, the outer-most molecular layer(s) hydrolyze to provide ultra low fouling zwitterionic groups by converting hydrophobic hydrolysable esters into carboxyl (COO—) groups. In this way, there is no compromise between the nonfouling properties of the outer coating surfaces and the mechanical strengths of the entire coatings.

By examining the structure of a zwitterionic monomer, there are at least three parameters that can be adjusted: (a) hydrophobic ester groups (type and length), (b) the chain length between two charged sites, and (c) counter ions (hydrophilic or hydrophobic). By adjusting these three parameters, one may obtain homopolymer-based coatings.

As noted above, in a further embodiment, a hydrolysable zwitterionic nanoparticle-embedded coating is provided. By adding nanoparticles prepared from amphiphilic diblock copolymers containing hydrophilic zwitterionic and hydrophobic segments into a hydrolysable binder polymer, these nanoparticles are well dispersed within the hydrolysable polymer matrix. Upon the hydrolysis of the outer-most layer(s) of the coatings, nanoparticles will open up and inner hydrophilic zwitterionic groups will be exposed on the outer surface of the coatings, leading to a hydrophilic zwitterionic surface. This approach is more effective than conventional ways to form copolymers of hydrophobic hydrolysable and hydrophilic zwitterionic segments.

In a further embodiment, hydrolysable zwitterionic precursor polymers disclosed above may be used as the hydrolysable polymer binder, into which zwittterionic nanoparticles may be embedded.

Approach 1

Figure 24:
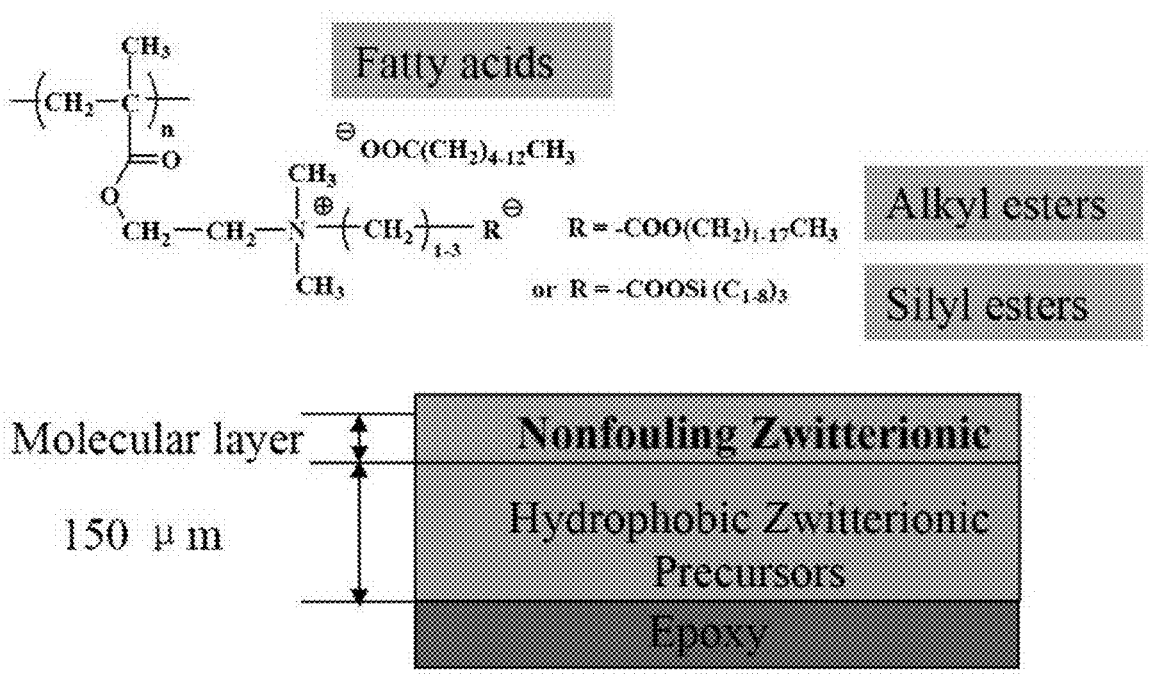
FIG. 24 illustrates representative hydrolyzable hydrophobic zwitterionic precursors having strong mechanical properties. These precursors provide self-polishing ultra low fouling zwitterionic coatings on hydrolysis in seawater. Once the hydrophilic surface layer swells, this layer peels off to reveal a "fresh" surface before severe biofouling occurs on the surface. This layer-by-layer peeling action leads to self-polishing effects.

The first milestone in the development of ultra low fouling marine coatings is the discovery of ultra low fouling zwitterionic materials. However, zwitterionic polymers are superhydrophilic and do not have mechanical properties when they are coated onto a surface directly. Also, it is not expected that non-hydrolysable zwitterionic coatings will be able to resist the attachment of marine organisms for years. The second milestone is the discovery of hydrolysable hydrophobic zwitterionic precursors and their unique properties (FIG. 24), enabling the development of long-lasting self-polishing ultra low fouling zwitterionic coatings. These coatings are hydrophobic and have strong mechanical properties as coatings. At the same time, the outer-most layers of these coating polymers will be hydrolyzed in seawater and turned into superhydrophilic zwitterionic groups, which are inherently ultra low biofouling even under static conditions. Once the hydrophilic surface layer swelled, this layer peels off to reveal a "fresh" surface before severe biofouling occurs on the surface. This layer-by-layer peeling action leads to self-polishing effects. The hydrolysis rate of the coatings can be adjusted. Thus, these novel coatings can be prepared without compromise between strong mechanical properties and excellent nonfouling properties.

Self-polishing zwitterionic-based homopolymer coatings are based on the homopolymers of hydrolysable zwitterionic precursor monomers. The flexibility of the molecular design of the monomers allows for the preparation of a variety of hydrolysable hydrophobic zwitterionic CBMA monomer precursors. Hydrophobic monomers can be prepared by introducing hydrophobic ester groups such as alkyl esters [—COO(CH$_2$)$_{1-17}$CH$_3$] and silyl esters [—COOSi(C1-7)$_3$]. Results show that the alkyl ester has a slower hydrolysis rate than its silyl counterpart. Furthermore, hydrophobic counter anions [CH$_3$(CH$_2$)$_{4-12}$COO—] can be used to increase the hydrophobic properties of the monomers.

Figure 25:
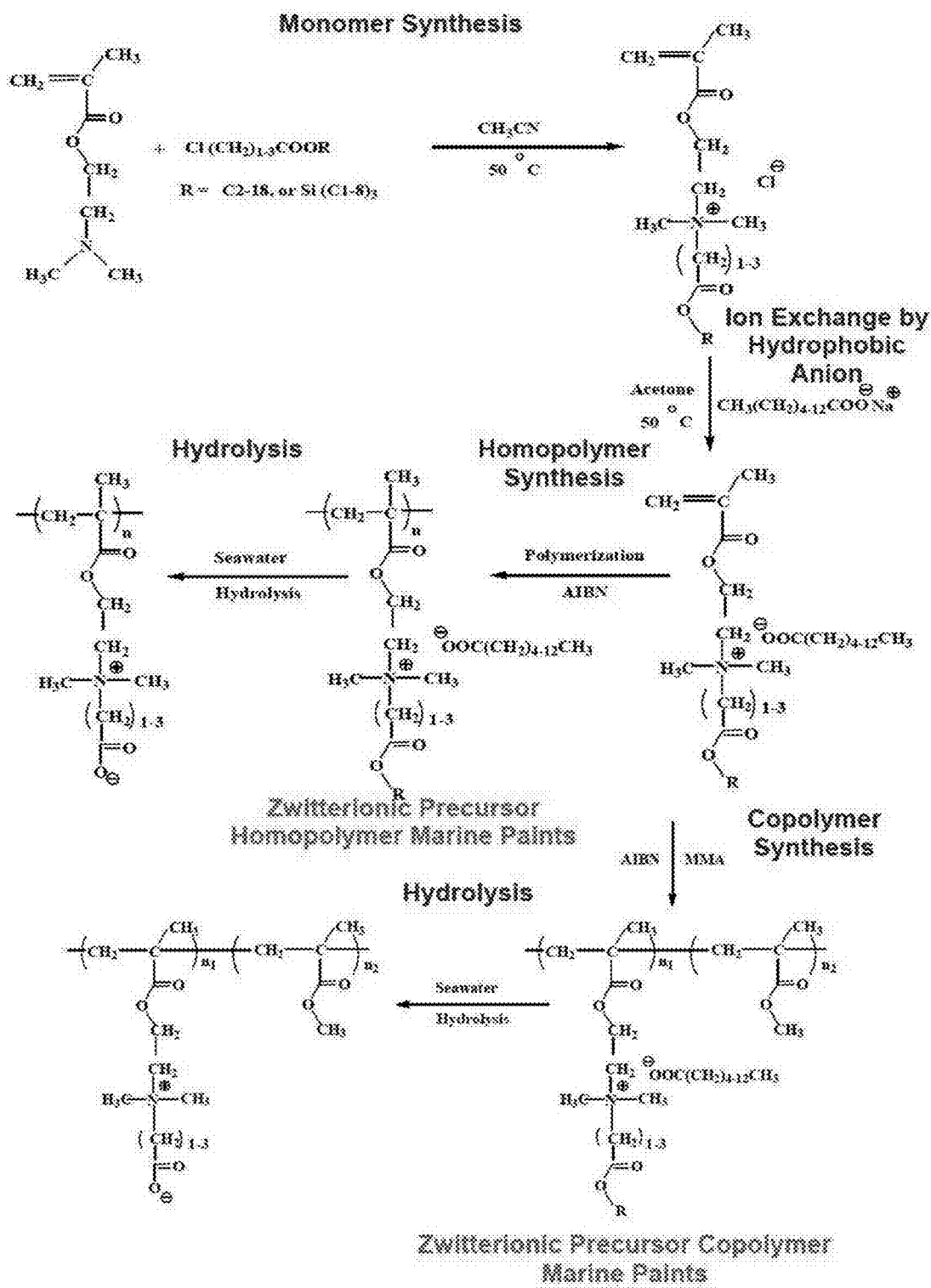
FIG. 25 illustrates methods for making representative self-polishing zwitterionic-based copolymer coatings of the invention via the copolymerization of hydrolysable zwitterionic CBMA monomer precursors with hydrophobic MMA.

Most of the cationic monomers/or polymers containing counter anions, such as Cl—, Br—, SO$_4^{2-}$, are hydrophilic. If hydrophobic anions are introduced to the cationic monomers, the corresponding polymers will have excellent hydrophobic properties. The spacer between two charged groups [N$_+$(CH$_2$)$_{1-3}$COOR] can significantly affect their hydrolysis rate. Shorter distance will lead to higher hydrolysis rate. The corresponding homopolymers can be synthesized via the free radical polymerization of the hydrolysable zwitterionic precursor monomers. Typical monomer and homopolymer synthesis routes are shown in FIG. 25.

Self-polishing zwitterionic-based copolymer coatings can also be obtained via the copolymerization of hydrolysable zwitterionic CBMA monomer precursors with hydrophobic MMA. Through copolymerization with MMA, the hydrolysis behavior and mechanical properties of copolymers can be further adjusted. Typical copolymer synthesis routes are also shown in FIG. 25. For commercial SPC coatings, the copolymer approach was also adopted. However, self-polishing zwitterionic-based copolymer coating is biocide free and inherently biofouling resistant. Different spacers [N+(CH$_2$)$_{1-3}$COOR], ester groups [—COO(CH$_2$)$_{1-17}$CH$_3$] and [—COOSi(C1-7)$_3$], and counter anions [CH$_3$(CH$_2$)$_{4-12}$COO—] for hydrolysable zwitterionic precursor monomers are evaluated along with different random copolymer compositions (5-50% mol) and molecular weights (5K-200K) in the case of copolymers. These parameters influence the hydrolysis rates and mechanical properties of coating polymers.

Figure 26:
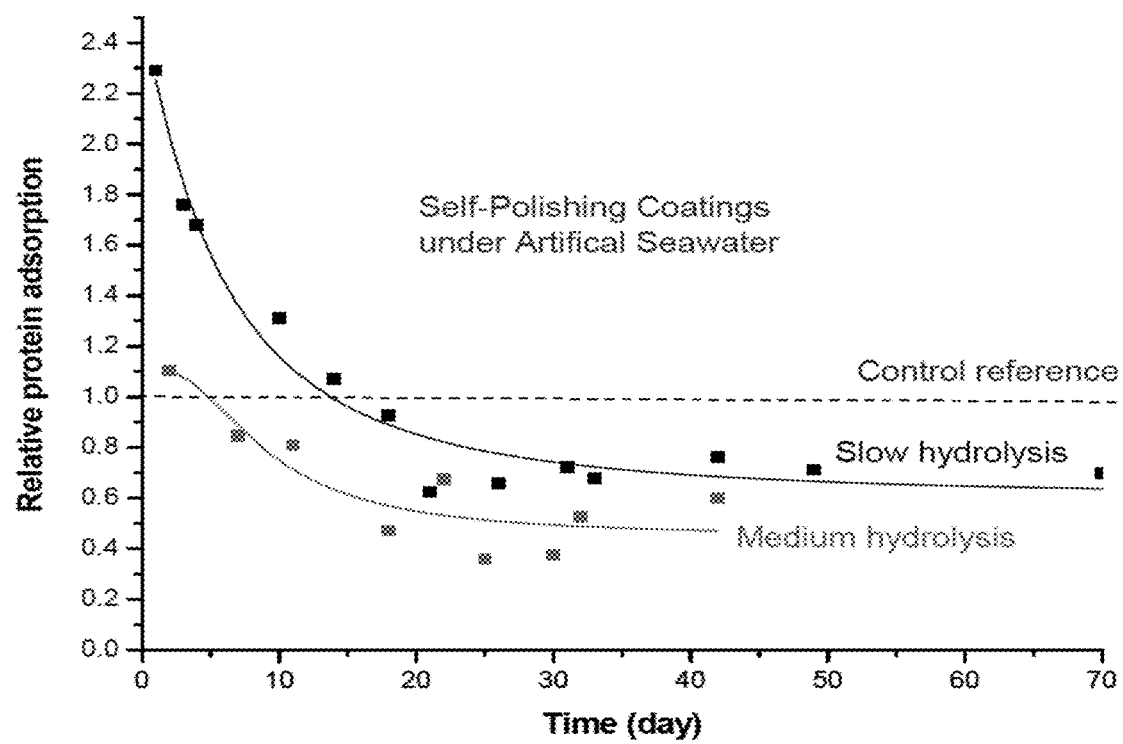
FIG. 26 presents ELISA results of representative self-polishing zwitterionic-based homopolymer coatings with different alkyl esters and demonstrating protein adsorption decrease over time due to hydrolysis of the outermost coating layer.

These polymers may be coated on silane-treated glass slides (1'×3') using a spincoater or on epoxy-coated panels (4'×8') using a sprayer. Hydrolysis rate were tested in artificial seawater and the film thickness was measured by ellipsometry. These parameters will influence the chemical, physical and hydrolysis properties of the coatings. Results in FIG. 26 demonstrate the feasibility of this approach. Results show that zwitterionic precursor polymers (while dissolved in organic solvent) do not dissolve in artificial seawater (0.6M NaCl) under pH at 2-12. Results further show that these zwitterionic precursors coated onto a plate gradually hydrolyze and resist nonspecific protein adsorption over a period of 50-70 days tested. The coatings hydrolyze to form ultra low fouling zwitterionic groups at their outer-most layers once they are in contact with seawater. The chemical and physical properties of coatings will be changed due to hydrolysis.

Approach 2

In a further embodiment, the invention provides a self-polishing zwitterionic nanoparticle-embedded polymer coating. Nanoparticles are prepared from amphiphilic diblock copolymers containing a hydrophilic polymer, for example pSBMA or pCBMA, with alkyl methacrylate monomers. These nanoparticles are then mixed with a hydrophobic hydrolyzable acrylic binder copolymer. Binder copolymer can be hydrolyzed by seawater because it contains water reactive groups.

Figure 27:
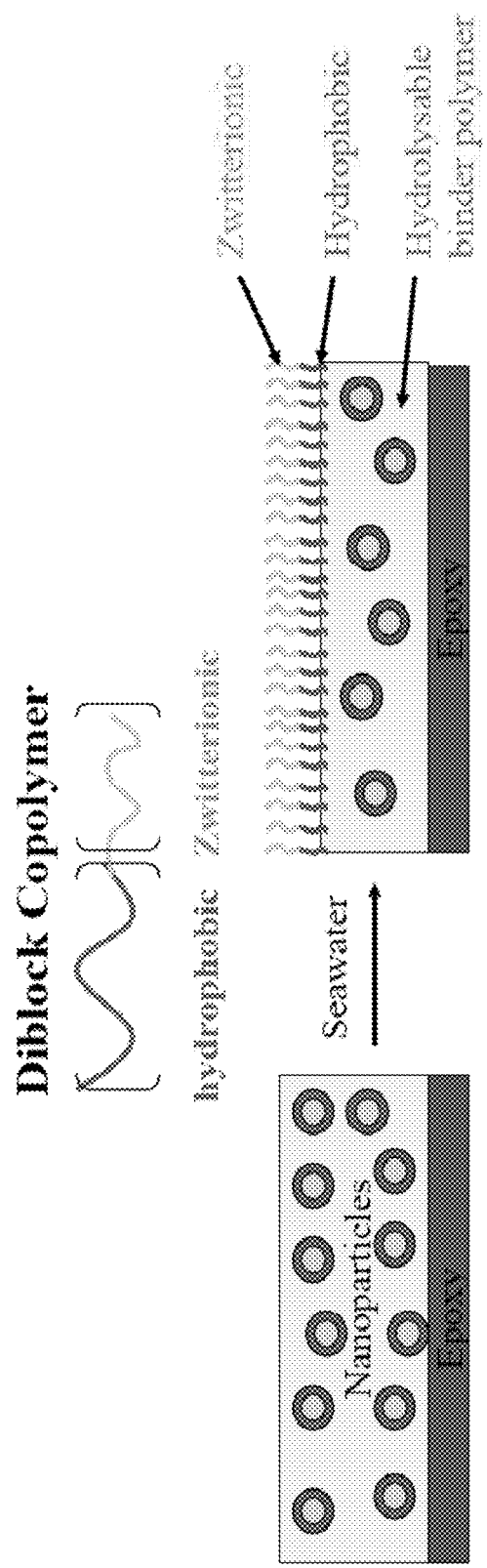
FIG. 27 is a schematic illustration of a representative marine coating having an epoxy base and a hydrolyzable binder polymer having dispersed therein nanoparticles formed from amphiphilic diblock copolymers a hydrophobic block and a zwitterionic hydrophilic block. On hydrolysis, the coating presents the zwitterionic hydrophilic block of diblock copolymer.

Once nanoparticles are exposed to an aqueous solution, the hydrophilic zwitterionic block will be rearranged to the coating surface to resist biofouling (FIG. 27). The resulting hydrolyzed polymer surface layer becomes hydrophilic, swells with water, and is peeled off to reveal a "fresh" surface. Hydrolysable zwitterionic precursor polymers described above in the first approach can serve as the hydrolysable binder for nanoparticles, leading to more effective polymer coatings than those from both approaches individually. The first and second approaches may be combined to develop an even more effective self-polishing zwitterionic coatings.

Nanoparticles are prepared from diblock copolymers of zwitterionic SBMA or CBMA with alkyl methacrylate monomers. The diblock copolymers of SBMA and alkyl methacrylates can be synthesized by the living/controlled atom radical polymerization (ATRP) of the first block (alkyl methacrylates) using ethyl 2-bromoisobutyrate as initiator and then the second block (2-(dimethylamino)ethyl methacrylate), followed by quaternization with 1,3-propanesultone or β-propiolactone to obtain corresponding zwitterion-containing diblock copolymers in high yield.

Figure 28:
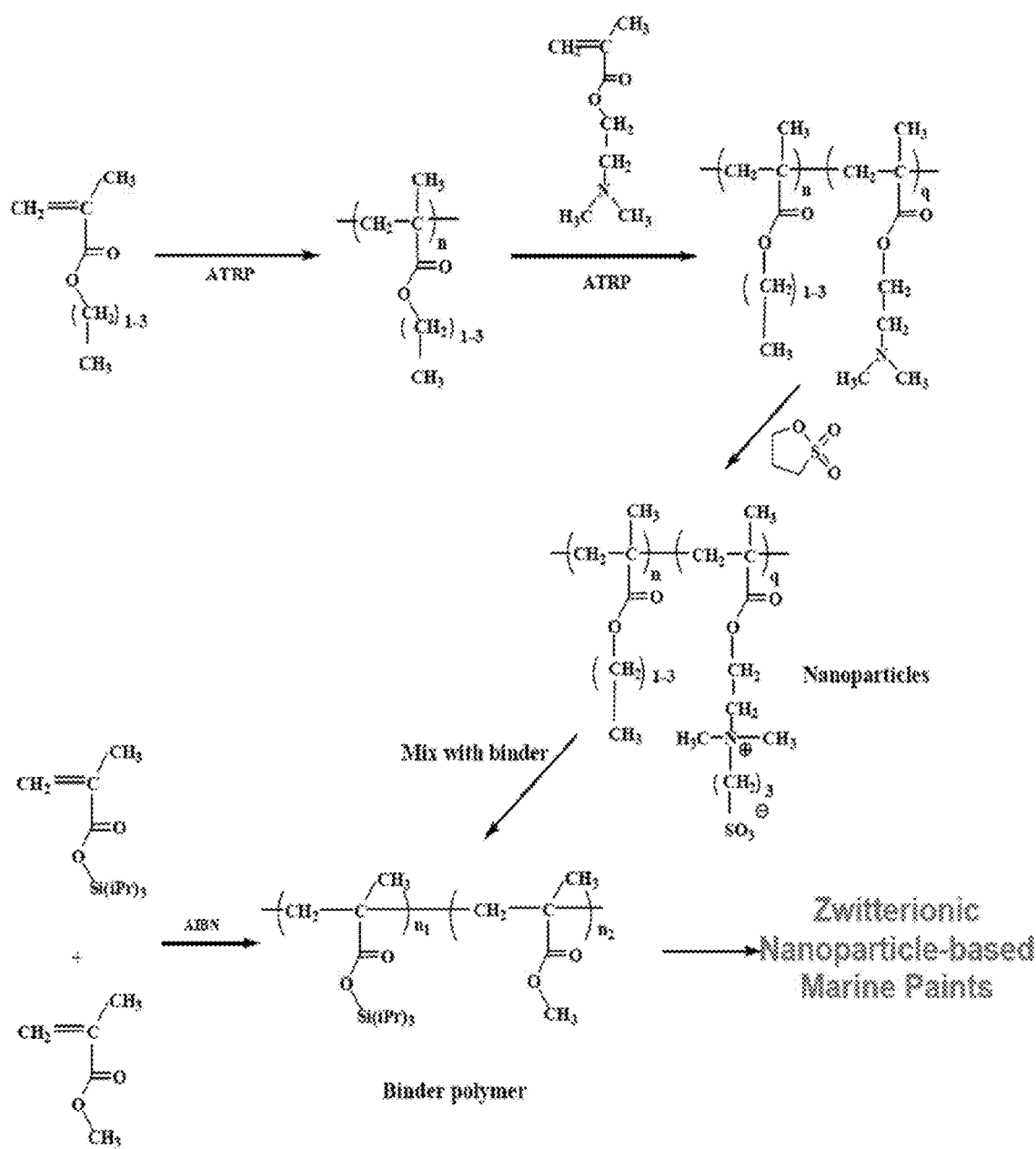
FIG. 28 is a schematic illustration of a synthesis route of a representative block copolymer of dodecyl methacrylate and sulfobetaine methacrylate by ATRP method, which undergo spontaneous self-assembly in hydrophobic organic solvents to form nanoparticles, and a synthesis route of a representative binder polymer synthesized from silyl ($Bu_3Si$ or $iPr_3Si$) methacrylate and methyl methacrylate using the free radical copolymerization method.
Figure 29:
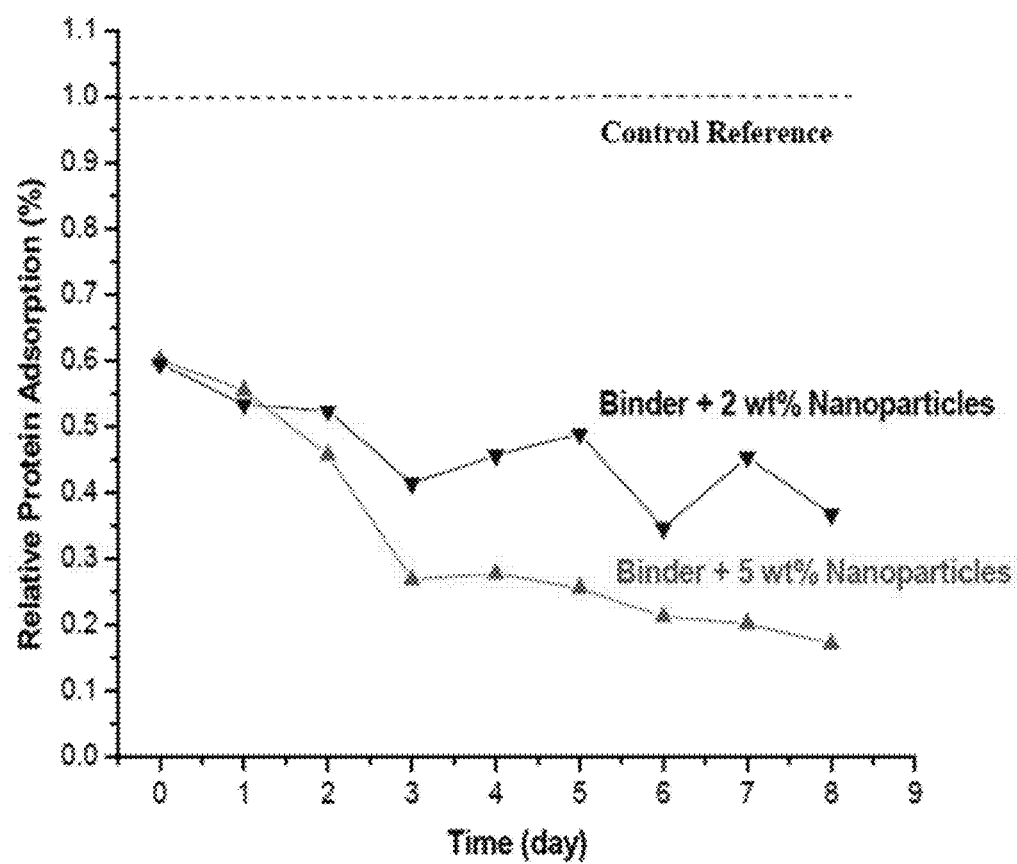
FIG. 29 compares protein adsorption as a function of time for representative coatings of the invention (2 and 5 weight percent nanoparticles) to control. The results indicate that the surface coating containing zwitterionic-based nanoparticles rapidly lead to low protein adsorption on a coating surface with time for 8 days.

A typical synthesis route of the block copolymer of dodecyl methacrylate and sulfobetaine methacrylate by ATRP method is shown in FIG. 28. The obtained diblock copolymers undergo spontaneous self-assembly in hydrophobic organic solvents to form nanoparticles. Compositions of block copolymers of 5-50% (mol) determined by NMR and molecular weights of the diblock copolymers of 5K-20K determined by GPC, can be varied to optimize the formation of nanoparticles. The size of nanoparticles of 20-200 nm can be determined by DLS. Similar procedures are applied to pCBMA nanoparticle based coatings. Binder polymers are synthesized from silyl ($Bu_3Si$ or $iPr_3Si$) methacrylate and methyl methacrylate (30%:70% in mol) using the free radical copolymerization method. Nanoparticles of different concentrations are mixed with binder copolymer in various solvents. These polymers are coated on silane-treated glass slides using a spin-coater (1'×3') or on epoxy-coated panels (4'×8') using a sprayer. Results from ELISA experiments are shown in FIG. 29. The results indicate that the surface coating containing zwitterionic-based nanoparticles can quickly lead to low protein adsorption on a coating surface with time for 8 days.

Figure 30:
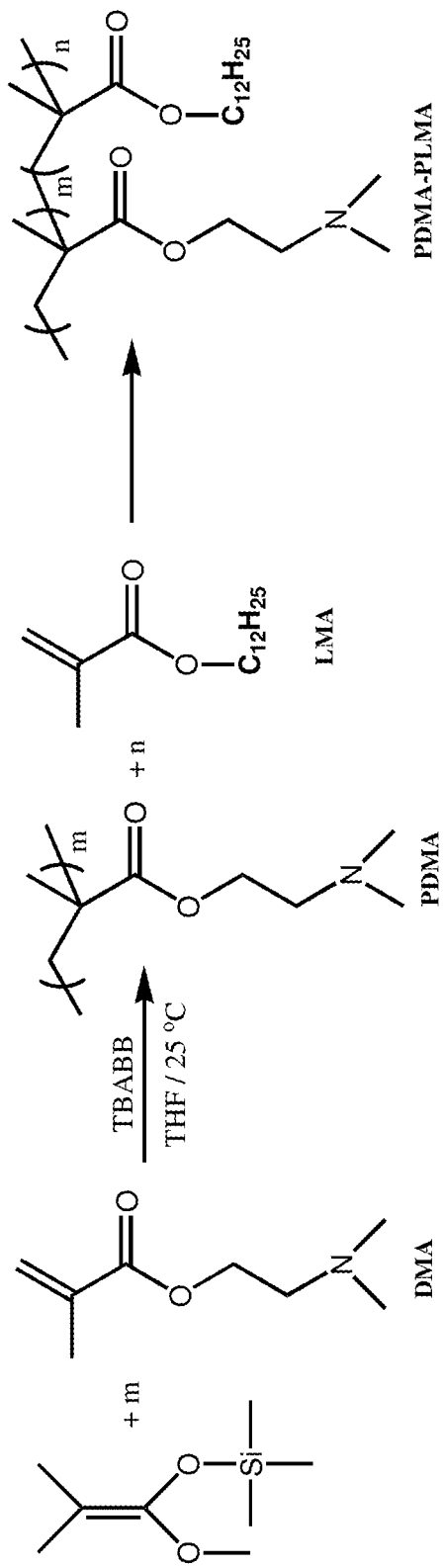
FIG. 30 illustrates the synthesis of the PDMA-PLMA block copolymer precursor via group transfer polymerization.
Figure 31:
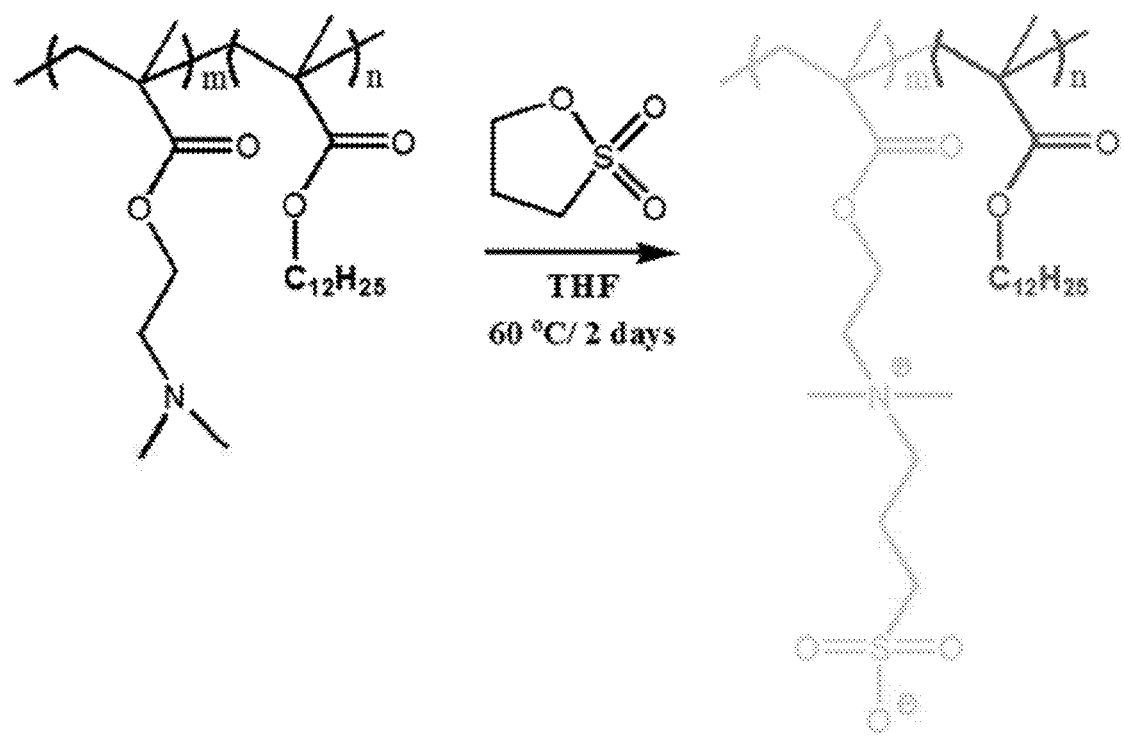
FIG. 31 illustrates the in situ quaternization of the PDMA-PLMA block copolymer and the self assembly into nanoparticle.

Group transfer polymerization was used to synthesis the PDMA-PLMA diblock copolymer (FIG. 30) to provide a series of PDMA-PLMA diblock copolymers. These PDMA-PLMA diblock copolymer were quaternized with propanesultone in THF solvent for the in situ formation of the nanoparticles (FIG. 31). The nanoparticle stability varies based on the nanoparticle composition (FIG. 32). Very stable and higher concentration (up to 5%) nanoparticles can be obtained when the nanoparticles have the suitable block length.

Figure 33:
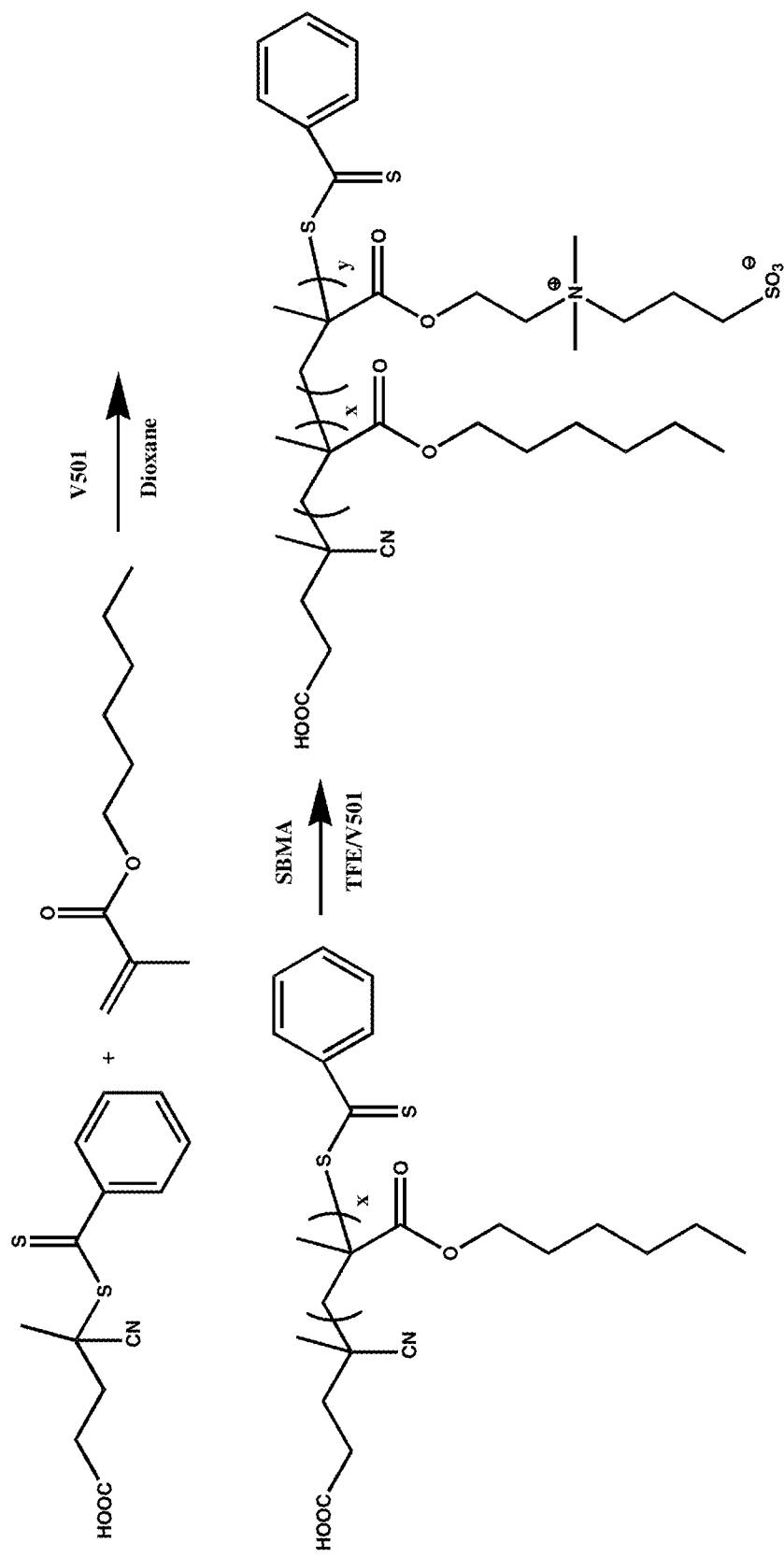
FIG. 33 illustrates the synthesis of the PHMA-PSBMA diblock copolymers via RAFT polymerization.

Another method for the synthesis of nanoparticle is via reversible addition-fragmentation chain transfer (RAFT) shown in FIG. 33. CTP was used to control the RAFT polymerization of LMA. PLMA was then used as macroCTA for the RAFT polymerization of SBMA. PLMA-PSBMA with different compositions can be obtained by varying the feeding SBMA monomer ratios (FIG. 34).

Figure 35:
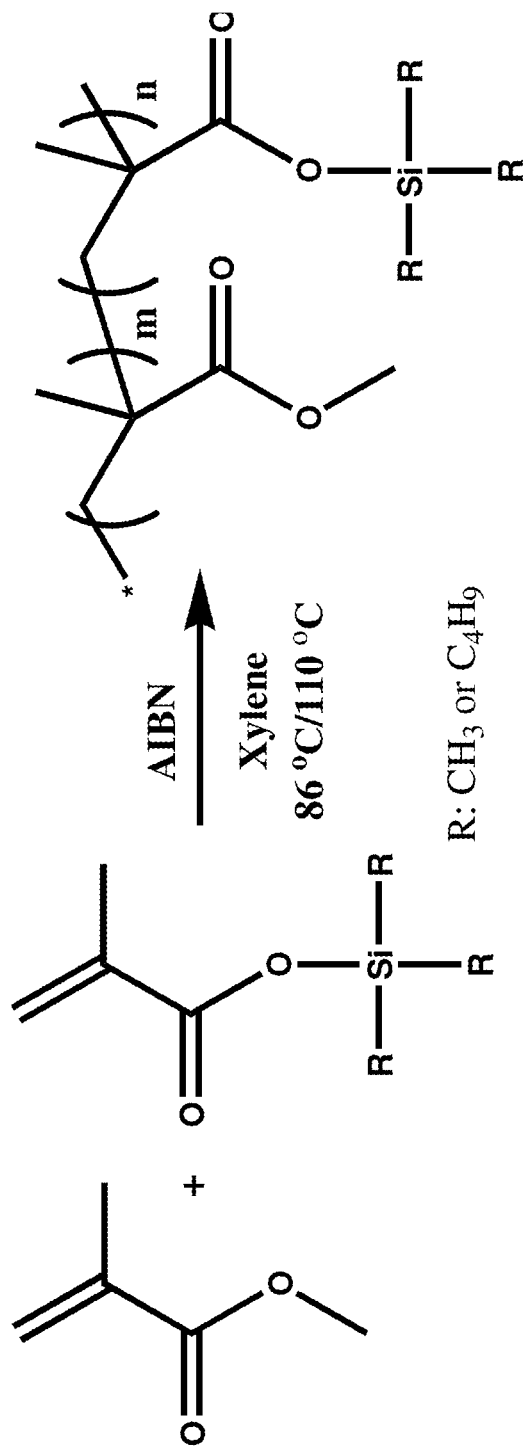
FIG. 35 illustrates the synthesis of silyl-based hydrolysable base coatings via free radical copolymerization of MMA and TBSMA.
Figure 37:
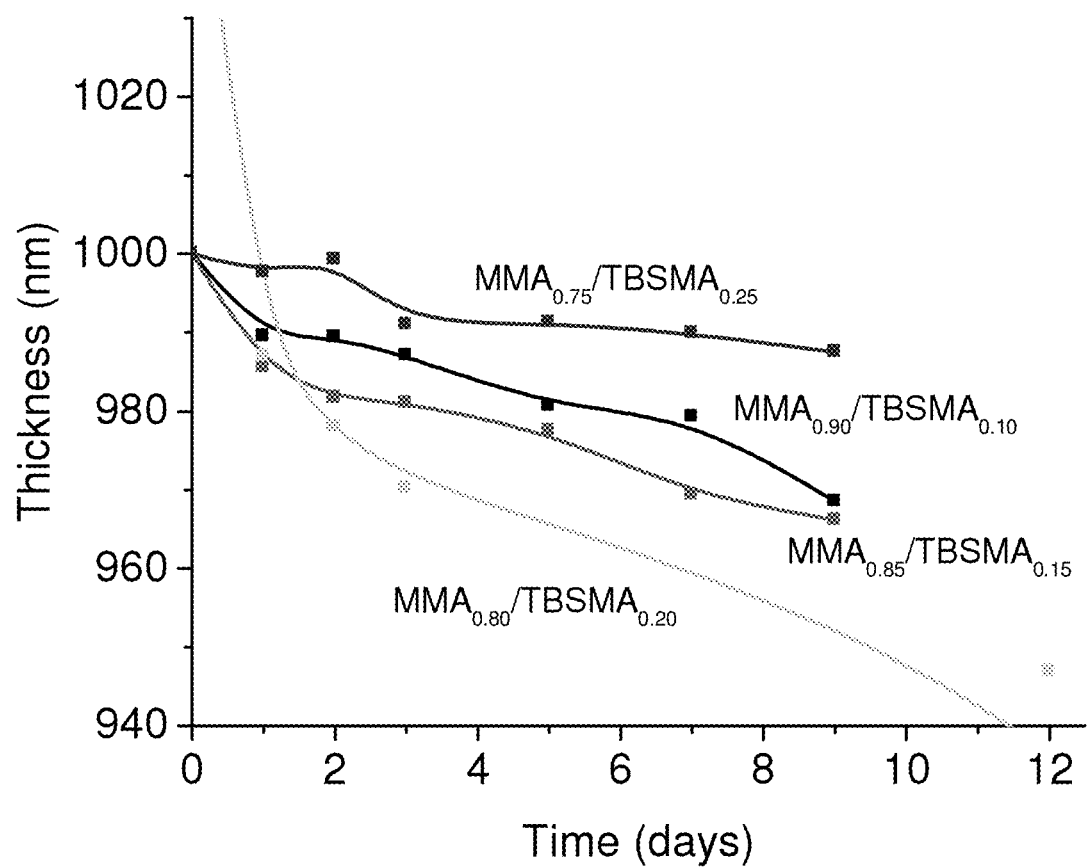
FIG. 37 compares the hydrolysis rate of representative base coatings under seawater conditions.

Hydrolysable base coatings can be obtained by copolymerizing the methyl methacrylate (MMA) with tributylsilyl methacrylate (TBSMA) via free radical polymerization as shown in FIG. 35 to provide a series of MMA/TBSMA copolymers (FIG. 36). These base coatings can be hydrolyzed under seawater conditions (FIG. 37). A suitable hydrolysis rate can be obtained by varying the base coating composition.

Figure 38:
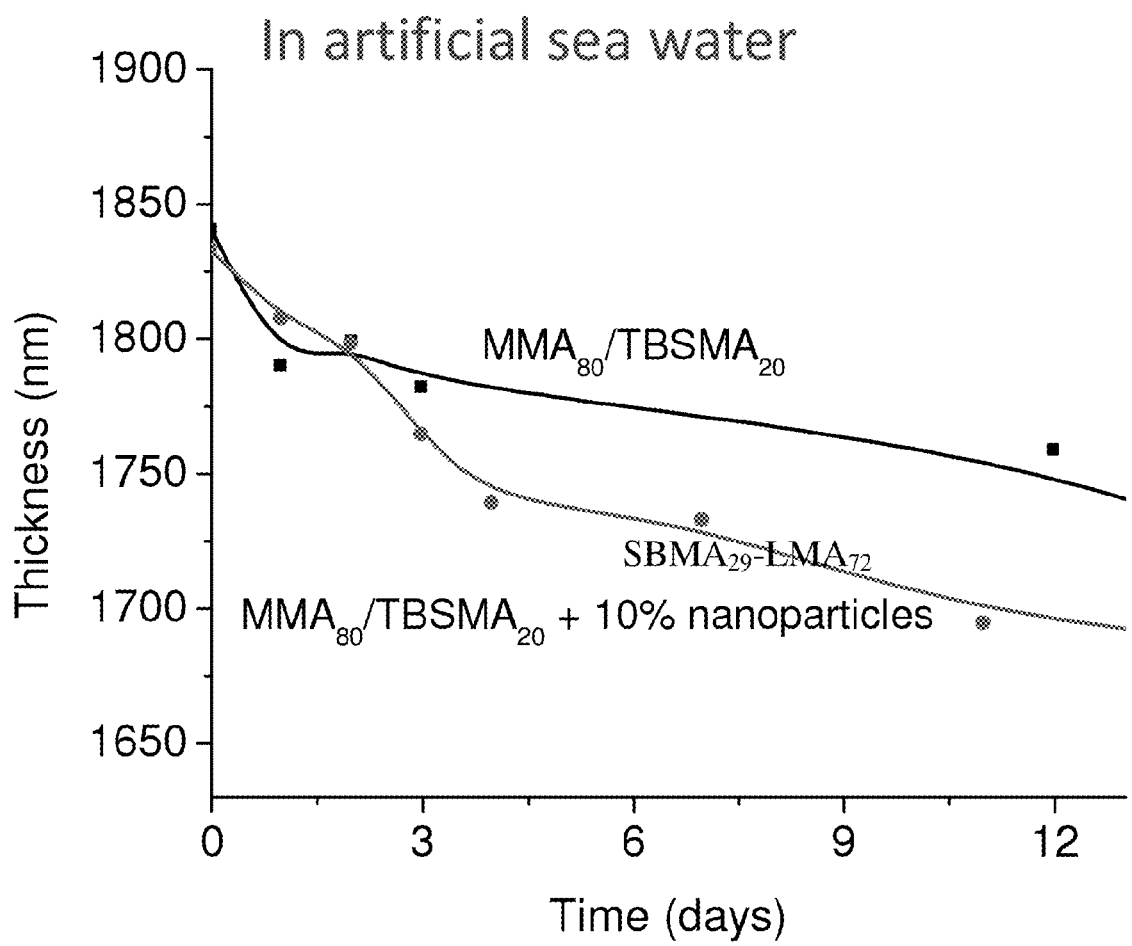
FIG. 38 compares the hydrolysis rate of representative base coatings with and without nanoparticles.
Figure 39:
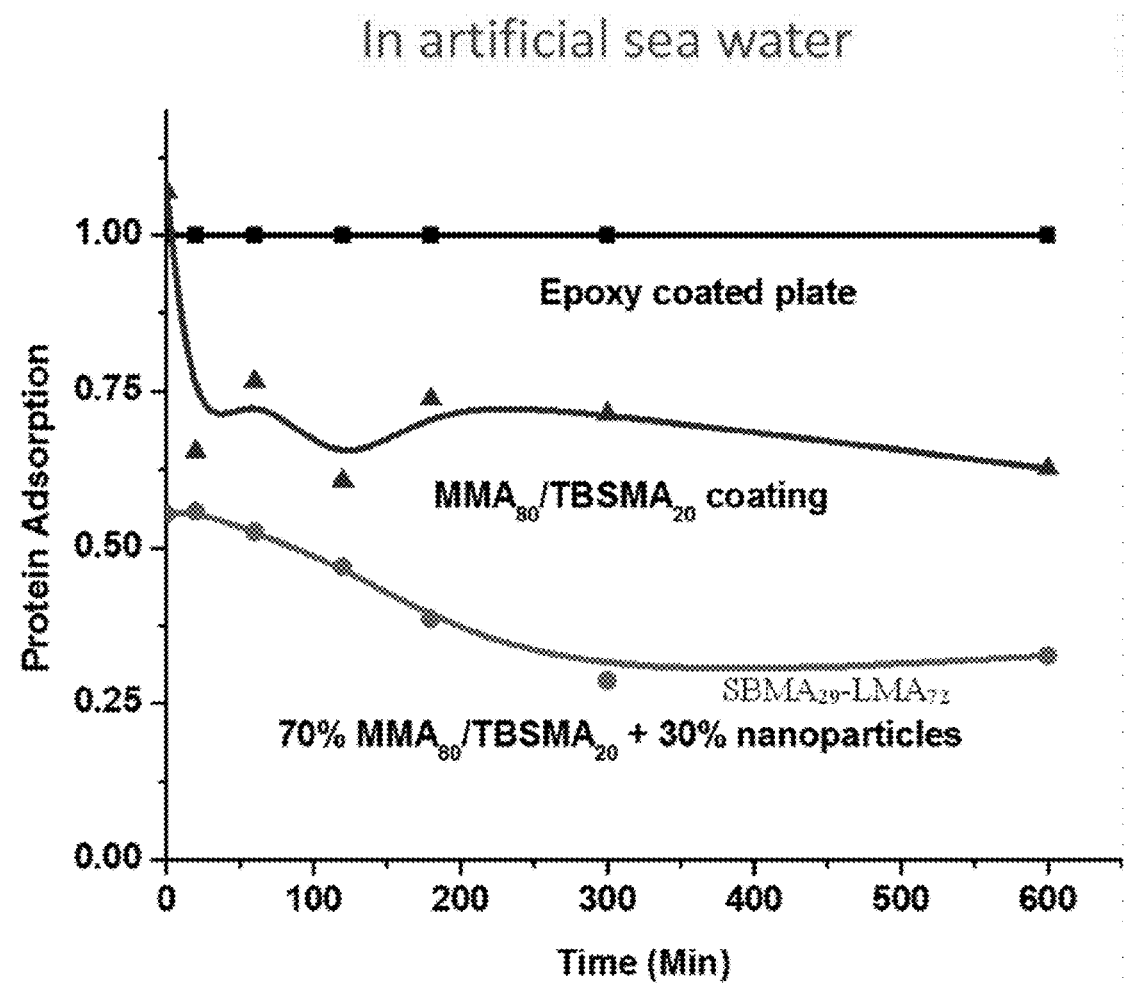
FIG. 39 compares protein adsorption on an epoxy surface and an epoxy surface coated with representative hydrolyzable base coatings with and without nanoparticles.

Nanoparticles can be added to these hydrolysable base coatings to improve their nonfouling properties. The hydrolysis rate changes with the addition of the nanoparticles (FIG. 38). The protein adsorption can be significantly decreased by adding these nanoparticles to the base coating (FIG. 39).

Figure 40:
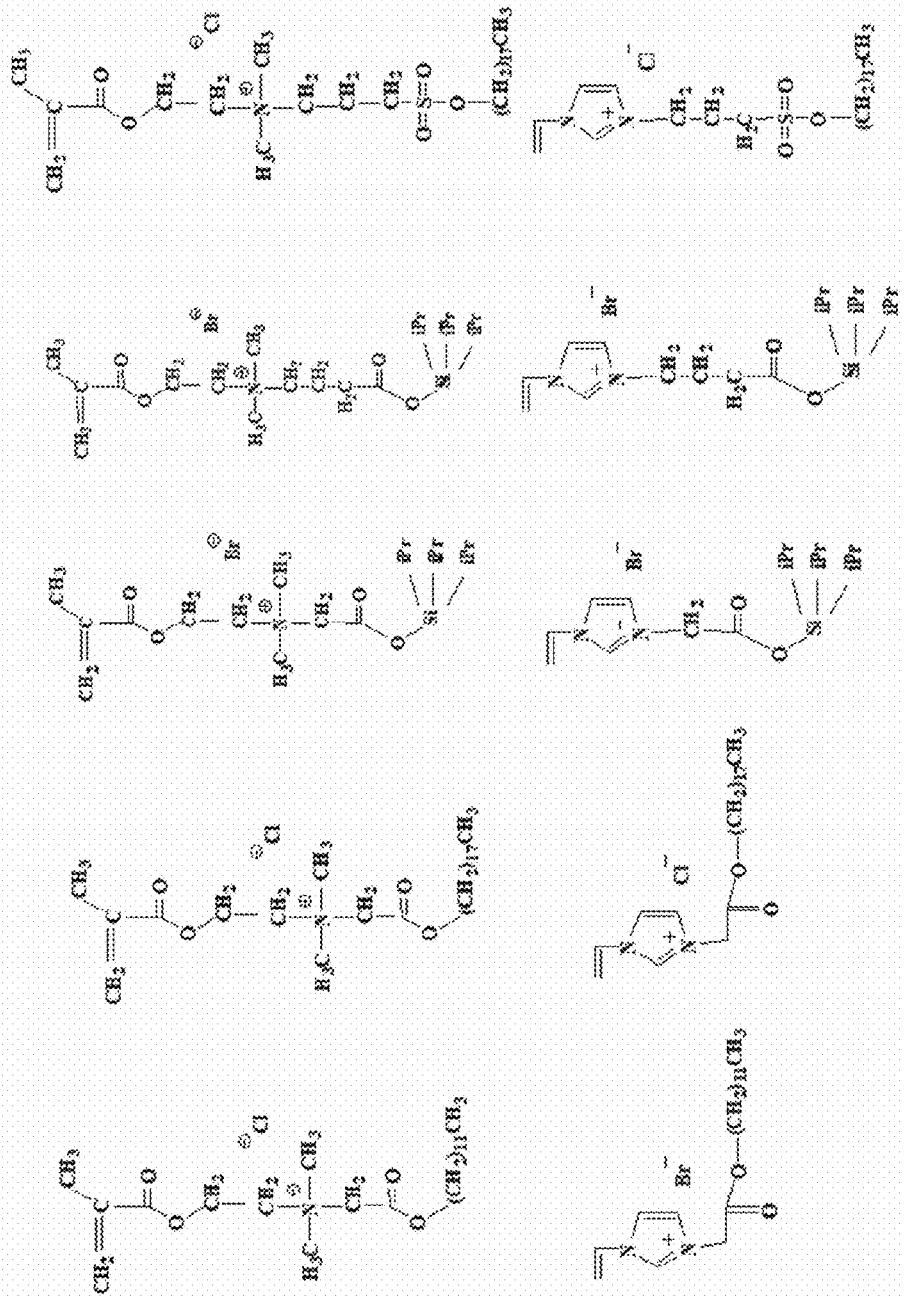
FIG. 40 illustrates representative hydrolyzable zwitterionic monomer precursors.
Figure 41:
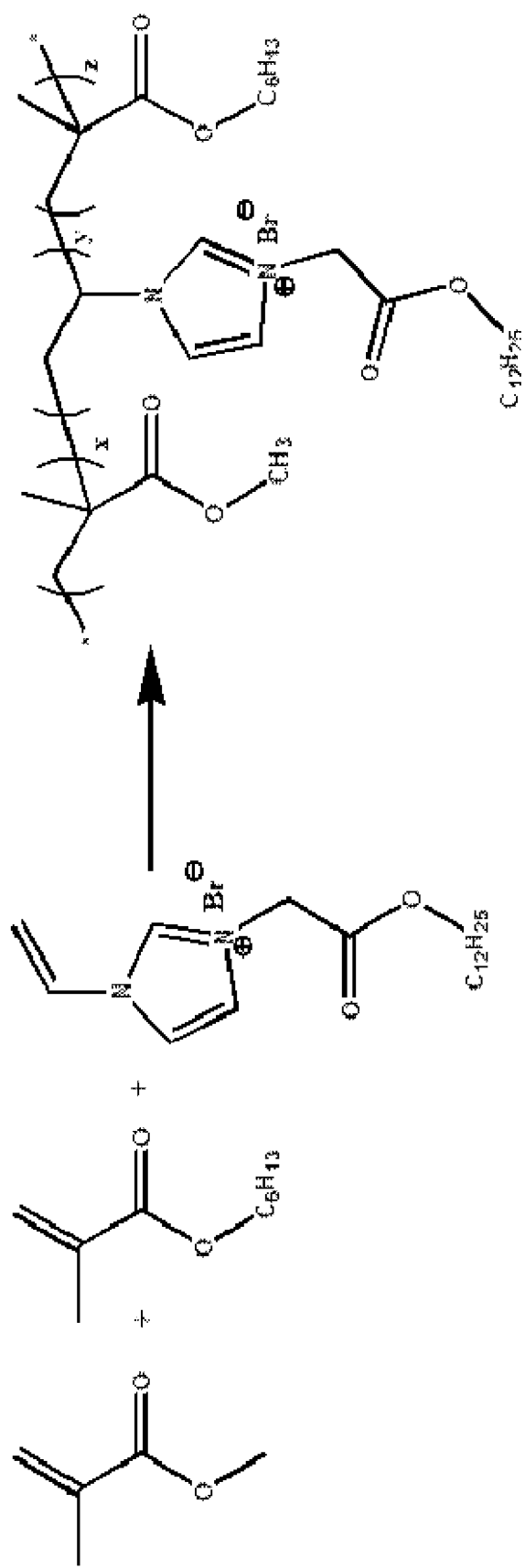
FIG. 41 illustrates the synthesis of a representative hydrolyzable base coating via the copolymerization of MMA, HMA and a hydrolyzable zwitterionic monomer precursor.

Representative hydrolysable zwitterionic monomer precursors are shown in FIG. 40. These monomers can be homopolymerized or copolymerized with other hydrophobic monomers to afford the hydrolysable base coating (FIG. 41). A series of hydrolysable base coatings with different compositions were prepared and are tabulated in FIG. 42.

Figure 43:
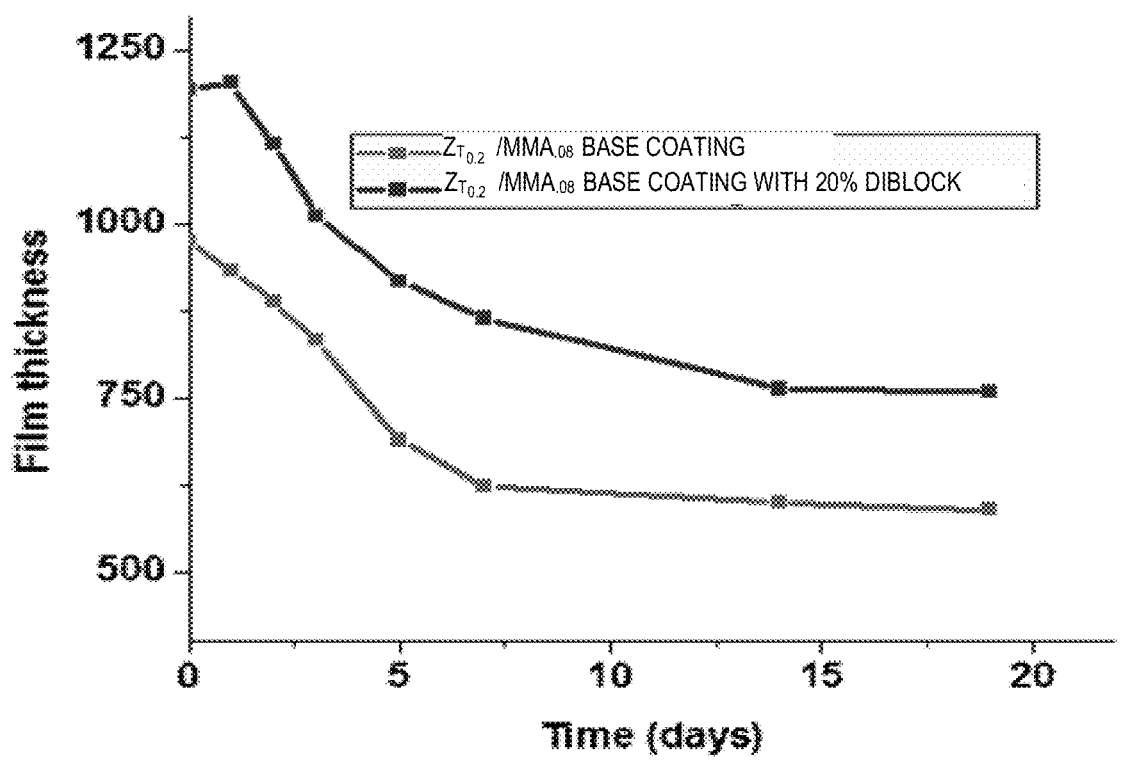
FIG. 43 compares hydrolysis rates of representative zwitterionic monomer precursor base coating with and without nanoparticles.
Figure 44:
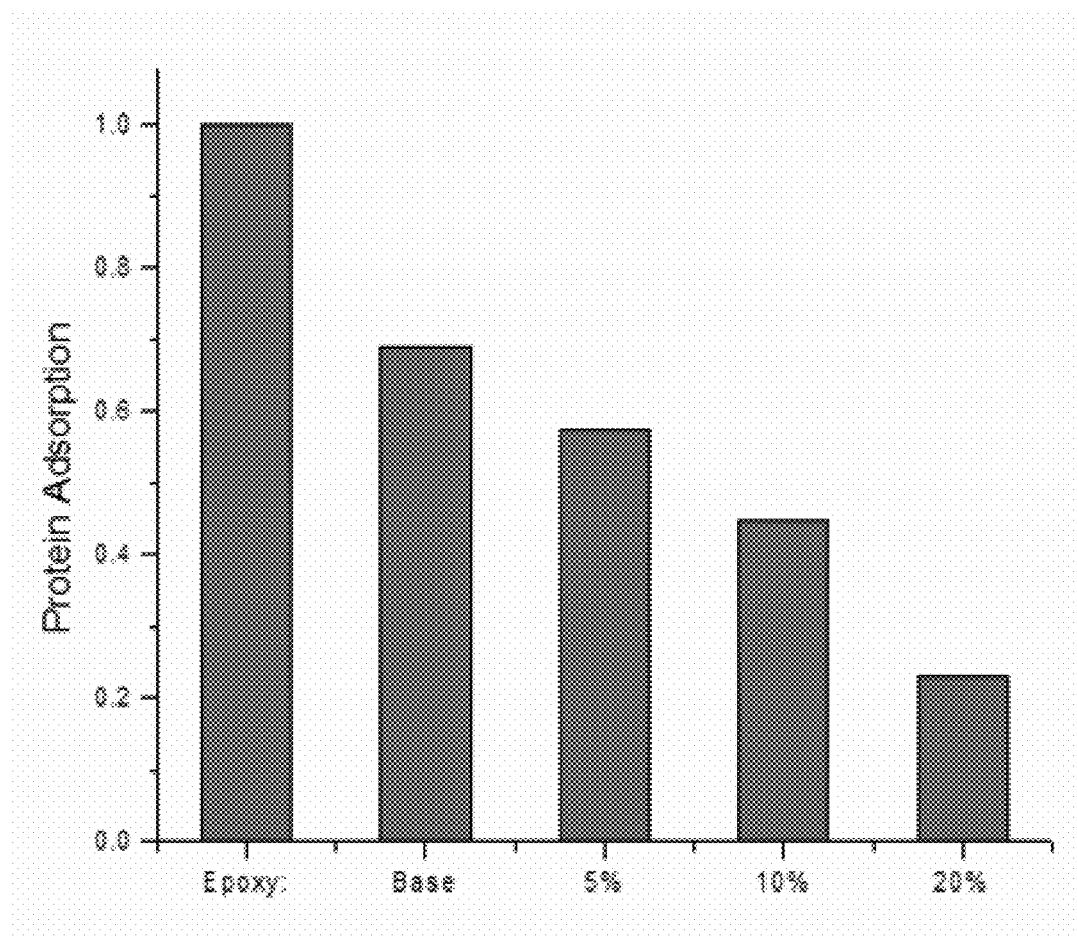
FIG. 44 compares the effect of nanoparticle concentration on surface protein adsorption.

The zwitterionic base coatings hydrolyze under seawater conditions (FIG. 43). Nanoparticles can be added into these base coatings to improve the coating's nonfouling properties (FIG. 44).

A series of base coating formulations were tested to evaluate their hydrolysis rates and nonfouling properties and the results are tabulated in FIG. 45. Protein adsorption can be decreased to 23% compared to the epoxy control coating.

Protein adsorption on these coatings can be significantly decreased after hydrolysis under seawater conditions (FIG. 46).

Figure 47:
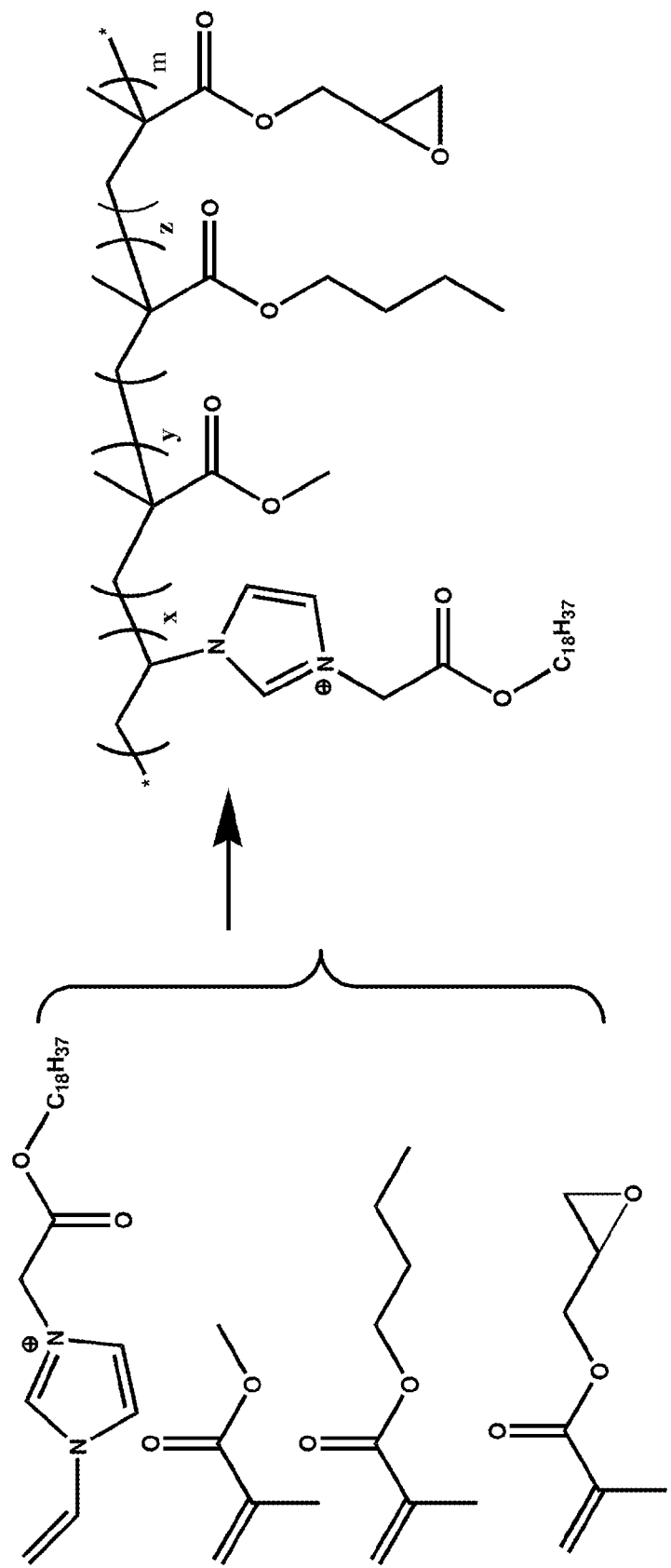
FIG. 47 illustrates the synthesis of a representative hydrolyzable base coating via the copolymerization of MMA, HMA, GMA and a hydrolyzable zwitterionic monomer precursor.

A GMA monomer can be incorporated into the base coating system to increase the coating's adhesive stabilities (FIG. 47).

Figure 48:
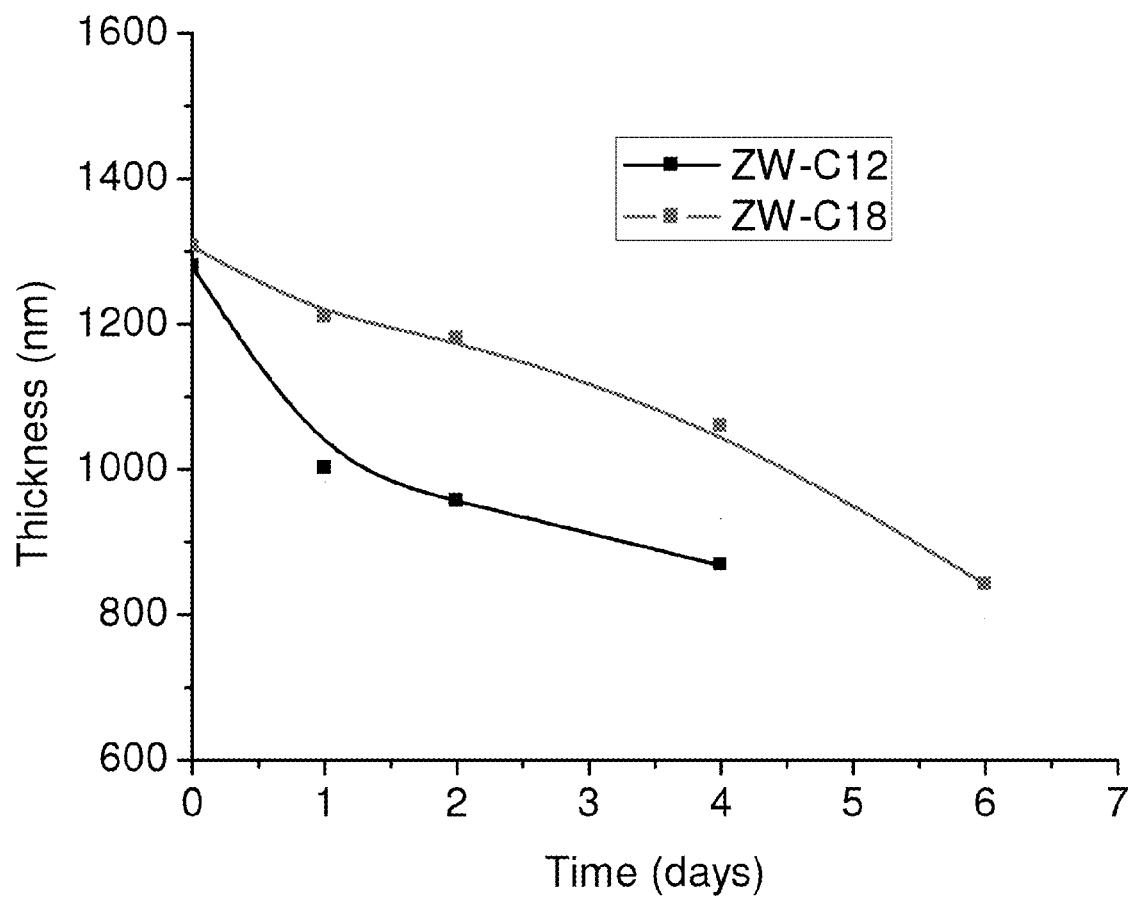
FIG. 48 compares the self-polishing marine coating hydrolysis rate with two representative polymer structures.
Figure 49:
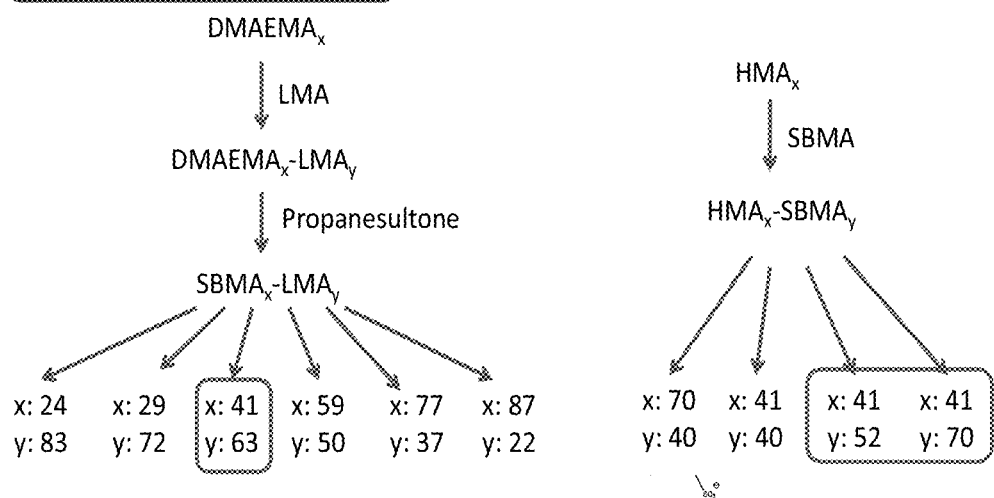
FIG. 49 is a schematic illustration of the synthesis of representative nanoparticles of the invention: GTP and RAFT methods.
Figure 50:
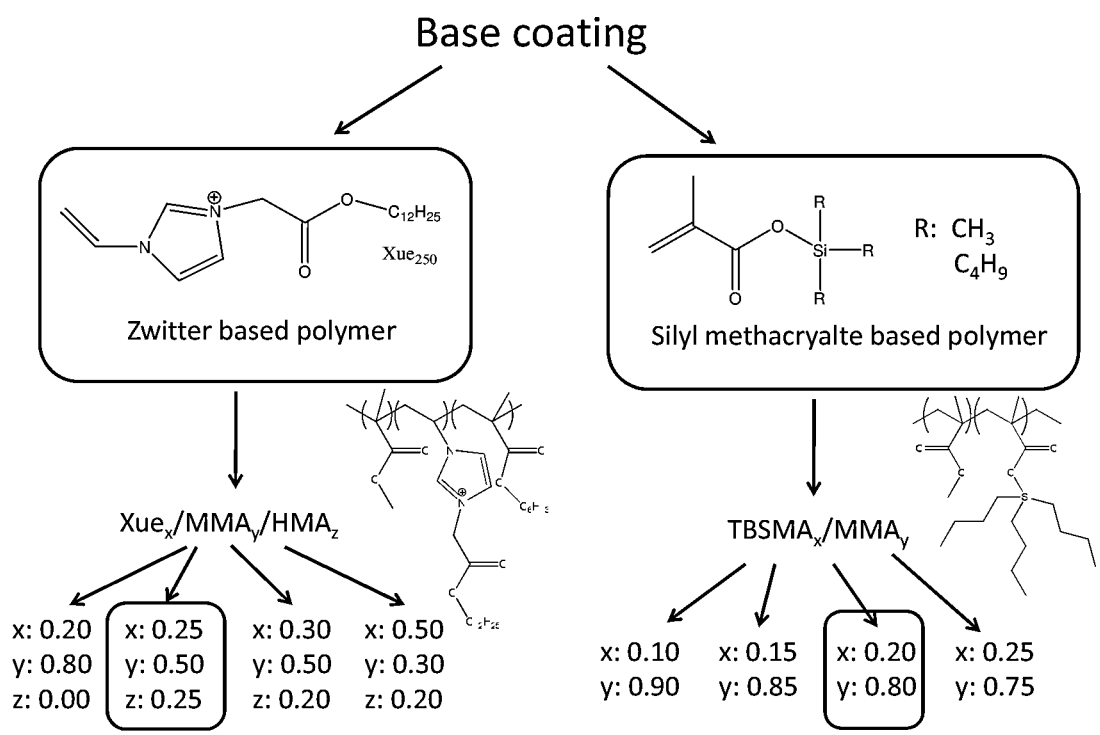
FIG. 50 is a schematic illustration of the synthesis of representative base coatings of the invention: $Xue_x/MMA_y/HMA_z$ and $TBSMA_x/MMA_y$.
Figure 51:
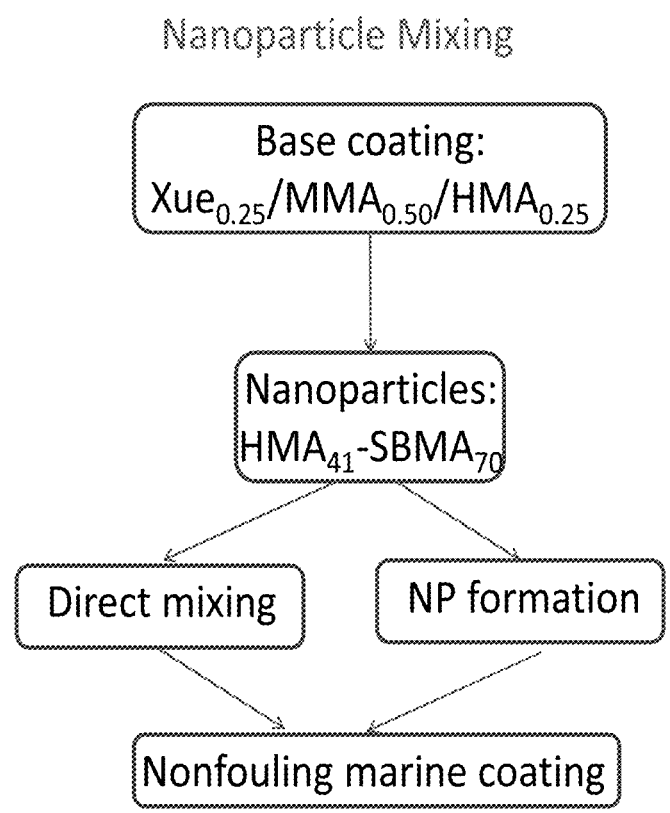
FIG. 51 is a schematic illustration of the process for nanoparticle mixing to provide a representative marine coating of the invention.
Figure 52:
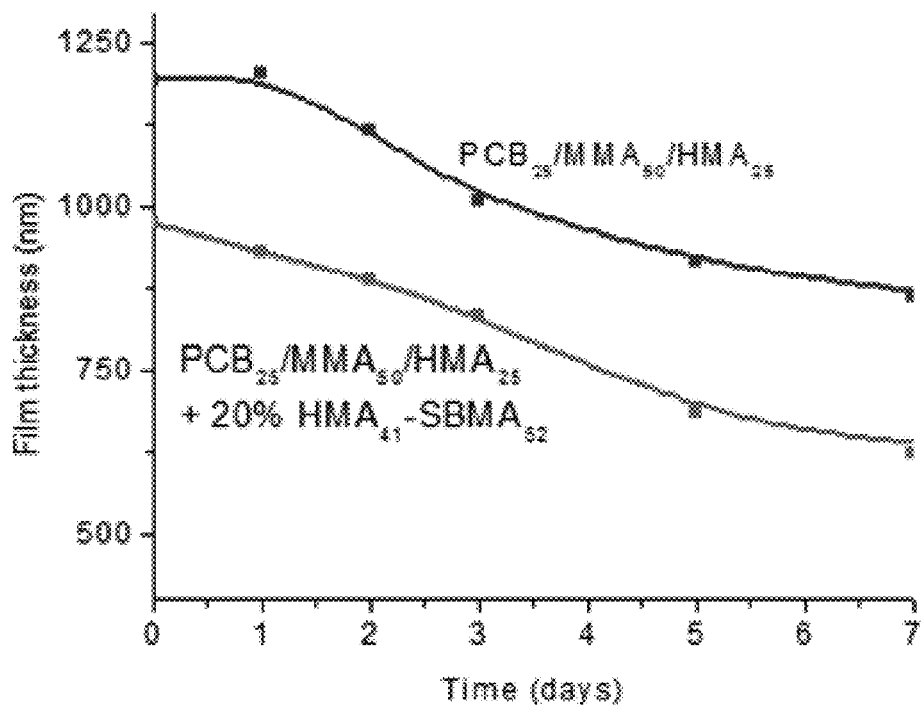
FIG. 52 compares representative coatings erosion (film thickness as a function of time).
Figure 53:
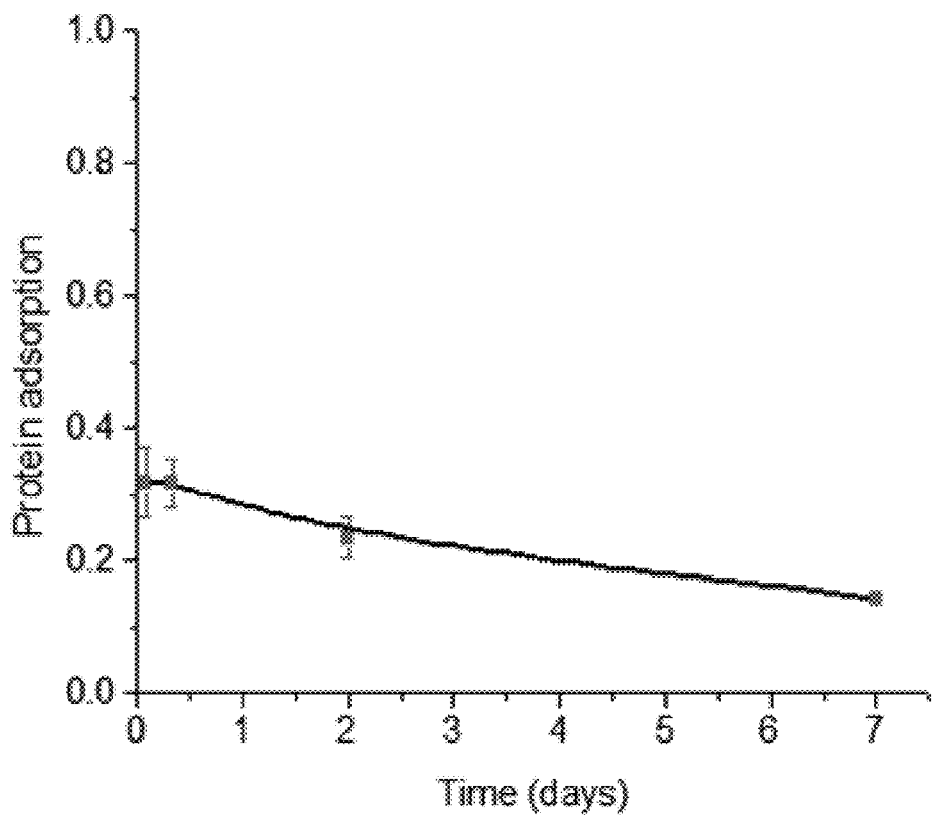
FIG. 53 illustrates protein adsorption as a function of time for a representative coating of the invention.

Increasing the zwitterionic monomer precursor's hydrophobicity increases the coating's stability while maintaining its hydrolysis abilities (FIG. 48).

In another aspect, the invention provides amphiphilic copolymers which may be utilized to prepare non-fouling coatings. The amphiphilic copolymers of the invention described herein can be used in the copolymer-based coatings described above. Some embodiments include amphiphilic copolymers comprising hydrophilic zwitterionic polymers. Such zwitterionic polymers may include all types of zwitterionic polymers, for example, pSBMA, pCBMA, pMPC, and mixed charge polymers. Hydrophobic copolymers may include any hydrophobic polymer such as polymethacrylate, polyacrylate, polyacrylamide, polyester, polyurethane, polystyrene, and including fluorinated polymers. Synthetic methods include direct polymerization of zwitterionic monomer in mixed solvent (for both components) and protecting carboxyl groups to render a hydrophobic zwitterionic precursor, polymerization of the precursor, and then deprotection to form provide the zwitterionic form.

Amphiphilic copolymer structures have various complex structures including diblock, triblock, random, grafting, and star-shape. Certain embodiments include stable nanostructured objects comprising amphiphilic copolymers.

Figure 85:
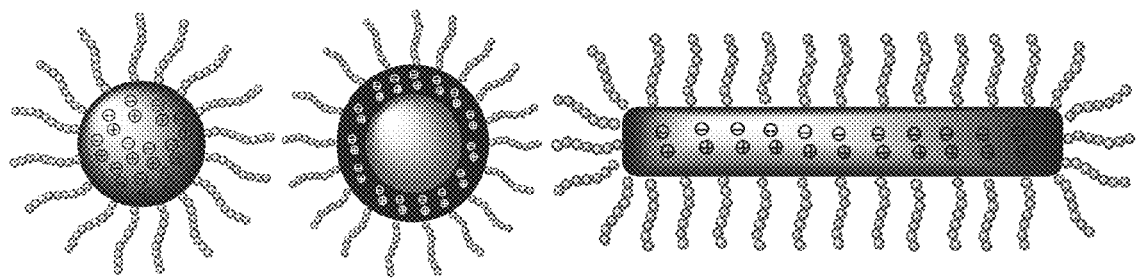
FIG. 85 illustrates self-assembled nanostructures by amphiphilic copolymer in selective solvent (micelle, vesicle, worm-like) (hydrophilic core and hydrophobic shell in organic solvent).
Figure 86:
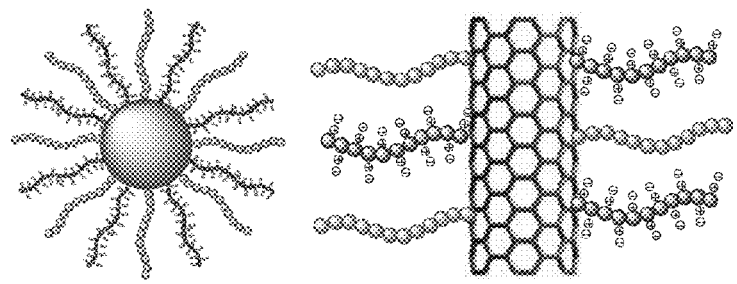
FIG. 86 hydrophobic PDMS and hydrophilic zwitterionic polymer modified silica nanoparticles (left) and carbon nanotubes (right).
Figure 87:
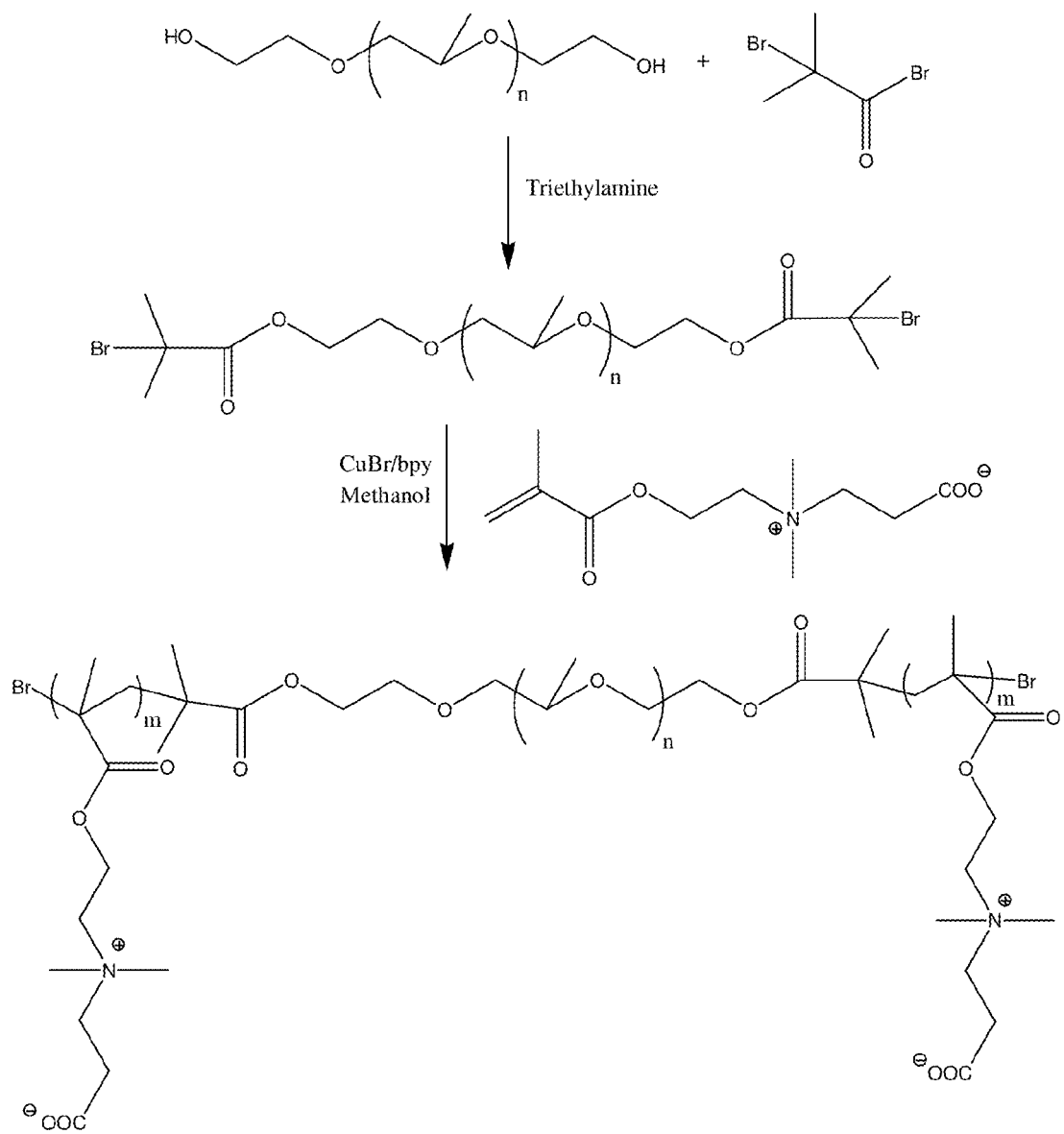
FIG. 87 illustrates the synthesis of the bifunctional PPO-based ATRP macroinitiator and the corresponding CBMA-PPO-CBMA triblock copolymers.
Figure 88:
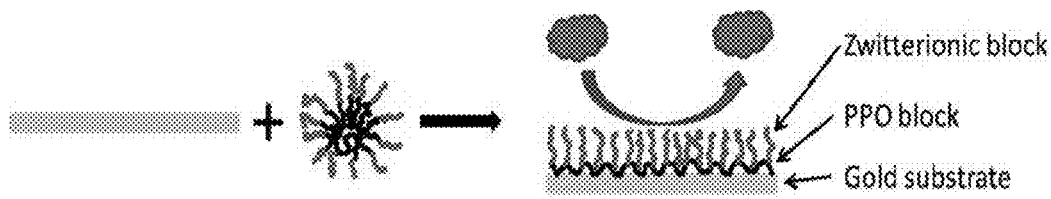
FIG. 88 illustrates the self-assembly of the CBMA-PPO-CBMA triblock copolymer onto gold surface to afford an ultralow fouling surface coating.

Methods for formation of various nanostructured objects include directly dissolving copolymers in organic solvent or dissolving copolymers in suitable solvent. In certain embodiments, low polarity solvent may then be slowly added to form self-assembled structures with hydrophilic core and hydrophobic shell. Depending upon the method of fabrication, the shapes of the nanostructured objects may include spherical micelles, vesicles, rod-like objects, worm-like objects, and other structures. See FIG. 85. In certain embodiments, amphiphilic copolymers may be functionalized onto silica nanoparticles or carbon nanotubes. See FIG. 86.

The present invention describes different approaches for preparation of non-fouling coatings. Nanostructured objects of the invention may be incorporated into different base coatings, including, for instance, PDMS coatings, polyurethane coatings, or epoxy coatings. In embodiments that use a PDMS coating, an additional curing system using, for instance, a platinum catalyst and condensation curing system using a tin catalyst may be used.

Coating preparation approaches may include cast coating, spin coating, and spray coating.

A representative super-amphiphilic copolymer, diblock copolymer PDMS-PCBMA, was prepared via reversible addition-fragmentation chain transfer (RAFT) polymerization of CBMA monomers in the presence of macro chain transfer agent, PDMS-4-cyano-4-(phenylcarbonothioylthio) pentanoic acid (PDMS-CTP). The diblock copolymer was self-assembled into nano-structured objects in THF. These nano-structured objects were further incorporated into an addition cured silicone coating to prepare a novel marine coating. During the curing process, phase separation was induced by these nanostructured objects. The coating with nanopatterned surface has excellent anti-fouling and fouling-release properties. The coatings may be useful for the applications where anti-fouling and fouling-release properties are desired, such as medical device and marine coating.

Zwitterionic Triblock Copolymers

The present invention provides zwitterionic-based triblock co-polymerzation with PPO as the middle block. In some embodiments, the zwitterionic triblock copolymers can be self-assembled onto hydrophobic gold surfaces using a "graft to" method. This process can generate well-ordered, polymer brush structures with zwitterionic, hydrophilic segments facing towards aqueous, solutions and hydrophobic segments may be bound to a substrate. The performance of the non-fouling surface may be enhanced by adjusting one or more of the hydrophilic CBMA block length, polymer film thickness, and the surface packing densities. Compared to the commercially available PEO-PPO-PEO triblock copolymers, which can only prevent diluted plasma adsorption to a certain level on gold surface, the zwitterionic triblock co-polymer disclosed herein when coated onto, for instance, a gold surface has excellent ultralow fouling properties even for undiluted human plasma. The copolymer-coated gold surface can also be easily functionalized with, for instance, antibody, and be used as biosensor for the detection of antigen. In certain embodiments, such a functionalized zwitterionic triblock copolymers can be used to detect analytes in undiluted biological specimens, such as human plasma.

Such zwitterionic triblock copolymers may include poly(carboxybetaine methacrylate)-poly(propylene oxide)-poly(carboxybetaine methacrylate) or CBMA-PPO-CBMA. These embodiments may be synthesized via solution ATRP. Such zwitterionic triblock copolymers may be attached onto gold surfaces with "graft to" methods. Such zwitterionic triblock copolymer coated gold surfaces have excellent non-fouling properties. Additionally, such surfaces can be easily functionalized via the EDC/NHS chemistry.

In one embodiment, the hydroxyl group of a dihydroxy group terminated PPO was esterified with bromoisobutyryl bromide to afford the PPO based difunctional ATRP initiator. It was then used to initiate the ATRP polymerization of CBMA. A CBMA25-PPO48-CBMA25 triblock co-polymer can be obtained. $^1$H NMR analysis shows the polymerization conversion was higher than 99%.

Figure 70:
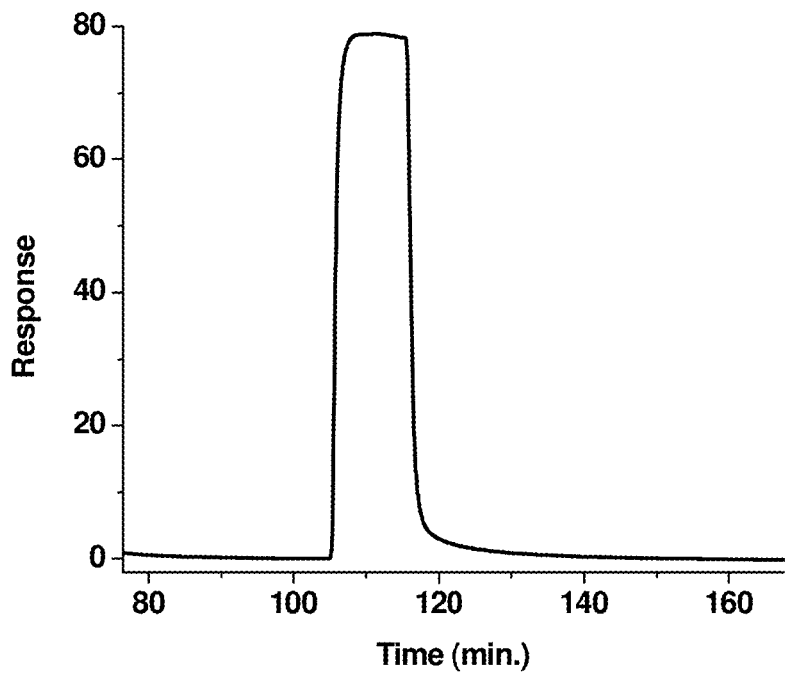
FIG. 70 is an SPR sensor grams of undiluted human plasma over the $CBMA_{40}$-$PPO_{48}$-$CBMA_{40}$ coated gold surface.

Fibrinogen and plasma adsorption was measured by SPR, which is based on wavelength interrogation. The chip was first cleaned with UV ozone, and then immersed into 1-undecanethiol solution overnight to form a self-assembled monolayer (SAM) on the gold surface. The chip was then attached to the base of the prism. The optical contact was established by using a refractive index matching fluid (Cargille). A baseline signal was established by flowing PBS buffer at a rate of 50 μL min-1 through the sensor for 10 min. Freshly prepared 1 mg/mL triblock copolymer solution was then flowed through the SPR channels for 2 hours, followed by PBS buffer solution (2 hours) to remove loosely bounded polymers, and to re-establish the baseline. Freshly prepared 1 mg/mL protein solutions of fibrinogen and undiluted blood plasma were flowed through independent channels for 10 min, followed by PBS buffer solution to remove unbound protein molecules and to re-establish the baseline. Adsorption was quantified by measuring the change in wavelength in the buffer baselines before and after protein adsorption. The wavelength change was converted to an amount of adsorbed protein. For the SPR sensor, a 1 nm SPR wavelength shift at 750 nm represents a surface coverage of approximately 17 ng/cm$^2$ of adsorbed protein. A temperature controller was employed to maintain the temperature during experiments. FIG. 70 shows a typical SPR curve for the plasma adsorption on these CBMA40-PPO48-CBMA40 triblock copolymer coated gold surface. The fibrinogen and lysozyme adsorption (FIGS. 73 and 74) is essentially zero on these surfaces while the undiluted plasma adsorption is only 0.65 nm, which corresponds to 11 ng/cm$^2$ nonspecific protein adsorption. CBMA40-PPO48-CBMA40 triblock copolymer can be coated onto the gold surface to afford an ultralow fouling surface, these polymer coated gold chips can be used as SPR sensor chips for the detection of antibody/antigen in biomedical application (FIG. 70). It should be mentioned that the triblock copolymer composition has an influence on the self-assembly of the copolymer on the gold surface, which will eventually affect its fouling resistant properties.

Figure 75:
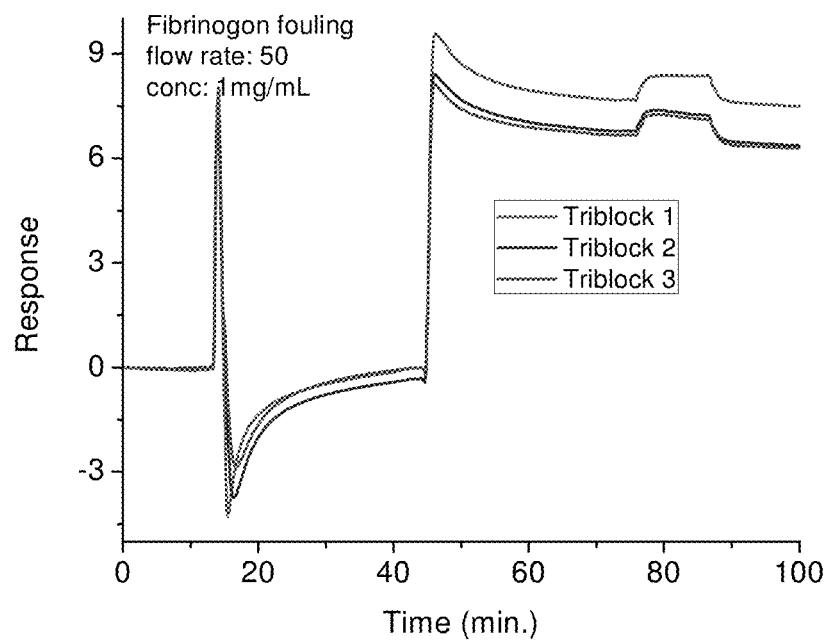
FIG. 75 compares fibrinogen fouling test results for three triblock copolymer coated gold chips.
Figure 76:
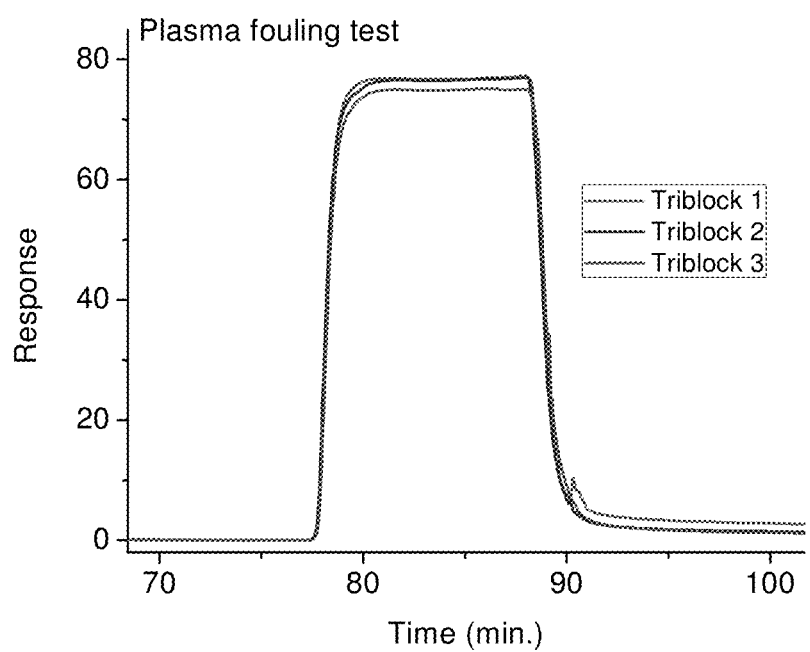
FIG. 76 compares plasma fouling test results for three triblock polymer coated gold chips.

Adsorption of poly(ethylene oxide)-poly(propylene oxide)-poly-(ethylene oxide) (or PEO-PPO-PEO) triblock copolymers (Pluronics™, BASF Co.) on the polystyrene surface via SPR has been studied and the results show that the hydrophobic PPO block provides an anchor which allows polymer molecules to remain adsorbed onto the interface and the PEO chains extend into the solvent phase. Without being bound by theory, it is likely the same mechanism being utilized with CBMA-PPO$_{48}$-CBMA triblock copolymer system of the invention: the hydrophobic PPO block adsorbs onto the hydrophobic gold surface, while the super-hydrophilic zwitterionic CBMA block chain extended into the solvent phase. If the zwitterionic block is not long enough the adsorbed polymer layer is not sufficient to prevent plasma fouling occur on the surface. For example, a zwitterionic triblock co-polymer comprising CBMA$_{15}$-PPO$_{48}$-CBMA$_{15}$ results in a fouling level 1.88 nm, which represent 32 ng/cm$^2$ fouling (FIG. 75). An increase the zwitterionic block length to 25 can significantly improve the coating surface's non-fouling properties (with 11 ng/cm$^2$) (FIG. 76). In order to form a dense polymer layer onto the hydrophobic surface, the PPO block need to pass through the hydrophilic CBMA layer (when a loosely packed polymer layer has been formed) before it can reach the hydrophobic substrate surface. If the hydrophilic block is too long, it will prevent the high density polymer brush layer formation on the surface, which will eventually decrease the surface coating's fouling resistant properties.

A commercially available PEO-PPO-PEO triblock co-polymer (Pluronic™ F108) has been used to coat the CH$_3$-terminated SAM layer on a gold surface. The results showed the PEO-PPO-PEO polymer is able to achieve ultra-low fouling surface via surface modification by controlling surface packing density of polymers. However, the polymer coated surface can only tolerate diluted 20% plasma adsorption. Previous studies have shown that while pCB-coated and PEG-coated surfaces or gold nanoparticles have similar stability in 10% blood serum, pCB-coated surfaces 14 and GNPs 24 are more stable than PEG-coated GNPs in 100% blood serum. The CBMA-PPO-CBMA triblock copolymer of the present invention is the first composition that can be grafted to the hydrophobic surface to achieve ultralow fouling level even for undiluted human plasma.

The self-assembly of the zwitterionic triblock co-polymer onto the hydrophobic surface is also rapid. In some embodiments within 20 minutes, a relatively densely packed polymer brush layer can be formed as evidenced by the SPR adsorption curve. In other embodiments, a zwitterionic copolymer solution may be allowed to flow over a hydrophobic surface 2 hours or more to achieve a high-density polymer brush layer. Most of the loosely adsorbed polymers may be washed away with PBS buffer solution within 20 minutes of buffer flow.

Thickness and surface packing of non-fouling polymer brushes contribute to non-fouling properties of the brush-functionalized surfaces. The performance of the non-fouling surface may be enhanced by adjusting the hydrophilic CBMA block length, polymer film thickness, and the surface packing densities.

Functionalization

Unlike many other low fouling materials, pCB groups exhibit an acid-base equilibrium and can be transformed to functionalizable intermediates. Various molecules containing primary amines, such as proteins and antibodies, can be covalently attached to the carboxylic acid residues by commonly used amino coupling chemistries (e.g., NHS/EDC) to create the ligand-functionalized solid substrates. Unreacted functionalized groups can be converted back to zwitterionic groups, ensuring the excellent non-fouling properties of post-functionalized surfaces.

It should be mentioned that the gold surface was first modified with a hydrophobic SAM layer before treated with CBMA-PPO-CBMA triblock co-polymer, so the current CBMA-PPO-CBMA triblock copolymer system can be applied onto other hydrophobic surface such as polypropylene and polystyrene surfaces.

Figure 71:
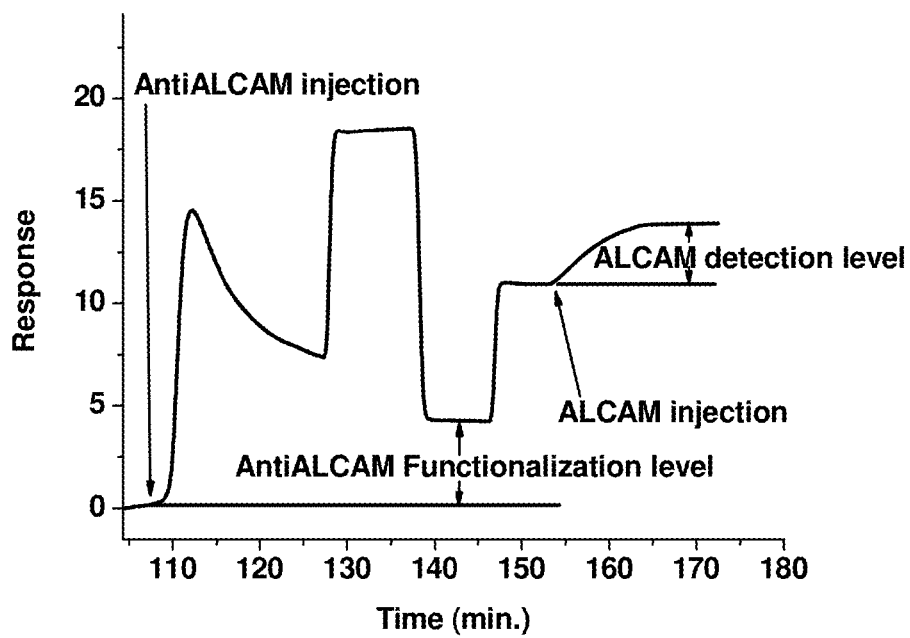
FIG. 71 is an SPR curve for a surface functionalized with antiALCAM and corresponding ALCMA detection. Functionalization level: 70.6±5.0 ng/cm2. Antigen response: 58.2±2.0/cm$^2$.
Figure 72:
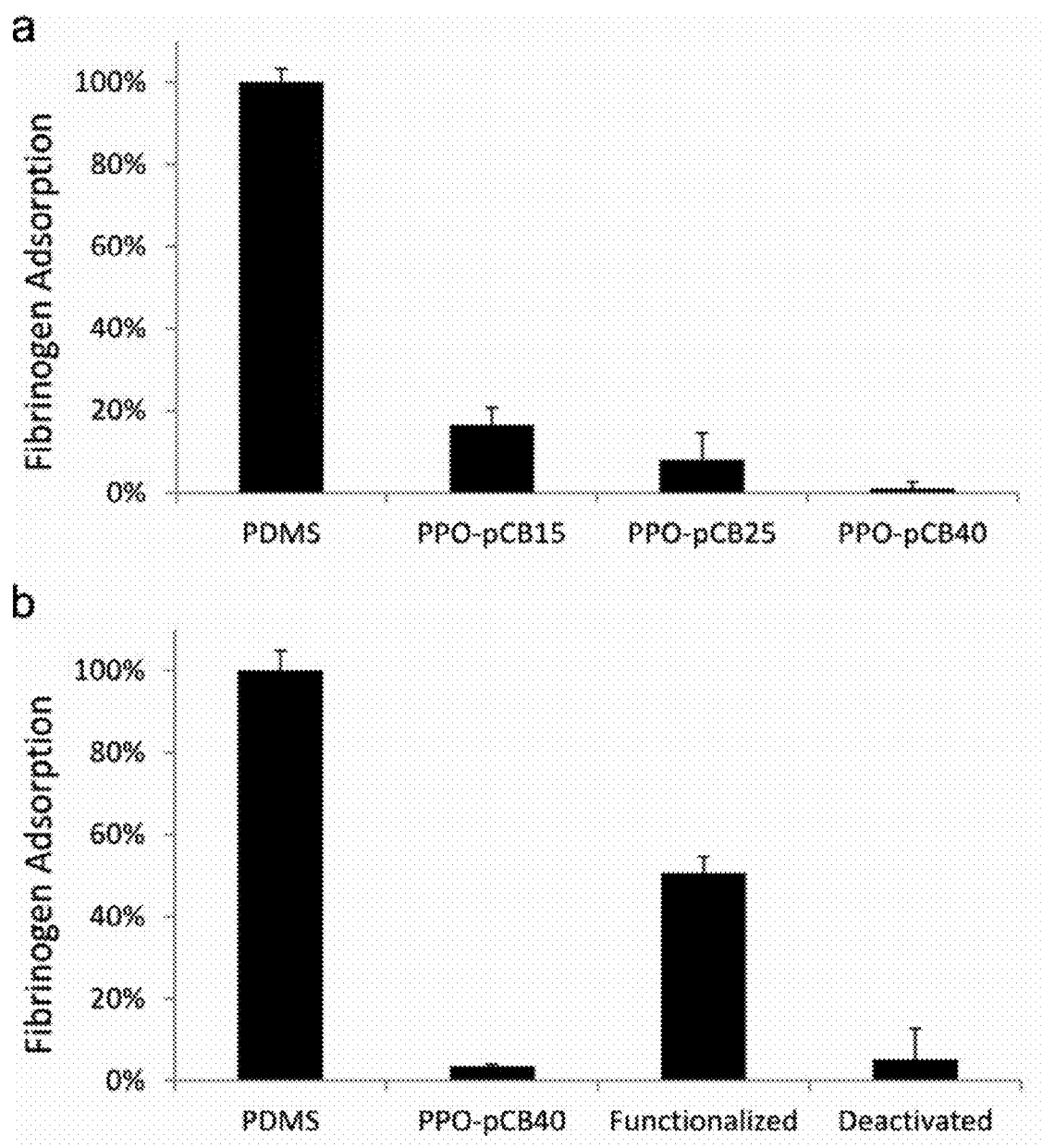
FIGS. 72A and 72B compare the amounts of adsorbed human fibrinogen (Fg) measured from ELISA.

These CBMA-PPO-CBMA triblock copolymers can be easily coated onto hydrophobic surfaces, such as poly(dimethyl siloxane) (PDMS) by simply dipping the hydrophobic materials into the aqueous polymer solution. PDMS is commonly used for the fabrication of medical device, artificial plant and microfluidic devices. A dense polymer layer with PPO block stick to the hydrophobic PDMS materials while CBMA block facing the aqueous solution can be formed quickly. These CBMA polymer protected surfaces can significantly suppress the nonspecific protein adsorption. FIG. 71 shows the fibrinogen adsorption level measured by ELISA on pure PDMS and PDMS surface coated by all three synthesized triblock copolymers. Clearly the triblock copolymer coated PDMS can significantly decrease the protein adsorption with increasing length of PCBMA block, with $CBMA_{40}$-$PPO_{48}$-$CBMA_{40}$ showing the greatest resistance to protein fibrinogen adsorption.

Unlike all other low fouling materials, PCB groups exhibit an acid-base equilibrium and can be transformed to functionalizable intermediates. Various molecules containing primary amines, such as proteins and antibodies, can be covalently attached to the carboxylic acid residues by commonly used EDC/NHS chemistries to create the ligand-functionalized solid substrates. Unreacted functionalized groups can be converted back to zwitterionic groups, ensuring the excellent nonfouling properties of post-functionalized surfaces. FIG. 71 demonstrates the ability to functionalize a PDMS surface coated with the $CBMA_{40}$-$PPO_{48}$-$CBMA_{40}$ triblock copolymer: after activation with EDC/NHS chemistry, the surfaces can be easily functionalized with bioactive molecules such as fibrinogen. After functionalization, the EDC/NHS activated surface can be deactivated with pH 10 buffer solution, regenerating a nonfouling surface again with fibrinogen adsorption as low as 5% compared to uncoated PDMS surface.

Figure 73A:
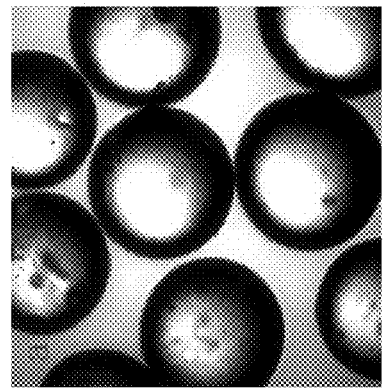
FIG. 73A-73H are images of hydrophobic glass beads coated and uncoated with triblock copolymers and their reaction with fluorescent proteins.
Figure 73E:
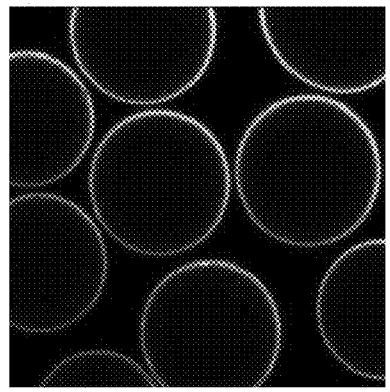
Figure 73B:
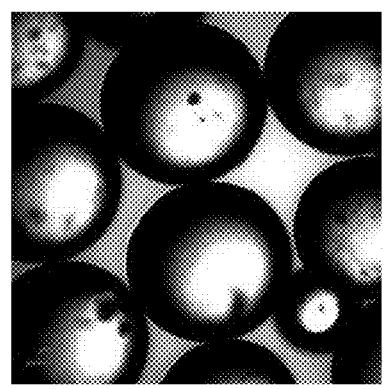
Figure 73F:
Figure 73C:
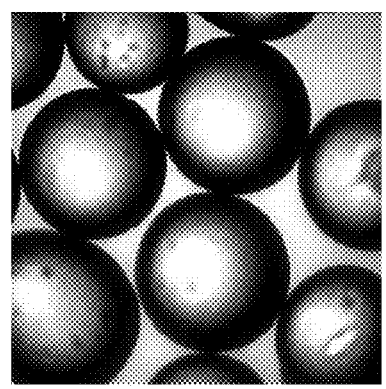
Figure 73G:
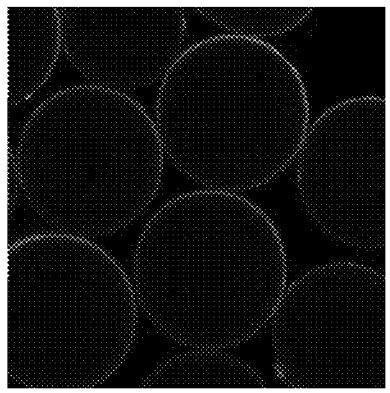
Figure 73D:
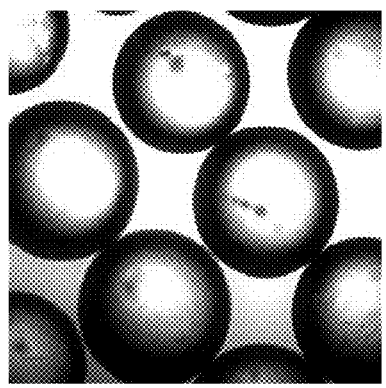
Figure 73H:
Figure 74:
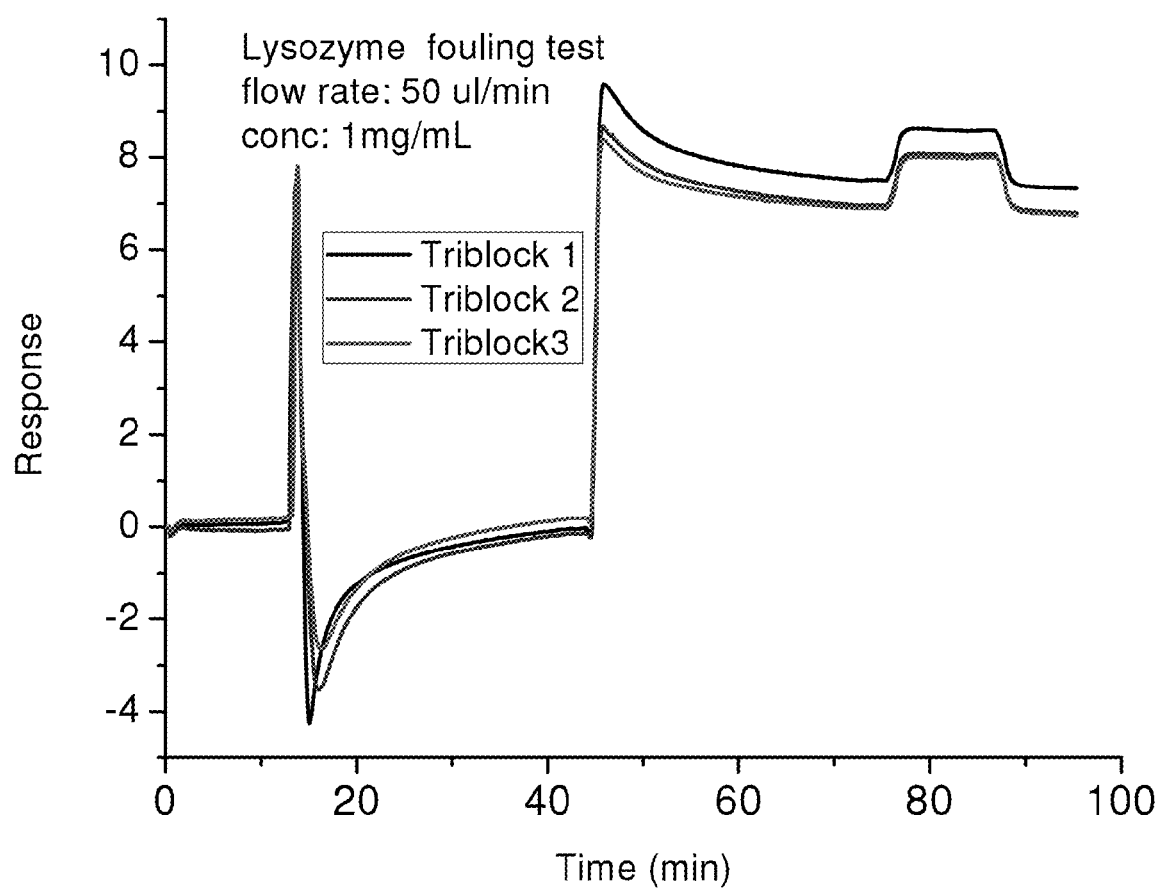
FIG. 74 compares lysozyme fouling test results for three triblock copolymer coated gold chips.

These triblock copolymers can also be coated onto other hydrophobic surfaces easily. FIG. 73 shows the fluorescence images of the triblock copolymer coated and uncoated hydrophobic glass beads. Shown in FIG. 73A are glass beads that have not been treated with the triblock copolymers, fluorescence tagged proteins can adsorption to the hydrophobic surfaces easily, as evidenced by the strong fluorescence image. After coating with triblock copolymers, no protein adsorption can be detected (see FIG. 73B); the triblock copolymer coated surfaces can also be easily functionalized with antibodies after EDC/NHS activation (see FIG. 73C); and after deactivation with pH 10 buffer solution, the nonfouling properties of these surfaces can be recovered as shown in FIG. 73D.

Zwitterionic Hydrogel with Modulus Matching PDMS

Figure 83:
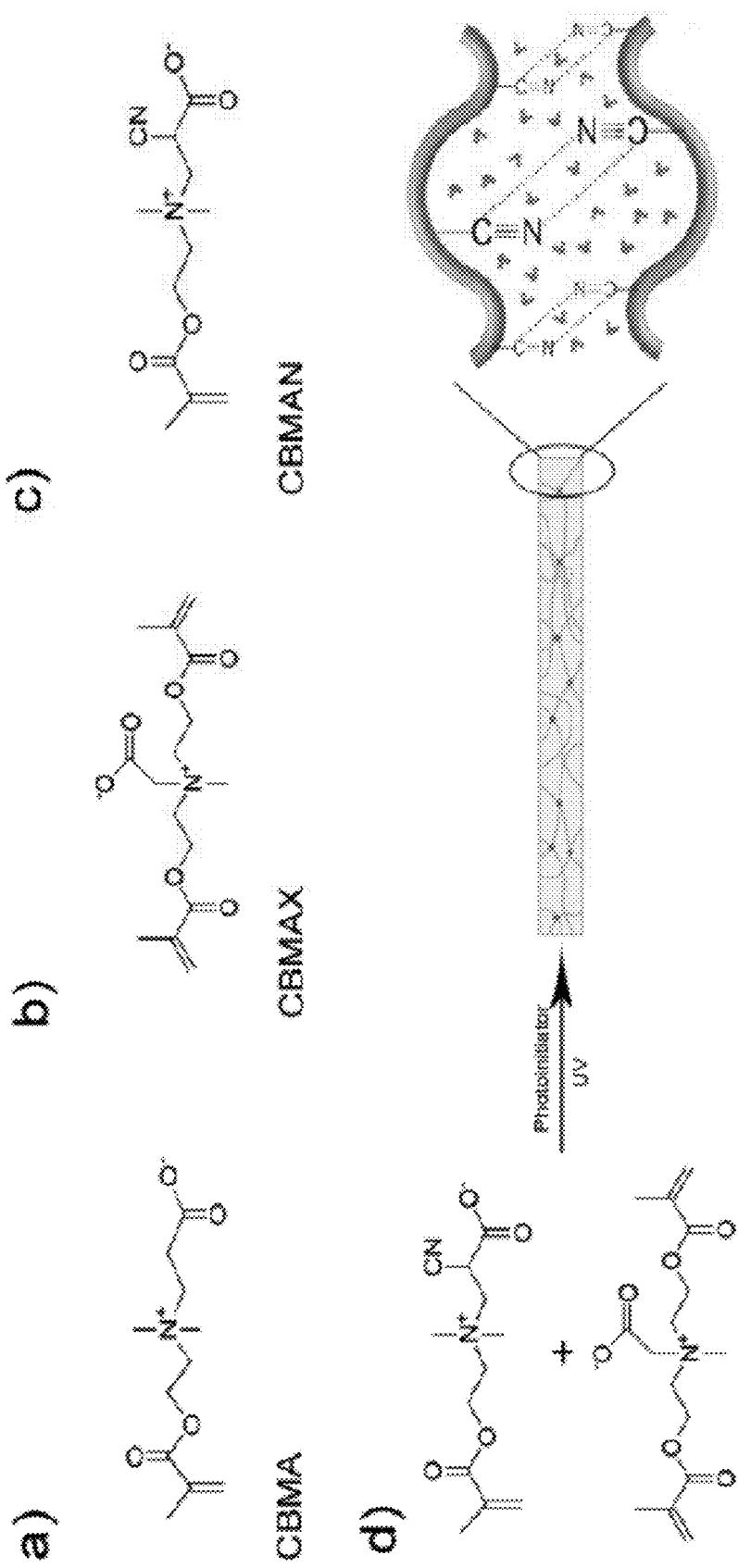
FIGS. 83A-83D illustrate structures of carboxybetaine methacrylate (CBMA) (83A); carboxybetainedimethacrylate (CBMAX) (83B); nitrile-containing CBMA (CBMAN) (83C); and hydrogel synthesis and illustration of the dipole-dipole reinforced CBMA hydrogel (83D).
Figure 84:
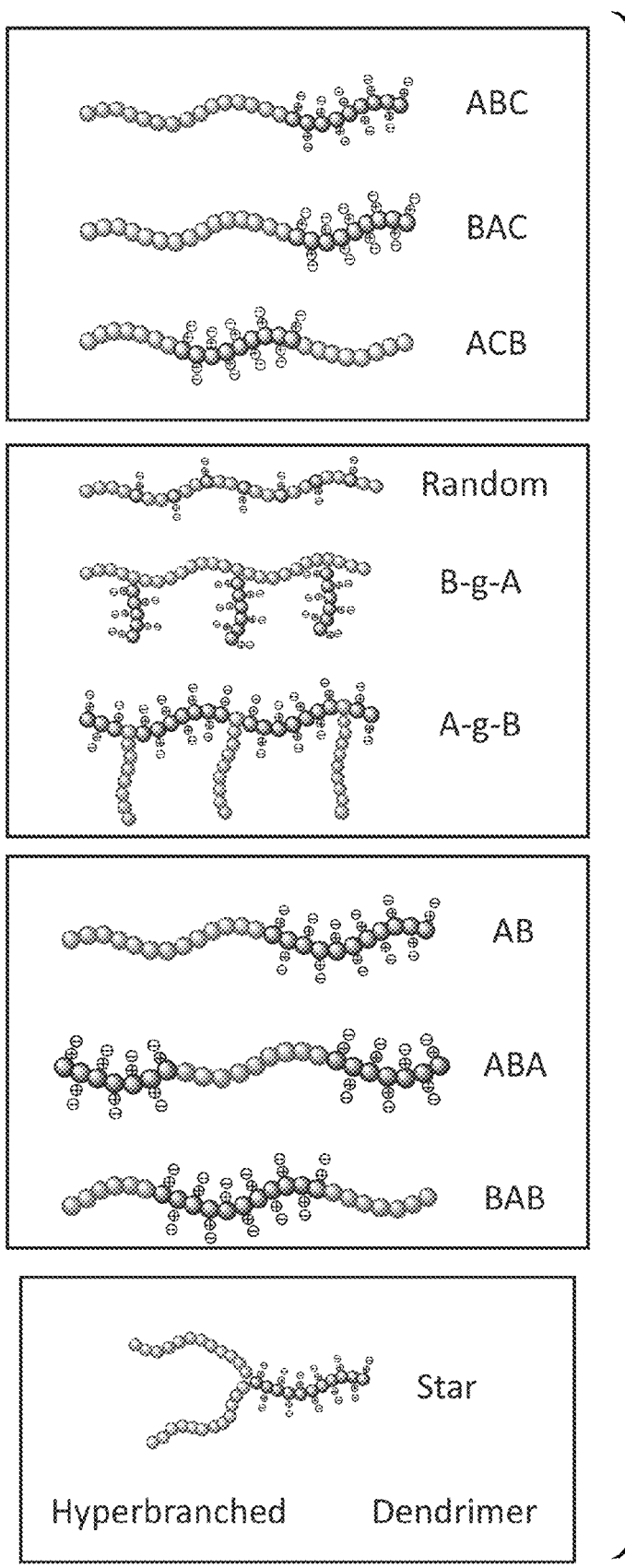
FIG. 84 illustrates structures of amphiphilic copolymer (diblock, triblock, random, star-shape, grafting).

To mimic systems in which a hydrophobic polymer is used, certain embodiments of the invention provide a one-pot synthesis of high strength and low modulus PCBMA hydrogel. The surface of such a hydrogel surfaces may be covered by PCBMA wherein the bulk modulus may also be easily tuned via crosslinking density. Conventional PCBMA hydrogels cannot match the mechanical properties of PDMS (low modulus and high strength). Conventional low-crosslinked PCBMA hydrogels have low modulus but are weak in strength due to high dilution of polymer chains in the swollen state. To improve the hydrogel strength, such an embodiment may utilize a crosslinker with a zwitterionic side chain, such carboxybetainedimethacrylate (CBMAX) (FIG. 83). For example, by further increasing the crosslinking density of CBMA with CBMAX results in high strength hydrogels with compressive strength at break of several MPas, without scarifying nonfouling properties (due to the carboxybetaine group in CBMAX). However, these high strength hydrogels exhibited high elastic modulus (e.g., 90 MPa). According to Rubinstein and Colby's scaling predictions, the modulus of a gel has strong power-law dependence over the polymer fraction, that is, $E \sim \epsilon 3$ ($\epsilon$: polymer fraction). This means the hydrogel is hard and similar to plastic due to the compact network and low water content resulting from high concentration of chemical crosslinkers. Due to the property difference between PDMS (a soft elastomer) and PCBMA, it is very challenging to prepare PCBMA hydrogels with comparable mechanical properties (low modulus and high strength).

To solve this challenge, one may use, for example a derivative of CBMA monomer which contains nitrile groups (nitrile-containing CBMA (CBMAN)), and to construct hydrogels using CBMAN and CBMAX (FIG. 83). The use of nitrile groups is inspired by nitrile-containing materials such as polyacrylonitrile (PAN), which have been used as high strength fibers due to strong dipole-dipole interactions between nitrile groups. When nitrile groups were engineered into the network of hydrogels, adjacent CN groups align anti-parallel to form pairs of molecules as suggested by earlier theoretical calculation and experimental data. These dipole-dipole interactions may serve as energy absorbers due to the displacement of dipole pairs, enabling soft hydrogels with high mechanical strength.

The following examples are provided for the purpose of illustrating, not limiting, the claimed invention.

EXAMPLES

Example 1

The Synthesis and Characterization of Representative Cationic Polymers

Materials.

N-(3-dimethylaminopropyl) acrylamide (>98%) was purchased from TCI America, Portland, Oreg. Methyl bromoacetate (97%), ethyl 4-bromobutyrate (≥97.0%), ethyl 6-bromohexanoate (99%), copper (I) bromide (99.999%), bromoisobutyryl bromide (BIBB 98%), 11-mercapto-1-undecanol (97%), and 2,2'-bipyridine (BPY 99%), and 2,2'-azobis(2-methylpropionitrile) (AIBN 98%) were purchased from Sigma-Aldrich. Fibrinogen (fraction I from bovine plasma) and phosphate buffer saline (PBS, pH 7.4, 0.15 M, 138 mM NaCl, 2.7 mM KCl) were purchased from Sigma Chemical Co. Ethanol (absolute 200 proof) was purchased from AAPER Alcohol and Chemical Co. Water used in experiments was purified using a Millipore water purification system with a minimum resistivity of 18.0 MΩ·cm.

ω-Mercaptoundecyl bromoisobutyrate (1) was synthesized through reaction of BIBB and (2) using a method described in Ilker, M. F.; Nuesslein, K.; Tew, G. N.; Coughlin, E. B., "Tuning the Hemolytic and Antibacterial Activities of Amphiphilic Polynorbornene Derivatives," *Journal of the American Chemical Society* 126(48):15870-15875, 2004. 1H NMR (300 MHz, CDCl$_3$): 4.15 (t, J=6.9, 2H, OCH$_2$), 2.51 (q, J=7.5, 2H, SCH$_2$), 1.92 (s, 6H, CH$_3$), 1.57-1.72 (m, 4H, CH$_2$), and 1.24-1.40 (m, 16H, CH$_2$).

Cationic Monomer Syntheses

CBAA-1-ester: (2-carboxymethyl)-3-acrylamidopropyldimethylammonium bromide, methyl ester N-(3-dimethylaminopropyl)acrylamide (25 mmol), methyl bromoacetate (37.5 mmol), and acetonitrile (25 mL) were added into a 100-mL round-bottom flask. The mixture was stirred under a nitrogen atmosphere for 6 hr at room temperature. The precipitate was collected, washed with ca 500 mL of anhydrous acetone. The solvent was removed on a rotary evaporator to get a white powder (96% yield). 1H NMR (300 MHz, D$_2$O): 2.02 (m, 2H, —CH$_2$—), 3.25 (s, 6H, N$^+$(CH$_3$)$_2$), 3.37 (t, 2H, CH$_2$—N$^+$), 3.58 (m, 2H, CH$_2$—N), 3.79 (s, 3H, O—CH$_3$), 4.29 (s, 2H, CH$_2$—C=O), 5.77 (m, 1H, CH=C—CON-trans); 6.19 (m, 1H, CH=C—CON— cis), 6.23 (m, 1H, =CH—CON—).

CBAA-3-ester: (4-carboxypropyl)-3-acrylamidopropyldimethylammonium bromide, ethyl ester N-(3-dimethylaminopropyl)acrylamide (50 mmol), ethyl 4-bromobutyrate (60 mmol), and acetonitrile (25 mL) were added into a 100-mL round-bottom flask. The mixture was stirred under a nitrogen atmosphere for three days at room temperature. The solvent was removed on a rotary evaporator to get a colorless oil (92% yield). $^1$H NMR (300 MHz, D$_2$O): 1.22 (t, 3H CH$_3$), 2.00 (m, 4H, C—CH$_2$—C), 2.47 (t, 2H, CH$_2$—C=O), 3.06 (s, 6H, N$^+$(CH$_3$)$_2$), 3.28-3.35 (6H, CH$_2$—N and CH$_2$—N$^+$—CH$_2$), 4.14 (q, 2H, O—CH$_2$), 5.75 (m, 1H, CH=C—CON-trans); 6.19 (m, 1H, CH=C—CON— cis), 6.26 (m, 1H, =CH—CON—).

CBAA-5-ester: (6-carboxypentyl)-3-acrylamidopropyldimethylammonium bromide, ethyl ester N-(3-dimethylaminopropyl)acrylamide (50 mmol), ethyl 6-bromohexanoate (55 mmol), and acetonitrile (25 mL) were added into a 100-mL round-bottom flask. The mixture was stirred under a nitrogen atmosphere for five days at 45° C. The solvent was removed on a rotary evaporator to get a slightly yellowish oil (87% yield). 1H NMR (300 MHz, D$_2$O): 1.20 (t, 3H CH$_3$), 1.34 (m, 2H, C—C—CH$_2$—C—C), 1.60-1.72 (4H, C—CH$_2$—C—CH$_2$—C), 2.00 (m, 2H, N—C—CH$_2$—C—N), 2.34 (t, 2H, CH$_2$—C=O), 3.04 (s, 6H, N$^+$(CH$_3$)$_2$), 3.24-3.37 (6H, CH$_2$—N and CH$_2$—N$^+$—CH$_2$), 4.12 (q, 2H, O—CH$_2$), 5.75 (m, 1H, CH=C—CON-trans); 6.20 (m, 1H, CH=C—CON— cis), 6.24 (m, 1H, =CH—CON—).

Representative Cationic Polymer Syntheses

Surface-Initiated ATRP. Three monomers, CBAA-1-ester, CBAA-3-ester, and CBAA-5-ester, were grafted onto gold-coated SPR sensor chips or gold-coated silicon chips using surface-initiated ATRP. The preparation and characterization of the polymer brushes is described in Zhang, Z.; Chen, S.; Chang, Y.; Jiang, S., "Surface Grafted Sulfobetaine Polymers via Atom Transfer Radical Polymerization as Superlow Fouling Coatings" *Journal of Physical Chemistry B* 110(22): 10799-10804, 2006, and Zhang, Z.; Chen, S.; Jiang, S., "Dual-Functional Biomimetic Materials: Nonfouling Poly (carboxybetaine) with Active Functional Groups for Protein Immobilization" *Biomacromolecules* 7(12):3311-3315, 2006. previous publications. Briefly, CuBr (1 mmol) and a SPR chip or a gold disk with a Br-thiol SAM was placed in a nitrogen-purged reaction tube. Degassed solution (pure water and methanol in a 1:1 volume ratio, 10 mL) with CBAA ester (6.5 mmol), and BPY (2 mmol, in 5 mL degassed methanol) were transferred to the tube using a syringe. After reaction for more than 1 hour under nitrogen, the SPR chip or gold disk was removed and rinsed with ethanol, water and PBS solution. The samples were stored in PBS solutions before testing.

Polymer Synthesis and Characterization

CBAA-1-ester solution of ca. 0.3 M in methanol was purged with nitrogen for 30 min. The polymerization was then performed at 60° C. for ca 48 hours under nitrogen using 3 mol % AIBN as an initiator to provide polyCBAA-1-ester. Similar methods were applied for preparation of polyCBAA-3-ester or polyCBAA-5-ester using ethanol as a solvent. The polymers were washed with ethyl ether and the solvent was then removed. The structures of the polymers were confirmed by NMR. 1H NMR (300 MHz, D$_2$O): polyCBAA-1-ester: 1.62 (br, 2H), 2.05 (br, 3H), 3.25-3.32 (br, 8H), 3.62 (br, 2H), 3.83 (s, 3H), 4.38 (s, 2H); poly-CBAA-3-ester 1.21 (t, 3H), 1.61 (br, 2H), 2.04 (br, 5H), 2.50 (t, 2H), 3.37 (br, 6H), 3.12 (s, 6H), 4.14 (q, 2H); polyCBAA-5-ester: 1.22 (t, 3H), 1.37 (m, 2H), 1.62-1.80 (br m, 6H), 2.01 (br, 3H), 2.39 (t, 2H), 3.03 (s, 6H), 3.24 (br m, 6H), 4.12 (q, 2H).

The molecular weight of linear polyCBAA was estimated using a Waters Alliance 2695 Separations Module equipped with a Waters Ultrahydrogel 1000 column and detected with a Waters 2414 Reflex Detector. The mobile phase was an aqueous solution at a flow rate of 0.5 mL/min. The instrument and column were calibrated with poly(ethylene oxide) standards from Polymer Laboratories. All measurements were performed at 35° C. The molecular weight of the polymer was calculated using Empower Pro from Waters.

Example 2

Representative Cationic Polymer Hydrolysis

The cationic polymers prepared as described in Example 1 were dissolved in NaOH solutions with different concentration (10 mM, 100 mM, and 1 M) in a concentration of 50 mg/mL. After an appropriate time interval, the polymer solutions were neutralized with dilute HCl solution and the water was removed by vacuum. 1H NMR spectroscopy ($D_2O$) was performed to measure the degradation rate by determining the amount of intact ester groups and comparing with other non-hydrolyzable pendant groups as inner standards. The results are illustrated in FIG. 3.

Example 3

Representative Cationic Polymer Protein Adsorption and Release

The cationic polymers prepared as described in Example 1 were evaluated for protein adsorption by surface plasmon resonance (SPR).

Protein adsorption was measured with a custom-built SPR sensor, which is based on wavelength interrogation. A SPR chip was attached to the base of the prism, and optical contact was established using refractive index matching fluid (Cargille). A dual-channel flow cell with two independent parallel flow channels was used to contain liquid sample during experiments. A peristaltic pump (Ismatec) was utilized to deliver liquid sample to the two channels of the flow cell. Fibrinogen solution of 1.0 mg/mL in PBS (0.15M, pH 7.4) was flowed over the surfaces at a flow rate of 0.05 mL/min. A surface-sensitive SPR detector was used to monitor protein-surface interactions in real time. Wavelength shift was used to measure the change in surface concentration (mass per unit area). The results are illustrated in FIGS. 5A-5C.

Example 4

Representative Cationic Polymer Antimicrobial Properties

The cationic polymers prepared as described in Example 1 were evaluated for their antimicrobial properties.

*E. coli* K12 were first cultured in separate pure cultures overnight at 37° C. on LB agar plates, which was then incubated with shaking at 37° C. for 24 h. Cultures on agar plates can be used for two weeks, if kept at 4° C. Several colonies were used to inoculate 25 ml of LB (20 g/L). These initial cultures were incubated at 37° C. with shaking at 100 rpm for 18 hours and were then used to inoculate a second culture of each species in 200 ml of appropriate medium. When the second suspended culture reached an optical density of 1.0 at 600 nm, bacteria were collected by centrifugation at 8,000×g for 10 min at 4° C. Cell pellets were washed three times with sterile phosphate buffered saline (PBS, pH7.4) and subsequently suspended in PBS to a final concentration of $10^8$ cells/mL.

Figure 6:
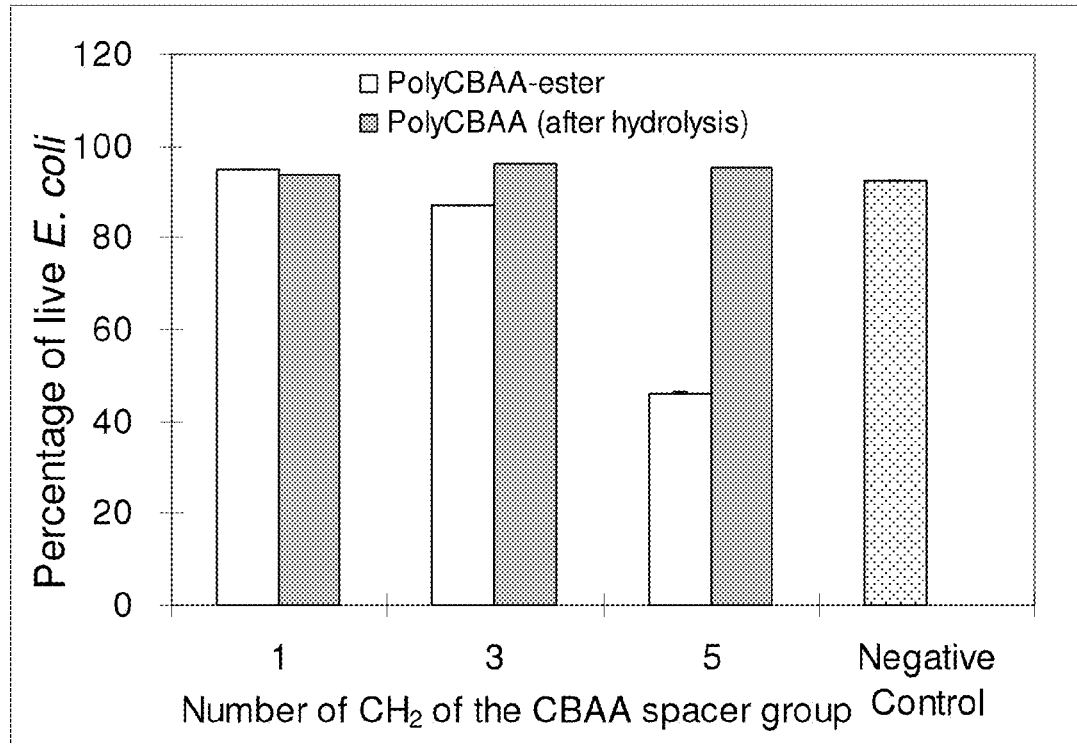
FIG. 6 is a graph comparing antimicrobial activities of three representative cationic polymers useful in the invention, polyCBAA-esters, before and after hydrolysis. *E. coli* ($10^8$ cells/mL) was incubated with each polymer solution (repeat unit molar concentration: 2 mM) for 30 min. PBS buffer (pH 7.4 and 150 mM) is used as a negative control.

Exposure of bacterial cells to representative polymer solutions was started when the culture containing bacterial cells was added to above polymer suspension which was pre-equilibrated and shaken at 30° C., and the mixture were incubated at room temperature for 30 min. The final solution contains ca. $10^8$ cells/mL *E. coli* and 2 mM repeat unit concentration, which is the molar concentration of the repeat unit of the polymers (ca. 0.6-0.76 mg/mL based on molecular weight of CBAAs and CBAA-esters). Bacteria were stained with Live/Dead BacLight™ (Invitrogen, USA), and bacterial suspension was subsequently filtered through a polycarbonate membrane filter with 0.2 μm pore size (Millipore, USA), and observed directly with a CCD-Cool SNAP camera (Roper scientific, Inc., USA) mounted on Nikon Eclipse 80i with 100× oil lens. The number of live and dead cells was determined, respectively, through FITC and Rhodamine filters with the same microscope described in Cheng, G.; Zhang, Z.; Chen, S.; Bryers, J. D.; Jiang, S., "Inhibition of Bacterial Adhesion and Biofilm Formation on Zwitterionic Surfaces," *Biomaterials* 28(29):4192-4199, 2007. The results are illustrated in FIG. 6.

Example 5

Preparation and Properties of a Representative Marine Coating Composition: Cationic Polymer Having Hydrophobic Counter Ion The preparation of a representative cationic polymer having a hydrophobic counter ion and that is useful as a component in a marine coating is described. The hydrolysis, self-polishing, and nonfouling properties of the coating are also described.

Figure 16:
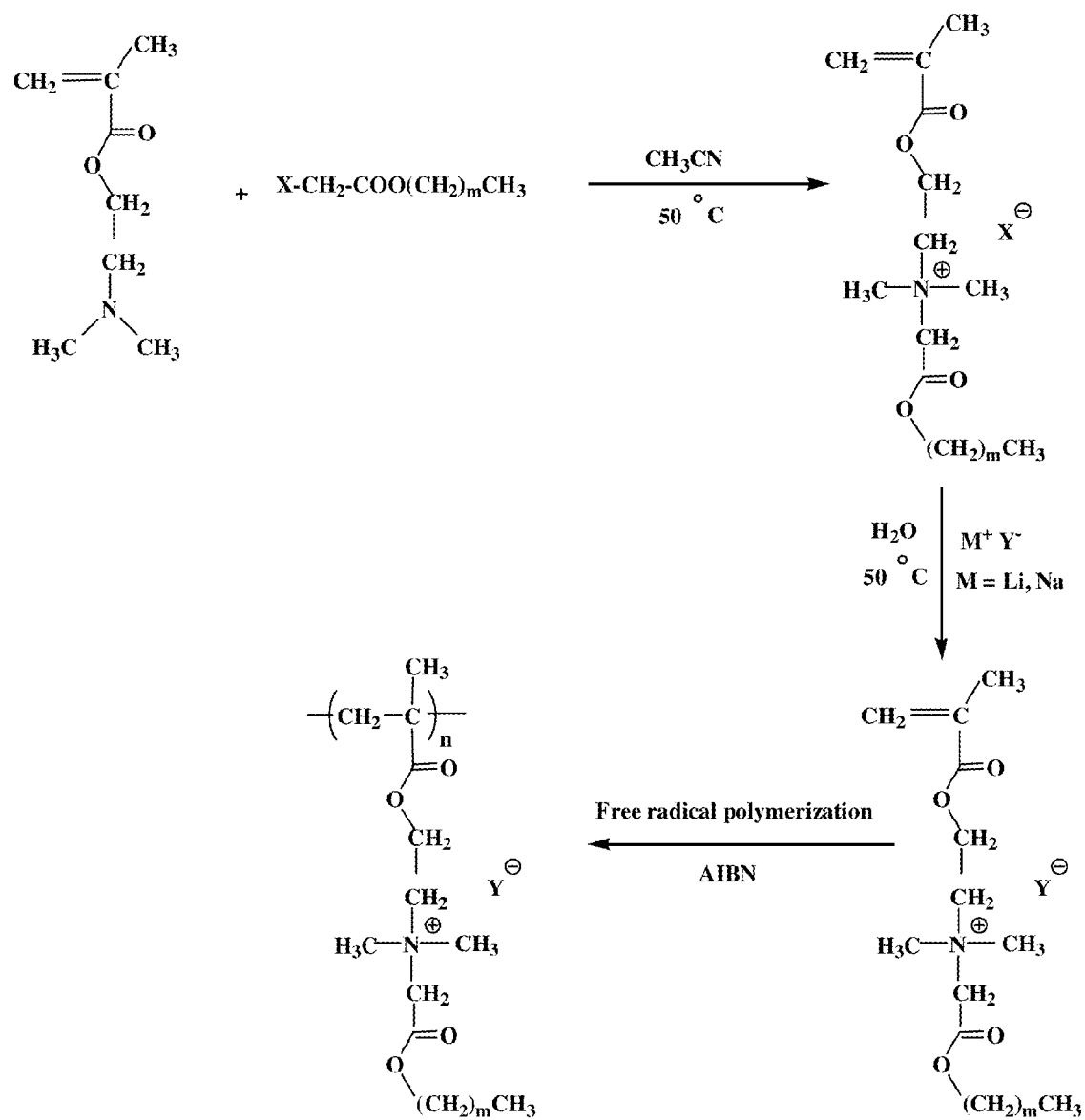
FIG. 16 is a schematic illustration of the preparation of representative cationic monomers and polymers useful in the invention having ion exchanged counter ions Y$^-$ (e.g., hydrophobic counter ions).

The preparation of the representative cationic monomer and polymer (i.e., carboxybetaine methacrylate ester (CBMA-ester) monomer and polymer) and ion exchange with hydrophobic ions are illustrated in FIG. 16 and described below.

Alkyl Chloroacetates.

Alkyl chloroacetates were prepared by refluxing chloroacetate acid with corresponding alkyl alcohol in the presence of sulfuric acid and benzene as solvent for overnight. The obtained esters of chloroacetic acid were purified by vacuum distillation and obtained in yields around 70~95%.

Dodecyl chloroacetate. The mixture of 1-dodecanol (0.2 mol, 37.27 g), chloroacetic acid (0.2 mol, 18.9 g), benzene (200 ml) and sulfuric acid (2 ml) was refluxed for 12 hrs. After the reaction, the mixture was washed with 25% $Na_2CO_3$ (100 ml). The organic layer was dried with magnesium sulfate and then evaporated, the remaining liquid was distilled under vacuum to provide a colorless oil (bp 150° C./3 mmHg) in 90% yield.

N-(methacryloxyethyl-N-(alkyl acetate)-N,N-dimethyl-ammonium chloride

The cationic compounds of N-(methacryloxyethyl-N-(alkyl acetate)-N,N-dimethyl-ammonium chloride were prepared in nearly quantitative yields from alkyl chloroacetates and 2-(dimethylamino)ethyl methacrylate.

N-(methacryloxyethyl-N-(dodecyl acetate)-N,N-dimethyl-ammonium chloride 2-(dimethylamino)ethyl methacrylate (0.05 mol, 7.86 g), dodecyl chloroacetate (0.06 mol, 15.75 g), acetonitrile (50 ml) were heated to 50° C. for two days. After reaction the solvent was evaporated and the remaining compound was washed with ether to provide a white solid in 98% yield.

CBMA-Ester Monomers with Hydrophobic Ions.

The carboxybetaine methacrylate ester (CBMA-ester) monomers with hydrophobic anions were synthesized with metathesis reaction method.

N-(methacryloxyethyl-N-(dodecyl acetate)-N,N-dimethyl-ammonium salicylate A mixture of N-(methacryloxyethyl-N-(dodecylacetate)-N,N-dimethylammonium chloride (0.1 mol, 41.9 g), salicylic acid sodium (0.12 mol, 19.2 g), and water (400 ml) was heated to 50° C. for two days. After reaction, the mixture was extracted with chloroform (500 ml) and the chloroform extract dried with magnesium sulfate, filtered, and then evaporated to dryness to provide a white solid, N-(methacryloxyethyl-N-(dodecyl acetate)-N, N-dimethyl-ammonium salicylate, in 90% yield.

CBMA-Ester Polymers.

The carboxybetaine methacrylate ester (CBMA-ester) monomers were polymerized by the free radical polymerization method.

Polymerization of N-(methacryloxyethyl-N-(dodecylacetate)-N,N-dimethyl-ammonium salicylate. Under the protection of nitrogen gas, monomer N-(methacryloxyethyl-N-(dodecylacetate)-N,N-dimethyl-ammonium salicylate (0.1 mol, 46.4 g) was placed in a 500 ml flask and chloroform (250 ml) was added. After heating the mixture to 65° C. for 10 min, initiator AIBN (2,2'-azo-bis(isobutyronitrile)) (0.47 g) was added to the solution. The reaction was run for 24 hr, then poured into hexane (2 L). The polymer was precipitated in the solution. After filtering and drying, the polymer was obtained as white solid in 85% yield.

Figure 17:
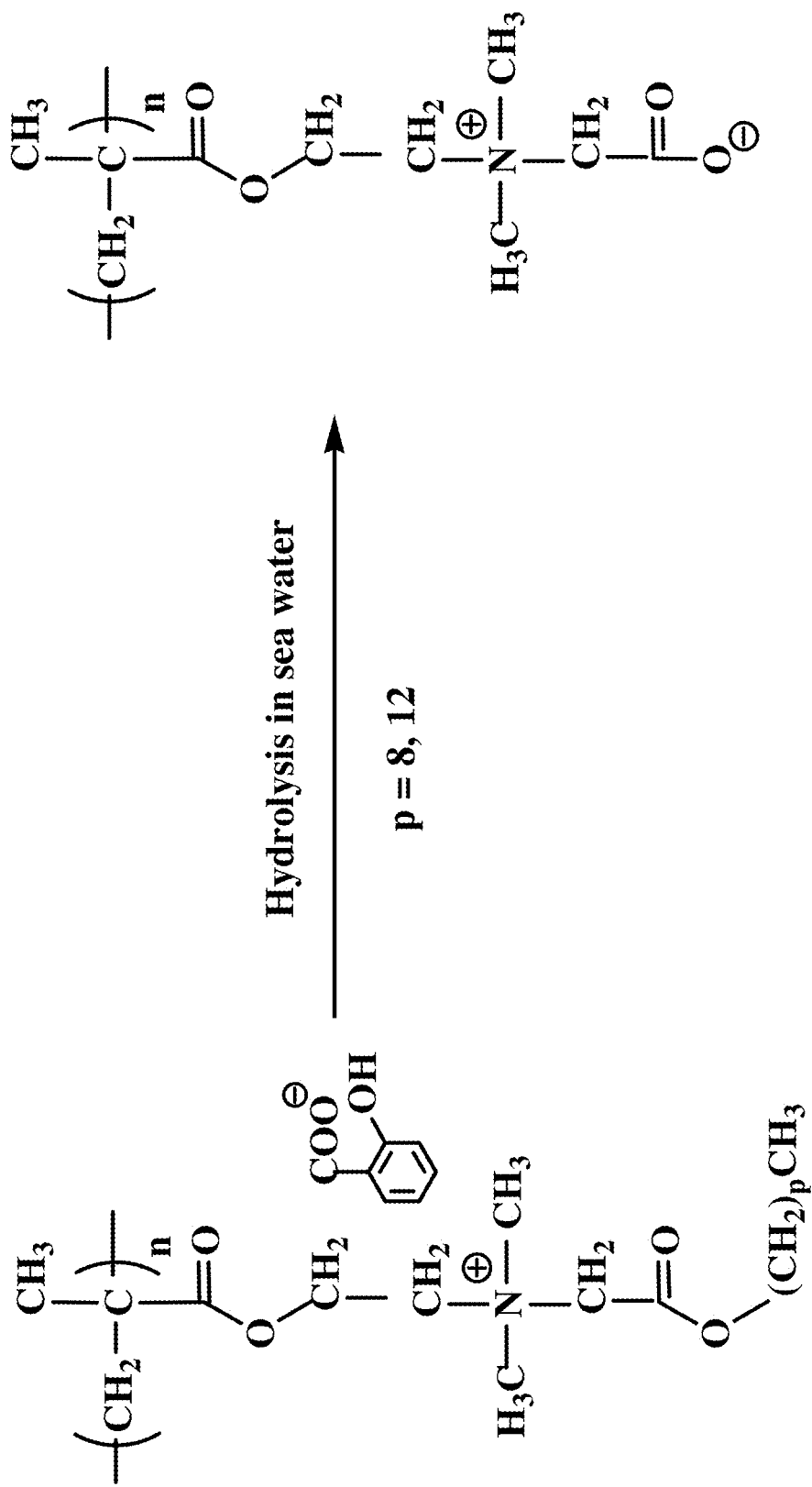
FIG. 17 illustrates the seawater hydrolysis of representative cationic polymers useful in the invention having hydrophobic counter ion (salicylate) and leaving group, $CH_3(CH_2)_7OH$ or $CH_3(CH_2)_{11}OH$: hydrolysis of cationic polycarboxybetaine esters to zwitterionic polycarboxybetaine.

The obtained polymers, such as poly(N-(methacryloxyethyl-N-(dodecyl acetate)-N,N-dimethylammonium salicylate), are hydrophobic and, depending on the size of the ester group and the type of hydrophobic ion, may not dissolve in water. These hydrophobic polymers can be hydrolyzed to hydrophilic poly(carboxybetaine methacrylate) (CBMA) under seawater conditions (see FIG. 17). The solubility of representative cationic polymers useful in the invention in water is set forth in Table 2.

Nonfouling Properties of Representative Marine Coating.

Figure 18:
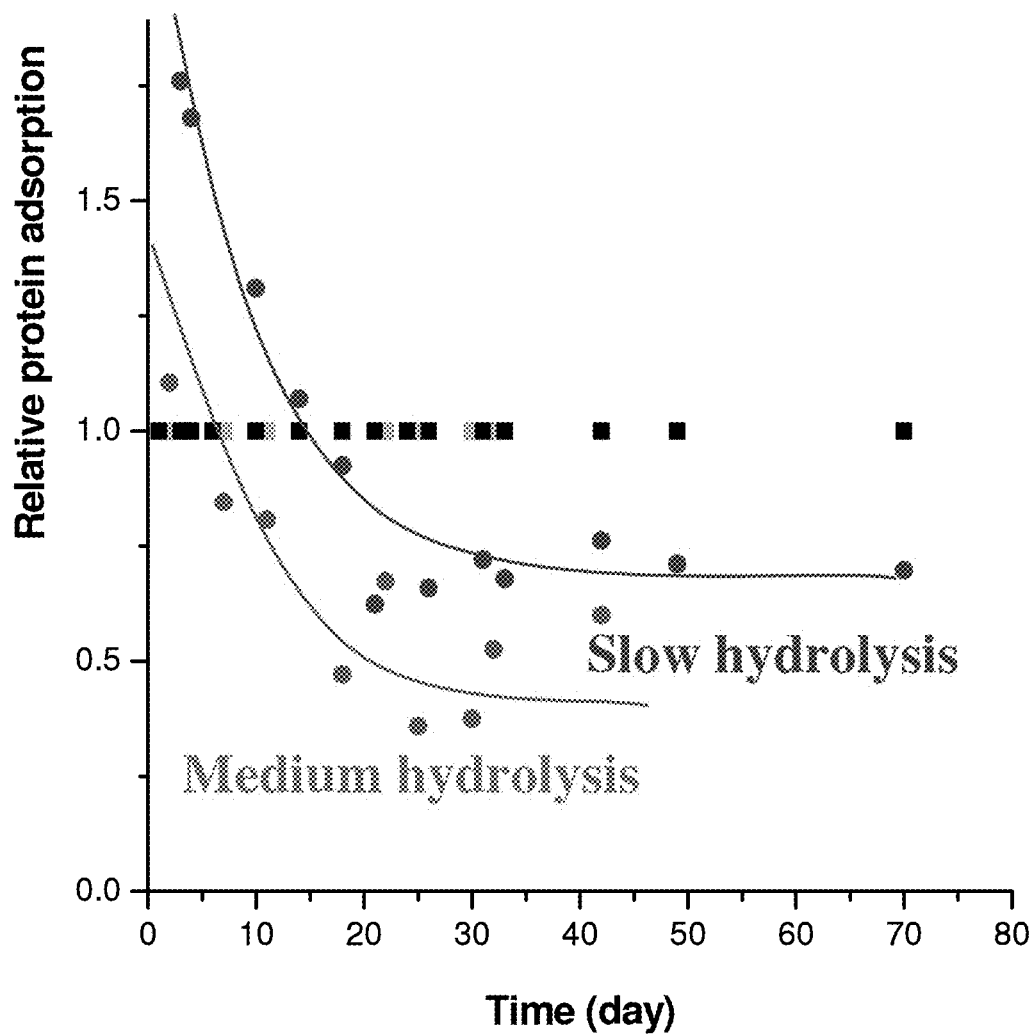
FIG. 18 compares relative protein adsorption as a function of hydrolysis (time exposed to artificial seawater, 0.6 M sodium chloride at pH 8.2) for surfaces coated with cationic polymers illustrated in FIG. 17 (m=7 and m=11), slow hydrolysis for cationic polymer with m=11 and medium hydrolysis for cationic polymer with m=7. Relative protein adsorption was determined by horseradish peroxidase-anti-fibrinogen ELISA.
Figure 19:
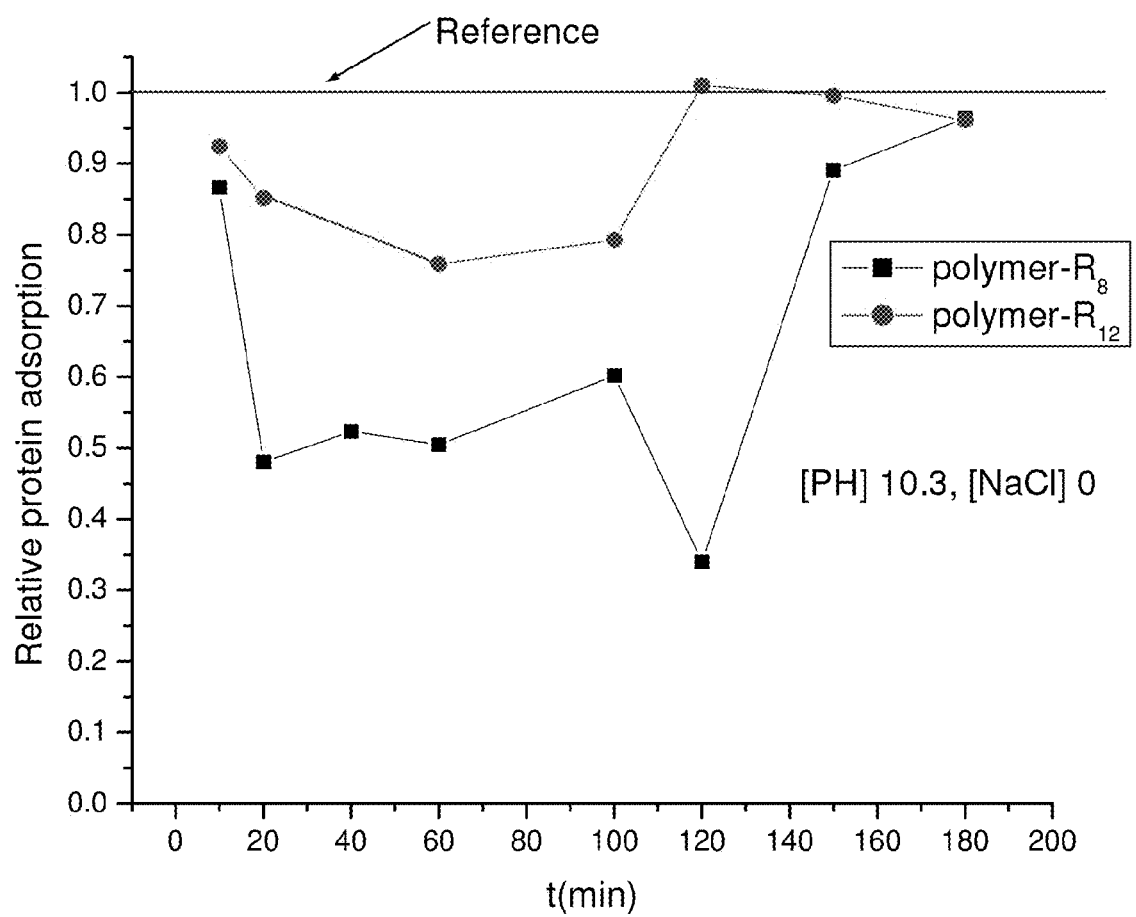
FIG. 19 compares relative protein adsorption as a function of time (solution at pH 10.3) for surfaces coated with cationic polymers illustrated in FIG. 17 (m=7 and m=11). Relative protein adsorption was determined by horseradish peroxidase-anti-fibrinogen ELISA.
Figure 20A:
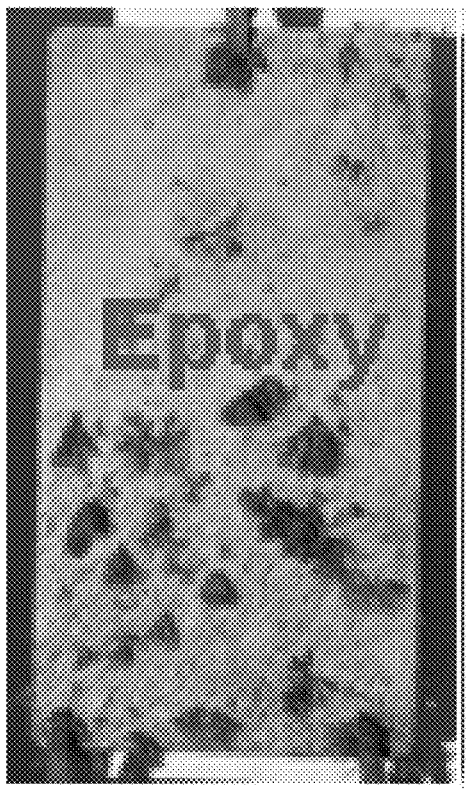
Figure 20B:
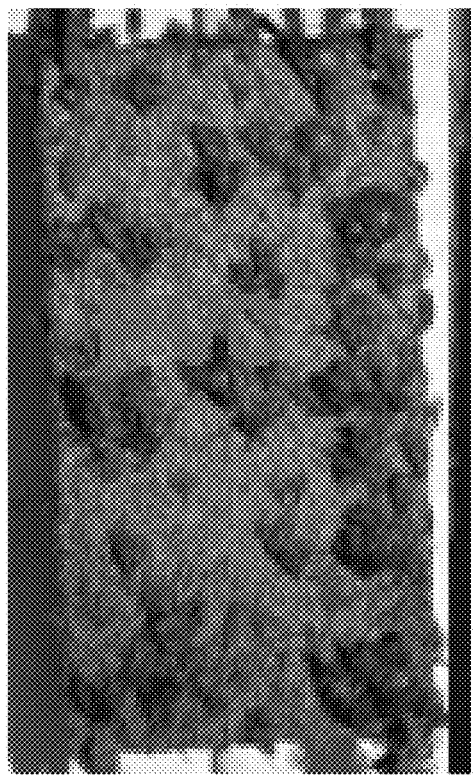
Figure 20F:

The hydrophobic poly(CBMA-ester)s were spin-coated onto panels (10 mm×10 mm) for protein adsorption experiments, which were tested with enzyme linked immunosorbent assay (ELISA). It was found that fibrinogen adsorption could be reduced to a level of 30~40% with increasing hydrolysis time in artificial sea water (see FIG. 18) and in basic solution (accelerated experiments, see FIG. 19). These hydrophobic polymers (with p=2-18 and Y=salicylate ion, see Table 2 and FIG. 17) were spray-coated onto panels (4"×8") with epoxy as primer. Examples for results from field tests in Florida are shown in FIG. 20. For field tests in Florida, static immersion panels were exposed in the Indian River Lagoon near Sebastian Inlet between April and May 2008. All panels were held 1 meter under the surface within ½" galvanized mesh caging. Digital photographs were taken of these panels (see FIG. 20).

Example 6

Preparation and Properties of a Representative Marine Coating Composition

Nanoparticles from Block Copolymers

The preparation of a representative nanoparticles that are useful as a component in a marine coating is described. The nonfouling properties of the coating are also described.

Figure 21:
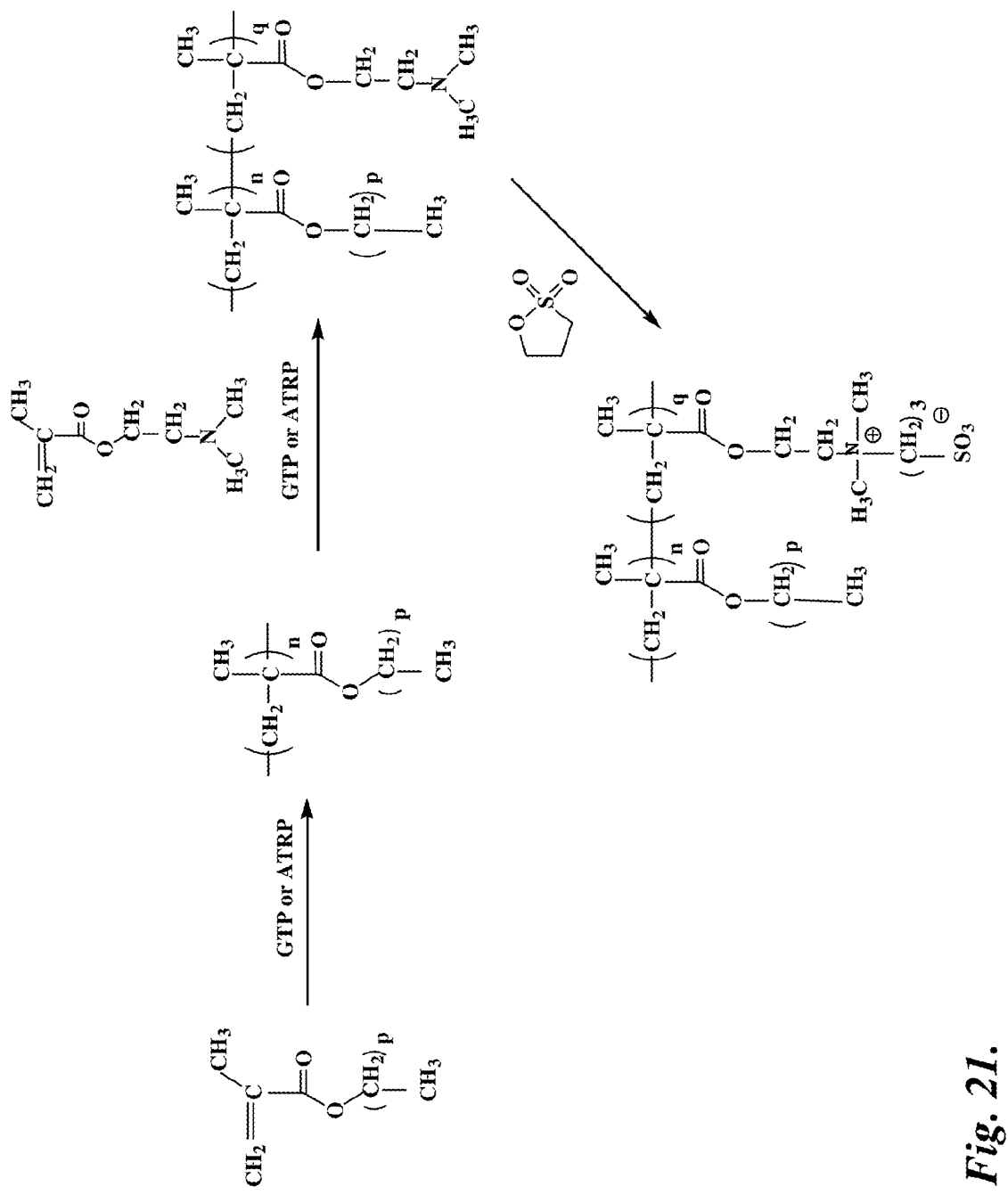
FIG. 21 is a schematic illustration of the preparation of representative block polymer of the invention having a zwitterionic block (sulfobetaine) and a hydrophobic block (methacrylate $C_p$ ester).

The preparation of the representative block copolymer having a zwitterionic block (sulfobetaine) and a hydrophobic block is illustrated in FIG. 21 and described below. Referring to FIG. 21, the hydrophobic block is prepared by polymerization of alkyl methacrylate. The hydrophobic block can be prepared by group transfer polymerization (GTP) or atom transfer radical polymerization (ATRP) method. The diblock copolymer is prepared by GTP or ATRP with the hydrophobic block and an amine monomer to provide a diblock copolymer that is then quaternized to provide the diblock copolymer having a zwitterionic block and a hydrophobic block.

The diblock copolymers of sulfobetaine methacrylate and alkyl methacrylates can be synthesized by group transfer polymerization (GTP) or atom transfer radical polymerization (ATRP) method followed by quaternization with 1,3-propanesultone to obtain corresponding zwitterion-containing diblock copolymers in high yield.

On approach for the synthesis of block copolymer of dodecyl methacrylate and sulfobetaine methacrylate by ATRP method is as follows.

Block 1.

To a Schlenk flask containing toluene (100 ml) was added Cu(I)Br (0.002 mol, 0.29 g), 2,2'-dipyridyl (0.006 mol, 0.95 g) and dodecyl methacrylate (0.1 mol, 25 g). The solution was degassed for 15 min and heated to 90° C. for 10 min. Then, methyl 2-bromopropionate (0.002 mol, 0.334 g) was added to the solution. After reaction, the catalyst residues were removed by filtering through a column of basic alumina prior to gel permeation chromatographic (GPC) analysis. The polymers were isolated by precipitation into methanol. Conversion was measured by gravimetry by drying to constant weight in a vacuum oven at 50° C.

Block 2.

To a Schlenk flask containing toluene (100 ml) was added Cu(I)Cl (0.002 mol, 0.20 g), PMDETA (1,1,4,7,7-pentamethyl diethylene triamine) (0.002 mol, 0.35 g) and polymer obtained from Block 1 (20 g). The solution was degassed for 15 min and heated to 90° C. for 10 min. Then, monomer 2-(dimethylamino)ethyl methacrylate (0.13 mol, 20 g) was added to the solution. After reaction, the catalyst residues were removed by filtering through a column of basic alumina prior to GPC analysis. The polymers were isolated by precipitation into methanol. Conversion was measured by gravimetry by drying to constant weight in a vacuum oven at 50° C. The obtained block polymer was added to THF (200 ml), and excess 1,3-propanesulfone was added. The mixture was stirred at room temperature for 24 hr to obtain the corresponding zwitterion-containing diblock copolymer. The obtained block copolymer undergoes spontaneous self-assembly in hydrophobic organic solvents or in aqueous solution to form nanoparticles.

Marine Coating.

The nanoparticles were mixed with hydrolyzable silyl ester binder polymers and coated on panels. Results from field tests in Hawaii are illustrated in FIG. 22. For field tests in Hawaii, the test site was a pier on the south side of Ford Island, Pearl Harbor, Honolulu, Hi. Panels were hung from racks mounted on pilings beneath the pier. Panels were exposed to a diverse community of fouling organisms and recruitment between May and June 2008.

Example 7

Preparation and Properties of a Representative

Marine Coating Composition: Siloxane Coating

The preparation of a zwitterionic graft polymer of fluorinated carboxybetaine and polymethylhydrosiloxane that is useful as a component in a marine coating is described.

Figure 23:
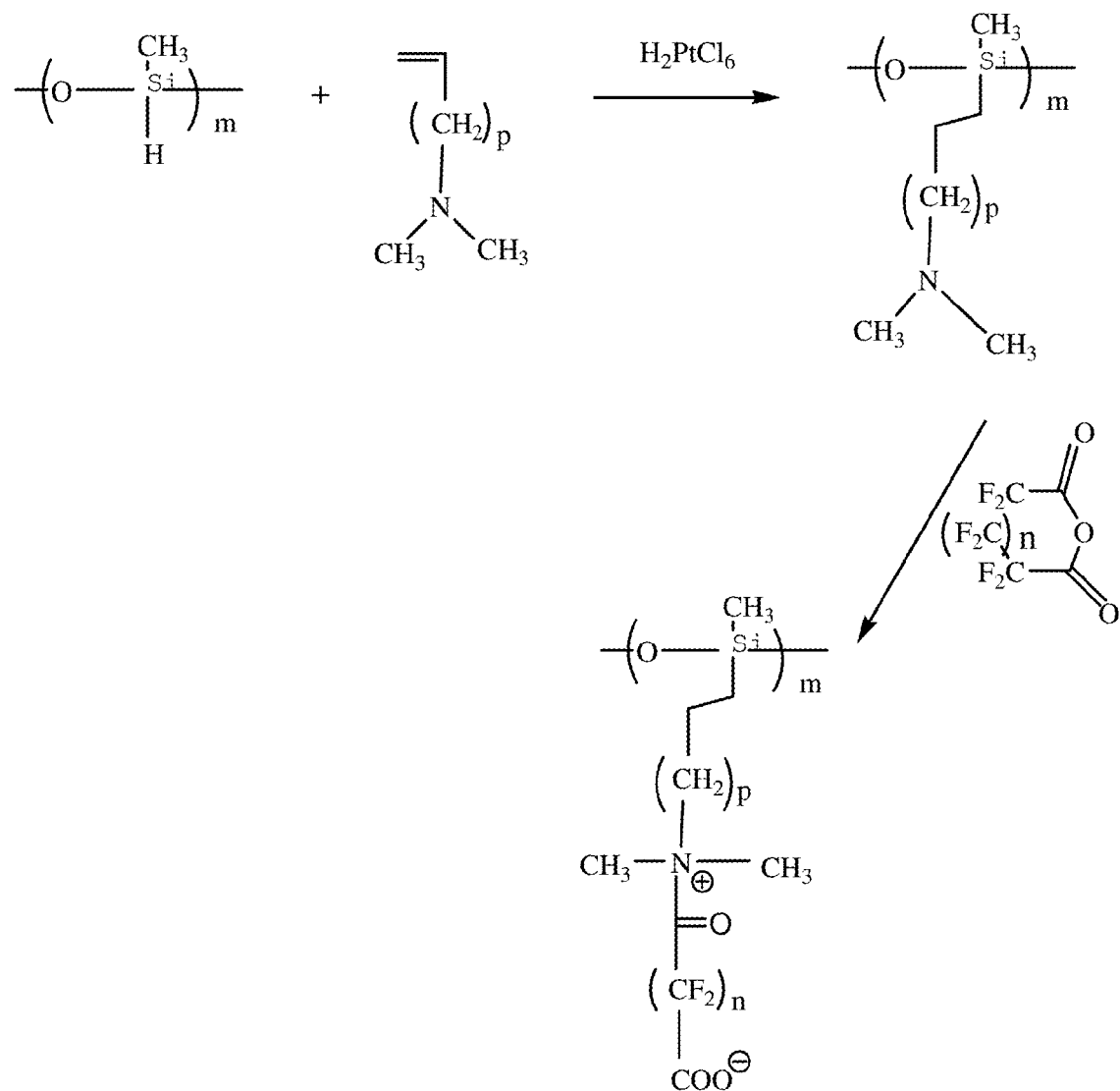
FIG. 23 is a schematic illustration of the preparation of representative siloxane polymer of the invention having a zwitterionic pendant group containing a fluoroalkyl moiety ($-CF_2)_n-$).

The preparation of the representative zwitterionic graft polymer is illustrated in FIG. 23 and described below.

Fluorine-containing zwitterionic alkenes can be added to polymethylhydrosiloxane or other silicone derivatives using $H_2PtCl_6$ as a catalyst. The obtained polymers have amphiphilic characteristics with good antifouling and fouling release properties. One approach for the preparation of grafting fluorine-containing zwitterionic compound to polymethylhydrosiloxane is as follows.

Synthesis of poly(methylalkylsiloxanes) was performed by a hydrosilation reaction of poly(methylhydrosiloxane) with α-olefins of varying lengths. A three-necked round-bottomed flask equipped with a thermometer, a mechanical agitator, and a nitrogen purge was charged with poly(methylhydrosiloxane) (20 g) and excess α-olefin in dry toluene (100 ml). Chloroplatinic acid (hydrogen hexachloroplatinate (IV) (150 ppm) was then added to the reaction mixture, which was maintained at 60° C. for 3 days. The reaction mixture was filtered to remove the catalyst, refluxed with activated charcoal for 1 h and filtered. The solvent was removed under reduced pressure. Excess α-olefin was removed under a vacuum. Finally, the polymer was dissolved in dry toluene (100 ml) again, excess multrifluoroglutaric anhydride was added to the solution and heated at room temperature for 2 days to obtain the final fluorinated zwitterionic graft polymer.

Example 8

Preparation, Characterization, and Use as Marine Coating of Representative Amphiphilic Diblock Copolymer: PDMS-PCBMA Materials.

N,N'-dicyclohexylcarbodiimide (DCC, 99%), 4-(dimethylamino) pyridine (DMAP), 4-cyano-4-(phenylcarbonothioylthio)pentanoic acid (chain transfer agent, CTP), 4-cyano-4-[(dodecylsulfanylthiocarbonyl)sulfanyl]pentanoic acid (chain transfer agent, DMP), 2,2'-azobis(2-methylpropionitrile) (AIBN 98%) were purchased from Sigma-Aldrich. Monocarbinol terminated polydimethylsiloxane (MCR-C18, Mn=5,000), addition cure PDMS system (HMS-151, HMS-301, DMS-V03, DMS-V05, DMS-V21) were purchased from Gelest Inc. Water used in experiments was purified using a Millipore water purification system with a minimum resistivity of 18.0 MΩ·cm.

Figure 55:
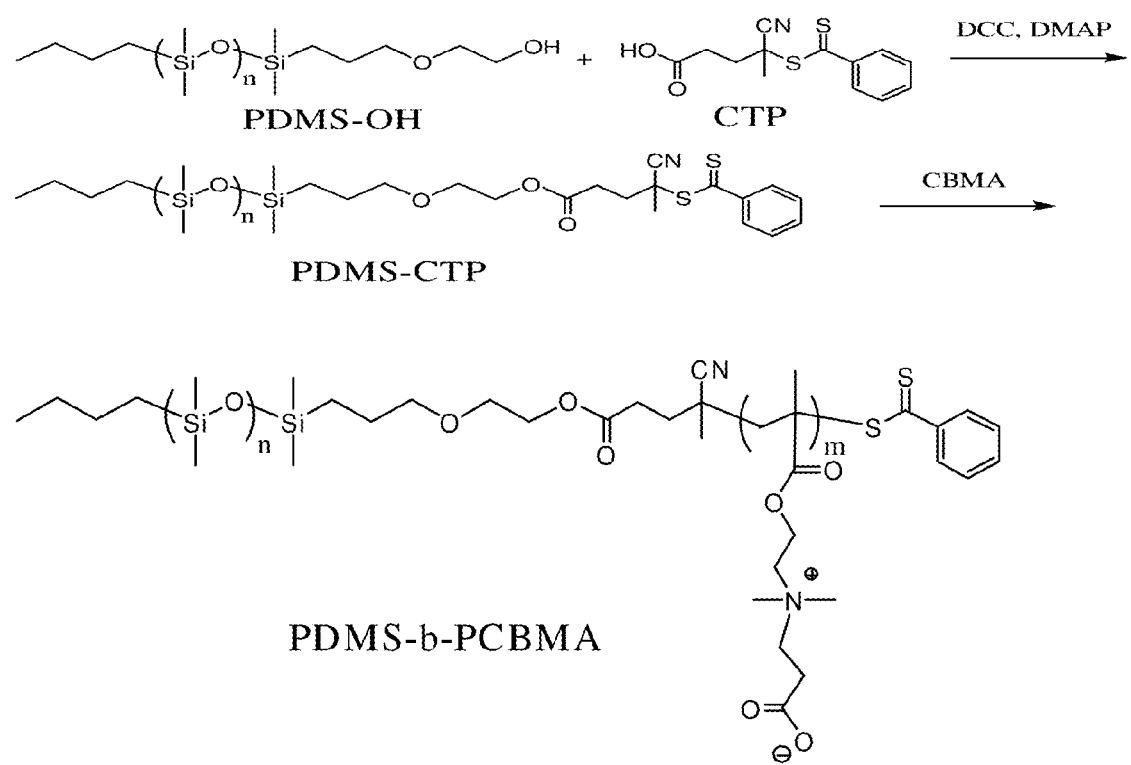
FIG. 55 illustrates the synthetic route for making a representative diblock copolymer, PDMS-b-PCBMA, using a mixed solvent strategy.

The synthesis of diblock copolymer PDMS-b-PCBMA is shown in FIG. 55.

PDMS-Based Macro RAFT Agent.

In a 150 mL one-neck round-bottom flask equipped with a magnetic stirring bar, PDMS-OH (Mn=5000 g/mol) (5.00 g, 1.0 mmol) was dissolved in 80 mL of toluene. After azeotropic distillation to remove traces of water, 4-cyano-4-(phenylcarbonothioylthio) pentanoic acid) (CTP) (0.28 g, 1.0 mmol), 4-(dimethylamino) pyridine (DMAP)(1.22 mg, 0.01 mmol), and methylene chloride (30 mL) were added. After the solution was homogenized by stirring, the flask was placed in an ice bath. Then, N,N'-dicyclohexylcarbodiimide (DCC) (0.21 g, 1.0 mmol) was added in portions. After 12 h of stirring at 0° C., the reaction mixture was increased to room temperature and stirred for another 20 hours. The precipitated dicyclohexylurea was filtered off. PDMS-based macro-CTA PDMS-CTP was obtained as yellow oil-like liquid. The crude product was purified by column chromatography on silica gel with a mobile phase of diethyl ether/hexane (1/2, v/v). The product (3.65 g, yield: 69%) was stored away from light at 4° C. in a sealed bottle. $^1$H NMR (CDCl$_3$): 0.10 (s, 402H, Si—CH3), 0.56 (m, 3H, —CH2-CH3), 0.92 (m, 2H, —CH2-CH2-CH3), 1.34 (m, 4H, Si—CH2-), 1.68 (m, 4H, Si—CH2-CH2-), 1.96 (s, 3H, (N≡C)C—CH3), 2.40-2.80 (m, 4H, (—O—C(=O)—CH2-CH2-), 3.46 (m, 2H, —CH2-CH2-O—CH2-), 3.67 (m, 2H, —O—CH2-CH2-O—C=O), 4.30 (m, 2H, —O—CH2-CH2-O—C=O), 7.42 (m, 2H, m-ArH), 7.60 (m, 1H, p-ArH) and 7.91 (m, 2H, o-ArH).

Synthesis of Diblock Copolymer PDMS-b-PCBMA Using Mixed Solvent Strategy.

CBMA (22.90 g, 100.0 mmol) and mPDMS-CTP (5.30 g, 1.0 mmol) were added along with chloroform/methanol mixture (150 mL, volume ratio=1:1) to an ampule. AIBN (54.7 mg, 0.33 mmol) dissolved in methanol (1.0 mL) was then added. The solution was stirred until all the CBMA monomer was dissolved. The ampule contents were purged with nitrogen for 30 min, and then the ampule was placed in a preheated oil bath at 70° C. The reaction was terminated after 4 h by cooling the reaction tube in an ice bath followed by exposure to air. The product was purified by dialysis against water and isolated by lyophilization.

Synthesis Route of Triblock Copolymer PDMS-PEGMA-PCBMA Using Sequential RAFT Polymerization.

In a 150 mL one-neck round-bottom flask equipped with a magnetic stirring bar, PDMS-OH (Mn=5000 g/mol) (5.00 g, 1.0 mmol) was dissolved in 80 mL of toluene. After azeotropic distillation to remove traces of water, 4-cyano-4-[(dodecylsulfanylthiocarbonyl)sulfanyl]pentanoic acid (DMP) (0.40 g, 1.0 mmol), 4-(dimethylamino) pyridine (DMAP) (1.22 mg, 0.01 mmol), and methylene chloride (30 mL) were added. After the solution was homogenized by stirring, the flask was placed in an ice bath. Then, N,N'-dicyclohexylcarbodiimide (DCC) (0.21 g, 1.0 mmol) was added in portions. After 12 h of stirring at 0° C., the reaction mixture was increased to room temperature and stirred for another 20 hours. The precipitated dicyclohexylurea was filtered off. PDMS-based macro-CTA PDMS-CTP was obtained as yellow oil-like liquid. The crude product was purified by column chromatography on silica gel with a mobile phase of diethyl ether/hexane (1/2, v/v). The product (4.25 g, yield: 79%) was stored away from light at 4° C. in a sealed bottle.

PEGMA (30.0 g, 100.0 mmol) and mPDMS-CTP (5.30 g, 1.0 mmol) were added along with chloroform/methanol mixture (150 mL, volume ratio=1:1) to an ampule. AIBN (54.7 mg, 0.33 mmol) was then added. The ampule contents were purged with nitrogen for 30 min, and then the ampule was placed in a preheated oil bath at 70° C. The reaction was terminated after 4 h by cooling the reaction tube in an ice bath followed by exposure to air. The product was purified by dialysis against water and isolated by lyophilization to obtain PDMS$_{67}$-PEGMA$_{50}$-DMP diblock copolymer.

In the last step, CBMA (2.29 g, 100. mmol) and PDMS$_{67}$-PEGMA$_{50}$-DMP (2.0 g, 0.10 mmol) were added along with chloroform/methanol mixture (50 mL, volume ratio=1:1) to an ampule. AIBN (5.47 mg, 0.033 mmol) dissolved in methanol (1.0 mL) was then added. The solution was stirred until all the CBMA monomer was dissolved. The ampule contents were purged with nitrogen for 30 min, and then the ampule was placed in a preheated oil bath at 70° C. The reaction was terminated after 3 h by cooling the reaction tube in an ice bath followed by dialysis against water and isolated by lyophilization to obtain PDMS$_{67}$-PEGMA$_{50}$-PCBMA$_{25}$ diblock copolymer.

Self-Assembly of Amphiphilic Copolymer

It is well known that amphiphilic block copolymers can undergo self-assembly in aqueous media. The diblock copolymer PDMS-b-PCBMA (0.1 g) was dissolved in 1.0 mL chloroform/methanol (1:1, v/v) mixture. The diblock solution was then slowly dropped into 9.0 mL of toluene to form the stable nanostructured objects, including micelles, vesicles, and rod-like and worm-like micelles, which consist of PCBMA core and PDMS shell. These stable nanostructured objects are ready to be applied onto the glass and/or epoxy coating surface to prepare a non-fouling coating.

Coating Preparation

The non-fouling coatings were prepared using a two-layer manner which were prepared by first additional-curing a PDMS bottom layer and then coating on top of it the block co-polymer in a blend with PDMS (see FIG. 59) The bottom layer was the same for all the samples and made from commercial SYLGARD 184 silicone elastomer. 5.0 g of SYLGARD 184 silicone elastomer mixture was dissolved in 10 mL of MIBK. Then 1.5 mL of this solution was drop casted onto an allyltrimethoxysilane treated microscopy glass slides. The bottom coating was cured at room temperature for 24 h, and then annealed under vacuum at 60° C.

For the top layer, a solution of block co-polymer $PDMS_{67}$-$PCBMA_{10}$ (0.20 g), HMS-301 (0.80 g), DMS-V05 (1.12 g) and Karstedt's catalyst (4.0 µL) in THF (6.0 ml) was subsequently spray coated on the bottom layer using a Badger model 250 airbrush (40 psi air pressure). The coating was cured at room temperature for 24 h and then at 60° C. for 12 h. The blend coating contained around 10 wt % PDMS67-b-PCBMA10 (with respect to the PDMS matrix) in the top layer and is named here B-10.10. Other formulations are listed in Table 3.

TABLE 3

Marine coatings prepared by PDMS-PCBMA incorporated in additioncure PDMS matrix

|  | B-10.10 | B-15.5 | B-15.10 |
| --- | --- | --- | --- |
| HMS-301 | 0.80 g | 0.80 g | 0.80 g |
| DMS-V05 | 1.12 g | 1.12 g | 1.12 g |
| Karstedt's Catalyst | 4.0 µL | 4.0 µL | 4.0 µL |
| $PDMS_{67}$-$PCBMA_{10}$ | 0.20 g | — | — |
| $PDMS_{67}$-$PCBMA_{15}$ | — | 0.10 g | 0.20 g |

Nanopatterns on Coating Surfaces

Figure 59:
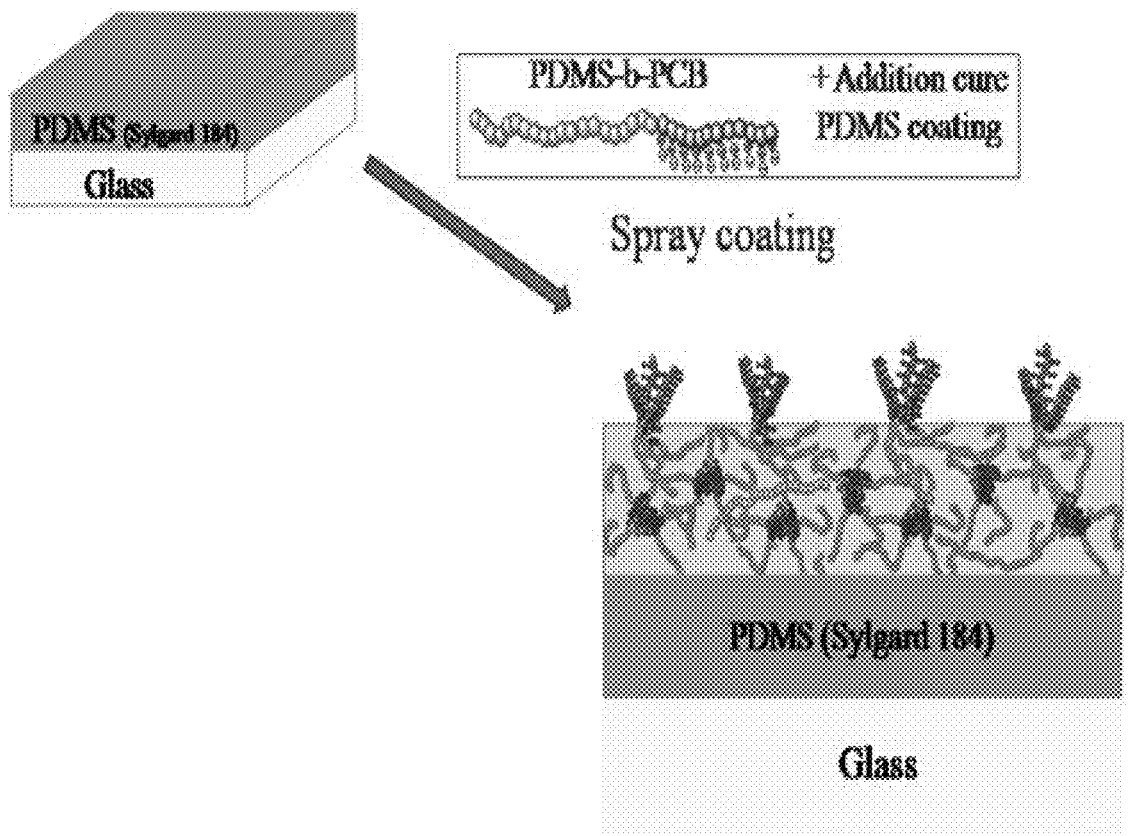
FIG. 59 illustrates the preparation of a PDMS coating filled with PDMS-PCBMA diblock copolymer with nanostructured surface.

The amphiphilic $PDMS_{67}$-$PCBMA_{10}$ diblock co-polymer can form uniform spherical nanoparticles in THF. The formed nanoparticles may be incorporated into addition cure silicone via spray coating method (FIG. 59). Thus, the PDMS-PCBMA nanoparticles with PCBMA core and PDMS shell are dispersed in the PDMS matrix. When the coating is immersed in an aqueous solution, PCBMA chains migrate to the water interface, resulting in PCBMA/PDMS composite coatings. The polar incompatibility between the two blocks of PCBMA-PDMS copolymer strongly enhances the PCBMA/PDMS phase separation. The nanoparticles close to the surface will reverse and formed uniform PCBMA domains on the surface. The scanning electron microscope (SEM) images clearly showed the sizes of these PCBMA domains are around 100 nm in diameter (FIG. 60). The whole surface is smooth with a nanopattern.

Protein Adsorption

Protein Adsorption Evaluated by Enzyme-Linked Immunosorbent Assay (ELISA): To measure fibrinogen (Fg) adsorption, the coating samples were first incubated with 1 mg/ml Fg for 1.5 hours, followed by 5 washes with PBS buffer. Samples were then incubated with horseradish peroxidase (HRP) conjugated anti-fibrinogen (10 µg/ml) for 1.5 hours in a buffer under a desirable conditions followed by another 5 washes with the same buffer. The hydrogel disks, dip coated panels and TCPS substrates were taken out and put into 24 wells plates. 800 µl 1.0 mg/ml o-phenylenediamine (OPD) 0.1 M citrate-phosphate pH 5.0 buffer, containing 0.03% hydrogen peroxide was added. Enzyme activity was stopped by adding an equal volume of 2N $H_2SO_4$ after 15 minutes. The tangerine color is measured at 492 nm. To measure anti-Fg adsorption, samples are directly incubated with horseradish peroxidase (HRP) conjugated anti-Fg, following the same steps for the measurements of Fg adsorption.

Figure 61:
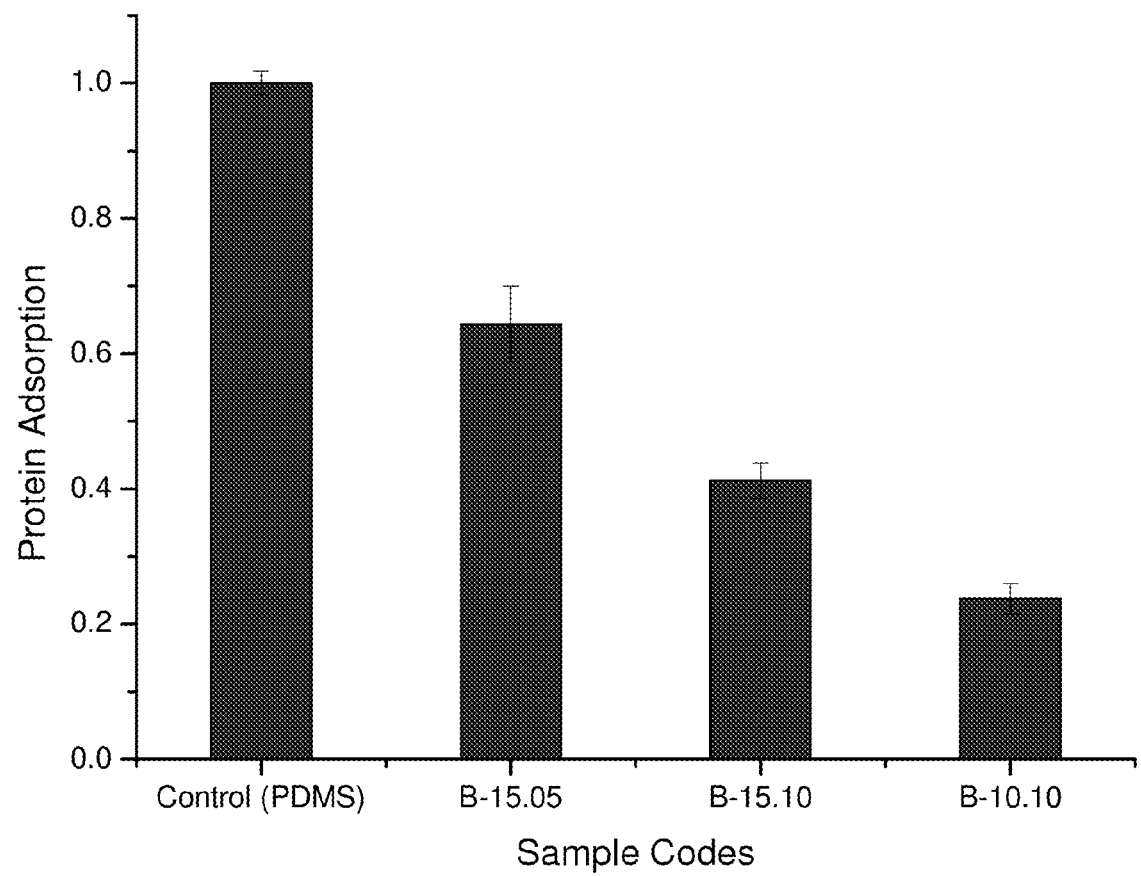
FIG. 61 compares relative protein adsorption as a function of block length and coating composition for surfaces coated with diblock copolymer PDMS-b-PCBMA incorporated in a PDMS matrix. Relative protein adsorption was determined by Enzyme-Linked Immunosorbent Assay (ELISA).

Herein, three non-fouling polymer coatings with different compositions (TABLE 1) were tested in the mean of anti-Fg adsorption. FIG. 61 shows that all the coatings with PDMS-PCBMA diblock co-polymers are more resistant to fibrinogen adsorption than the PDMS control. For the B-10.10 sample, fibrinogen adsorption is about 23% of PDMS control which indicates the coating has anti-fouling property.

Marine Microorganism Assay

For non-fouling polymer coatings applied in a marine setting, the anti-fouling and fouling-release properties are evaluated using spore (sporeling) of Ulva and/or diatom (Navicula). The coating was immersed in sea water with certain amount of spores of Ulva for 1 h. Then non-settled spores was washed away. The settled spores were quantified to determine the anti-fouling of the coating.

After the spores of Ulva are settled on the coating surface, the coating was incubated for 7 days to culture sporelings. The number of sporelings was determined by fluorescence measurement. Percentage removal (fouling release property) was calculated from the fluorescence reading before and after exposure to the water jet.

Figure 62:
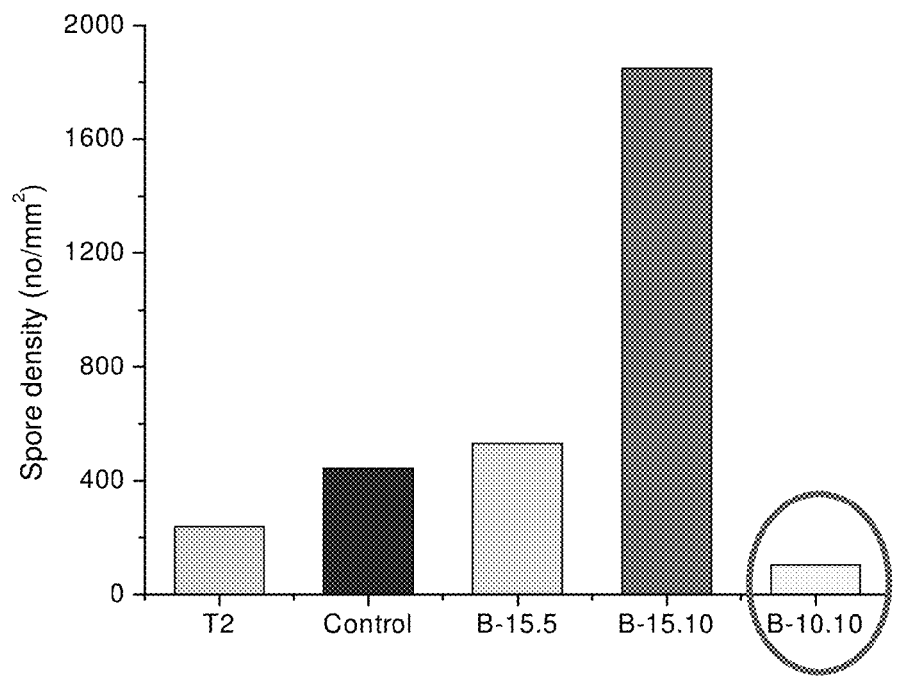
FIG. 62 illustrates the density of Ulva spores after 45 minute settlement. Each point is the mean from 90 counts on 3 replicate slides. Bars show 95% confidence limits. (T2, Commercial Silastic T2 coating; Control, SYLGARD 184 PDMS coating; B-15.5, 5% PDMS67-PCBMA15 in PDMS matrix; B-15.10, 10% PDMS67-PCBMA15 in PDMS matrix; B-10.10, 10% PDMS67-PCBMA10 in PDMS matrix).
Figure 63:
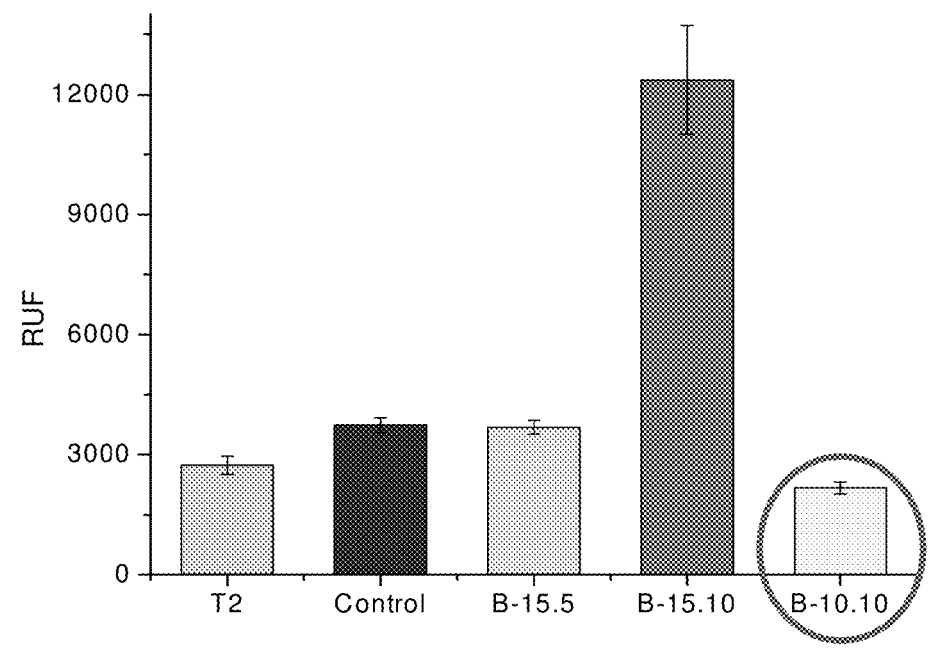
FIG. 63 illustrates the growth of Ulva sporelings after 6 days. Each point is the mean biomass from 6 replicate slides measured using a fluorescence plate reader (RFU; relative fluorescence unit). Bars show standard error of the mean.
Figure 64:
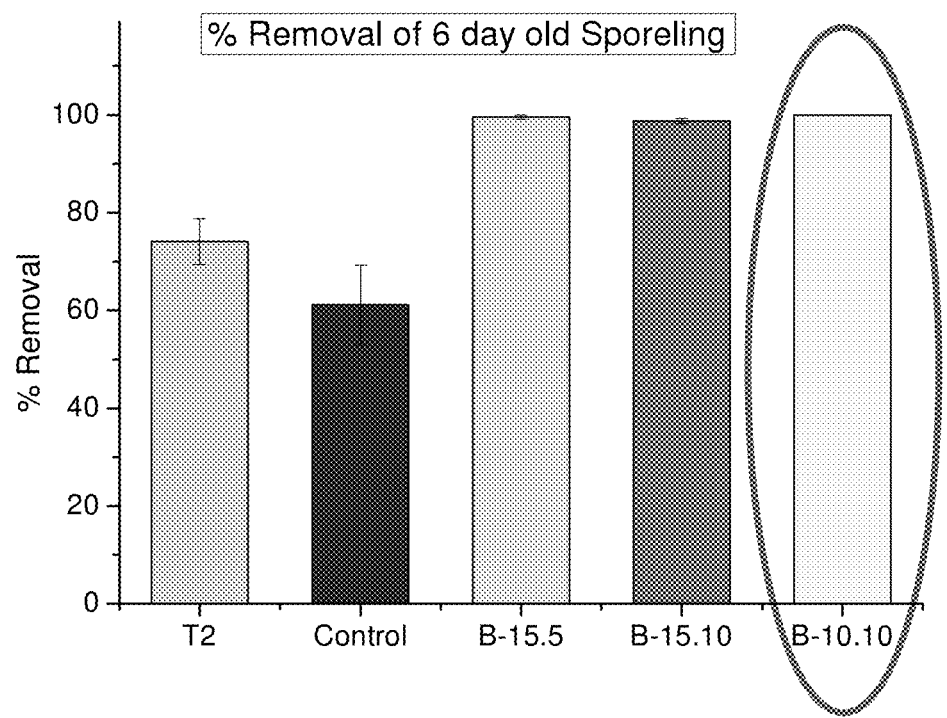
FIG. 64 illustrates the average percentage of Ulva sporelings biomass removal from the surfaces T2, Control, B-15.5, B-15.10, and B-10.10 following exposure to a wall shear stress of 52 Pa.
Figure 66:
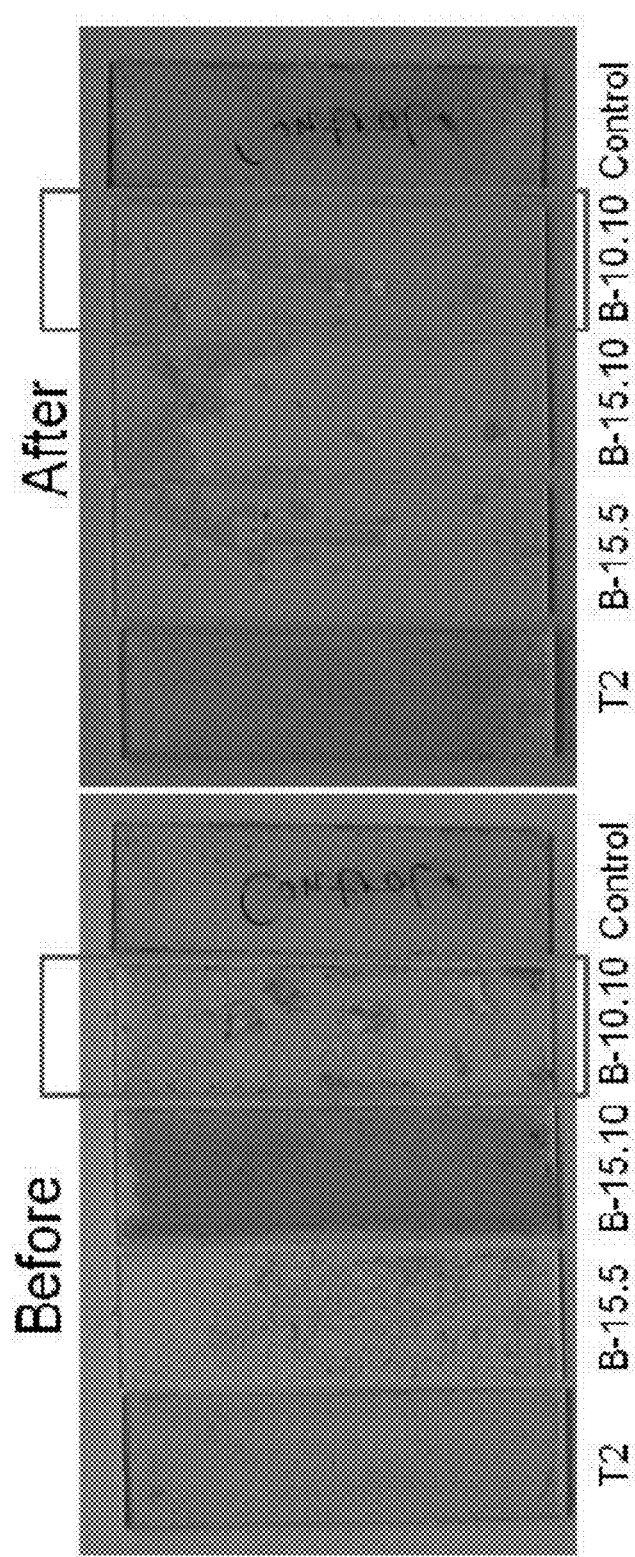
FIG. 66 are photographs of PDMS/PCBMA composite surfaces before (left) and after (right) exposure to a wall shear stress of 24 Pa.

The results shown in FIG. 62 clearly indicate that the amount of attached Ulva spores on the PDMS/PCBMA composite coating surface (circle in FIG. 62) is only 22% compared to the control (commercial PDMS SYLGARD 184). Then, all the coating samples were cultured in sea water for 6 days. More sporelings were observed to have grown on the surfaces. After exposure to a wall shear stress of 24 Pa, essentially all the attached sporelings were removed from the PDMS/PCBMA coating (B-15.5, B-15.10 and B-10.10) surfaces (FIG. 64) which correlates to approximately 100% release. These results demonstrate excellent non-fouling and fouling-release properties of the tested composite surfaces.

As shown in FIG. 64B, increasing the amount of $PDMS_{67}$-$PCBMA_{10}$ nanoparticles incorporated in addition curable PDMS lead to lower Ulva spore settlement and higher removal percentage. For example, when 50 wt % of $PDMS_{67}$-$PCBMA_{10}$ nanoparticles were mixed in the PDMS matrix, it reduced 57% of initial Ulva spore settlement on the PCBMA/PDMS composite surface, compared to Sylgard 184 control. Meanwhile, when exposure to a wall shear stress of 8 Pa, the PCBMA/PDMS composite removed 81% of attached sporelings, while Sylgard 184 control only removed 28%. This clearly indicated that the PCBMA/PDMS composites have low fouling settlement and high fouling-release property.

Field Test

All the coatings were applied to standard 10.16×20.32 cm (4×8 in) test panels with 9.5 mm (⅜ in) holes at each corner to facilitate attachment to the test frames. These were immersed at the Florida Institute of Technology (FIT) static exposure site which is located in the Indian River Lagoon, Melbourne, Fla. The panels were suspended at about 0.5 m depth and caged. Immersion time ranks between 2 weeks to 1 month, depending on coating types. The panels were removed when it is observed that the control coatings have achieved at least 30-50% fouling cover, or greater than 20 organisms>2 mm are present. The fouling assessment is carried out on the center 5 cm×1.5 cm area (=7.5 sq cm), either as % cover or counts of organisms present. For fouling-release coatings, water jet cleaning may be applied and a fouling assessment carried out after cleaning.

Figure 67:
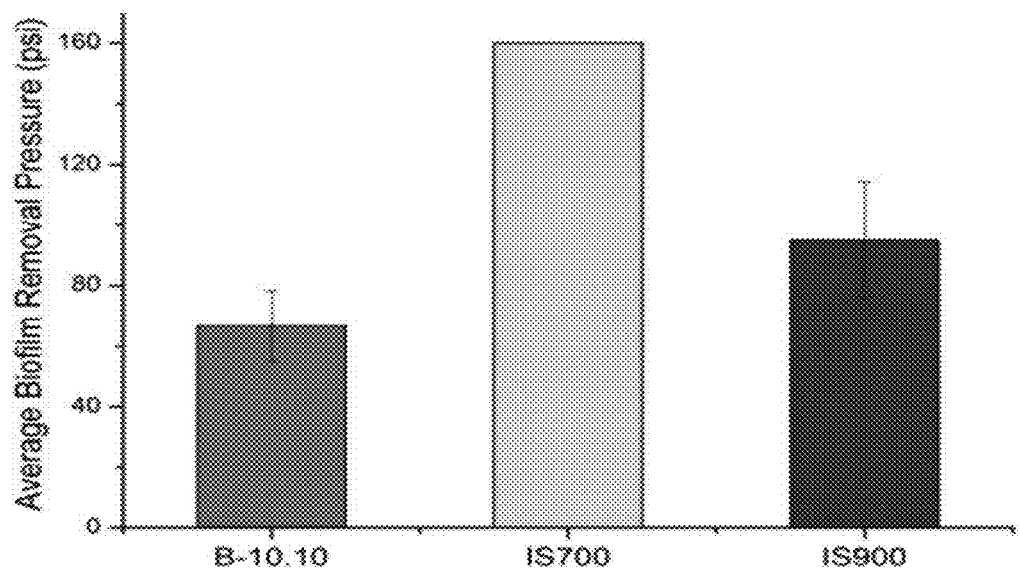
FIG. 67 compares the average biofilm removal pressure from the surface B-10.10 coating, Intersleek® 700 (IS700), and Intersleek® 900 (IS900).

The fouling-release data are shown in FIG. 67. The average biofilm removal pressure for the B-10.10 coating is around 66 psi which is significantly lower that commercial Intersleek® 700 (IS700) (160 psi). It is even lower than another commercial coating, Intersleek® 900 (IS900) (about 95 psi).

Figure 68:
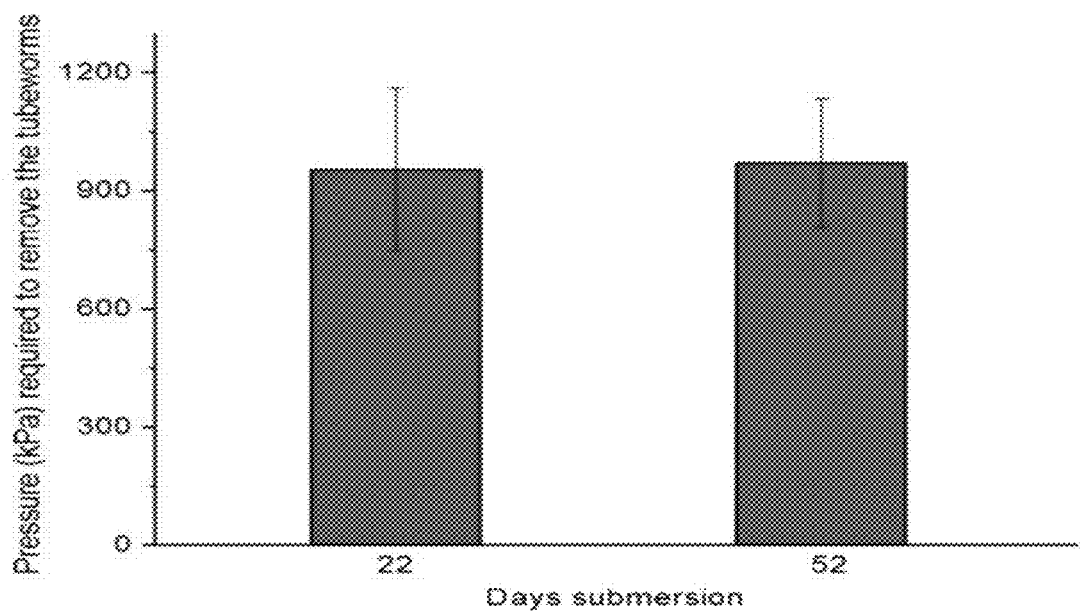
FIG. 68 compares the average pressure (kPa) required to remove tubeworms (Hydroideselegans) from B-10.10 coatings after submission in the ocean for 22 days (left) and 52 days (right). Error bars=1 standard error.
Figure 69:
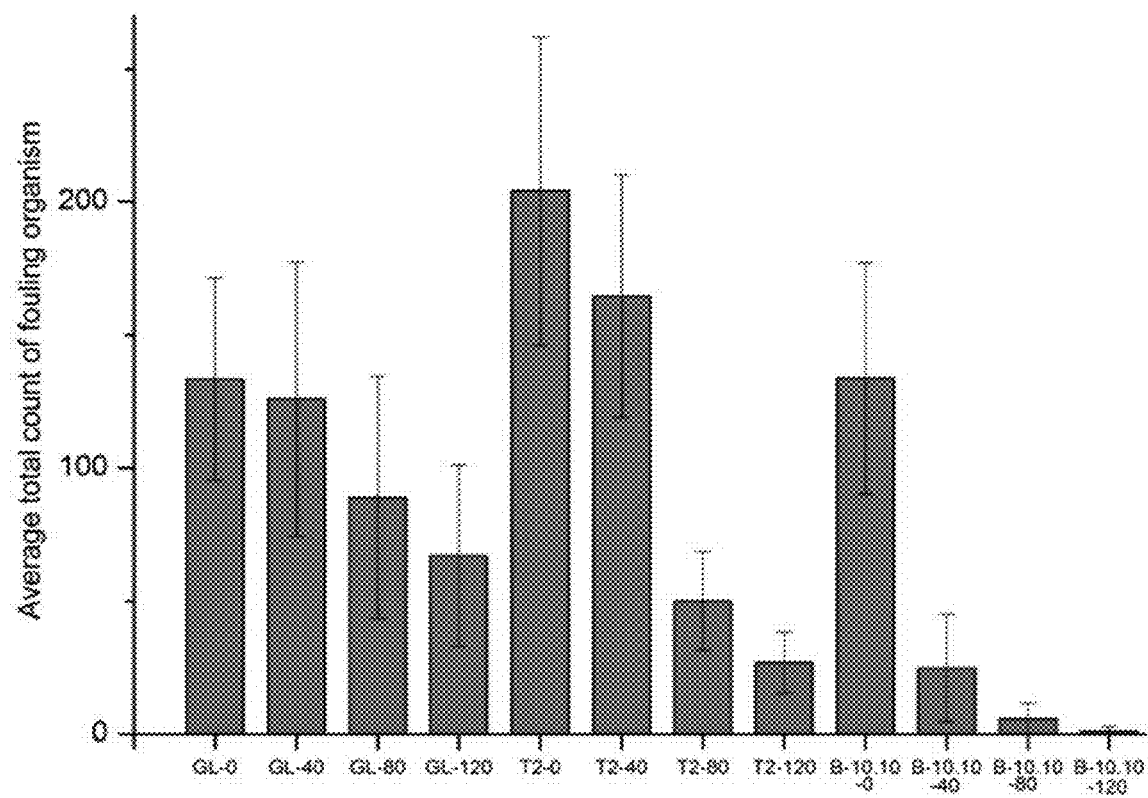
FIG. 69 compares the average total count of fouling organisms on the coating surface after water jet cleanings with different pressures (40, 80 and 120 psi, respectively). The coatings were immersed at test site for 3 weeks. GL, glass; T2, Silastic T2; B-10.10, PDMS/zwitterionic coating.

Another field test was performed in Hawaii. The coated panels were submerged at the Ford Island site where the polychaete tubeworm Hydroideselegansis major colonist of submerged surfaces. After submission in the sea water for 22 days and 52 days, respectively, the coated panels were evaluated for the durability of the panel coating and for the ease of removal of fouling. All the panels exhibit no defects to the surface after submission for 22 days and 52 days which indicates that the B-10.10 is durable and can last a long time. As a test of fouling-release performance, the pressure required to remove individual tubeworms (Hydroideselegans) from the test panels was estimated. Force was measured using a hand-held Shimpo MF push scale that measures force up to 5 lbs. To calculate pressure as psi and in kPa, the basal area was also estimated. Length and width were measured for tubeworms that were not coiled. The basal area for uncoiled tubeworms was calculated as a rectangle. Up to three individuals of each organism were sampled per panel. As shown in FIG. 68, the average pressure required to remove the tubeworms were 954+/−206 kPa (22 days submission) and 971+/−163 (52 days submission), respectively. The values for Intersleek® 700, considered the best fouling-release paint commercially available now, were measured to be about 2.5 megapascals (MPa). Thus, the B-10.10 coating has significantly higher fouling-release capability.

These coatings were also tested following the protocol established at the National University of Singapore. Standard microscopy slides were coated with our PDMS/zwitterionic coating. These coated slides were held in a slide holder and suspended at 0.5-1 m depth, with 3 weeks immersion. The coated side is usually oriented to face downwards so as to reduce accumulation of microalgal slime and detritus. Immersion time lasts between 2 weeks-1 month, depending on coating types. The slides are removed when it is observed that the control coatings have achieved at least 30-50% fouling cover, or greater than 20 organisms>2 mm present. The slides are photographed under magnification and fouling assessment is carried out on the center 5 cm×1.5 cm area (=7.5 $cm^2$) as counts of organisms present. For fouling-release coatings, water jet cleaning may be applied and a fouling assessment carried out after cleaning. After immersion for 3 weeks, the coatings were analyzed and the fouling-release property was evaluated under different water jet pressure, 0, 40, 80 and 120 psi, respectively. As shown in FIG. 68, the overall fouling organisms on the B-10.10 coating is about 74.7% of that on Silastic T2 control. It indicates that the B-10.10 coating can resist the settlement of fouling organisms. After 40, 80 and 120 psi water jet cleaning was applied, only 53.2%, 86.1% and 96.2% of fouling organisms were removed from the coating surface. For the Silastic T2 control coating, the percentages of removal are 21.5% (40 psi), 68.2% (80 psi) and 80.2% (120 psi), respectively. These results clearly showed that the B-10.10 coating has significantly higher fouling-release capability.

Example 9

Figure 56:
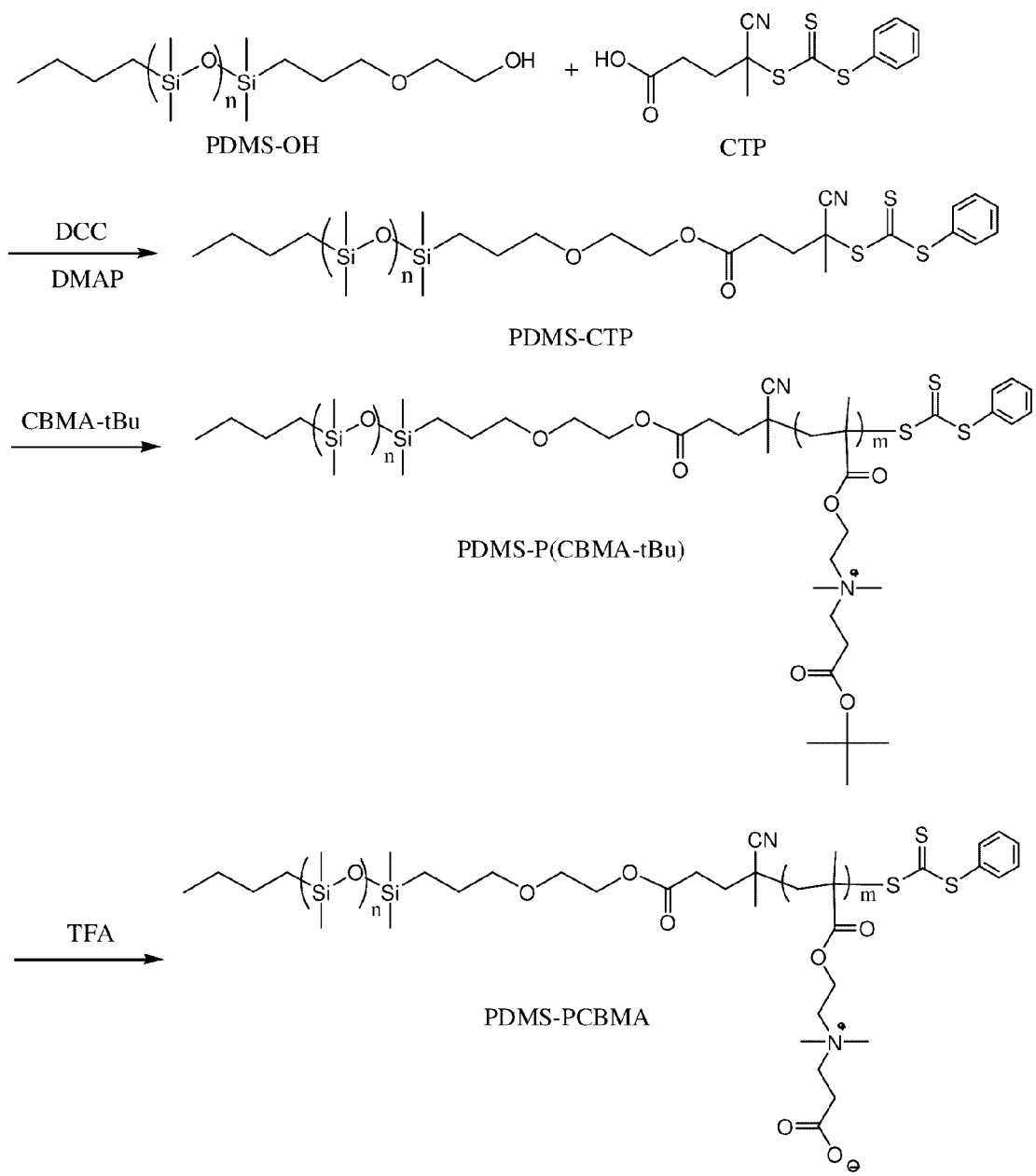
FIG. 56 illustrates the synthesis route for making a representative diblock copolymer, PDMS-b-PCBMA, using a hydrolysable precursor strategy.
Figure 57:
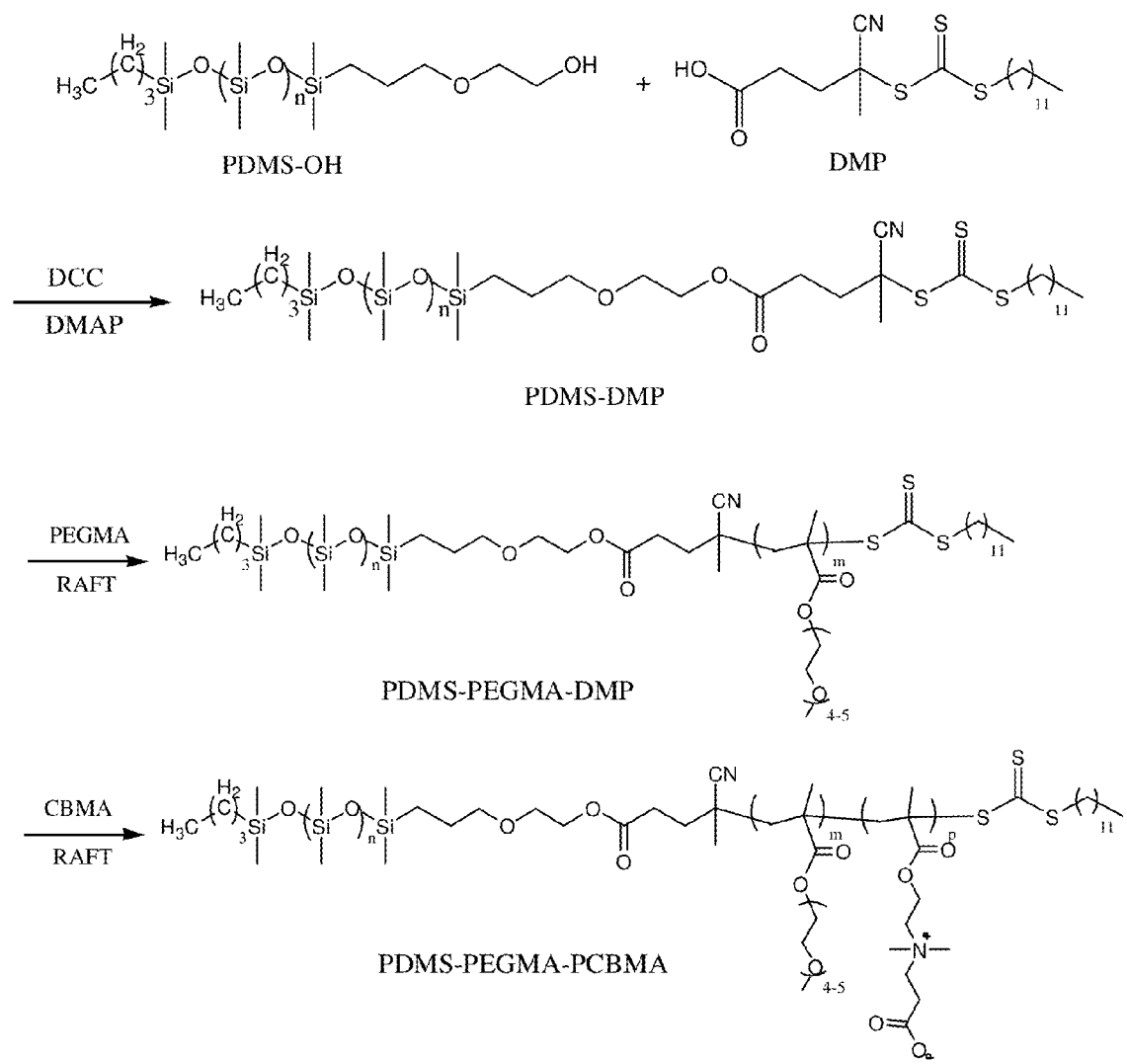
FIG. 57 illustrates the synthesis route for making a representative triblock copolymer, PDMS-PEGMA-PCBMA, using sequential RAFT polymerization.

Preparation of Representative Amphiphilic Diblock Copolymer: PDSM-PCBMA Hydrolysable Precursor Strategy The synthesis of PCBMA-PDMS copolymers follows three steps (FIG. 56). In step 1, the macro-chain transfer agent (macro-CTA) PDMS-CTP was synthesized as described above. In step 2, RAFT polymerization of CBMA-tBu (CBMA precursor) in chloroform was conducted in the presence of PDMS-CTP macro-CTA, using AIBN as an initiator. CBMA-tBu (28.50 g, 100.0 mmol) and PDMS-CTP (5.30 g, 1.0 mmol) were added along with dioxane (150 mL) to an ampule. AIBN (54.7 mg, 0.33 mmol) dissolved in dioxane (1.0 mL) was then added. The solution was stirred until essentially all the CBMA-tBu monomer was dissolved. The ampule contents were sparged with nitrogen for 30 min, and then the ampule was placed in a preheated oil bath at 70° C. The reaction was terminated after 4 h by cooling the reaction tube in an ice bath followed by exposure to air. The resulting PDMS-PCBMA-tBu was obtained by precipitation in acetonitrile.

In step 3, PDMS-PCBMA-tBu diblock copolymer will be treated with TFA to efficiently remove tert-butyl protecting group. PDMS-PCBMA-tBu (1.0 g) were dissolved in 20 mL of $CHCl_3$, then 2.0 mL of TFA was added in the solution. The hydrolysis reaction was completed after 2 h at room temperature. After addition of 100 mL of ethyl ether to the reaction mixture, the formed white powder was isolated and dried. The resulting PDMS-PCBMA copolymer was purified by dialysis against water and isolated by lyophilization.

Example 10

Preparation Representative Amphiphilic Graft Copolymer: PHMS-g-CB

Figure 58:
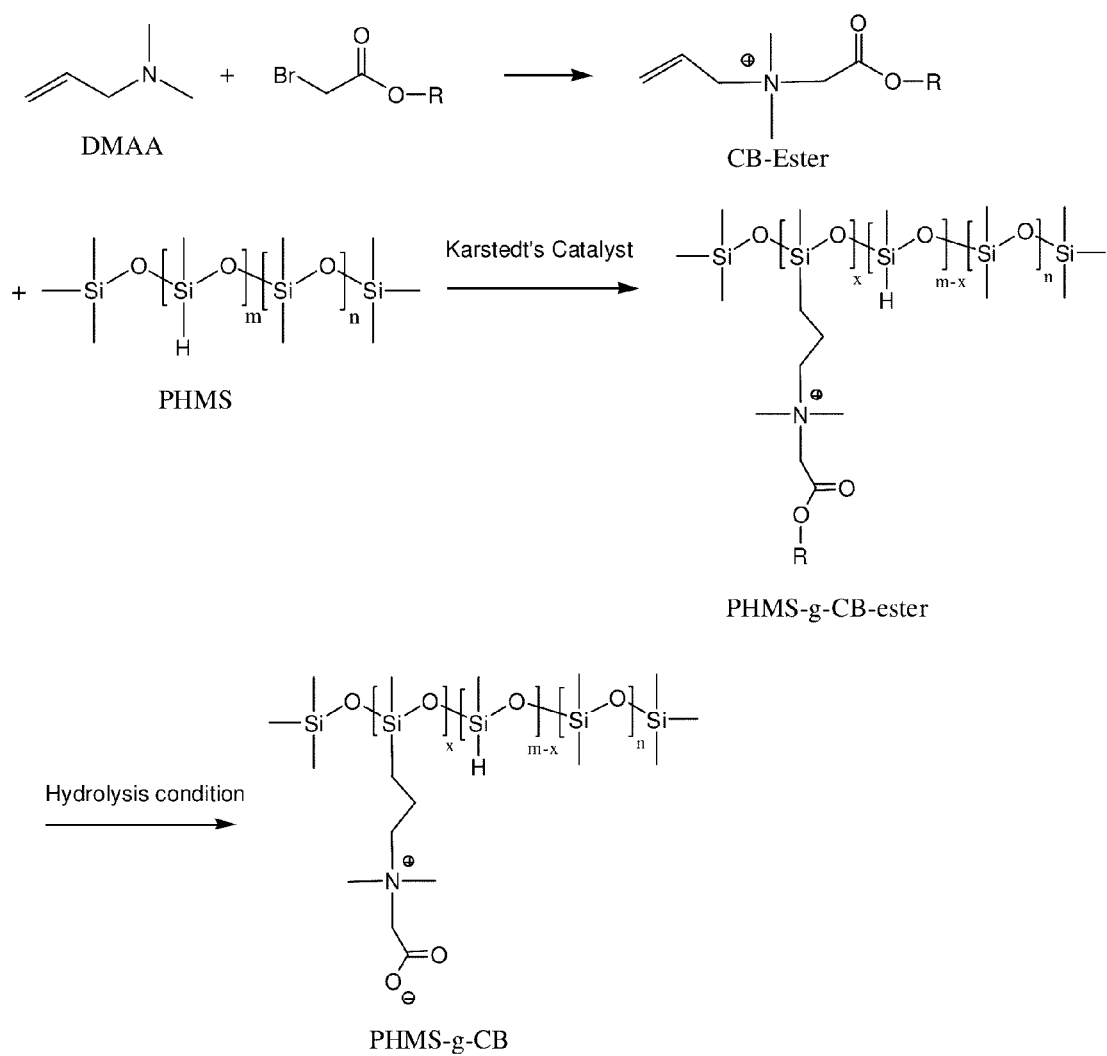
FIG. 58 illustrates the synthesis route of a representative graft copolymer, PHMS-g-CB, of the invention.

A representative procedure for synthesis of PHMS-g-CB grafting copolymer is illustrated in FIG. 58 and described below. First, 4.26 g DMAA and 11.70 gtert-butyl bromoacetate were reacted in 25 mL acetonitrile for 24 h at 50° C. under $N_2$ protection. Upon addition of 250 mL ethyl ether to the reaction mixture, the formed white crystals were isolated and dried. This product was directly used in the next step. Second, to a 100 mL round bottom flask equipped with a nitrogen inlet, condenser, and temperature controller, 5.0 g of PHMS possessing a hydride equivalent weight of 135 g/mol (0.037 mol of hydride) and 5.21 g of CB-ester (0.026 mol) were dissolved in 20 mL of toluene. Once dissolved, approximately 2.00 g of platinum oxide catalyst was added to the reaction mixture and the reaction mixture vigorously stirred for 16 h at 60° C. After completion of the reaction, platinum oxide was removed by filtration. The product was obtained as oil-like after concentrated by rotary evaporation. Third, the final product was obtained after removal of tert-butyl protecting group. The oil-like product PHMS-g-CB-ester (2.0 g) was dissolved in 30 mL chloroform. Then 3.0 mL of TFA was added in the solution. The hydrolysis reaction was completed after 2 h at room temperature. After addition of 100 mL of ethyl ether to the reaction mixture, the formed white powder was isolated and dried. The resulting PHMS-g-CB copolymer was stored in a desiccator at room temperature.

Example 11

Hydrophobic Polymer Patterned with Zwitterionic Polymer of Controlled Coverage To construct a model system with fixed super-hydrophobic polymer modulus and varied surface energy certain embodiments of the present disclosure may take the form of super-hydrophobic polymer substrates with patterned zwitterionic brushes on the surface. Accurate control of the zwitterionic polymer coverage can finely tune the surface energy. In such embodiments the initiators will not fully cover the PDMS substrate, but form patterns before grafting zwitterionic brush. For example, a PDMS substrate with the optimized elastic modulus can be synthesized. The PDMS surface can be treated with concentrated ozone gas to introduce reactive oxygen containing groups. To make a pattern of the initiators attached, plastic sheets (e.g., Mylar®) may be processed via a programmed laser cutter to prepare physical masks with patterned circle or bar shaped holes. The size of the holes and their separation distance can be at the micrometer level or smaller. The mask may be applied on the PDMS surface, and trichlorosilane can filter through the holes via solvent-free chemical vapor deposition, forming initiator patterns. PCBMA will be grafted from these initiator patterns via ATRP, and the PCBMA film thickness and density will be controlled (targeted film thickness is 10-100 nm). By making masks with various types of patterns, the PCBMA coverage (or surface energy) is tuned.

Example 12

Preparation and Characterization of PCBMA Modification of PDMS Surface Via "Grafting-From" Approach Materials.

Copper(I) bromide (99.999%), copper(II) bromide (>99.0%), allytrimethoxysilane, 1,1,4,7,10,10-hexamethyl-triethylene tetramine (HMTETA), human plasma fibrinogen, and phosphate-buffered saline (PBS, 0.01 M phosphate, 0.138 M sodium chloride, 0.0027 M potassium chloride, pH 7.4) were purchased from Sigma Chemical Co. N-(3-Dimethylaminopropyl)-N'-ethylcarbodiimide hydrochloride (EDC), N-hydroxysuccinimide (NHS), and fluorescein isothiocyanate were purchased from Acros Organics. Sylgard® 184 Silicone Elastomer Kit was used from Dow Corning.

Figure 77:
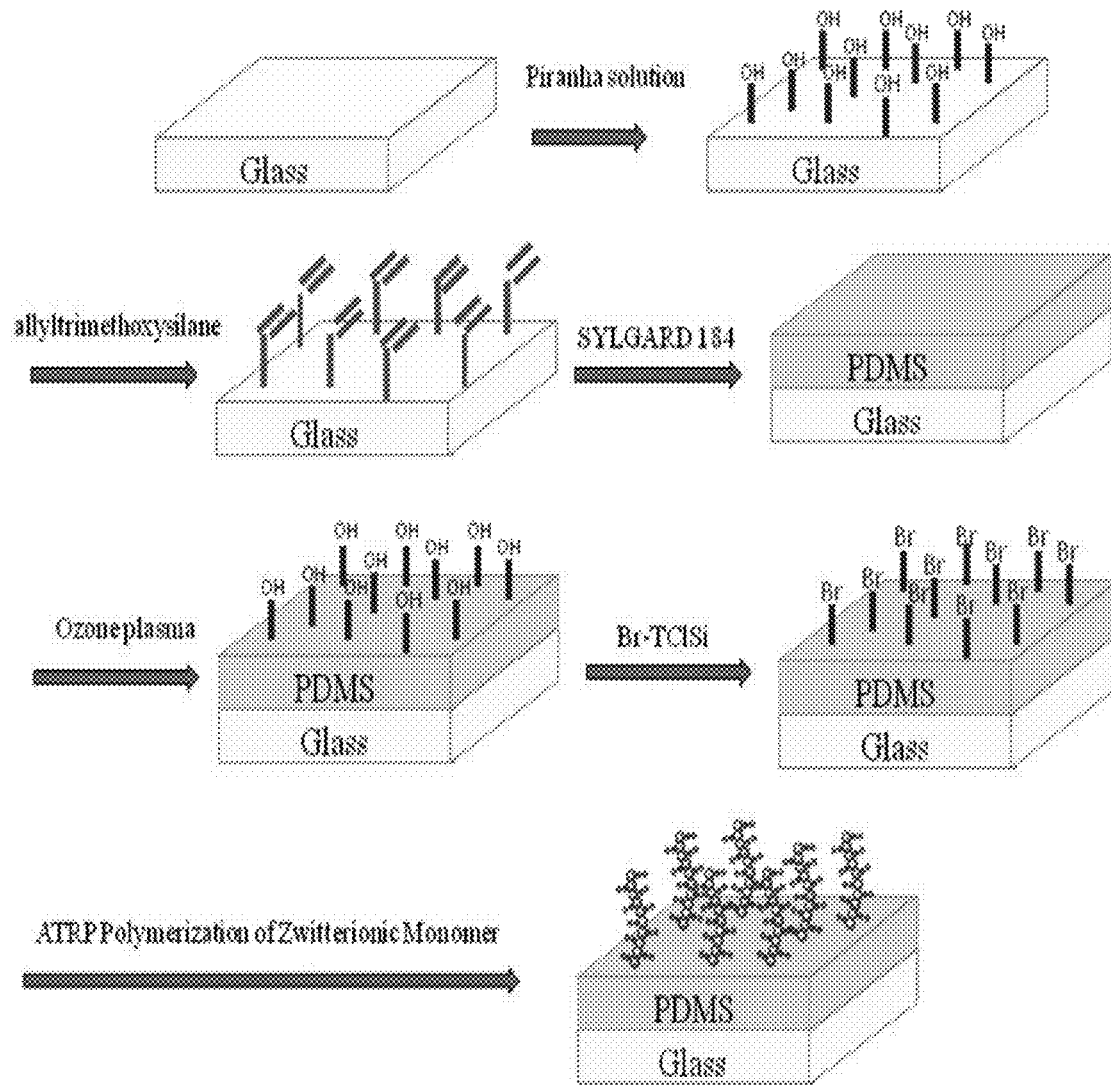
FIG. 77 illustrates the preparation of PDMS coated glass slides and subsequent modification of PDMS surface by zwitterionic polymers via surface ATRP.

Modification of PDMS surface using zwitteroinic polymers is another way to prepare non-fouling polymer coatings (FIG. 77). To accomplish this, PDMS coated glass slides was prepared first. The glass slides were cleaned using acetone and then air dried. The cleaned glass slides were then soaked in piranha solution (125 mL concentrated $H_2SO_4$ and 75 $H_2O_2$) for 2 h. The glass slides were washed to neutral using DI water. The glass slide surfaces were then covered by vinyl groups by soaking in allytrimethoxysilane/ethanol (1 g/100 mL) solution for 4 h. Then, SYLGARD 184 PDMS were then casted onto the glass slides to form PDMS layer. The PDMS surface was then treated with ozone to introduce reactive oxygen containing groups: hydroxyls and peroxides. These were used to attach an atom transfer radical polymerization (ATRP) trichlorosilane initiator to the surface by chemical vapour deposition or traditional solution method. The deposited initiator was then used to polymerize CBMA from the surface via ATRP in water/methanol mixture. The typical polymerization procedure are as follows: Cu(I)Br (7.17 mg, 0.0500 mmol) and Cu(II)Br$_2$ (2.79 mg, 0.0125 mmol) were placed in a small test tube under nitrogen protection and sealed with a rubber septum. 1.375 g (6 mmol) CBMA monomer and a PDMS substrate with immobilized initiator were placed in a large test tube, also under nitrogen protection and sealed with a rubber septum. Both test tubes were deoxygenated by five repetitions of a strong vacuum followed by nitrogen backfill. Deoxygenated water (deoxygenated by bubbling with N$_2$ gas) was then added to both test tubes (2 mL to the small tube, 30 mL to the large tube). While stirring, 17 uL of HMTETA was added to the copper solution and stirred for 30 min for ligand complexation. To initiate polymerization, 1.2 mL of the copper catalyst solution was added to the CBMA monomer and PDMS/glass substrate. Polymerization time was controlled to adjust film thickness.

Characterization.

Figure 78:
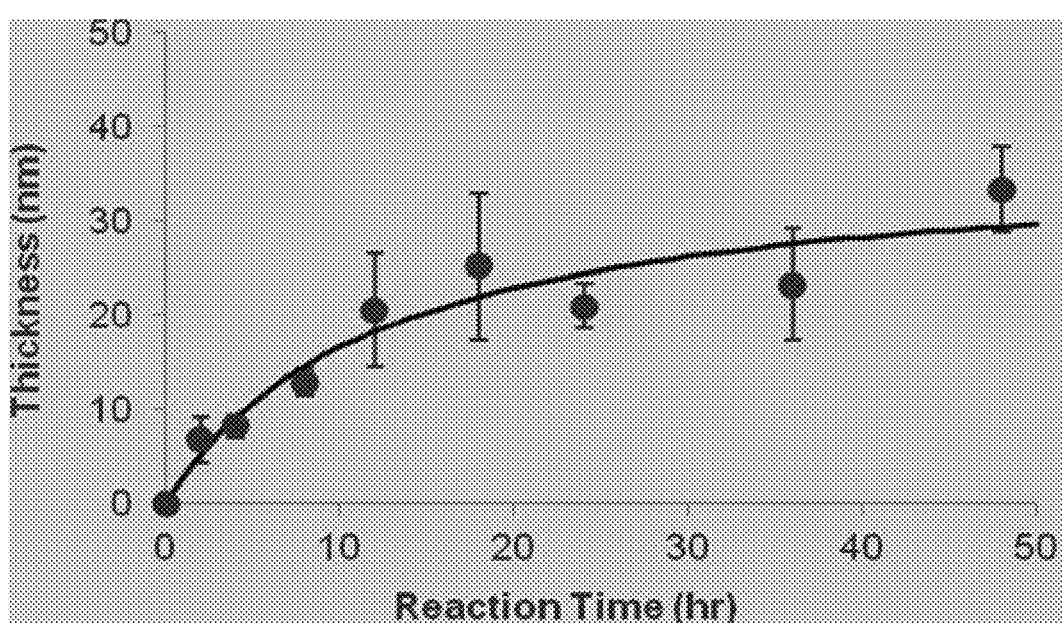
FIG. 78 compares PCBMA film thickness as a function of reaction time as measured by ellipsometry. Error bars represent standard deviation.
Figure 79:
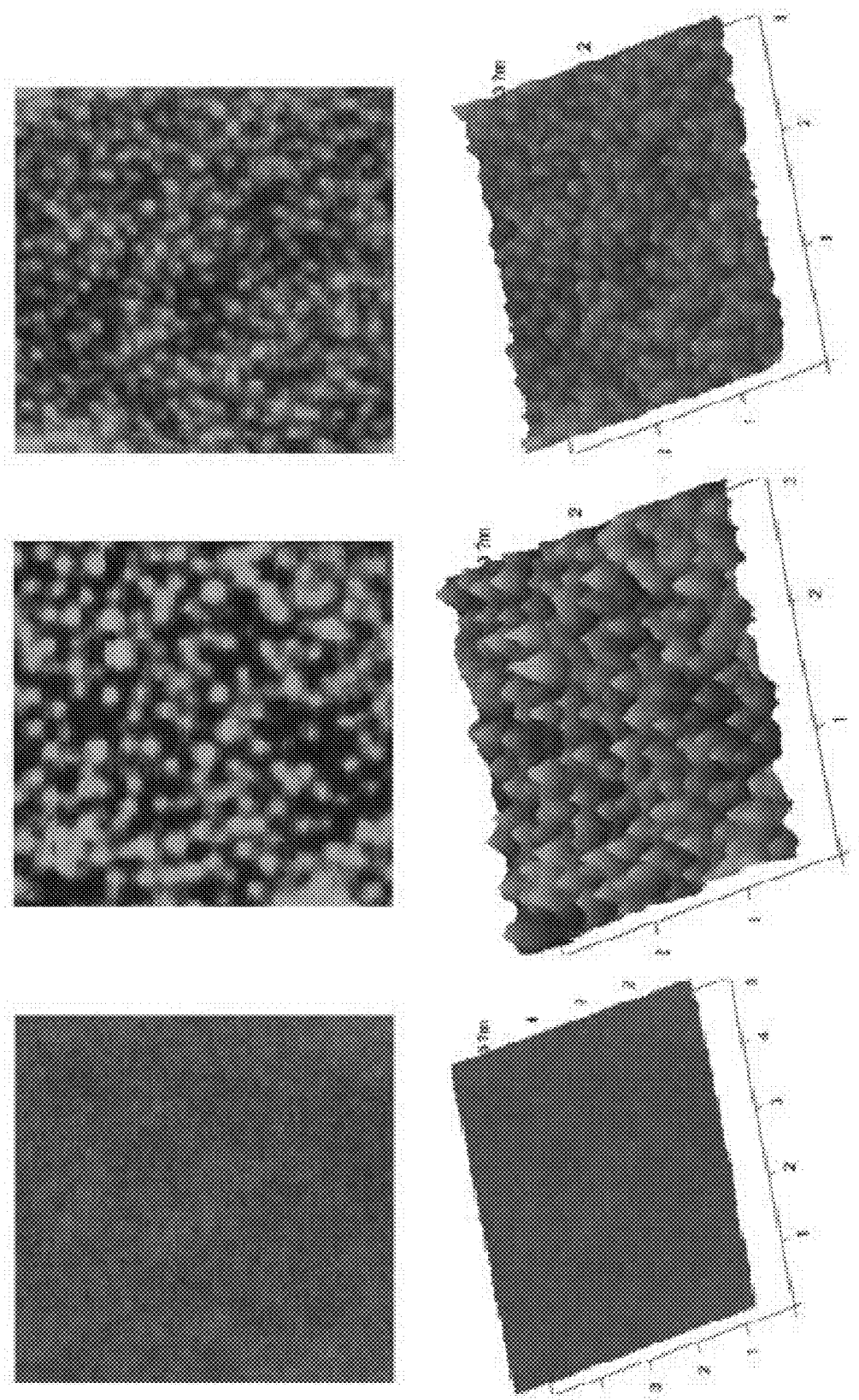
FIG. 79 illustrates AFM images for unmodified PDMS (left) and PCBMA covered PDMS surface under dry (middle) and wet (right) conditions.

Polymer film thickness was measured as a function of reaction time using ellipsometry. As seen in FIG. 78, increase polymerization time results in higher film thickness. A final film thickness around 30 nm was achieved after polymerization for 50 h. PCBMA modified PDMS was imaged by atomic force microscopy (AFM) to evaluate the structure of the modified surface in both wet and dry conditions. When compared to unmodified PDMS (FIG. 78), dry PCBMA had a roughened surface with visible polymer domain formations. In wet conditions, the domains are much smaller.

ELISA.

Figure 80:
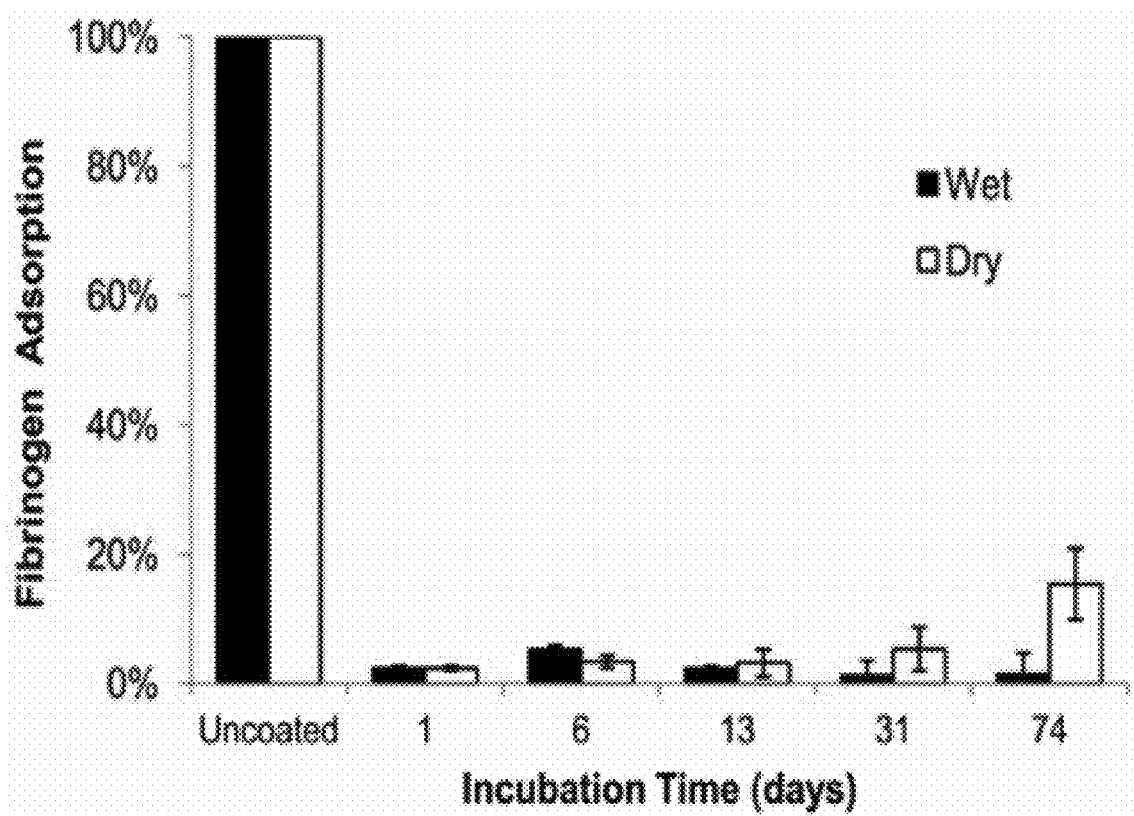
FIG. 80 compares fouling data for fibrinogen adsorption on zwitterionic/PDMS surfaces measured by ELISA as a function of incubation time in dry conditions in a desiccator and wet conditions in phosphate buffered saline solution.

Protein fouling was measured as a function of polymerization time using a fibrinogen adsorption ELISA assay described above. The results are shown in FIG. 80. The coatings were incubated in either wet conditions in phosphate buffered saline (PBS) or dry conditions in a desiccator. Low protein adhesion was seen for up to 31 days for samples incubated under dry conditions. When incubated in wet conditions, on the other hand, the nonfouling properties of PCBMA-coated PDMS appeared to improve with time, with <2% protein adsorption after 74 days.

Functionalization.

Figure 81:
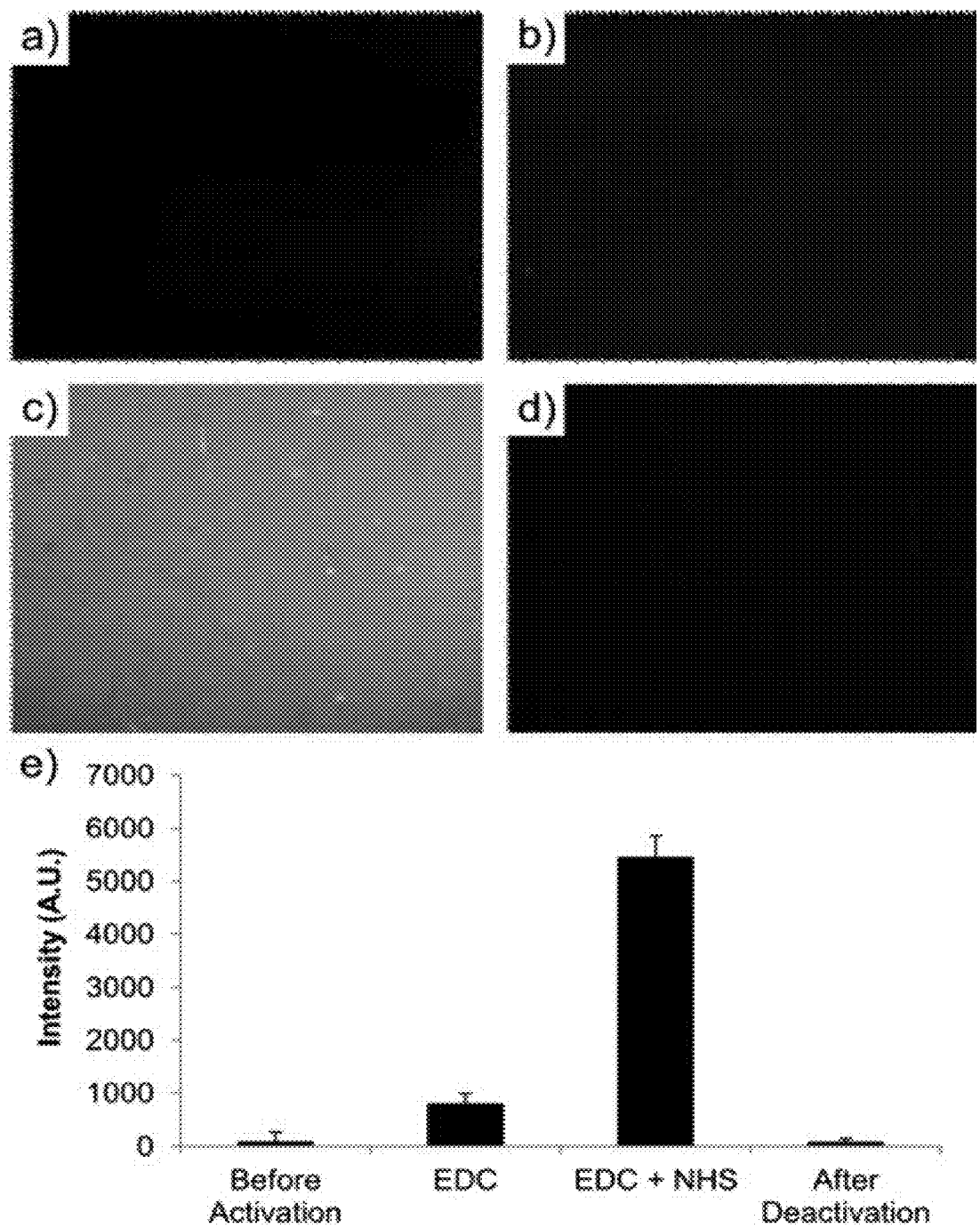
FIGS. 81A-81E are images of unmodified PCBMA-PDMS surface exposed to FITC-BSA showed no protein binding (81A); EDC activated pCBMA-PDMS surface showed little protein attachment (81B); NHS+EDC activated pCBMA-PDMS surface exhibited high levels of controlled protein attachment (81C); NHS+EDC activated pCBMA-PDMS surface followed by deactivation demonstrated no protein binding (81D); and values of image intensities of 27A-27D (81E).

The unique structure of PCBMA allows for covalent immobilization of biomolecules such as RGD-containing peptides for cell adhesion or antibodies for biomarker detection, without sacrificing the nonfouling characteristics of the surface. FITC-labeled bovine serum albumin (FITC-BSA) was chosen as an example biomolecule to demonstrate functionality. This was done first by activating the exposed carboxylic acid groups with reactive N-hydroxysuccinimide (NHS) esters using 1-ethyl-3-(3-dimethylaminopropyl) carbodiimide hydrochloride (EDC). The activated NHS groups are able to react with biomolecules containing accessible primary amines. Once the proteins are covalently bound to the surface, the surface can be deactivated under slightly basic conditions (pH 10) to hydrolyze unreacted NHS groups back to carboxylic acids, thereby restoring the nonfouling background. The typical functionalization procedure is as follows: 57.4 mg EDC and 7.67 mg NHS were dissolved in 1.5 mL ultrapure (18.2 MΩ) water. PCBMA-coated PDMS was incubated in the activation solution for 10 minutes. The sample was removed, rinsed with water and dried with air. Next, 2 μL of FITC-BSA at 1 mg/mL in 10 mM phosphate, pH 7.4, was spotted on the activated PCBMA-PDMS surface and allowed to react for 30 min. The surface was then rinsed with PBS and incubated in 300 mM NaCl and 10 mM Na$_2$CO$_3$, pH 10.0, for 1 hour to deactivate any unreacted NHS ester groups still remaining on the surface. A similar procedure was followed, but without NHS in the activation solution, as a control. Another control was performed where FITC-BSA was not spotted on the activated surface, but instead the surface was deactivated first with basic solution. FITC-BSA was then spotted to test the effectiveness of deactivation. As shown in FIG. 81A, a pCBMA-modified surface is shown that was exposed to FITC-BSA without any activation by EDC/NHS. This surface exhibits no protein adhesion, confirming the nonfouling characteristics of the non-activated surface. FIGS. 81B and 81C show the PCBMA-modified surface exposed to FITC-BSA, previously activated with EDC and EDC+NHS, respectively. The surface activated with EDC showed minimal functionalization due to the short half-life of the EDC based esters. NHS greatly improves the stability of the active ester, providing increased time between activation and biomolecule conjugation, resulting in greatly improved levels of protein attachment. A surface once activated, then deactivated with basic conditions (10 mM sodium carbonate, pH 10.0), returns to being nonfouling and no longer is able to conjugate to FITC-BSA (FIG. 81D). Values of intensity for all surfaces can be seen in FIG. 81E.

Marine Microorganism Assay.

Figure 82:
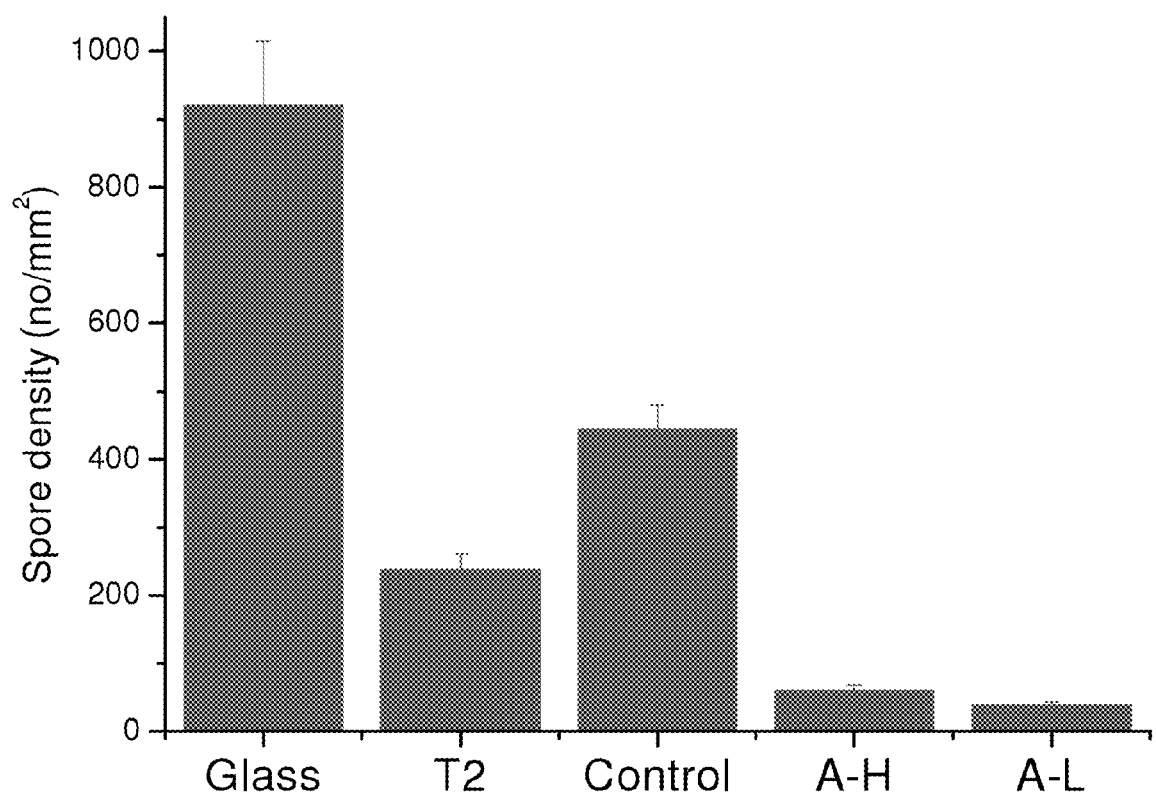
FIG. 82 compares the density of Ulva spores after 45 minute settlement on the PCBMA modified PDMS surfaces (T2, Silastic T2; Control, SYLGARD 184; A-H and A-L, PCBMA modified PDMS).

For non-fouling polymer coatings applied in a marine setting, the PCBMA coated PDMS is evaluated using spore (sporeling) of Ulva. The coating is immersed in sea water with certain amount of spores of Ulva for 45 min. Then non-settled spores will be washed away. The settled spores will be quantified to determine the anti-fouling of this coating. The results shown in FIG. 82 clearly indicate that the amount of attached Ulva spores on the PCBMA coated PDMS surface is only about 10% compared to the control (commercial PDMS SYLGARD 184). Thus, PCBMA coated PDMS has excellent low-fouling property.

Example 13

Preparation of Representative Zwitterionic Hydrogels

CBMAN Preparation.

Commercially available isobutyl cyanoacetate is alkylated with dibromomethane in a potassium carbonate/dimethyl formamide two-phase system to give 1-bromo-2-cyano-2-isobutyl cyanoacetate. The purified product reacts with dimethylaminoethyl methacrylate in acetonitrile at 60° C. and results in a cationic tert-butyl ester compound. Then the tert-butyl ester moiety is removed by trifluoroacetic acid (TFA) treatment in dichloromethane for 2 days. The solvent is removed under vacuum and replaced with acetonitrile. The solution is neutralized over an ion exchange resin (IRA 4000H form), subsequently concentrated and precipitated into ether, and finally vacuum dried to obtain a solid.

Zwitterionic hydrogels can be prepared via photopolymerization of hydrogel components (monomer, CBMAN; crosslinker, CBMAX) in 1M NaCl. Total concentration of monomer and crosslinker ranges from 10% to 65% (wt/vol). This solution is mixed by sonication in an ice bath and 2-hydroxy-2-methylpropiophenone (photoinitiator) is added at 1% (wt/wt). This final solution is homogenized by gentle mixing and polymerized between glass microscope slides separated by 0.5 or 1.5 mm-thick polytetrafluoroethylene (PTFE) spacers, under 362 nm UV light. After 30 minutes, the hydrogel is removed and immersed in phosphate-buffered saline (PBS) to hydrate. PBS is refreshed daily for 5 days to remove unreacted chemicals.

The resulting hydrogels can be characterized for equilibrium water content (EWC) and compressive modulus and strength. By varying crosslinker density, the hydrogels are expected to have modulus matching that of PDMS as well as reasonably high mechanical strength enabling their uses in practical situations.

While illustrative embodiments have been illustrated and described, it will be appreciated that various changes can be made therein without departing from the spirit and scope of the invention.

The embodiments of the invention in which an exclusive property of priviledge is claimed are defined as follows:

1. A marine coating composition, comprising:
    (a) a plurality of nanoparticles, each nanoparticle comprising a plurality of copolymers, wherein each copolymer comprises a zwitterionic component and a hydrophobic component, wherein the zwitterionic component comprises repeating units selected from the group consisting of carboxybetaine, sulfobetaine, phosphobetaine, and mixtures thereof, and wherein the hydrophobic component comprises repeating units produced from hydrophobic monomers; and
    (b) a solid polymeric matrix, wherein the solid polymeric matrix comprises a polymer selected from the group consisting of rosins, polyesters, amino resins, polyurethanes, polyamides, polyimides, epoxy and phenolic resins, alkyd resins, polyphosphazenes, polysiloxanes, fluorinated polymers, and mixtures thereof,
    wherein the nanoparticles are embedded in the solid polymeric matrix.

2. The composition of claim 1, wherein the plurality of copolymers are block copolymers.

3. The composition of claim 1 further comprising biocide.

4. The composition of claim 1, wherein each copolymer is a block copolymer, a random copolymer, or a graft copolymer.

5. The composition of claim 1, wherein each copolymer is a polydimethylsiloxane-b-polycarboxybetaine methacrylate (PDMS-b-PCBMA) or a polydimethylsiloxane-b-polysulfobetaine methacrylate (PDMS-b-PSBMA) diblock copolymer.

6. The composition of claim 1, wherein each copolymer is a polydimethylsiloxane-polyethyleneglycol monomethyl ether methacrylate-polycarboxybetaine methacrylate (PDMS-PEGMA-PCBMA) or a polydimethylsiloxane-polyethyleneglycol monomethyl ether methacrylate-polysulfobetaine methacrylate (PDMS-PEGMA-PSBMA) triblock copolymer.

7. A surface of a marine substrate treated with the composition of claim 1.

8. The surface of claim 7, wherein the substrate is a marine structure.

9. The surface of claim 8, wherein the marine structure is a vessel hull, a propeller, a periscope, a sensor, a fish net, or a bridge.

10. A method for treating a surface of a marine substrate, comprising applying the composition of claim 1 to a surface of a marine substrate.

11. The method of claim 10, wherein applying the composition comprises spraying or painting.

12. The composition of claim 1, wherein the copolymer is a triblock copolymer, wherein the zwitterionic component is a first block, and the hydrophobic component is a second block.

13. The composition of claim 12, wherein the second block comprises siloxane repeating units, and wherein the triblock copolymer further comprises a third block comprising neutral hydrophilic repeating units.

14. The composition of claim 12, wherein the triblock copolymer is a poly(carboxybetaine methacrylate)-poly(p-phenylene oxide)-poly(carboxybetaine methacrylate) (PCBMA PPO PCBMA), a poly(carboxybetaine methacrylate)-poly(ethylene oxide)-poly(carboxybetaine methacrylate) (PCBMA-PEO-PCBMA), a poly(sulfobetaine methacrylate)-poly(p-phenylene oxide)-poly(sulfobetaine methacrylate) (PSBMA-PPO-PSBMA), a poly(sulfobetaine methacrylate)-poly(ethylene oxide)-poly(sulfobetaine methacrylate) (PSBMA-PEO-PSBMA), a poly(carboxybetaine methacrylate)-poly(p phenylene oxide)-poly(sulfobetaine methacrylate) (PCBMA-PPO-PSBMA), or a poly(carboxybetaine methacrylate) poly(ethylene oxide) poly(sulfobetaine methacrylate) (PCBMA-PEO-PSBMA).

* * * * *

UNITED STATES PATENT AND TRADEMARK OFFICE
CERTIFICATE OF CORRECTION

PATENT NO. : 9,533,006 B2  
APPLICATION NO. : 13/692958  
DATED : January 3, 2017  
INVENTOR(S) : S. Jiang et al.

Page 1 of 1

It is certified that error appears in the above-identified patent and that said Letters Patent is hereby corrected as shown below:

In the Specification

| Column | Lines | |
|---|---|---|
| 1 | 21-26 | Delete "This invention was made with Government support under Grant Numbers N00014-04-1-0409, N00014-07-1036, N000141010631, and N000141210441 awarded by Office of Naval Research and Grant Number HDTRA1-10-1-0074 awarded by the Defense Threat Reduction Agency. The Government has certain rights in the invention." and insert --This invention was made with Government support under Grant Numbers N00014-04-1-0409, N00014-07-1-1036, N00014-10-1-0631, and N00014-12-1-0441 awarded by Office of Naval Research. The Government has certain rights in the invention.-- |

Signed and Sealed this  
Twelfth Day of September, 2017

Joseph Matal  
*Performing the Functions and Duties of the*  
*Under Secretary of Commerce for Intellectual Property and*  
*Director of the United States Patent and Trademark Office*